United States Patent [19]

Oberdorf et al.

[11] Patent Number: 5,489,605
[45] Date of Patent: Feb. 6, 1996

[54] CYANOOXIME ETHERS, THEIR PREPARATION, AGENTS CONTAINING THEM AND THEIR USE

[75] Inventors: Klaus Oberdorf, Heidelberg; Uwe Kardorff, Mannheim; Hans Theobald, Limburgerhof; Albrecht Harreus, Ludwigshafen; Hartmann Koenig, Limburgerhof; Volker Harries, Frankenthal, all of Germany

[73] Assignee: BASF Aktiengesellschaft, Ludwigshafen, Germany

[21] Appl. No.: 290,938

[22] PCT Filed: Feb. 17, 1993

[86] PCT No.: PCT/EP93/00371

§ 371 Date: Aug. 24, 1994

§ 102(e) Date: Aug. 24, 1994

[87] PCT Pub. No.: WO93/16985

PCT Pub. Date: Sep. 2, 1993

[30] Foreign Application Priority Data

Feb. 29, 1992 [DE] Germany .................. 42 06 353.1

[51] Int. Cl.⁶ .............. C07C 255/64; C07D 261/08; C07D 263/32; A01N 43/74
[52] U.S. Cl. .............. 514/374; 514/378; 514/523; 548/236; 548/247; 558/391
[58] Field of Search ................... 548/236, 247; 558/391; 514/523, 374, 378

[56] References Cited

U.S. PATENT DOCUMENTS

| | | |
|---|---|---|
| 4,327,213 | 4/1982 | Van Zorge . |
| 4,347,372 | 8/1982 | Fory et al. . |
| 4,363,041 | 12/1982 | Lelandais . |
| 4,424,215 | 1/1984 | Buerstinghaus et al. . |
| 4,451,286 | 5/1984 | Martin . |
| 4,568,668 | 2/1986 | Bürstinghaus et al. . |
| 4,760,056 | 7/1988 | Bürstinghaus et al. . |
| 4,612,306 | 9/1986 | Bürstinghaus et al. . |
| 4,670,425 | 6/1987 | Büerstinghaus et al. . |
| 4,857,524 | 8/1989 | Furukawa et al. . |
| 5,055,471 | 10/1991 | de Fraine et al. . |

FOREIGN PATENT DOCUMENTS

| | | |
|---|---|---|
| 1228244 | 7/1971 | Canada . |
| 129889 | 6/1984 | European Pat. Off. . |
| 2051038 | 9/1978 | United Kingdom . |

OTHER PUBLICATIONS

J. Smiti et al., Arch. Pharm. 304 (1971), 425–429.

Rec. Trav. Chim. Pays–Bas 91 (1972), 711.

J. Org. Chem, 25 (19) (1960).

*Primary Examiner*—Robert Gerstl
*Attorney, Agent, or Firm*—Keil & Weinkauf

[57] ABSTRACT

Cyanooxime ethers of the formula I $$R^1R^2CH-ON=C(CN)-R^3 \qquad I$$

where
  $R^1$ is hydrogen or $C_1$–$C_4$-alkyl;
  $R^2$ is an unsubstituted or substituted mononuclear to trinuclear aliphatic or aromatic ring system which, in addition to carbon atoms, may contain from one to four nitrogen atoms or from one to three hetero atoms selected from the group consisting of oxygen, sulfur and nitrogen and
  $R^3$ is unsubstituted or substituted alkyl or an unsubstituted or substituted aliphatic ring system which, in addition to carbon atoms, may contain one or two hetero atoms selected from the group consisting of oxygen, sulfur and nitrogen,
processes for their preparation, agents containing them and their use.

24 Claims, No Drawings

CYANOOXIME ETHERS, THEIR PREPARATION, AGENTS CONTAINING THEM AND THEIR USE

The present invention relates to cyanooxime ethers of the formula I $$R^1R^2CH-ON=C(CN)-R^3 \qquad \text{I}$$

where
$R^1$ is hydrogen or $C_1-C_4$-alkyl;
$R^2$ is a mononuclear to trinuclear aliphatic or aromatic ring system which is bonded via a carbon atom and may contain, in addition to carbon atoms, from one to four nitrogen atoms or from one to three hetero atoms selected from the group consisting of oxygen, sulfur and nitrogen, where this ring system may carry from one to five halogen atoms and/or from one to four of the following radicals: cyano, cyanato, thiocyanato, nitro, amino, hydroxyl, carboxyl, $C_1-C_6$-alkyl, $C_1-C_4$-haloalkyl, $C_1-C_6$-alkoxy, $C_1-C_4$-haloalkoxy, $C_1-C_4$-alkoxy-$C_1-C_4$-alkyl, $C_1-C_6$-alkylthio, $C_1-C_4$-haloalkylthio, $C_1-C_4$-alkylthio-$C_1-C_4$-alkyl, $C_3-C_{15}$-alkenyl, $C_3-C_{15}$-alkenyloxy, $C_3-C_8$-cycloalkyl, $C_3-C_8$-cycloalkenyl, $C_3-C_8$-cycloalkoxy, $C_5-C_8$-cycloalkenyloxy, $C_1-C_6$-alkylamino, di-$C_1-C_6$-alkylamino, $C_1-C_6$-alkylcarbonyl, $C_1-C_6$-alkoxycarbonyl, $C_1-C_6$-alkylaminocarbonyl, di-$C_1-C_6$-alkylaminocarbonyl, $C_1-C_6$-alkylcarboxyl, phenyl, phenoxy, phenylthio, phenylamino, phenyl-$C_1-C_4$-alkyl, phenoxy-$C_1-C_4$-alkyl, phenylthio-$C_1-C_4$-alkyl or phenylamino-$C_1$–$C_4$-alkyl, where the aromatic rings in turn may carry from one to five halogen atoms and/or from one to three of the following radicals: cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, where this ring system may carry from one to four halogen atoms and/or from one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

$R^3$ is unsubstituted or substituted alkyl or an unsubstituted or substituted aliphatic ring system which is bonded via a carbon atom and, in addition to carbon atoms, may contain one or two hetero atoms selected from the group consisting of oxygen, sulfur and nitrogen.

The present invention furthermore relates to a process for the preparation of these compounds, to pesticides containing the compounds I and to their use.

The literature discloses cyanooxime ethers as active ingredients for protecting plants and as drugs (fungicides: EP-A 370 629; growth regulators: U.S. Pat. No. 4,451,286; antidotes: EP-A 12 158, EP-A 122 231; insecticides: EP-A 303 934; herbicides: DE-A 28 37 857; drugs: DE-A 28 00 316).

Furthermore, EP-A 463 488 discloses phenylacetic acid derivatives which have oxime ether groups and are suitable for controlling pests and are noteworthy for their fungicidal.

It is an object of the present invention to provide novel compounds suitable for controlling pests.

We have found that this object is achieved by the cyanooxime ethers of the formula I which are defined at the outset. We have also found processes for the preparation of these compounds, pesticides containing these compounds and their use.

The novel compounds are obtained in general by etherifying a cyanooxime of the formula II in a conventional manner, in an inert organic solvent, with a compound III.

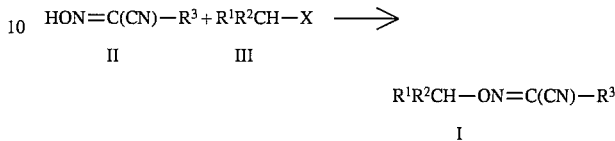

In the formula III, X is a nucleofugic leaving group, such as halogen, for example chlorine, bromine or iodine, an aromatic or aliphatic sulfonate, for example p-toluenesulfonate, methanesulfonate or triflate, or carboxylate, such as acetate, in particular chlorine or bromine.

This reaction is usually carried out at from −20° to 100° C., preferably from 20° to 80° C.

Suitable solvents are aliphatic hydrocarbons, such as pentane, hexane, cyclohexane and petroleum ether, aromatic hydrocarbons, such as toluene, o-, m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, nitriles, such as acetonitrile and propionitrile, ketones, such as acetone, methyl ethyl ketone, diethyl ketone and tert-butyl methyl ketone, and dimethyl sulfoxide and dimethylformamide, particularly preferably dimethylformamide, N-methylpyrrolidone, pyridine, acetonitrile and tetrahydrofuran.

Mixtures of the stated solvents may also be used.

The reaction may furthermore be carried out in a two-phase solvent system, for example methylene chloride/water, with the addition of a suitable phase transfer Catalyst. Examples of suitable phase transfer catalysts are trimethylammonium salts, such as benzyltrimethylammonium chloride, and crown ethers, such as 18-crown-6.

The starting materials are generally reacted with one another in equimolar amounts. It may be advantageous for the yield if one of the starting materials is used in an excess of from 0.1 to 10, preferably from 0.2 to 2, molar equivalents, based on the coreactant.

As a rule, it is advantageous to carry out the reaction in the presence of a base.

Suitable bases are in general inorganic compounds, such as alkali metal and alkaline earth metal hydroxides, e.g. lithium hydroxide, sodium hydroxide, potassium hydroxide and calcium hydroxide, alkali metal and alkaline earth metal oxides, such as lithium oxide, sodium oxide, calcium oxide and magnesium oxide, alkali metal and alkaline earth metal hydrides, such as lithium hydride, sodium hydride, potassium hydride and calcium hydride, alkali metal amides, such as lithium amide, sodium amide and potassium amide, alkali metal and alkaline earth metal carbonates, such as lithium carbonate and calcium carbonate, alkali metal bicarbonates, such as sodium bicarbonate, and alkali metal and alkaline earth metal alcoholates, such as sodium methylate, sodium ethylate, potassium ethylate, potassium tert-butylate and dimethoxymagnesium, as well as organic bases, for example tertiary amines, such as trimethylamine, triethylamine, triisopropylethylamine and N-methylpiperidine, pyridine, substituted pyridines, such as collidine, lutidine and 4-dimethylaminopyridine, and bicyclic amines.

Potassium carbonate, sodium methylate, sodium ethylate and sodium hydride are particularly preferably used.

The bases are used in general in equimolar amounts but may also be employed in excess or, if necessary, as a solvent.

The reaction mixtures are worked up in a conventional manner, for example by mixing with water, separating the phases and, if required, purifying the crude products by chromatography. Some of the intermediates and end products are obtained in the form of colorless or slightly brownish, viscous oils, which can be freed from volatile components or purified under reduced pressure and at moderately elevated temperatures. If the intermediates and end products are obtained as solids, purification may also be effected by recrystallization or digestion.

Owing to the C=N double bonds, the novel compounds of the general formula I may be obtained in the preparation in the form of E/Z isomer mixtures. These can be separated into the individual components in the conventional manner, for example by crystallization or chromatography. Both the individual isomeric compounds and mixtures thereof are subjects of the invention and can be used as pesticides.

The cyanooximes II required for the preparation of the compounds I are known in the literature or can be prepared by processes similar to known ones (J. Org. Chem. 25(9) (1960), 1471; Rec. Tray. Chim. Pays-Bas 91 (1972), 711; EP-A 031,754; EP-A 074,047; EP-A 115,318; EP-A 129,889; EP-A 150,822; EP-A 201,764; EP-A 201,807).

The compounds of the general formula III which are required for the preparation of the compounds of the general formula I are either described in the literature or can be prepared by processes similar to known ones.

The compounds of the general formula III which are required for the preparation of the compounds of the general formula I and in which $R^2$ is 4-oxazolyl and the ring may be substituted as described above are either described in the literature or can be prepared by the methods described there (for example: J. Simiti and E. Chindris, Arch. Pharm. 304 (1971), 425–429).

The compounds of the general formula III which are required for the preparation of the compounds of the general formula I and in which $R^2$ is 5-isoxazolyl and the ring may be substituted as described above are either described in the literature or can be prepared by the methods described there (for example G. A. Lec, Synthesis 1982, 508–509).

In view of their use for controlling pests, preferred compounds of the formula I are those in which the substituents have the following meanings:

$R^1$ is hydrogen or $C_1$–$C_4$-alkyl, such as methyl, ethyl, propyl, 1-methylethyl, butyl, 1-methylpropyl, 2-methylpropyl or 1,1-dimethylethyl, preferably hydrogen or methyl, in particular hydrogen;

a mononuclear to trinuclear aliphatic or aromatic ring system which is bonded via a carbon atom and, in addition to carbon atoms, may contain from one to four nitrogen atoms or from one to three hereto atoms selected from the group consisting of oxygen, sulfur and nitrogen, for example $C_3$–$C_8$-cycloalkyl such as cyclopropyl, cyclobutyl, cyclopentyl, cyclohexyl, cycloheptyl or cyclooctyl, preferably cyclopropyl, cyclopentyl or cyclohexyl, in particular cyclopropyl or cyclohexyl;

$C_5$–$C_8$-cycloalkenyl, such as cyclopent-1-enyl, cyclopent-2-enyl, cyclopent-3-enyl, cyclohex-1-enyl, cyclohex-2-enyl, cyclohex- 3-enyl, cyclohept-1-enyl, cyclohept-2-enyl, cyclohept-3-enyl, cyclohept-4-enyl, cyclooct-1-enyl, cyclooct-2-enyl, cyclooct- 3-enyl or cyclooct-1-enyl, preferably cyclopent-1-enyl, cyclopent-3-enyl or cyclohex-1-enyl, in particular cyclopent- 3-enyl;

$C_5$–$C_8$-cycloalkadienyl, such as cyclopenta-1,3-dien-1-yl, cyclopenta- 1,3-dien-2-yl, cyclopenta-1,3-dien-5-yl, cyclohexa- 1,3-dien-1-yl, cyclohexa-1,3-dien-2-yl, cyclohexa-1,3-dien-5-yl, cyclohexa-1,4-dien-1-yl, cyclohexa-1,4-dien-3-yl, cyclohepta- 1,3-dien-1-yl, cyclohepta-1,3-dien-2-yl, cyclohepta-1,3-dien- 5-yl, cyclohepta-1,3-dien-6-yl, cyclohepta-1,4-dien-1-yl, cyclohepta-1,4-dien-2-yl, cyclohepta-1,4-dien-3-yl, cyclohepta- 1,4-dien-6-yl, cycloocta-1,3-dien-1-yl, cycloocta-1,3-dien-2-yl, cycloocta-1,3-dien-5-yl, cycloocta-1,3-dien-6-yl, cycloocta- 1,4-dien-1-yl, cycloocta-1,4-dien-2-yl, cycloocta-1,4-dien-3-yl, cycloocta-1,4-dien-6-yl, cycloocta-1,4-dien-7-yl, cycloocta- 1,4-dien-1-yl or cycloocta-1,4-dien-3-yl;

3-membered to 6-membered, saturated or unsaturated heterocycles containing from one to three nitrogen atoms and/or one oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin- 2-yl, 1,3,4-triazolidin-2-yl, 2,3-dihydrofur-2-yl, 2,3-dihydrofur-3-yl, 2,5-dihydrofur-2-yl, 2,5-dihydrofur-3-yl, 2,3-dihydrothien- 2-yl, 2,3-dihydrothien-3-yl, 2,5-dihydrothien-2-yl, 2,5-dihydrothien- 3-yl, 2,3-pyrrolin-2-yl, 2,3-pyrrolin-3-yl, 2,5-pyrrolin- 2-yl, 2,5-pyrrolin-3-yl, 2,3-isoxazolin-3-yl, 2,5-isoxazolin- 3-yl, 4,5-isoxazolin-3-yl, 2,3-isoxazolin-4-yl, 2,5-isoxazolin- 4-yl, 4,5-isoxazolin-4-yl, 2,3-isoxazolin-5-yl, 2,5-isoxazolin- 5-yl, 4,5-isoxazolin-5-yl, 2,3-isothiazolin-3-yl, 2,5-isothiazolin-3-yl, 4,5-isothiazolin-3-yl, 2,3-isothiazolin-4-yl, 2,5-isothiazolin- 4-yl, 4,5-isothiazolin-4-yl, 2,3-isothiazolin-4-yl, 2,5-isothiazolin-5-yl, 4,5-isothiazolin-5-yl, 2,3-dihydropyrazol- 3-yl, 2,3-dihydropyrazol-4-yl, 2,3-dihydropyrazol-5-yl, 3,4-dihydropyrazol-3-yl, 3,4-dihydropyrazol-4-yl, 3,4-dihydropyrazol- 5-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol- 4-yl, 2,3-dihydrooxazol-5-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl or 1,2,4-tetrahydrotriazin-3-yl, 1,3-dihydrooxazin-2-yl, 1,3-dithian- 2-yl, 2-tetrahydropyranyl, 1,3-dioxolan-2-yl, thiazol- 2-in-2-yl, 3,4,5,6-tetrahydropyridin-2-yl, 4H-1,3-thiazin-2-yl, oxiranyl or 1,3-dithian-2-yl;

heteroaromatics having a five-membered ring and containing from one to three nitrogen atoms and/or an oxygen or sulfur atom, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol- 3-yl, 1,2,4-thiadiazol-5-yl, 1,2,4-triazol-3-yl, 1,3,4-oxadiazol- 2-yl, 1,3,4-thiadiazol-2-yl or 1,3, 4-triazol-2-yl, 1,2,3-oxadiazol- 4-yl, 1,2,3-oxadiazol-5-yl, 1,2,5-triazol-3-yl, 1,2,3-triazol-4-yl, 1,2,3-triazol-5-yl, 5-tetrazolyl, 1,2,3,4-thiatriazol-5-yl or 1,2,3,4-oxatriazol-5-yl, in particular 3-isoxazolyl, 5-isoxazolyl, 4-oxazolyl or 4-thiazolyl;

or heteroaromatics having a six-membered ring containing from one to three nitrogen atoms as hetero atoms, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin- 2-yl or 1,2,4-triazin-3-yl, in particular 2-pyridinyl, 3-pyridinyl, 2-pyrimidinyl, 3-pyrimidinyl or 1,3,5-triazin-2-yl, or phenyl, 1-naphthyl, 2-naphthyl, 1-anthracenyl, 2-anthracenyl, 9-anthracenyl, 1-phenanthrenyl, 2-phenanthrenyl, 3-phenanthrenyl, 4-phenanthrenyl or 9-phenanthrenyl, in particular phenyl;

where these abovementioned ring systems may carry from one to five halogen atoms, such as fluorine, chlorine, bromine and iodine, in particular fluorine or chlorine, and/or from one to four of the following radicals:

cyano, cyanato, thiocyanato, nitro, amino, hydroxyl, carboxyl, $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, 1-methylethyl, 1-methylpropyl or 1,1-dimethylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_6$-alkoxy, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular methoxy, ethoxy or 1-methylethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2 -fluoroethoxy, 2-chloro-2,2-difluoroethoxy, 2,2-dichloro- 2-fluoroethoxy, 2,2,2-trichloroethoxy or pentafluoroethoxy;

$C_1$–$C_4$-alkoxy-$C_1$–$C_4$-alkyl, such as methoxymethyl, ethoxymethyl, propoxymethyl, 1-methylethoxymethyl, butoxymethyl, 1-methylpropoxymethyl, 2-methylpropoxymethyl, 1,1-dimethylethoxymethyl, 1-methoxyethyl, 1-ethoxyethyl, 1-propoxyethyl, 1-(1-methylethoxy)ethyl, 1-butoxyethyl, 1-(1-methylpropoxy)ethyl, 1-(2-methylpropoxy) ethyl, 1-(1,1-dimethylethoxy) ethyl, 2-methoxyethyl, 2-ethoxyethyl, 2-propoxyethyl, 2-(1-methylethoxy)ethyl, 2-butoxyethyl, 2-(1-methylpropoxy) ethyl, 2-(2-methylpropoxy)ethyl, 2-(1,1-dimethylethoxy) ethyl, 1-methoxypropyl, 1-ethoxypropyl, 1-propoxypropyl, 1-(1-methylethoxy)propyl, 1-butoxypropyl, 1-(1-methyl-propoxy)propyl, 1-(2-methylpropoxy)propyl, 1-(1,1-dimethylethoxy)propyl, 2-methoxypropyl, 2-ethoxypropyl, 2-propoxypropyl, 2-(1-methylethoxy)propyl, 2-butoxypropyl, 2-(1-methylpropoxy)propyl, 2-(2-methylpropoxy)propyl, 2-(1,1-dimethylethoxy)propyl, 3-methoxypropyl, 3-ethoxypropyl, 3-propoxypropyl, 3-(1-methylethoxy)propyl, 3-butoxypropyl, 3-(1-methylpropoxy)propyl, 3-(2-methylpropoxy)propyl, 3-(1,1-dimethylethoxy)propyl, 1-methoxy-1-methylethyl, 1-ethoxy-1-methylethyl, 1-propoxy-1-methylethyl, 1-(1-methylethoxy)-1-methylethyl, 1-butoxy-1-methylethyl, 1-(1-methylpropoxy)-1-methylethyl, 1-(2-methylpropoxy)-1-methylethyl, 1-(1,1-dimethylethoxy)- 1-methylethyl, 2-methoxy-1-methylethyl, 2-ethoxy-1-methylethyl, 2-propoxy-1-methylethyl, 2-(1-methylethoxy)-1-methylethyl, 2-butoxy-1-methylethyl, 2-(1-methylpropoxy)-1-methylethyl, 2-(2-methylpropoxy)-1-methylethyl, 2-(1,1-dimethylethoxy)- 1-methylethyl, 1-methoxybutyl, 1-ethoxybutyl, 1-propoxybutyl, 1-(1-methylethoxy)-butyl, 1-butoxybutyl, 1-(1-methylpropoxy)-butyl, 1-(2-methylpropoxy)-butyl, 1-(1,1-dimethylethoxy)-butyl, 2-methoxybutyl, 2-ethoxybutyl, 2-propoxybutyl, 2-(1-methylethoxy)-butyl, 2-butoxybutyl, 2-(1-methylpropoxy)-butyl, 2-(2-methylpropoxy)-butyl, 2-(1,1-dimethylethoxy)-butyl, 3-methoxybutyl, 3-ethoxybutyl, 3-propoxybutyl, 3-(1-methylethoxy)-butyl, 3-butoxybutyl, 3-(1-methylpropoxy)-butyl, 3-(2-methylpropoxy)-butyl, 3-(1,1-dimethylethoxy)-butyl, 4-methoxybutyl, 4-ethoxybutyl, 4-propoxybutyl, 4-(1-methylethoxy)-butyl, 4-butoxybutyl, 4-(1-methylpropoxy)-butyl, 4-(2-methylpropoxy)-butyl, 4-(1,1-dimethylethoxy)-butyl, 1-methoxy-1-methylpropyl, 1-ethoxy-1-methylpropyl, 1-propoxy-1-methylpropyl, 1-(1-methylethoxy)- 1-methylpropyl, 1-butoxy-1-methylpropyl, 1-(1-methylpropoxy)-1-methylpropyl, 1-(2-methylpropoxy)-1-methylpropyl, 1-(1,1-dimethylethoxy)-1-methylpropyl, 2-methoxy-1-methylpropyl, 2-ethoxy-1-methylpropyl, 2-propoxy-1-methylpropyl, 2-(1-methylethoxy)- 1-methylpropyl, 2-butoxy-1-methylpropyl, 2-(1-methylpropoxy)- 1-methylpropyl, 2-(2-methylpropoxy)-1-methylpropyl, 2-(1,1-dimethylethoxy)-1-methylpropyl, 3-methoxy-1-methylpropyl, 3-ethoxy-1-methylpropyl, 3-propoxy-1-methylpropyl, 3-(1-methylethoxy)- 1-methylpropyl, 3-butoxy-1-methylpropyl, 3-(1-methylpropoxy)- 1-methylpropyl, 3-(2-methylpropoxy)-1-methylpropyl, 3-(1,1-dimethylethoxy)-1-methylpropyl, 1-methoxy-2-methylpropyl, 1-ethoxy-2-methylpropyl, 1-propoxy-2-methylpropyl, 1-(1-methylethoxy)-2-methylpropyl, 1-butoxy-2-methylpropyl, 1-(1-methylpropoxy)- 2-methylpropyl, 1-(2-methylpropoxy)-2-methylpropyl, 1-(1,1-dimethylethoxy)-2-methylpropyl, 2-methoxy-2-methylpropyl, 2-ethoxy-2-methylpropyl, 2-propoxy-2-methylpropyl, 2-(1-methylethoxy)- 2-methylpropyl, 2-butoxy-2-methylpropyl, 2-(1-methylpropoxy)- 2-methylpropyl, 2-(2-methylpropoxy)-2-methylpropyl, 2-(1,1-dimethylethoxy)-2-methylpropyl, 3-methoxy-2-methylpropyl, 3-ethoxy-2-methylpropyl, 3-propoxy-2-methylpropyl, 3-(1-methylethoxy)- 2-methylpropyl, 3-butoxy-2-methylpropyl, 3-(1-methylpropoxy)- 2-methylpropyl, 3-(2-methylpropoxy)-2-methylpropyl, 3-(1,1-dimethylethoxy)-2-methylpropyl, 2-methoxy-1,1-dimethylethyl, 2-ethoxy-1,1-dimethylethyl, 2-propoxy-1,1-dimethylethyl, 2-(1-methylethoxy)-1,1-dimethylethyl, 2-butoxy-1,1-dimethylethyl, 2-(1-methylpropoxy)-1,1-dimethylethyl, 2-(2-methylpropoxy)-1,1-dimethylethyl, 2-(1,1-dimethylethoxy)-1,1-dimethylethyl, in particular methoxymethyl;

$C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1- dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, in particular methylthio, ethylthio or 1-methylethylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio; $C_1$–$C_4$-alkylthio-$C_1$–$C_4$-alkyl, such as methylthiomethyl, ethylthiomethyl, propylthiomethyl, 1-methylethylthiomethyl, butylthiomethyl, 1-methylpropylthiomethyl, 2-methylpropylthiomethyl, 1,1-dimethylethylthiomethyl, 1-methylthioethyl, 1-ethylthioethyl, 1-propylthioethyl, 1-(1-methylethylthio)ethyl, 1-butylthioethyl, 1-(1-methylpropylthio)ethyl, 1-(2-methylpropylthio)ethyl, 1-(1,1-dimethylethylthio)ethyl, 2-methylthioethyl, 2-ethylthioethyl, 2-propylthioethyl, 2-(1-methylethylthio)ethyl, 2-butylthioethyl, 2-(1-methylpropylthio)ethyl, 2-(2-methylpropylthio)ethyl, 2-(1,1-dimethylethylthio)ethyl, 1-methylthiopropyl, 1-ethylthiopropyl, 1-propylthiopropyl, 1-(1-methylethylthio)propyl, 1-butylthiopropyl, 1-(1-methylpropylthio)propyl, 1-(2-methylpropylthio)propyl, 1-(1,1-dimethylethylthio)propyl, 2-methylthiopropyl, 2-ethylthiopropyl, 2-propylthiopropyl, 2-(1-methylethylthio)propyl, 2-butylthiopropyl, 2-(1-methylpropylthio)propyl, 2-(2-methylpropylthio)propyl, 2-(1,1-dimethylethylthio)propyl, 3-methylthiopropyl, 3-ethylthiopropyl, 3-propylthiopropyl, 3-(1-methylethylthio)propyl, 3-butylthiopropyl, 3-(1-methylpropylthio)propyl, 3-(2-methylpropylthio)propyl, 3-(1,1-dimethylethylthio)propyl, 1-methylthio-1-methylethyl, 1-ethylthio-1-methylethyl, 1-propylthio-1-methylethyl, 1-(2-methylethylthio)-1-methylethyl, 1-butylthio-(1-methylethyl, 1-(1-methylpropylthio)-1-methylethyl, 1-(2-methylpropylthio)- 1-methylethyl, 1-(1,1-dimethylethylthio)-1-methylethyl, 2-methylthio- 1-methylethyl, 2-ethylthio-1-methylethyl, 2-propylthio- 1-methylethyl, 2-(1-methylethylthio)-1-methylethyl, 2-butylthio- 1-methylethyl, 2-(1-methylpropylthio)-1-methylethyl, 2-(2-methylpropylthio)-1-methylethyl, 2-(1,1-dimethylethylthio)- 1-methylethyl, 1-methylthiobutyl, 1-ethylthiobutyl, 1-propylthiobutyl, 1-(1-methylethylthio)butyl, 1-butylthiobutyl, 1-(1-methylpropylthio)butyl, 1-(2-methylpropylthio)butyl, 1-(1,1-dimethylethylthio)butyl, 2-methylthiobutyl, 2-ethylthiobutyl, 2-propylthiobutyl, 2-(1-methylethylthio)butyl, 2-butylthiobutyl, 2-(1-methylpropylthio)butyl, 2-(2-methylpropylthio)butyl, 2-(1,1-dimethylethylthio)butyl, 3-methylthiobutyl, 3-ethylthiobutyl, 3-propylthiobutyl, 3-(1-methylethylthio)butyl, 3-butylthiobutyl, 3-(1-methylpropylthio)butyl, 3-(2-methylpropylthio)butyl, 3-(1,1-dimethylethylthio)butyl, 4-methylthiobutyl, 4-ethylthiobutyl, 4-propylthiobutyl, 4-(1-methylethylthio)butyl, 4-butylthiobutyl, 4-(1-methylpropylthio)butyl, 4-(2-methylpropylthio)butyl, 4-(1,1-dimethylethylthio)butyl, 1-methylthio- 1-methylpropyl, 1-ethylthio-1-methylpropyl, 1-propylthio- 1-methylpropyl, 1-(1-methylethylthio)-1-methylpropyl, 1-butylthio- 1-methylpropyl, 1-(1-methylpropylthio)-1-methylpropyl, 1-(2-methylpropylthio)-1-methylpropyl, 1-(1,1-dimethylethylthio)- 1-methylpropyl, 2-methylthio-1-methylpropyl, 2-ethylthio- 1-methylpropyl, 2-propylthio-1-methylpropyl, 2-(1-methylethylthio)- 1-methylpropyl, 2-butylthio-1-methylpropyl, 2-(1-methylpropylthio)-1-methylpropyl, 2-(2-methylpropylthio)- 1-methylpropyl, 2-(1,1-dimethylethylthio)-1-methylpropyl, 3-methylthio-1-methylpropyl, 3-ethylthio-1-methylpropyl, 1-propylthio-1-methylpropyl, 3-(1-methylethylthio)-1-methylpropyl, 3-butylthio-1-methylpropyl, 3-(1-methylpropylthio)- 1-methylpropyl, 3-(2-methylpropylthio)-1-methylpropyl, 3-(1,1-dimethylethylthio)- 1-methylpropyl, 1-methylthio-2-methylpropyl, 1-ethylthio-2-methylpropyl, 1-propylthio-2-methylpropyl, 1-(1-methylethylthio)-2-methylpropyl, 1-butylthio-2-methylpropyl, 1-(1-methylpropylthio)-2-methylpropyl, 1-(2-methylpropylthio)- 2-methylpropyl, 1-(1,1-dimethylethylthio)-2-methylpropyl, 2-methylthio-2-methylpropyl, 2-ethylthio-2-methylpropyl, 2-propylthio-2-methylpropyl, 2-(1-methylethylthio)-2-methylpropyl, 2-butylthio-2-methylpropyl, 2-(1-methylpropylthio)- 2-methylpropyl, 2-(2-methylpropylthio)-2-methylpropyl, 2-(1,1-dimethylethylthio)- 2-methylpropyl, 3-methylthio-2-methylpropyl, 3-ethylthio-2-methylpropyl, 3-propylthio-2-methylpropyl, 3-(1-methylethylthio)-2-methylpropyl, 3-butylthio-2-methylpropyl, 3-(1-methylpropylthio)-2-methylpropyl, 3-(2-methylpropylthio)- 2-methylpropyl, 3-(1,1-dimethylethylthio)-2-methylpropyl, 2-methylthio-1,1-dimethylethyl, 2-ethylthio-1,1-dimethylethyl, 2-propylthio-1,1-dimethylethyl, 2-(1-methylethylthio)-1,1-dimethylethyl, 2-butylthio-1,1-dimethylethyl, 2-(1-methylpropylthio)- 1,1-dimethylethyl, 2-(2-methylpropylthio)-1,1-dimethylethyl, 2-(1,1-dimethylethylthio)-1,1-dimethylethyl;

$C_3$–$C_{15}$-alkenyl, in particular $C_3$–$C_6$-alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl- 2-butenyl, 3-methyl-2-butenyl, 1-methyl-3-butenyl, 2-methyl- 3-butenyl, 3-methyl-3-butenyl, 1,1-dimethyl-2-propenyl, 1,2-dimethyl- 2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl- 3-butenyl, 1,2-dimethyl-2-butenyl, 1,2-dimethyl-3-butenyl, 1,3-dimethyl-2-butenyl, 1,3-dimethyl-3-butenyl, 2,2-dimethyl- 3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl;

$C_3$–$C_{15}$-alkenyloxy, in particular $C_3$–$C_{15}$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl- 2-butenyloxy, 1-methyl-3-butenyloxy, 2-methyl-3-butenyloxy, 3-methyl-3-butenyloxy, 1,1-dimethyl-2-propenyloxy, 1,2-dimethyl- 2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl- 2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl- 2-butenyloxy, 1,3-dimethyl-3- butenyloxy, 2,2-dimethyl- 3-butenyloxy, 2,3-dimethyl-2-butenyloxy, 2,3-dimethyl-3-butenyloxy, 3,3-dimethyl-2-butenyloxy, 1-ethyl-2-butenyloxy, 1-ethyl- 3-butenyloxy, 2-ethyl-2-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy;

$C_3$–$C_8$-cycloalkyl, such as cyclopropyl, cyclobutyl, cyclopentyl, cyclohexyl, cycloheptyl or cyclooctyl, in particular cyclopropyl or cyclohexyl;

$C_5$–$C_8$-cycloalkenyl, such as cyclopent-1-enyl, cyclopent-2-enyl, cyclopent-3-enyl, cyclohex-1-enyl, cyclohex-2-enyl, cyclohex- 3-enyl, cyclohept-1-enyl, cyclohept-2-enyl, cyclohept-3-enyl, cyclohept-4-enyl, cyclooct-1-enyl, cyclooct-2-enyl, cyclooct- 3-enyl or cyclooct-1-enyl;

$C_3$–$C_8$-cycloalkoxy, such as cyclopropoxy, cyclobutoxy, cyclopentyloxy, cyclohexyloxy, cycloheptyloxy or cyclooctyloxy;

$C_5$–$C_8$-cycloalkenyloxy, such as cyclopent-1-enyloxy, cyclopent- 2-enyloxy, cyclopent-3-enyloxy, cyclohex-1-enyloxy, cyclohex- 2-enyloxy, cyclohex-3-enyloxy, cyclohept-1-enyloxy, cyclohept- 2-enyloxy, cyclohept-3-enyloxy, cyclohept-4-enyloxy, cyclooct-1-enyloxy, cyclooct-2-enyloxy, cyclooct-3-enyloxy or cyclooct-1-enyloxy;

$C_1$–$C_6$-alkylamino, such as methylamino, ethylamino, propylamino, 1-methylethylamino, butylamino, 1-methylpropylamino, 2-methylpropylamino, 1,1-dimethylethylamino, pentylamino, 1-methylbutylantino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino, in particular methylamino, or ethylamino;

di-$C_1$–$C_6$-alkylamino, particularly di-$C_1$–$C_4$-alkylamino, such as N,N-dimethylamino, N,N-diethylamino, N,N-dipropylamino, N,N-di-( 1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-( 1-methylethyl)amino, N-butyl-N-methylamino, N-methyl-N-( 1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-( 1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-( 1-methylpropyl)amino, N-(1-methylethyl)-N-(2-methylpropyl)amino, N-(1,1-dimethylethyl)-N-(1-methylethyl)amino, N-butyl-N-( 1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino, in particular dimethylamino or diethylamino;

$C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl- 2-methylpropylcarbonyl, in particular methylcarbonyl or ethylcarbonyl;

$C_1$–$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentyloxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, in particular methoxycarbonyl or ethoxycarbonyl;

$C_1$–$C_6$-alkylaminocarbonyl, such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, in particular methylaminocarbonyl;

di-$C_1$–$C_6$-alkylaminocarbonyl, particularly di-$C_1$–$C_4$-alkylaminocarbonyl, such as N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-( 2-methylpropyl)aminocarbonyl, N-(1,1-dimethylethyl)-N-( 1-methylpropyl)aminocarbonyl or N-(1,1-dimethylethyl)-N-( 2-methylpropyl)aminocarbonyl, in particular dimethylaminocarbonyl;

$C_1$–$C_6$-alkylcarboxyl, such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl or 1-ethyl- 2-methylpropylcarboxyl, in particular methylcarboxyl;

phenyl, phenoxy, phenylthio, phenylamino;

phenyl-$C_1$–$C_4$-alkyl, such as benzyl, 1-phenylethyl, 2-phenylethyl, 1-phenylpropyl, 2-phenylpropyl, 3-phenylpropyl, 1-methyl- 1-phenylethyl, 1-methyl-2-phenylethyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl- 1-phenylpropyl, 2-methyl-2-phenylpropyl, 2-methyl-3-phenylpropyl or 1,1-dimethyl-2-phenylethyl, preferably benzyl;

phenoxy-$C_1$–$C_4$-alkyl, such as phenoxymethyl, 1-phenoxyethyl, 2-phenoxyethyl, 1-phenoxypropyl, 2-phenoxypropyl, 3-phenoxypropyl, 1-methyl-1-phenoxyethyl, 1-methyl-2-phenoxyethyl, 1-phenoxybutyl, 2-phenoxybutyl, 3-phenoxybutyl, 4-phenoxybutyl, 1-methyl-1-phenoxypropyl, 1-methyl-2-phenoxypropyl, 1-methyl- 3-phenoxypropyl, 2-methyl-1-phenoxypropyl, 2-methyl-2-phenoxypropyl, 2-methyl-3-phenoxypropyl or 1,1-dimethyl-2-phenoxyethyl;

phenylthio-$C_1$–$C_4$-alkyl, such as phenylthiomethyl, 1-phenylthioethyl, 2-phenylthioethyl, 1-phenylthiopropyl, 2-phenylthiopropyl, 3-phenylthiopropyl, 1-methyl-1-phenylthioethyl, 1-methyl- 2-phenylthioethyl, 1-phenylthiobutyl, 2-phenylthiobutyl, 3-phenylthiobutyl, 4-phenylthiobutyl, 1-methyl-1-phenylthiopropyl, 1-methyl-2-phenylthiopropyl, 1-methyl-3-phenylthiopropyl, 2-methyl-1-phenylthiopropyl, 2-methyl-2-phenylthiopropyl, 2-methyl-3-phenylthiopropyl or 1,1-dimethyl-2-phenylthioethyl;

phenylamino-$C_1$–$C_4$-alkyl, such as phenylaminomethyl, 1-phenylaminoethyl, 2-phenylaminoethyl, 1-phenylaminopropyl, 2-phenylaminopropyl, 3-phenylaminopropyl, 1-methyl-1-phenylaminoethyl, 1-methyl-2-phenylaminoethyl, 1-phenylaminobutyl, 2-phenylaminobutyl, 3-phenylaminobutyl, 4-phenylaminobutyl, 1-methyl-1 -phenylaminopropyl, 1-methyl-2-phenylaminopropyl, 1-methyl- 3-phenylaminopropyl, 2-methyl-1-phenylaminopropyl, 2-methyl-2-phenylaminopropyl, 2-methyl-3-phenylaminopropyl or 1,1-dimethyl- 2-phenylaminoethyl;

where the aromatic rings in turn may carry from one to five halogen atoms, such as fluorine, chlorine, bromine or iodine, in particular fluorine or chlorine, and/or from one to three of the following radicals: cyano, nitro, $C_1$–$C_4$-alkyl, such as methyl, ethyl, propyl, 1-methylethyl, butyl, 1-methylpropyl, 2-methylpropyl or 1,1-dimethylethyl, preferably cyano, methyl, or 1-methylethyl, in particular methyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy, ethoxy or 1-methylethoxy, in particular methoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro- 2-fluoroethoxy, 2-chloro-2,2-difluoroethoxy, 2,2-dichloro- 2-fluoroethoxy, 2,2,2-trichloroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

or $C_1$–$C_4$-haloalkylthio, particularly $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, for example heteroaromatics having a five-membered ring and containing from one to three nitrogen atoms and/or one oxygen or sulfur atom, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl or 1,3,4-triazol-2-yl;

or heteroaromatics having a six-membered ring containing from one to three nitrogen atoms, such as 2-pyridyl, 3-pyridyl, 4-pyridyl, 3-pyridazinyl, 4-pyridazinyl, 2-pyrimidinyl, 4-pyrimidinyl, 5-pyrimidinyl, 2-pyrazinyl, 1,3,5-triazin-2-yl or 1,2,4-triazin-3-yl;

where these ring systems may carry from one to four halogen atoms, such as fluorine, chlorine, bromine or iodine, preferably fluorine, chlorine and bromine and/or from one to three of the following radicals:

$C_1$–$C_4$-alkyl, such as methyl, ethyl, propyl, 1-methylethyl, butyl, 1-methylpropyl, 2-methylpropyl or 1,1-dimethylethyl, in particular methyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro- 2-fluoroethoxy, 2-chloro-2,2-difluoroethoxy, 2,2-dichloro- 2-fluoroethoxy, 2,2,2-trichloroethoxy or pentafluoroethoxy, in particular trifluoromethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

or $C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, in particular trifluoromethylthio;

$R^3$ is unsubstituted or substituted alkyl of one to ten carbon atoms, in particular $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl, ethyl or 1-methylethyl;

where these groups may carry from one to nine halogen atoms, such as fluorine, chlorine, bromine and iodine, preferably fluorine, chlorine and bromine, in particular chlorine and bromine, and/or one of the radicals stated in general and in particular for $R^2$ or one of the following radicals:

$C_1$–$C_6$-alkoxy, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular $C_1$–$C_4$-alkoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro- 2-fluoroethoxy, 2-chloro-2,2-difluoroethoxy, 2,2-dichloro- 2-fluoroethoxy, 2,2,2-trichloroethoxy or pentafluoroethoxy, preferably trifluoromethoxy;

$C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-di- methylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, preferably $C_1$–$C_3$-alkylthio, in particular methylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio, preferably trifluoromethylthio;

$C_3$–$C_8$-cycloalkoxy, such as cyclopropoxy, cyclobutoxy, cyclopentyloxy, cyclohexyloxy, cycloheptyloxy or cyclooctyloxy, in particular cyclopropoxy or cyclohexyloxy;

di-$C_1$–$C_6$-alkylamino, particularly di-$C_1$–$C_4$-alkylamino, such as N,N-dimethylamino, N,N-diethylamino, N,N-dipropylamino, N,N-di-( 1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-( 1-methylethyl)amino, N-butyl-N-methylamino, N-methyl-N-( 1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-( 1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-( 1-methylpropyl)amino, N-(1-methylethyl)-N-(2-methylpropyl)amino, N-(1,1-dimethylethyl)-N-(1-methylethyl)amino, N-butyl-N-( 1-methylpropyl)amino, N-butyl-N-(2-methylpropyl)amino, N-butyl-N-(1,1-dimethylethyl)amino, N-(1-methylpropyl)-N-( 2-methylpropyl)amino, N-(1,1-dimethylethyl)-N-(1-methylpropyl)amino or N-(1,1-dimethylethyl)-N-(2-methylpropyl)amino, in particular dimethylamino, diethylamino, in particular dimethylamino;

$C_1$–$C_6$-alkylcarbonyl, such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl- 2-methylpropylcarbonyl, preferably methylcarbonyl or ethylcarbonyl;

$C_1$–$C_6$-alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentyloxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentyloxycarbonyl, 2-methylpentyloxycarbonyl, 3-methylpentyloxycarbonyl, 4-methylpentyloxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl, preferably methoxycarbonyl;

$C_1$–$C_6$-alkylaminocarbonyl, such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl, preferably methylaminocarbonyl;

di-$C_1$–$C_6$-alkylaminocarbonyl, particularly di-$C_1$–$C_4$-alkylaminocarbonyl, such as N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-( 2-methylpropyl)aminocarbonyl, N-(1,1-dimethylethyl)-N-( 1-methylpropyl)aminocarbonyl or N-(1,1-dimethylethyl)-N-( 2-methylpropyl)aminocarbonyl, preferably dimethylaminocarbonyl;

$C_1$–$C_6$-alkylcarboxyl, such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl or 1-ethyl-2-methylpropylcarboxyl, preferably methylcarboxyl; phenyl, phenoxy, phenylthio or phenylamino, where the aromatic rings in turn may carry from one to five halogen atoms, such as fluorine, chlorine, bromine or iodine, preferably fluorine, chlorine or bromine, in particular fluorine or chlorine, and/or from one to three of the following radicals:

cyano, nitro, $C_1$–$C_4$-alkyl, such as methyl, ethyl, propyl, 1-methylethyl, butyl, 1-methylpropyl, 2-methylpropyl or 1,1-dimethylethyl, preferably cyano or methyl, in particular methyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, in particular methoxy or ethoxy;

$C_1$–$C_4$-haloalkyl, in particular $C_1$ or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroehtyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1$–$C_4$-haloalkoxy, in particular $C_1$- to $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro- 2-fluoroethoxy, 2-chloro-2,2-difluoroethoxy, 2,2-dichloro- 2-fluoroethoxy, 2,2,2-trichloroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio, in particular methylthio;

and $C_1$–$C_4$-haloalkylthio, in particular $C_1$- to $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

$R^3$ is furthermore an unsubstituted or substituted aliphatic ring system which is bonded via a carbon atom and, in addition to carbon atoms, may contain one or two hetero atoms selected from the group consisting of oxygen, sulfur and nitrogen; examples of such ring systems are:

$C_3$–$C_8$-cycloalkyl, such as cyclopropyl, cyclobutyl, cyclopentyl, cyclohexyl, cycloheptyl or cyclooctyl, preferably cyclopropyl, cyclopentyl or cyclohexyl, in particular cyclopropyl;

$C_5$–$C_8$-cycloalkenyl, such as cyclopent-1-enyl, cyclopent-2-enyl, cyclopent-3-enyl, cyclohex-1-enyl, cyclohex-2-enyl, cyclohex- 3-enyl, cyclohept-1-enyl, cyclohept-2-enyl, cyclohept-3-enyl, cyclohept-4-enyl, cyclooct-1-enyl, cyclooct-2-enyl, cyclooct- 3-enyl or cyclooct-1-enyl;

$C_5$–$C_8$-cycloalkadienyl, such as cyclopenta-1,3-dien-1-yl, cyclopenta- 1,3-dien-2-yl, cyclopenta-1,3-dien-5-yl, cyclohexa- 1,3-dien-1-yl, cyclohexa-1,3-dien-2-yl, cyclohexa-1,3-dien-5-yl, cyclohexa-1,4-dien-1-yl, cyclohexa-1,4-dien-3-yl, cyclohepta- 1,3-dien-1-yl, cyclohepta-1,3-dien-2-yl, cyclohepta-1,3-dien- 5-yl, cyclohepta-1,3-dien-6-yl, cyclohepta-1,4-dien-1-yl, cyclohepta- 1,4-dien-2-yl, cyclohepta-1,4-dien-3-yl, cyclohepta- 1,4-dien-6-yl, cycloocta-1,3-dien-1-yl, cycloocta-1,3-dien-2-yl, cycloocta-1,3-dien-5-yl, cycloocta-1,3-dien-6-yl, cycloocta- 1,4-dien-1-yl, cycloocta-1,4-dien-2-yl, cycloocta-1,4-dien-3-yl, cycloocta-1,4-dien-6-yl, cycloocta-1,4-dien-7-yl, cycloocta- 1,4-dien-1-yl or cycloocta-1,4-dien-3-yl;

3-membered to 6-membered, saturated or unsaturated heterocycles containing from one to three nitrogen atoms and/or one oxygen or sulfur atom, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin- 2-yl, 1,3,4-triazolidin-2-yl, 2,3-dihydrofur-2-yl, 2,3-dihydrofur-3-yl, 2,5-dihydrofur-2-yl, 2,5-dihydrofur-3-yl, 2,3-dihydrothien- 2-yl, 2,3-dihydrothien-3-yl, 2,5-dihydrothien-2-yl, 2,5-dihydrothien- 3-yl, 2,3-pyrrolin-2-yl, 2,3-pyrrolin-3-yl, 2,5-pyrrolin- 2-yl, 2,5-pyrrolin-3-yl, 2,3-isoxazolin-3-yl, 2,4-isoxazolin- 3-yl, 4,5-isoxazolin-3-yl, 2,3-isoxazolin-4-yl, 2,5-isoxazolin- 4-yl, 4,5-isoxazolin-4-yl, 2,3-isoxazolin-5-yl, 3,4-isoxazolin- 5-yl, 4,5-isoxazolin-5-yl, 2,3-isothiazolin-3-yl, 2,5-isothiazolin- 3-yl, 4,5-isothiazolin-3-yl, 2,3-isothiazolin-4-yl, 2,5-isothiazolin-4-yl, 4,5-isothiazolin-4-yl, 2,3-isothiazolin- 5-yl, 2,5-isothiazolin-5-yl, 4,5-isothiazolin-5-yl, 2,3-dihydropyrazol- 3-yl, 2,3-dihydropyrazol-4-yl, 2,3-dihydropyrazol- 5-yl, 3,4-dihydropyrazol-3-yl, 3,4-dihydropyrazol-4-yl, 3,4-dihydropyrazol- 5-yl, 4,5-dihydropyrazol-3-yl, 4,5-dihydropyrazol- 4-yl, 4,5-dihydropyrazol-5-yl, 2,3-dihydrooxazol-2-yl, 2,3-dihydrooxazol- 4-yl, 2,3-dihydrooxazol-5-yl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin- 2-yl or 1,2,4-tetrahydrotriazin-3-yl, 1,3-dithianyl, 2-tetrahydropyranyl, 3-tetrahydropyranyl, 1,3-dioxolauryl, oxiranyl, preferably 2-tetrahydrofuranyl, 3-tetrahydrofuranyl or 2-tetrahydropyranyl, in particular 2-tetrahydrofuranyl or 2-tetrahydropyranyl;

where these abovementioned ring systems may carry from one to five halogen atoms, such as fluorine, chlorine, bromine and iodine, preferably fluorine, chlorine and bromine, in particular chlorine, and/or from one to four of the following radicals:

cyano, nitro, amino, $C_1$–$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl- 2-methylpropyl, in particular methyl, ethyl or 1-methylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, preferably trichloromethyl or trifluoromethyl, in particular trifluoromethyl;

$C_1$–$C_6$-alkoxy, such as methoxy, ethoxy, propoxy, 1-methylethoxy, butoxy, 1-methylpropoxy, 2-methylpropoxy, 1,1-dimethylethoxy, pentyloxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy, in particular methoxy, ethoxy, 1-methylethoxy or propoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2,2-difluoroethoxy, 2,2,2-trifluoroethoxy, 2-chloro-2-fluoroethoxy, 2,-chloro,-2,2-difluoroethoxy, 2,2-dichloro-2-fluoroethoxy, 2,2,2-trichloroethoxy or pentafluoroethoxy;

$C_1$–$C_4$-alkoxy-$C_1$–$C_4$-alkyl, such as methoxymethyl, ethoxymethyl, propoxymethyl, 1-methylethoxymethyl, butoxymethyl, 1-methylpropoxymethyl, 2-methylpropoxymethyl, 1,1-dimethylethoxymethyl, 1-methoxyethyl, 1-ethoxyethyl, 1-propoxyethyl, 1-(1-methylethoxy)ethyl, 1-butoxyethyl, 1-(1-methylpropoxy)ethyl, 1-(2-methylpropoxy)ethyl, 1-(1,1-dimethylethoxy)ethyl, 2-methoxyethyl, 2-ethoxyethyl, 2-propoxyethyl, 2-(1-methylethoxy)ethyl, 2-butoxyethyl, 2-(1-methylpropoxy)ethyl, 2-(2-methylpropoxy)ethyl, 2-(1,1-dimethylethoxy)ethyl, 1-methoxypropyl, 1-ethoxypropyl, 1-propoxypropyl, 1-(1-methylethoxy)propyl, 1-butoxypropyl, 1-(1-methylpropoxy)propyl, 1-(2-methylpropoxy)propyl, 1-(1,1-dimethylethoxy)propyl, 2-methoxypropyl, 2-ethoxypropyl, 2-propoxypropyl, 2-(1-methylethoxy)propyl, 2-butoxypropyl, 2-(1-methylpropoxy)propyl, 2-(2-methylpropoxy)propyl, 2-(1,1-dimethylethoxy)propyl, 3-methoxypropyl, 3-ethoxypropyl, 3-propoxypropyl, 3-(1-methylethoxy)propyl, 3-butoxypropyl, 3-(1-methylpropoxy)propyl, 3-(2-methylpropoxy)propyl, 3-(1,1-dimethylethoxy)propyl, 1-methoxy-1-methylethyl, 1-ethoxy-1-methylethyl, 1-propoxy-1-methylethyl, 1-(1-methylethoxy)-1-methylethyl, 1-butoxy-1-methylethyl, 1-(1-methylpropoxy)-1-methylethyl, 1-(2-methylpropoxy)-1-methylethyl, 1-(1,1-dimethylethoxy)- 1-methylethyl, 2-methoxy-1-methylethyl, 2-ethoxy-1-methylethyl, 2-propoxy-1-methylethyl, 2-(1-methylethoxy)-1-methylethyl, 2-butoxy-1-methylethyl, 2-(1-methylpropoxy)-1-methylethyl, 2-(2-methylpropoxy)-1-methylethyl, 2-(1,1-dimethylethoxy)- 1-methylethyl, 1-methoxybutyl, 1-ethoxybutyl, 1-propoxybutyl, 1-(1-methylethoxy)butyl, 1-butoxybutyl, 1-(1-methylpropoxy)butyl, 1-(2-methylpropoxy)butyl, 1-(1,1-dimethylethoxy)butyl, 2-methoxybutyl, 2-ethoxybutyl, 2-propoxybutyl, 2-(1-methylethoxy)butyl, 2-butoxybutyl, 2-(1-methylpropoxy)butyl, 2-(2-methylpropoxy)butyl, 2-(1,1-dimethylethoxy)butyl, 3-methoxybutyl, 3-ethoxybutyl, 3-propoxybutyl, 3-(1-methylethoxy)butyl, 3-butoxybutyl, 3-(1-methylpropoxy)butyl, 3-(2-methylpropoxy)butyl, 3-(1,1-dimethylethoxy)butyl, 4-methoxybutyl, 4-ethoxybutyl, 4-propoxybutyl, 4-(1-methylethoxy)butyl, 4-butoxybutyl, 4-(1-methylpropoxy)butyl, 4-(2-methylpropoxy)butyl, 4-(1,1-dimethylethoxy)butyl, 1-methoxy-1-methylpropyl, 1-ethoxy-1-methylpropyl, 1-propoxy-1-methylpropyl, 1-(1-methylethoxy)-1-methylpropyl, 1-butoxy-1-methylpropyl, 1-(1-methylpropoxy)-1-methylpropyl, 1-(2-methylpropoxy)-1-methylpropyl, 1-(1,1-dimethylethoxy)-1-methylpropyl, 2-methoxy-1-methylpropyl, 2-ethoxy-1-methylpropyl, 2-propoxy-1-methylpropyl, 2-(1-methylethoxy)-1-methylpropyl, 2-butoxy-1-methylpropyl, 2-(1-methylpropoxy)-1-methylpropyl, 2-(2-methylpropoxy)-1-methylpropyl, 2-(1,1-dimethylethoxy)- 1-methylpropyl, 3-methoxy-1-methylpropyl, 3-ethoxy- 1-methylpropyl, 3-propoxy-1-methylpropyl, 3-(1-methylethoxy)- 1-methylpropyl, 3-butoxy-1-methylpropyl, 3-(1-methylpropoxy)- 1-methylpropyl, 3-(2-methylpropoxy)-1-methylpropyl, 3-(1,1-dimethylethoxy)- 1-methylpropyl, 1-methoxy-2-methylpropyl, 1-ethoxy-2-methylpropyl, 1-propoxy-2-methylpropyl, 1-(1-methylethoxy)- 2-methylpropyl, 1-butoxy-2-methylpropyl, 1-(1-methylpropoxy)- 2-methylpropyl, 1-(2-methylpropoxy)-2-methylpropyl, 1-(1,1-dimethylethoxy)-2-methylpropyl, 2-methoxy-2-methylpropyl, 2-ethoxy-2-methylpropyl, 2-propoxy-2-methylpropyl, 2-(1-methylethoxy)- 2-methylpropyl, 2-butoxy-2-methylpropyl, 2-(1-methylpropoxy)- 2-methylpropyl, 2-(2-methylpropoxy)-2-methylpropyl, 2-(1,1-dimethylethoxy)-2-methylpropyl, 3-methoxy-2-methylpropyl, 3-ethoxy-2-methylpropyl, 3-propoxy-2-methylpropyl, 3-(1-methylethoxy)-2-methylpropyl, 3-butoxy-2-methylpropyl, 3-(1-methylpropoxy)- 2-methylpropyl, 3-(2-methylpropoxy)-2-methylpropyl, 3-(1,1-dimethylethoxy)-2-methylpropyl, 2-methoxy-1, 1-dimethylethyl, 2-ethoxy-1,1-dimethylethyl, 2-propoxy-1, 1-dimethylethyl, 2-(1-methylethoxy)-1,1-dimethylethyl, 2-butoxy-1,1-dimethylethyl, 2-(1-methylpropoxy)-1,1-dimethylethyl, 2-(2-methylpropoxy)- 1,1-dimethylethyl, 2-(1,1-dimethylethoxy)-1,1-dimethylethyl, in particular methoxymethyl;

$C_1$–$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio, preferably $C_1$–$C_3$-alkylthio, in particular methylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio;

$C_1$–$C_4$-alkylthio-$C_1$–$C_4$-alkyl, such as methylthiomethyl, ethylthiomethyl, propylthiomethyl, 1-methylethylthiomethyl, butylthiomethyl, 1-methylpropylthiomethyl, 2-methylpropylthiomethyl, 1,1-dimethylethylthiomethyl, 1-methylthioethyl, 1-ethylthioethyl, 1-propylthioethyl, 1-(1-methylethylthio)ethyl, 1-butylthioethyl, 1-(1-methylpropylthio)ethyl, 1-(2-methylpropylthio)ethyl, 1-(1,1-dimethylethylthio)ethyl, 2-methylthioethyl, 2-ethylthioethyl, 2-propylthioethyl, 2-(1-methylethylthio)ethyl, 2-butylthioethyl, 2-(1-methylpropylthio)ethyl, 2-(2-methylpropylthio)ethyl, 2-(1,1-dimethylethylthio)ethyl, 1-methylthiopropyl, 1-ethylthiopropyl, 1-propylthiopropyl, 1-(1-methylethylthio)propyl, 1-butylthiopropyl, 1-(1-methylpropylthio)propyl, 1-(2-methylpropylthio)propyl, 1-(1,1-dimethylethylthio)propyl, 2-methylthiopropyl, 2-ethylthiopropyl, 2-propylthiopropyl, 2-(1-methylethylthio)propyl, 2-butylthiopropyl, 2-(1-methylpropylthio)propyl, 2-(2-methylpropylthio)propyl, 2-(1,1-dimethylethylthio)propyl, 3-methylthiopropyl, 3-ethylthiopropyl, 3-propylthiopropyl, 3-(1-methylethylthio)propyl, 3-butylthiopropyl, 3-(1-methylpropylthio)propyl, 3-(2-methylpropylthio)propyl, 3-(1,1-dimethylethylthio)propyl, 1-methylthio-1-methylethyl, 1-ethylthio-1-methylethyl, 1-propylthio-1-methylethyl, 1-(2-methylethylthio)-1-methylethyl, 1-butylthio-1-methylethyl, 1-(1-methylpropylthio)-1-methylethyl, 1-(2-methylpropylthio)- 1-methylethyl, 1-(1,1-dimethylethylthio)-1-methylethyl, 2-methylthio- 1-methylethyl, 2-ethylthio-1-methylethyl, 2-propylthio- 1-methylethyl, 2-(1-methylethylthio)-1-methylethyl, 2-butylthio- 1-methylethyl, 2-(1-methylpropylthio)-1-methylethyl, 2-(2-methylpropylthio)- 1-methylethyl, 2-(1,1-dimethylethylthio)-1-methylethyl, 1-methylthiobutyl, 1-ethylthiobutyl, 1-propylthiobutyl, 1-(1-methylethylthio)butyl, 1-butylthiobutyl, 1-(1-methylpropylthio)butyl, 1-(2-methylpropylthio)butyl, 1-(1, 1-dimethylethylthio)butyl, 2-methylthiobutyl, 2-ethylthiobutyl, 2-propylthiobutyl, 2-(1-methylethylthio)butyl, 2-butylthiobutyl, 2-(1-methylpropylthio)butyl, 2-(2-methylpropylthio)butyl, 2-(1,1-dimethylethylthio)butyl, 3-methylthiobutyl, 3-ethylthiobutyl, 3-propylthiobutyl, 3-(1-methylethylthio)butyl, 3-butylthiobutyl, 3-(1-methylpropylthio)butyl, 3-(2-methylpropylthio)butyl, -(1,1-dimethylethylthio)butyl, 4-methylthiobutyl, 4-ethylthiobutyl, 4-propylthiobutyl, 4-(1-methylethylthio ) butyl, 4-butylthiobutyl, 4-(1-methylpropylthio ) butyl, 4-(2-methylpropylthio)-butyl, 4-(1,1-dimethylethylthio ) butyl, 1-methylthio-1-methylpropyl, 1-ethylthio-1-methylpropyl, 1-propylthio-1-methylpropyl, 1-(1-methylethylthio )-1-methylpropyl, 1-butylthio-1-methylpropyl, 1-(1-methylpropylthio )-1-methylpropyl, 1-(2-methylpropylthio)- 1-methylpropyl, 1-(1,1-dimethylethylthio )-1-methylpropyl, 2-methylthio-1-methylpropyl, 2-ethylthio-1-methylpropyl, 2-propylthio-1-methylpropyl, 2-(1-methylethylthio)-1-methylpropyl, 2-butylthio-1-methylpropyl, 2-(1-methylpropylthio)- 1-methylpropyl, 2-(2-methylpropylthio)-1-methylpropyl, 2-(1,1- dimethylethylthio)-1-methylpropyl, 3-methylthio-1-methylpropyl, 3-ethylthio-1-methylpropyl, 3-propylthio-1-methylpropyl, 3-(1-methylethylthio)-1-methylpropyl, 3-butylthio-1-methylpropyl, 3-(1-methylpropylthio)-1-methylpropyl, 3-(2-methylpropylthio)- 1-methylpropyl, 3-(1,1-dimethylethylthio )-1-methylpropyl, 1-methylthio-2-methylpropyl, 1-ethylthio-2-methylpropyl, 1-propylthio-2-methylpropyl, 1-(1-methylethylthio)-2-methylpropyl, 1-butylthio-2-methylpropyl, 1-(1-methylpropylthio)- 2-methylpropyl, 1-(2-methylpropylthio)-2-methylpropyl, 1-(1,1-dimethylethylthio)- 2-methylpropyl, 2-methylthio-2-methylpropyl, 2-ethylthio-2-methylpropyl, 2-propylthio-2-methylpropyl, 2-(1-methylethylthio)-2-methylpropyl, 2-butylthio-2-methylpropyl, 2-(1-methylpropylthio)-2-methylpropyl, 2-(2-methylpropylthio)- 2-methylpropyl, 2-(1,1-dimethylethylthio)-2-methylpropyl, 3-methylthio-2-methylpropyl, 3-ethylthio-2-methylpropyl, 3-propylthio-2-methylpropyl, 3-(1-methylethylthio)-2-methylpropyl, 3-butylthio-2-methylpropyl, 3-(1-methylpropylthio)- 2-methylpropyl, 3-(2-methylpropylthio)-2-methylpropyl, 3-(1,1-dimethylethylthio)- 2-methylpropyl, 2-methylthio-1,1-dimethylethyl, 2-ethylthio-1,1-dimethylethyl, 2-propylthio-1,1-dimethylethyl, 2- (1-methylethylthio)-1,1-dimethylethyl, 2-butylthio-1,1-dimethylethyl, 2-(1-methylpropylthio)-1,1-dimethylethyl, 2-(2-methylpropylthio)-1,1-dimethylethyl, 2-(1,1-dimethylethylthio)- 1,1-dimethylethyl, in particular methylthiomethyl;

$C_3–C_8$-cycloalkyl, such as cyclopropyl, cyclobutyl, cyclopentyl, cyclohexyl, cycloheptyl or cyclooctyl, in particular cyclopropyl or cyclohexyl;

di-$C_1–C_6$-alkylamino, particularly di-$C_1–C_4$-alkylamino, such as N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-( 1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-Ethyl-N-( 1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-( 1-methylpropyl)amino, N-(1-methylethyl)-N-(2-methylpropyl)amino, N-(1,1-dimethylethyl)-N-(1-methylethyl)amino, N-butyl-N-( 1-methylpropyl)amino, N-butyl-N-(2-methylpropyl)amino, N-butyl-N-(1,1-dimethylethyl)amino, N-(1-methylpropyl)-N-( 2-methylpropyl)amino, N-(1,1-dimethylethyl)-N-(1-methylpropyl)amino or N-(1,1-dimethylethyl)-N-(2-methylpropyl)amino, preferably dimethylamino or diethylamino, in particular dimethylamino;

$C_1–C_6$-alkylcarboxyl, such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimethylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl or 1-ethyl- 2-methylpropylcarboxyl, in particular methylcarboxyl;

phenyl, phenoxy, phenylthio;

phenyl-$C_1–C_4$-alkyl, such as benzyl, 1-phenylethyl, 2-phenylethyl, 1-phenylpropyl, 2-phenylpropyl, 3-phenylpropyl, 1-methyl- 1-phenylethyl, 1-methyl-2-phenylethyl, 1-phenylbutyl, 2-phenylbutyl, 3-phenylbutyl, 4-phenylbutyl, 1-methyl-1-phenylpropyl, 1-methyl-2-phenylpropyl, 1-methyl-3-phenylpropyl, 2-methyl- 1-phenylpropyl, 2-methyl-2-phenylpropyl, 2-methyl-3-phenylpropyl or 1,1-dimethyl-2-phenylethyl, preferably benzyl;

phenoxy-$C_1–C_4$-alkyl, such as phenoxymethyl, 1-phenoxyethyl, 2-phenoxyethyl, 1-phenoxypropyl, 2-phenoxypropyl, 3-phenoxypropyl, 1-methyl-1-phenoxyethyl, 1-methyl-2-phenoxyethyl, 1-phenoxybutyl, 2-phenoxybutyl, 3-phenoxybutyl, 4-phenoxybutyl, 1-methyl-1-phenoxypropyl, 1-methyl-2-phenoxypropyl, 1-methyl- 3-phenoxypropyl, 2-methyl-1-phenoxypropyl, 2-methyl-2-phenoxypropyl, 2-methyl-3-phenoxypropyl or 1,1-dimethyl-2-phenoxyethyl;

phenylthio-$C_1–C_4$-alkyl, such as phenylthiomethyl, 1-phenylthioethyl, 2-phenylthioethyl, 1-phenylthiopropyl, 2-phenylthiopropyl, 3-phenylthiopropyl, 1-methyl-1-phenylthioethyl, 1-methyl- 2-phenylthioethyl, 1-phenylthiobutyl, 2-phenylthiobutyl, 3-phenylthiobutyl, 4-phenylthiobutyl, 1-methyl-1-phenylthiopropyl, 1-methyl-2-phenylthiopropyl, 1-methyl-3-phenylthiopropyl, 2-methyl-1-phenylthiopropyl, 2-methyl-2-phenylthiopropyl, 2-methyl-3-phenylthiopropyl or 1,1-dimethyl-2-phenylthioethyl;

where the aromatic rings in turn may carry from one to five halogen atoms, such as fluorine, chlorine, bromine and iodine, preferably fluorine, chlorine and bromine, in particular fluorine and chlorine, and/or from one to three of the following radicals:

cyano, nitro;

$C_1–C_4$-alkyl, such as methyl, ethyl, propyl, 1-methylethyl, butyl, 1-methylpropyl, 2-methylpropyl or 1,1-dimethylethyl, preferably methyl or 1-methylethyl, in particular methyl;

$C_1–C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl, in particular trifluoromethyl;

$C_1–C_4$-alkoxy, such as methoxy, ethoxy, propoxy, 1-methylethoxy, butyloxy, 1-methylpropoxy, 2-methylpropoxy or 1,1-dimethylethoxy, preferably methoxy or ethoxy, in particular methoxy;

$C_1–C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro- 2-fluoroethoxy, 2-chloro-2,2-difluoroethoxy, 2,2-dichloro- 2-fluoroethoxy, 2,2,2-trichloroethoxy or pentafluoroethoxy;

$C_1–C_4$-alkylthio, such as methylthio, ethylthio, propylthio, 1-methylethylthio, butylthio, 1-methylpropylthio, 2-methylpropylthio or 1,1-dimethylethylthio, in particular methylthio;

and $C_1–C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio.

Preferred cyanooxime ethers of the formula I are those in which $R^3$ is $C_1-C_8$-alkyl as stated above in general and in particular, especially $C_1-C_3$-alkyl which may carry from one to nine halogen atoms as stated above in general and in particular, especially chlorine and bromine, and/or one of the following radicals:

cyano, nitro, amino;

$C_1-C_6$-alkoxy as stated above in general and in particular, especially $C_1-C_3$-alkoxy;

$C_1-C_4$-haloalkoxy as stated above in general and in particular;

$C_1-C_6$-alkylthio as stated above in general and in particular, especially $C_1$- or $C_2$-alkylthio;

$C_1-C_4$-haloalkylthio as stated above in general and in particular;

$C_3-C_8$-cycloalkyl as stated above in general and in particular, especially cyclopropyl;

$C_3-C_8$-cycloalkoxy as stated above in general and in particular, especially cyclopropoxy;

di-$C_1-C_6$-alkylamino as stated above in general and in particular, especially dimethylamino;

$C_1-C_6$-alkylcarbonyl as stated above in general and in particular, especially methylcarbonyl;

$C_1-C_6$-alkoxycarbonyl as stated above in general and in particular, especially methoxycarbonyl;

$C_1-C_6$-alkylaminocarbonyl as stated above in general and in particular, especially methylaminocarbonyl;

di-$C_1-C_6$-alkylaminocarbonyl as stated above in general and in particular, especially dimethylaminocarbonyl;

$C_1-C_6$-alkylcarboxyl as stated above in general and in particular, especially methylcarboxyl;

phenyl, phenoxy, phenylthio or phenyl-$C_1-C_4$-alkyl as stated above in general and in particular, especially phenyl or phenoxy;

phenoxy-$C_1-C_4$-alkyl as stated above in general and in particular, especially phenoxymethyl;

phenylthio-$C_1-C_4$-alkyl as stated above in general and in particular, especially phenylthiomethyl;

phenylamino-$C_1-C_4$-alkyl as stated above in general and in particular, especially phenylaminomethyl;

where the aromatic rings in turn may carry from one to five halogen atoms as stated above in general and in particular, especially fluorine and chlorine, and/or from one to three of the following radicals:

$C_1-C_4$-alkyl as stated above in general and in particular, especially methyl;

$C_1-C_4$-haloalkyl as stated above in general and in particular, especially trifluoromethyl;

$C_1-C_4$-alkoxy as stated above in general and in particular, especially methoxy or ethoxy;

$C_1-C_4$-haloalkoxy as stated above in general and in particular;

$C_1-C_4$-alkylthio as stated above in general and in particular, especially methylthio.

Other preferred cyanooxime ethers of the formula I are those in which $R^3$ is phenyl, 4-oxazolyl or 5-isoxazolyl, where these rings may carry from one to five halogen atoms as stated above in general and in particular, especially fluorine and chlorine, and/or from one to three of the following radicals:

cyano, cyanato, thiocyanato, nitro, amino, hydroxyl, carboxyl, $C_1-C_6$-alkyl as stated above in general and in particular, especially methyl, 1-methylethyl, 1,1-dimethylethyl, 1-methylpropyl;

$C_1-C_4$-haloalkyl as stated above in general and in particular, especially trifluoromethyl;

$C_1-C_6$-alkoxy as stated above in general and in particular, especially methoxy or ethoxy;

$C_1-C_4$-haloalkoxy as stated above in general and in particular;

$C_1-C_4$-alkoxy-$C_1-C_4$-alkyl as stated above in general and in particular, especially methoxymethyl;

$C_1-C_6$-alkylthio as stated above in general and in particular, especially methylthio;

$C_1-C_4$-haloalkylthio as stated above in general and in particular;

$C_1-C_4$-alkylthio-$C_1-C_4$-alkyl as stated above in general and in particular;

$C_3-C_{15}$-alkenyl as stated above in general and in particular;

$C_3-C_{15}$-alkenyloxy as stated above in general and in particular;

$C_3-C_8$-cycloalkyl as stated above in general and in particular, especially cyclopropyl or cyclohexyl;

$C_5-C_8$-cycloalkenyl as stated above in general and in particular;

$C_3-C_8$-cycloalkoxy as stated above in general and in particular;

$C_5-C_8$-cycloalkenyloxy as stated above in general and in particular;

$C_1-C_6$-alkylamino as stated above in general and in particular;

di-$C_1-C_6$-alkylamino as stated above in general and in particular;

$C_1-C_6$-alkylcarbonyl as stated above in general and in particular;

$C_1-C_6$-alkoxycarbonyl as stated above in general and in particular;

$C_1-C_6$-alkylaminocarbonyl as stated above in general and in particular;

di-$C_1-C_6$-alkylaminocarbonyl as stated above in general and in particular;

$C_1-C_6$-alkylcarboxyl as stated above in general and in particular;

phenyl, phenoxy, phenylthio, phenylamino, phenyl-$C_1-C_4$-alkyl as stated above in general and in particular, especially phenyl;

phenoxy-$C_1-C_4$-alkyl as stated above in general and in particular;

phenylthio-$C_1-C_4$-alkyl as stated above in general and in particular;

phenylamino-$C_1-C_4$-alkyl as stated above in general and in particular;

where the aromatic rings in turn may carry from one to five halogen atoms as stated above in general and in particular, especially fluorine, chlorine and bromine, and/or from one to three of the following radicals:

cyano, nitro, $C_1-C_4$-alkyl as stated above and in particular, especially methyl;

$C_1-C_4$-haloalkyl as stated above in general and in particular, especially trifluoromethyl;

$C_1-C_4$-alkoxy as stated above in general and in particular, especially methoxy;

$C_1-C_4$-haloalkoxy as stated above in general and in particular;

$C_1-C_4$-alkylthio as stated above in general and in particular, especially methylthio;

and C₁–C₄-haloalkylthio as stated above in general and in particular;

a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, as stated above, especially heteroaromatics having a five-membered ring, such as 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol- 5-yl, 1,2,4-triazol-3-yl, 1,3,4-oxadiazol-2-yl, 1,3,4-thiadiazol-2-yl and 1,3,4-triazol-2-yl, or heteroaromatics having a six-membered ring, such as 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, where these ring systems may carry from one to four halogen atoms as stated above in general and in particular, especially fluorine, chlorine and bromine, and/or from one to three of the following radicals:

C₁–C₄-alkyl as stated above in general and in particular, especially methyl;

C₁–C₄-haloalkyl as stated above in general and in particular, especially trifluromethyl;

C₁–C₄-alkoxy as stated above in general and in particular, especially methoxy;

C₁–C₄-haloalkoxy as stated above in general and in particular, especially trifluoromethoxy;

C₁–C₄-alkylthio as stated above in general and in particular, especially methylthio;

and C₁–C₄-haloalkylthio as stated above in general and in particular, especially trifluoromethylthio.

Other preferred cyanooxime ethers of the formula I are those in which $R^3$ is:

C₁–C₄-alkyl as stated above in general and in particular, especially methyl, ethyl or 1,1-dimethylethyl;

which may carry from one to nine halogen atoms as stated above in general and in particular, especially chlorine and bromine, and/or one of the following radicals:

C₁–C₄-alkoxy as stated above in general and in particular, especially methoxy, ethoxy, propoxy or 1-methylethoxy;

C₁–C₄-haloalkoxy as stated above in general and in particular;

C₁–C₄-alkylthio as stated above in general and in particular, especially methylthio or ethylthio;

C₃–C₈-cycloalkyl as stated above in general and in particular;

C₃–C₈-cycloalkoxy as stated above in general and in particular;

phenyl, phenoxy, phenylthio, phenylamino, phenyl-C₁–C₄-alkyl as stated above in general and in particular;

phenoxy-C₁–C₄-alkyl as stated above in general and in particular;

phenylthio-C₁–C₄-alkyl as stated above in general and in particular, where the aromatic rings in turn may carry from one to five halogen atoms as stated above in general and in particular, especially chlorine, and/or from one to three of the following radicals:

C₁–C₄-alkyl as stated above in general and in particular, especially methyl;

C₁–C₄-haloalkyl as stated above in general and in particular, especially trifluoromethyl;

C₁–C₄-alkoxy as stated above in general and in particular, especially methoxy;

C₁–C₄-haloalkoxy as stated above in general and in particular;

C₁–C₄-alkylthio as stated above in general and in particular;

or in which $R^3$ is a saturated or monounsaturated 3-membered to 7-membered ring system which is bonded via a carbon atom and, in addition to carbon atoms, may contain one or two hetero atoms selected from the group consisting of oxygen, sulfur and nitrogen, as stated above in general and in particular, especially cyclopropyl or 2-tetrahydropyranyl, where this ring system may carry from one to three of the following radicals:

C₁–C₄-alkyl as stated above in general and in particular, especially methyl;

C₁–C₄-alkoxy as stated above in general and in particular;

C₁–C₄-alkoxy-C₁–C₄-alkyl as stated above in general and in particular;

C₁–C₄-alkylthio as stated above in general and in particular;

C₁–C₄-alkylthio-C₁–C₄-alkyl as stated above in general and in particular;

phenyl, phenoxy, phenylthio;

phenyl-C₁–C₄-alkyl as stated above in general and in particular;

phenoxy-C₁–C₄-alkyl as stated above in general and in particular;

phenylthio-C₁–C₄-alkyl as stated above in general and in particular;

where the aromatic rings in turn may carry from one to five halogen atoms as stated above in general and in particular and/or from one to three of the following radicals:

C₁–C₄-alkyl as stated above in general and in particular;

C₁–C₄-haloalkyl as stated above in general and in particular;

C₁–C₄-alkoxy as stated above in general and in particular;

C₁–C₄-haloalkoxy as stated above in general and in particular, and C₁–C₄-alkylthio as stated above in general and in particular.

Particularly preferred compounds of the formula I are summarized in Tables A, B and C below:

TABLE A

| $R^1R^2CH$—ON=C(CN)—$R^3$ | $R^1$ = H | I |
| --- | --- | --- |
| $R^3$ | $R^2$ | |
| 2-Methoxyprop-2-yl | Phenyl | |
| 2-Methoxyprop-2-yl | 2-Chlorophenyl | |
| 2-Methoxyprop-2-yl | 3-Chlorophenyl | |
| 2-Methoxyprop-2-yl | 4-Chlorophenyl | |
| 2-Methoxyprop-2-yl | 2,6-Dichlorophenyl | |
| 2-Methoxyprop-2-yl | 2,4-Dichlorophenyl | |
| 2-Methoxyprop-2-yl | 2-Methylphenyl | |
| 2-Methoxyprop-2-yl | 3-Methylphenyl | |
| 2-Methoxyprop-2-yl | 4-Methylphenyl | |
| 2-Methoxyprop-2-yl | 2,5-Dimethylphenyl | |
| 2-Methoxyprop-2-yl | 2,4,6-Trimethylphenyl | |
| 2-Methoxyprop-2-yl | 3-Methoxyphenyl | |
| 2-Methoxyprop-2-yl | 4-Methoxyphenyl | |
| 2-Methoxyprop-2-yl | 2-Nitrophenyl | |
| 2-Methoxyprop-2-yl | 3-Nitrophenyl | |
| 2-Methoxyprop-2-yl | 4-Nitrophenyl | |
| 2-Methoxyprop-2-yl | 2-Bromophenyl | |
| 2-Methoxyprop-2-yl | 4-Bromophenyl | |
| 2-Methoxyprop-2-yl | 4-Cyanophenyl | |
| 2-Methoxyprop-2-yl | 4-Dimethylaminophenyl | |

TABLE A-continued

| R³ | R² |
|---|---|
| 2-Methoxyprop-2-yl | 4-Carbomethoxyphenyl |
| 2-Methoxyprop-2-yl | 2-Methoxy-5-nitrophenyl |
| 2-Methoxyprop-2-yl | 2-Trifluoromethylphenyl |
| 2-Methoxyprop-2-yl | 4-Trifluoromethylphenyl |
| 2-Methoxyprop-2-yl | 4-tert-Butylphenyl |
| 2-Methoxyprop-2-yl | 2-Chloro-6-nitrophenyl |
| 2-Methoxyprop-2-yl | 2-Fluorophenyl |
| 2-Methoxyprop-2-yl | 4-Fluorophenyl |
| 2-Methoxyprop-2-yl | 2,3,4,5,6-Pentafluorophenyl |
| 2-Methoxyprop-2-yl | 2-Chloro-3-isopropylphenyl |
| 2-Methoxyprop-2-yl | 2,6-Difluorophenyl |
| 2-Methoxyprop-2-yl | 2-Chloro-3-trifluoromethylphenyl |
| 2-Methoxyprop-2-yl | 2-Biphenyl |
| 2-Methoxyprop-2-yl | 3-Biphenyl |
| 2-Methoxyprop-2-yl | 4-Biphenyl |
| 2-Methoxyprop-2-yl | 4'-Chlorobiphenyl-4-yl |
| 2-Methoxyprop-2-yl | 3-Phenoxyphenyl |
| 2-Methoxyprop-2-yl | 3,4-Methylenedioxyphenyl |
| 2-Methoxyprop-2-yl | 1-Naphthyl |
| 2-Methoxyprop-2-yl | 2-Naphthyl |
| 2-Methoxyprop-2-yl | 9-Anthracenyl |
| 2-Methoxyprop-2-yl | 2-Furyl |
| 2-Methoxyprop-2-yl | 4-Isopropylfuran-2-yl |
| 2-Methoxyprop-2-yl | 5-Carboxymethylfuran-2-yl |
| 2-Methoxyprop-2-yl | 5-Methylfuran-2-yl |
| 2-Methoxyprop-2-yl | 5-Trifluoromethylfuran-2-yl |
| 2-Methoxyprop-2-yl | 3-Furyl |
| 2-Methoxyprop-2-yl | 2-Thienyl |
| 2-Methoxyprop-2-yl | 5-Chlorothien-2-yl |
| 2-Methoxyprop-2-yl | 3-Thienyl |
| 2-Methoxyprop-2-yl | 5-Bromothien-3-yl |
| 2-Methoxyprop-2-yl | Benzothiophen-3-yl |
| 2-Methoxyprop-2-yl | 2-Pyrrolyl |
| 2-Methoxyprop-2-yl | 1-Phenylpyrrol-2-yl |
| 2-Methoxyprop-2-yl | 3-Pyrrolyl |
| 2-Methoxyprop-2-yl | Isoxazol-5-yl |
| 2-Methoxyprop-2-yl | Isoxazol-3-yl |
| 2-Methoxyprop-2-yl | 3-Phenylisoxazol-5-yl |
| 2-Methoxyprop-2-yl | 3-Methylisoxazol-5-yl |
| 2-Methoxyprop-2-yl | 4-Chloro-3-methylisoxazol-5-yl |
| 2-Methoxyprop-2-yl | 4-Chloro-3-isopropylisoxazol-5-yl |
| 2-Methoxyprop-2-yl | 4-Chloro-3-sec-butylisoxazol-5-yl |
| 2-Methoxyprop-2-yl | 4-Chloro-3-tert-butylisoxazol-5-yl |
| 2-Methoxyprop-2-yl | 4-Chloro-3-cyclohexylisoxazol-5-yl |
| 2-Methoxyprop-2-yl | 4-Chloro-3-phenylisoxazol-5-yl |
| 2-Methoxyprop-2-yl | 4-Chloro-3-(4-methylphenyl)isoxazol-5-yl |
| 2-Methoxyprop-2-yl | 4-Chloro-3-(4-chlorophenyl)isoxazol-5-yl |
| 2-Methoxyprop-2-yl | 4-Chloro-3-(4-fluorophenyl)isoxazol-5-yl |
| 2-Methoxyprop-2-yl | 4-Chloro-3-(4-trifluoromethylphenyl)isoxazol-5-yl |
| 2-Methoxyprop-2-yl | 4-Chloro-3-(2,6-difluorophenyl)isoxazol-5-yl |
| 2-Methoxyprop-2-yl | 4-Chloro-3-phenyl-isoxazol-5-yl |
| 2-Methoxyprop-2-yl | 3,5-Dimethylisoxazol-4-yl |
| 2-Methoxyprop-2-yl | 3-Carboxyethylisoxazol-5-yl |
| 2-Methoxyprop-2-yl | 3-(3,4-Dichlorophenyl)isoxazol-5-yl |
| 2-Methoxyprop-2-yl | 3-(3-Nitrophenyl)isoxazol-5-yl |
| 2-Methoxyprop-2-yl | 3-(4-Chlorophenyl)isoxazol-5-yl |
| 2-Methoxyprop-2-yl | 3-(4-Fluorophenyl)isoxazol-5-yl |
| 2-Methoxyprop-2-yl | 3-(3,4-Difluorophenyl)isoxazol-5-yl |
| 2-Methoxyprop-2-yl | 3-Phenylisoxazol-5-yl |
| 2-Methoxyprop-2-yl | 3-Methoxymethylisoxazol-5-yl |
| 2-Methoxyprop-2-yl | 3-Methylisoxazol-5-yl |
| 2-Methoxyprop-2-yl | 3-Ethylisoxazol-5-yl |
| 2-Methoxyprop-2-yl | 3-n-Propylisoxazol-5-yl |
| 2-Methoxyprop-2-yl | 3-n-Butylisoxazol-5-yl |
| 2-Methoxyprop-2-yl | 3-Isopropylisoxazol-5-yl |
| 2-Methoxyprop-2-yl | 3-Isobutylisoxazol-5-yl |
| 2-Methoxyprop-2-yl | 3-tert-Butylisoxazol-5-yl |
| 2-Methoxyprop-2-yl | 3-sec-Butylisoxazol-5-yl |
| 2-Methoxyprop-2-yl | 3-Methoxyisoxazol-5-yl |
| 2-Methoxyprop-2-yl | 3-Cyclopropylisoxazol-5-yl |
| 2-Methoxyprop-2-yl | 3-Cyclopropylisoxazol-4-yl |
| 2-Methoxyprop-2-yl | 3-Cyclohexylisoxazol-5-yl |
| 2-Methoxyprop-2-yl | 3-(3-Methylphenyl)isoxazol-5-yl |
| 2-Methoxyprop-2-yl | 3-(3,4-Dichlorophenyl)isoxazol-5-yl |
| 2-Methoxyprop-2-yl | 3-(2,6-Dichlorophenyl)isoxazol-5-yl |
| 2-Methoxyprop-2-yl | 3-(3-Nitrophenyl)isoxazol-5-yl |
| 2-Methoxyprop-2-yl | 3-(2-Methoxyphenyl)isoxazol-5-yl |
| 2-Methoxyprop-2-yl | 3-(4-Trifluoromethylphenyl)isoxazol-5-yl |
| 2-Methoxyprop-2-yl | 3-(3-Trifluoromethylphenyl)isoxazol-5-yl |
| 2-Methoxyprop-2-yl | 3-(4-Bromophenyl)isoxazol-5-yl |
| 2-Methoxyprop-2-yl | 3-(3-Chlorophenyl)isoxazol-5-yl |
| 2-Methoxyprop-2-yl | 3-(2-Chlorophenyl)isoxazol-5-yl |
| 2-Methoxyprop-2-yl | 3-(3-Fluorophenyl)isoxazol-5-yl |
| 2-Methoxyprop-2-yl | 3-(3-Phenoxyphenyl)isoxazol-5-yl |
| 2-Methoxyprop-2-yl | 3-(2,6-Difluorophenyl)isoxazol-5-yl |
| 2-Methoxyprop-2-yl | 3-Trifluoromethylisoxazol-5-yl |
| 2-Methoxyprop-2-yl | 3-(2-Naphthyl)isoxazol-5-yl |
| 2-Methoxyprop-2-yl | 3-(1-Naphthyl)isoxazol-5-yl |
| 2-Methoxyprop-2-yl | 3-tert-Butyl-5-phenyl-isoxazol-4-yl |
| 2-Methoxyprop-2-yl | 5-Methylisoxazol-4-yl |
| 2-Methoxyprop-2-yl | 4-Ethoxycarbonylisoxazol-5-yl |
| 2-Methoxyprop-2-yl | 5-Cyclopropylisoxazol-3-yl |
| 2-Methoxyprop-2-yl | 4-Chloro-3-(4-bromophenyl)isoxazol-5-yl |
| 2-Methoxyprop-2-yl | 4-Chloro-3-(3-chlorophenyl)isoxazol-5-yl |
| 2-Methoxyprop-2-yl | 4-Chloro-3-(3-fluorophenyl)isoxazol-5-yl |
| 2-Methoxyprop-2-yl | 4-Chloro-3-(2-chlorophenyl)isoxazol-5-yl |
| 2-Methoxyprop-2-yl | 2-Phenyloxazol-4-yl |
| 2-Methoxyprop-2-yl | 2-(4-Fluorophenyl)oxazol-4-yl |
| 2-Methoxyprop-2-yl | 2-(4-Chlorophenyl)oxazol-4-yl |
| 2-Methoxyprop-2-yl | 2-(4-Bromophenyl)oxazol-4-yl |
| 2-Methoxyprop-2-yl | 2-(3-Chlorophenyl)oxazol-4-yl |
| 2-Methoxyprop-2-yl | 2-(4-Methylphenyl)oxazol-4-yl |
| 2-Methoxyprop-2-yl | 2-tert-Butyloxazol-4-yl |
| 2-Methoxyprop-2-yl | 2-(2,4-Dichlorophenyl)oxazol-4-yl |
| 2-Methoxyprop-2-yl | 2-(4-Methoxyphenyl)oxazol-4-yl |
| 2-Methoxyprop-2-yl | 2-(4-Chlorophenyl)-5-bromooxazol-4-yl |
| 2-Methoxyprop-2-yl | 2-Cyclopropyloxazol-4-yl |
| 2-Methoxyprop-2-yl | 2-Isopropyloxazol-4-yl |
| 2-Methoxyprop-2-yl | 2-tert-Butyloxazol-4-yl |
| 2-Methoxyprop-2-yl | 2-tert-Butyloxazol-5-yl |
| 2-Methoxyprop-2-yl | 2-Benzyloxazol-4-yl |
| 2-Methoxyprop-2-yl | 2-Methylthiazol-4-yl |
| 2-Methoxyprop-2-yl | 2-Isopropylthiazol-4-yl |
| 2-Methoxyprop-2-yl | 2-Cyclopropylthiazol-4-yl |
| 2-Methoxyprop-2-yl | 4-(4-Methoxyphenyl)thiazol-2-yl |
| 2-Methoxyprop-2-yl | 2-Acetamidothiazol-4-yl |
| 2-Methoxyprop-2-yl | 2-Phenylthiazol-4-yl |
| 2-Methoxyprop-2-yl | 2-(2-Chlorophenyl)thiazol-4-yl |
| 2-Methoxyprop-2-yl | 2-(4-Chlorophenyl)thiazol-4-yl |
| 2-Methoxyprop-2-yl | 2-(2,4-Dichlorophenyl)thiazol-4-yl |
| 2-Methoxyprop-2-yl | 2-(2,6-Dichlorophenyl)thiazol-4-yl |
| 2-Methoxyprop-2-yl | 2-(3-Fluorophenyl)thiazol-4-yl |
| 2-Methoxyprop-2-yl | 2-(3-Chlorophenyl)thiazol-4-yl |
| 2-Methoxyprop-2-yl | 2-(4-Trifluoromethylphenyl)thiazol-4-yl |
| 2-Methoxyprop-2-yl | 2-(3-Methylphenyl)thiazol-4-yl |
| 2-Methoxyprop-2-yl | 2-(4-Methoxyphenyl)thiazol-4-yl |
| 2-Methoxyprop-2-yl | 2-Methylthiazol-4-yl |
| 2-Methoxyprop-2-yl | 2-(4-Fluorophenyl)thiazol-4-yl |
| 2-Methoxyprop-2-yl | 2-Methyl-1,3,4-thiadiazol-5-yl |
| 2-Methoxyprop-2-yl | 2-Phenyl-1,3,4-thiadiazol-5-yl |
| 2-Methoxyprop-2-yl | 2-Cyclopropyl-1,3,4-thiadiazol-5-yl |
| 2-Methoxyprop-2-yl | 2-Isopropyl-1,3,4-thiadiazol-5-yl |
| 2-Methoxyprop-2-yl | 2-Phenoxymethyl-1,3,4-thiadiazol-5-yl |
| 2-Methoxyprop-2-yl | 2-(4-Chlorophenyl)-1,3,4-thiadiazol-5-yl |
| 2-Methoxyprop-2-yl | 2-Phenyl-1,3,4-oxadiazol-5-yl |
| 2-Methoxyprop-2-yl | 2-(4-Methoxyphenyl)-1,3,4-oxa |

TABLE A-continued $R^1R^2CH—ON=C(CN)—R^3$   $R^1 = H$   I

| R³ | R² |
|---|---|
| | diazol-5-yl |
| 2-Methoxyprop-2-yl | 2-(2-Methylphenyl)-1,3,4-oxadiazol-5-yl |
| 2-Methoxyprop-2-yl | 2-(4-Methylphenyl)-1,3,4-oxadiazol-5-yl |
| 2-Methoxyprop-2-yl | 2-(4-Cyanophenyl)-1,3,4-oxadiazol-5-yl |
| 2-Methoxyprop-2-yl | 2-(4-Nitrophenyl)-1,3,4-oxadiazol-5-yl |
| 2-Methoxyprop-2-yl | 2-(3-Nitrophenyl)-1,3,4-oxadiazol-5-yl |
| 2-Methoxyprop-2-yl | 2-(2-Chlorophenyl)-1,3,4-oxadiazol-5-yl |
| 2-Methoxyprop-2-yl | 2-(2,4-Dichlorophenyl)-1,3,4-oxadiazol-5-yl |
| 2-Methoxyprop-2-yl | 2-Ethyl-1,3,4-oxadiazol-5-yl |
| 2-Methoxyprop-2-yl | 2-Isopropyl-1,3,4-oxadiazol-5-yl |
| 2-Methoxyprop-2-yl | 2-Cyclopropyl-1,3,4-oxadiazol-5-yl |
| 2-Methoxyprop-2-yl | 3-(4-Chlorophenyl)-1,2,4-oxadiazol-5-yl |
| 2-Methoxyprop-2-yl | 3-(4-Fluorophenyl)-1,2,4-oxadiazol-5-yl |
| 2-Methoxyprop-2-yl | 3-n-Propyl-1,2,4-oxadiazol-5-yl |
| 2-Methoxyprop-2-yl | 3 Ethyl-1,2,4-oxadiazol-5-yl |
| 2-Methoxyprop-2-yl | 3-Methyl-1,2,4-oxadiazol-5-yl |
| 2-Methoxyprop-2-yl | 3-Isopropyl-1,2,4-oxadiazol-5-yl |
| 2-Methoxyprop-2-yl | 3-tert-Butylpropyl-1,2,4-oxadiazol-5-yl |
| 2-Methoxyprop-2-yl | 3-Cyclopropyl-1,2,4-oxadiazol-5-yl |
| 2-Methoxyprop-2-yl | 3-Cyclohexyl-1,2,4-oxadiazol-5-yl |
| 2-Methoxyprop-2-yl | 5-Isopropyl-1,2,4-oxadiazol-3-yl |
| 2-Methoxyprop-2-yl | 5-(4-Chlorophenyl)-1,2,4-oxadiazol-3-yl |
| 2-Methoxyprop-2-yl | 3-Carbomethoxy-1,2,4-oxadiazol-5-yl |
| 2-Methoxyprop-2-yl | 5-Chloro-1,2,3-thiadiazol-4-yl |
| 2-Methoxyprop-2-yl | 5-Methyl-1,2,3-thiadiazol-4-yl |
| 2-Methoxyprop-2-yl | 4-Methyl-1,2,3-thiadiazol-5-yl |
| 2-Methoxyprop-2-yl | 5-Chloro-1,2,4-thiadiazol-3-yl |
| 2-Methoxyprop-2-yl | Benzimidazol-2-yl |
| 2-Methoxyprop-2-yl | Benzoxazol-2-yl |
| 2-Methoxyprop-2-yl | Benzthiophen-3-yl |
| 2-Methoxyprop-2-yl | Benzofuran-2-yl |
| 2-Methoxyprop-2-yl | 5-Chlorobenzofuran 2-yl |
| 2-Methoxyprop-2-yl | 5-Chlorobenzoxazol-2-yl |
| 2-Methoxyprop-2-yl | 1-Methylpyrazol-3-yl |
| 2-Methoxyprop-2-yl | 1-(4-Methylphenyl)pyrazol-4-yl |
| 2-Methoxyprop-2-yl | 1,3-Dimethylpyrazol-5-yl |
| 2-Methoxyprop-2-yl | 1-Phenyl-3-ethoxypyrazol-5-yl |
| 2-Methoxyprop-2-yl | 1-Phenyl-3-methylpyrazol-5-yl |
| 2-Methoxyprop-2-yl | 3-Cyclopropyl-1-methyl-1,2,4-triazol-5-yl |
| 2-Methoxyprop-2-yl | 3-Cyclohexyl-1-methyl-1,2,4-triazol-5-yl |
| 2-Methoxyprop-2-yl | 1,3-Dimethyl-1,2,4-triazol-5-yl |
| 2-Methoxyprop-2-yl | 5-Phenyl-1,2,4-triazol-3-yl |
| 2-Ethoxyprop-2-yl | Phenyl |
| 2-Ethoxyprop-2-yl | 2-Chlorophenyl |
| 2-Ethoxyprop-2-yl | 3-Chlorophenyl |
| 2-Ethoxyprop-2-yl | 4-Chlorophenyl |
| 2-Ethoxyprop-2-yl | 2,6-Dichlorophenyl |
| 2-Ethoxyprop-2-yl | 2,4-Dichlorophenyl |
| 2-Ethoxyprop-2-yl | 2-Methylphenyl |
| 2-Ethoxyprop-2-yl | 3-Methylphenyl |
| 2-Ethoxyprop-2-yl | 4-Methylphenyl |
| 2-Ethoxyprop-2-yl | 2,5-Dimethylphenyl |
| 2-Ethoxyprop-2-yl | 2,4,6-Trimethylphenyl |
| 2-Ethoxyprop-2-yl | 3-Methoxyphenyl |
| 2-Ethoxyprop-2-yl | 4-Methoxyphenyl |
| 2-Ethoxyprop-2-yl | 2-Nitrophenyl |
| 2-Ethoxyprop-2-yl | 3-Nitrophenyl |
| 2-Ethoxyprop-2-yl | 4-Nitrophenyl |
| 2-Ethoxyprop-2-yl | 2-Bromophenyl |
| 2-Ethoxyprop-2-yl | 4-Bromophenyl |
| 2-Ethoxyprop-2-yl | 4-Cyanophenyl |
| 2-Ethoxyprop-2-yl | 4-Dimethylaminophenyl |
| 2-Ethoxyprop-2-yl | 4-Carbomethoxyphenyl |
| 2-Ethoxyprop-2-yl | 2-Methoxy-5-nitrophenyl |
| 2-Ethoxyprop-2-yl | 2-Trifluoromethylphenyl |
| 2-Ethoxyprop-2-yl | 4-Trifluoromethylphenyl |
| 2-Ethoxyprop-2-yl | 4-tert-Butylphenyl |
| 2-Ethoxyprop-2-yl | 2-Chloro-6-nitrophenyl |
| 2-Ethoxyprop-2-yl | 2-Fluorophenyl |
| 2-Ethoxyprop-2-yl | 4-Fluorophenyl |
| 2-Ethoxyprop-2-yl | 2,3,4,5,6-Pentafluorophenyl |
| 2-Ethoxyprop-2-yl | 2-Chloro-3-isopropylphenyl |
| 2-Ethoxyprop-2-yl | 2,6-Difluorophenyl |
| 2-Ethoxyprop-2-yl | 2-Chloro-3-trifluoromethylphenyl |
| 2-Ethoxyprop-2-yl | 2-Biphenyl |
| 2-Ethoxyprop-2-yl | 3-Biphenyl |
| 2-Ethoxyprop-2-yl | 4-Biphenyl |
| 2-Ethoxyprop-2-yl | 4'-Chlorobiphenyl-4-yl |
| 2-Ethoxyprop-2-yl | 3-Phenoxyphenyl |
| 2-Ethoxyprop-2-yl | 3,4-Methylenedioxyphenyl |
| 2-Ethoxyprop-2-yl | 1-Naphthyl |
| 2-Ethoxyprop-2-yl | 2-Naphthyl |
| 2-Ethoxyprop-2-yl | 9-Anthracenyl |
| 2-Ethoxyprop-2-yl | 2-Furyl |
| 2-Ethoxyprop-2-yl | 4-Isopropylfuran-2-yl |
| 2-Ethoxyprop-2-yl | 5-Carboxymethyl-furan-2-yl |
| 2-Ethoxyprop-2-yl | 5-Methylfuran-2-yl |
| 2-Ethoxyprop-2-yl | 5-Trifluoromethylfuran-2-yl |
| 2-Ethoxyprop-2-yl | 3-Furyl |
| 2-Ethoxyprop-2-yl | 2-Thienyl |
| 2-Ethoxyprop-2-yl | 5-Chlorothien-2-yl |
| 2-Ethoxyprop-2-yl | 3-Thienyl |
| 2-Ethoxyprop-2-yl | 5-Bromothien-3-yl |
| 2-Ethoxyprop-2-yl | Benzothiophen-3-yl |
| 2-Ethoxyprop-2-yl | 2-Pyrrolyl |
| 2-Ethoxyprop-2-yl | 1-Phenylpyrrol-2-yl |
| 2-Ethoxyprop-2-yl | 3-Pyrrolyl |
| 2-Ethoxyprop-2-yl | Isoxazol-5-yl |
| 2-Ethoxyprop-2-yl | Isoxazol-3-yl |
| 2-Ethoxyprop-2-yl | 3-Phenylisoxazol-5-yl |
| 2-Ethoxyprop-2-yl | 3-Methylisoxazol-5-yl |
| 2-Ethoxyprop-2-yl | 4-Chloro-3-methylisoxazol-5-yl |
| 2-Ethoxyprop-2-yl | 4-Chloro-3-isopropylisoxazol-5-yl |
| 2-Ethoxyprop-2-yl | 4-Chloro-3-sec-butylisoxazol-5-yl |
| 2-Ethoxyprop-2-yl | 4-Chloro-3-tert-butylisoxazol-5-yl |
| 2-Ethoxyprop-2-yl | 4-Chloro-3-cyclohexylisoxazol-5-yl |
| 2-Ethoxyprop-2-yl | 4-Chloro-3-phenylisoxazol-5-yl |
| 2-Ethoxyprop-2-yl | 4-Chloro-3-(4-methylphenyl)isoxazol-5-yl |
| 2-Ethoxyprop-2-yl | 4-Chloro-3-(4-chlorophenyl)isoxazol-5-yl |
| 2-Ethoxyprop-2-yl | 4-Chloro-3-(4-fluorophenyl)isoxazol-5-yl |
| 2-Ethoxyprop-2-yl | 4-Chloro-3-(4-trifluoromethylphenyl)-isoxazol-5-yl |
| 2-Ethoxyprop-2-yl | 4-Chloro-3-(2,6-difluorophenyl)isoxazol-5-yl |
| 2-Ethoxyprop-2-yl | 4-Chloro-3-phenylisoxazol-5-yl |
| 2-Ethoxyprop-2-yl | 3,5-Dimethylisoxazol-4-yl |
| 2-Ethoxyprop-2-yl | 3-Carboxyethylisoxazol-5-yl |
| 2-Ethoxyprop-2-yl | 3-(3,4-Dichlorophenyl)isoxazol-5-yl |
| 2-Ethoxyprop-2-yl | 3-(3-Nitrophenyl)isoxazol-5-yl |
| 2-Ethoxyprop-2-yl | 3-(4-Chlorophenyl)isoxazol-5-yl |
| 2-Ethoxyprop-2-yl | 3-(4-Fluorophenyl)isoxazol-5-yl |
| 2-Ethoxyprop-2-yl | 3-(3,4-Difluorophenyl)isoxazol-5-yl |
| 2-Ethoxyprop-2-yl | 3-Phenylisoxazol-5-yl |
| 2-Ethoxyprop-2-yl | 3-Methoxymethylisoxazol-5-yl |
| 2-Ethoxyprop-2-yl | 3-Methylisoxazol-5-yl |
| 2-Ethoxyprop-2-yl | 3-Ethylisoxazol-5-yl |
| 2-Ethoxyprop-2-yl | 3-n-Propylisoxazol-5-yl |
| 2-Ethoxyprop-2-yl | 3-n-Butylisoxazol-5-yl |
| 2-Ethoxyprop-2-yl | 3-Isopropylisoxazol-5-yl |
| 2-Ethoxyprop-2-yl | 3-Isobutylisoxazol-5-yl |
| 2-Ethoxyprop-2-yl | 3-tert-Butylisoxazol-5-yl |
| 2-Ethoxyprop-2-yl | 3-sec-Butylisoxazol-5-yl |
| 2-Ethoxyprop-2-yl | 3-Methoxyisoxazol-5-yl |
| 2-Ethoxyprop-2-yl | 3-Cyclopropylisoxazol-5-yl |
| 2-Ethoxyprop-2-yl | 3-Cyclopropylisoxazol-4-yl |
| 2-Ethoxyprop-2-yl | 3-Cyclohexylisoxazol-5-yl |
| 2-Ethoxyprop-2-yl | 3-(3-Methylphenyl)isoxazol-5-yl |
| 2-Ethoxyprop-2-yl | 3-(3,4-Dichlorophenyl)isoxazol-5-yl |
| 2-Ethoxyprop-2-yl | 3-(2,6-Dichlorophenyl)isoxazol-5-yl |
| 2-Ethoxyprop-2-yl | 3-(3-Nitrophenyl)isoxazol-5-yl |
| 2-Ethoxyprop-2-yl | 3-(2-Methoxyphenyl)isoxazol-5-yl |
| 2-Ethoxyprop-2-yl | 3-(4-Trifluoromethylphenyl)isoxa- |

TABLE A-continued

| | R¹R²CH—ON=C(CN)—R³   R¹ = H   I |
|---|---|
| R³ | R² |
| 2-Ethoxyprop-2-yl | 3-(3-Trifluoromethylphenyl)isoxazol-5-yl |
| 2-Ethoxyprop-2-yl | 3-(4-Bromophenyl)isoxazol-5-yl |
| 2-Ethoxyprop-2-yl | 3-(3-Chlorophenyl)isoxazol-5-yl |
| 2-Ethoxyprop-2-yl | 3-(2-Chlorophenyl)isoxazol-5-yl |
| 2-Ethoxyprop-2-yl | 3-(3-Fluorophenyl)isoxazol-5-yl |
| 2-Ethoxyprop-2-yl | 3-(3-Phenoxyphenyl)isoxazol-5-yl |
| 2-Ethoxyprop-2-yl | 3-(2,6-Difluorophenyl)isoxazol-5-yl |
| 2-Ethoxyprop-2-yl | 3-Trifluoromethylisoxazol-5-yl |
| 2-Ethoxyprop-2-yl | 3-(2-Naphthyl)isoxazol-5-yl |
| 2-Ethoxyprop-2-yl | 3-(1-Naphthyl)isoxazol-5-yl |
| 2-Ethoxyprop-2-yl | 3-tert-Butyl-5-phenylisoxazol-4-yl |
| 2-Ethoxyprop-2-yl | 5-Methylisoxazol-4-yl |
| 2-Ethoxyprop-2-yl | 4-Ethoxycarbonylisoxazol-5-yl |
| 2-Ethoxyprop-2-yl | 5-Cyclopropylisoxazol-3-yl |
| 2-Ethoxyprop-2-yl | 4-Chloro-3-(4-bromophenyl)isoxazol-5-yl |
| 2-Ethoxyprop-2-yl | 4-Chloro-3-(3-chlorophenyl)isoxazol-5-yl |
| 2-Ethoxyprop-2-yl | 4-Chloro-3-(3-fluorophenyl)isoxazol-5-yl |
| 2-Ethoxyprop-2-yl | 4-Chloro-3-(2-chlorophenyl)isoxazol-5-yl |
| 2-Ethoxyprop-2-yl | 2-Phenyloxazol-4-yl |
| 2-Ethoxyprop-2-yl | 2-(4-Fluorophenyl)oxazol-4-yl |
| 2-Ethoxyprop-2-yl | 2-(4-Chlorophenyl)oxazol-4-yl |
| 2-Ethoxyprop-2-yl | 2-(4-Bromophenyl)oxazol-4-yl |
| 2-Ethoxyprop-2-yl | 2-(3-Chlorophenyl)oxazol-4-yl |
| 2-Ethoxyprop-2-yl | 2-(4-Methylphenyl)oxazol-4-yl |
| 2-Ethoxyprop-2-yl | 2-tert-Butyloxazol-4-yl |
| 2-Ethoxyprop-2-yl | 2-(2,4-Dichlorophenyl)oxazol-4-yl |
| 2-Ethoxyprop-2-yl | 2-(4-Methoxyphenyl)oxazol-4-yl |
| 2-Ethoxyprop-2-yl | 2-(4-Chlorophenyl)-5-bromooxazol-4-yl |
| 2-Ethoxyprop-2-yl | 2-Cyclopropyloxazol-4-yl |
| 2-Ethoxyprop-2-yl | 2-Isopropyloxazol-4-yl |
| 2-Ethoxyprop-2-yl | 2-tert-Butyloxazol-4-yl |
| 2-Ethoxyprop-2-yl | 2-tert-Butyloxazol-5-y |
| 2-Ethoxyprop-2-yl | 2-Benzyloxazol-4-yl |
| 2-Ethoxyprop-2-yl | 2-Methylthiazol-4-yl |
| 2-Ethoxyprop-2-yl | 2-Isopropylthiazol-4-yl |
| 2-Ethoxyprop-2-yl | 2-Cyclopropylthiazol-4-yl |
| 2-Ethoxyprop-2-yl | 4-(4-Methoxyphenyl)thiazol-2-yl |
| 2-Ethoxyprop-2-yl | 2-Acetamidothiazol-4-yl |
| 2-Ethoxyprop-2-yl | 2-Phenylthiazol-4-yl |
| 2-Ethoxyprop-2-yl | 2-(2-Chlorophenyl)thiazol-4-yl |
| 2-Ethoxyprop-2-yl | 2-(4-Chlorophenyl)thiazol-4-yl |
| 2-Ethoxyprop-2-yl | 2-(2,4-Dichlorophenyl)thiazol-4-yl |
| 2-Ethoxyprop-2-yl | 2-(2,6-Dichlorophenyl)thiazol-4-yl |
| 2-Ethoxyprop-2-yl | 2-(3-Fluorophenyl)thiazol-4-yl |
| 2-Ethoxyprop-2-yl | 2-(3-Chlorophenyl)thiazol-4-yl |
| 2-Ethoxyprop-2-yl | 2-(4-Trifluoromethylphenyl)thiazol-4-yl |
| 2-Ethoxyprop-2-yl | 2-(3-Methylphenyl)thiazol-4-yl |
| 2-Ethoxyprop-2-yl | 2-(4-Methoxyphenyl)thiazol-4-yl |
| 2-Ethoxyprop-2-yl | 2-Methylthiazol-4-yl |
| 2-Ethoxyprop-2-yl | 2-(4-Fluorophenyl)thiazol-4-yl |
| 2-Ethoxyprop-2-yl | 2-Methyl-1,3,4-thiadiazol-5-yl |
| 2-Ethoxyprop-2-yl | 2-Phenyl-1,3,4-thiadiazol-5-yl |
| 2-Ethoxyprop-2-yl | 2-Cyclopropyl-1,3,4-thiadiazol-5-yl |
| 2-Ethoxyprop-2-yl | 2-Isopropyl-1,3,4-thiadiazol-5-yl |
| 2-Ethoxyprop-2-yl | 2-Phenoxymethyl-1,3,4-thiadiazol-5-yl |
| 2-Ethoxyprop-2-yl | 2-(4-Chlorophenyl)-1,3,4-thiadiazol-5-yl |
| 2-Ethoxyprop-2-yl | 2-Phenyl-1,3,4-oxadiazol-5-yl |
| 2-Ethoxyprop-2-yl | 2-(4-Methoxyphenyl)-1,3,4-oxadiazol-5-yl |
| 2-Ethoxyprop-2-yl | 2-(2-Methylphenyl)-1,3,4-oxadiazol-5-yl |
| 2-Ethoxyprop-2-yl | 2-(4-Methylphenyl)-1,3,4-oxadiazol-5-yl |
| 2-Ethoxyprop-2-yl | 2-(4-Cyanophenyl)-1,3,4-oxadiazol-5-yl |
| 2-Ethoxyprop-2-yl | 2-(4-Nitrophenyl)-1,3,4-oxadiazol-5-yl |
| 2-Ethoxyprop-2-yl | 2-(3-Nitrophenyl)-1,3,4-oxadiazol-5-yl |
| 2-Ethoxyprop-2-yl | 2-(2-Chlorophenyl)-1,3,4-oxadiazol-5-yl |
| 2-Ethoxyprop-2-yl | 2-(2,4-Dichlorophenyl)1,3,4-oxadiazol-5-yl |
| 2-Ethoxyprop-2-yl | 2-Ethyl-1,3,4-oxadiazol-5-yl |
| 2-Ethoxyprop-2-yl | 2-Isopropyl-1,3,4-oxadiazol-5-yl |
| 2-Ethoxyprop-2-yl | 2-Cyclopropyl-1,3,4-oxadiazol-5-yl |
| 2-Ethoxyprop-2-yl | 3-(4-Chlorophenyl)-1,2,4-oxadiazol-5-yl |
| 2-Ethoxyprop-2-yl | 3-(4-Fluorophenyl)-1,2,4-oxadiazol-5-yl |
| 2-Ethoxyprop-2-yl | 3-n-Propyl-1,2,4-oxadiazol-5-yl |
| 2-Ethoxyprop-2-yl | 3-Ethyl-1,2,4-oxadiazol-5-yl |
| 2-Ethoxyprop-2-yl | 3-Methyl-1,2,4-oxadiazol-5-yl |
| 2-Ethoxyprop-2-yl | 3-Isopropyl-1,2,4-oxadiazol-5-yl |
| 2-Ethoxyprop-2-yl | 3-tert-Butylpropyl-1,2,4-oxadiazol-5-yl |
| 2-Ethoxyprop-2-yl | 3-Cyclopropyl-1,2,4-oxadiazol-5-yl |
| 2-Ethoxyprop-2-yl | 3-Cyclohexyl-1,2,4-oxadiazol-5-yl |
| 2-Ethoxyprop-2-yl | 5-Isopropyl-1,2,4-oxadiazol-3-yl |
| 2-Ethoxyprop-2-yl | 5-(4-Chlorophenyl)-1,2,4-oxadiazol-3-yl |
| 2-Ethoxyprop-2-yl | 3-Carbomethoxy-1,2,4-oxadiazol-5-yl |
| 2-Ethoxyprop-2-yl | 5-Chloro-1,2,3-thiadiazol-4-yl |
| 2-Ethoxyprop-2-yl | 5-Methyl-1,2,3-thiadiazol-4-yl |
| 2-Ethoxyprop-2-yl | 4-Methyl-1,2,3-thiadiazol-5-yl |
| 2-Ethoxyprop-2-yl | 5-Chloro-1,2,4-thiadiazol-3 yl |
| 2-Ethoxyprop-2-yl | Benzimidazol-2-yl |
| 2-Ethoxyprop-2-yl | Benzoxazol-2-yl |
| 2-Ethoxyprop-2-yl | Benzthiophen-3-yl |
| 2-Ethoxyprop-2-yl | Benzofuran-2-yl |
| 2-Ethoxyprop-2-yl | 5-Chlorobenzofuran-2-yl |
| 2-Ethoxyprop-2-yl | 5-Chlorobenzoxazol-2-yl |
| 2-Ethoxyprop-2-yl | 1-Methylpyrazol-3-yl |
| 2-Ethoxyprop-2-yl | 1-(4-Methylphenyl)pyrazol-4-yl |
| 2-Ethoxyprop-2-yl | 1,3-Dimethylpyrazol-5-yl |
| 2-Ethoxyprop-2-yl | 1-Phenyl-3-ethoxypyrazol-5-yl |
| 2-Ethoxyprop-2-yl | 1-Phenyl-3-methylpyrazol-5-yl |
| 2-Ethoxyprop-2-yl | 3-Cyclopropyl-1-methyl-1,2,4-triazol-5-yl |
| 2-Ethoxyprop-2-yl | 3-Cyclohexyl-1-methyl-1,2,4-triazol-5-yl |
| 2-Ethoxyprop-2-yl | 1,3-Dimethyl-1,2,4-triazol-5-yl |
| 2-Ethoxyprop-2-yl | 5-Phenyl-1,2,4-triazol-3-yl |
| 2-n-Propoxyprop-2-yl | Phenyl |
| 2-n-Propoxyprop-2-yl | 2-Chlorophenyl |
| 2-n-Propoxyprop-2-yl | 3-Chlorophenyl |
| 2-n-Propoxyprop-2-yl | 4-Chlorophenyl |
| 2-n-Propgxyprop-2-yl | 2,6-Dichlorophenyl |
| 2-n-Propoxyprop-2-yl | 2,4-Dichlorophenyl |
| 2-n-Propoxyprop-2-yl | 2-Methylphenyl |
| 2-n-Propoxyprop-2-yl | 3-Methylphenyl |
| 2-n-Propoxyprop-2-yl | 4-Methylphenyl |
| 2-n-Propoxyprop-2-yl | 2,5-Dimethylphenyl |
| 2-n-Propoxyprop-2-yl | 2,4,6-Trimethylphenyl |
| 2-n-Propoxyprop-2-yl | 3-Methoxyphenyl |
| 2-n-Propoxyprop-2-yl | 4-Methoxyphenyl |
| 2-n-Propoxyprop-2-yl | 2-Nitrophenyl |
| 2-n-Propoxyprop-2-yl | 3-Nitrophenyl |
| 2-n-Propoxyprop-2-yl | 4-Nitrophenyl |
| 2-n-Propoxyprop-2-yl | 2-Bromophenyl |
| 2-n-Propoxyprop-2-yl | 4-Bromophenyl |
| 2-n-Propoxyprop-2-yl | 4-Cyanophenyl |
| 2-n-Propoxyprop-2-yl | 4-Dimethylaminophenyl |
| 2-n-Propoxyprop-2-yl | 4-Carbomethoxyphenyl |
| 2-n-Propoxyprop-2-yl | 2-Methoxy-5-nitrophenyl |
| 2-n-Propoxyprop-2-yl | 2-Trifluoromethylphenyl |
| 2-n-Propoxyprop-2-yl | 4-Trifluoromethylphenyl |
| 2-n-Propoxyprop-2-yl | 4-tert-Butylphenyl |
| 2-n-Propoxyprop-2-yl | 2-Chloro-6-nitrophenyl |
| 2-n-Propoxyprop-2-yl | 2-Fluorophenyl |
| 2-n-Propoxyprop-2-yl | 4-Fluorophenyl |
| 2-n-Propoxyprop-2-yl | 2,3,4,5,6-Pentafluorophenyl |
| 2-n-Propoxyprop-2-yl | 2-Chloro-3-isopropylphenyl |
| 2-n-Propoxyprop-2-yl | 2,6-Difluorophenyl |
| 2-n-Propoxyprop-2-yl | 2-Chloro-3-trifluoromethylphenyl |
| 2-n-Propoxyprop-2-yl | 2-Biphenyl |
| 2-n-Propoxyprop-2-yl | 3-Biphenyl |
| 2-n-Propoxyprop-2-yl | 4-Biphenyl |
| 2-n-Propoxyprop-2-yl | 4'-Chlorobiphenyl-4-yl |
| 2-n-Propoxyprop-2-yl | 3-Phenoxyphenyl |
| 2-n-Propoxyprop-2-yl | 3,4-Methylendioxyphenyl |
| 2-n-Propoxyprop-2-yl | 1-Naphthyl |
| 2-n-Propoxyprop-2-yl | 2-Naphthyl |
| 2-n-Propoxyprop-2-yl | 9-Anthracenyl |

TABLE A-continued $R^1R^2CH-ON=C(CN)-R^3$  $R^1 = H$  I

| R³ | R² |
|---|---|
| 2-n-Propoxyprop-2-yl | 2-Furyl |
| 2-n-Propoxyprop-2-yl | 4-Isopropylfuran-2-yl |
| 2-n-Propoxyprop-2-yl | 5-Carboxymethylfuran-2-yl |
| 2-n-Propoxyprop-2-yl | 5-Methylfuran-2-yl |
| 2-n-Propoxyprop-2-yl | 5-Trifluoromethylfuran-2-yl |
| 2-n-Propoxyprop-2-yl | 3-Furyl |
| 2-n-Propoxyprop-2-yl | 2-Thienyl |
| 2-n-Propoxyprop-2-yl | 5-Chlorothien-2-yl |
| 2-n-Propoxyprop-2-yl | 3-Thienyl |
| 2-n-Propoxyprop-2-yl | 5-Bromothien-3-yl |
| 2-n-Propoxyprop-2-yl | Benzothiophen-3-yl |
| 2-n-Propoxyprop-2-yl | 2-Pyrrolyl |
| 2-n-Propoxyprop-2-yl | 1-Phenylpyrrol-2-yl |
| 2-n-Propoxyprop-2-yl | 3-Pyrrolyl |
| 2-n-Propoxyprop-2-yl | Isoxazol-5-yl |
| 2-n-Propoxyprop-2-yl | Isoxazol-3-yl |
| 2-n-Propoxyprop-2-yl | 3-Phenylisoxazol-5-yl |
| 2-n-Propoxyprop-2-yl | 3-Methylisoxazol-5-yl |
| 2-n-Propoxyprop-2-yl | 4-Chloro-3-methylisoxazol-5-yl |
| 2-n-Propoxyprop-2-yl | 4-Chloro-3-isopropylisoxazol-5-yl |
| 2-n-Propoxyprop-2-yl | 4-Chloro-3-sec-butylisoxazol-5-yl |
| 2-n-Propoxyprop-2-yl | 4-Chloro-3-tert-butylisoxazol-5-yl |
| 2-n-Propoxyprop-2-yl | 4-Chloro-3-cyclohexylisoxazol-5-yl |
| 2-n-Propoxyprop-2-yl | 4-Chloro-3-phenylisoxazol-5-yl |
| 2-n-Propoxyprop-2-yl | 4-Chloro-3-(4-methylphenyl)-isoxazol-5-yl |
| 2-n-Propoxyprop-2-yl | 4-Chloro-3-(4-chlorophenyl)-isoxazol-5-yl |
| 2-n-Propoxyprop-2-yl | 4-Chloro-3-(4-fluorophenyl)-isoxazol-5-yl |
| 2-n-Propoxyprop-2-yl | 4-Chloro-3-(4-trifluoromethylphenyl)-isoxazol-5-yl |
| 2-n-Propoxyprop-2-yl | 4-Chloro-3-(2,6-difluorophenyl)-isoxazol-5-yl |
| 2-n-Propoxyprop-2-yl | 4-Chloro-3-phenylisoxazol-5-yl |
| 2-n-Propoxyprop-2-yl | 3,5-Dimethylisoxazol-4-yl |
| 2-n-Propoxyprop-2-yl | 3-Carboxyethylisoxazol-5-yl |
| 2-n-Propoxyprop-2-yl | 3-(3,4-Dichlorophenyl)isoxazol-5-yl |
| 2-n-Propoxyprop-2-yl | 3-(3-Nitrophenyl)isoxazol-5-yl |
| 2-n-Propoxyprop-2-yl | 3-(4-Chlorophenyl)isoxazol-5-yl |
| 2-n-Propoxyprop-2-yl | 3-(4-Fluorophenyl)isoxazol-5-yl |
| 2-n-Propoxyprop-2-yl | 3-(3,4-Difluorophenyl)isoxazol-5-yl |
| 2-n-Propoxyprop-2-yl | 3-Phenylisoxazol-5-yl |
| 2-n-Propoxyprop-2-yl | 3-Methoxymethylisoxazol-5-yl |
| 2-n-Propoxyprop-2-yl | 3-Methylisoxazol-5-yl |
| 2-n-Propoxyprop-2-yl | 3-Ethylisoxazol-5-yl |
| 2-n-Propoxyprop-2-yl | 3-n-Propylisoxazol-5-yl |
| 2-n-Propoxyprop-2-yl | 3-n-Butylisoxazol-5-yl |
| 2-n-Propoxyprop-2-yl | 3-Isopropylisoxazol-5-yl |
| 2-n-Propoxyprop-2-yl | 3-Isobutylisoxazol-5-yl |
| 2-n-Propoxyprop-2-yl | 3-tert-Butylisoxazol-5-yl |
| 2-n-Propoxyprop-2-yl | 3-sec-Butylisoxazol-5-yl |
| 2-n-Propoxyprop-2-yl | 3-Methoxyisoxazol-5-yl |
| 2-n-Propoxyprop-2-yl | 3-Cyclopropylisoxazol-5-yl |
| 2-n-Propoxyprop-2-yl | 3-Cyclopropylisoxazol-4-yl |
| 2-n-Propoxyprop-2-yl | 3-Cyclohexylisoxazol-5-yl |
| 2-n-Propoxyprop-2-yl | 3-(3-Methylphenyl)isoxazol-5-yl |
| 2-n-Propoxyprop-2-yl | 3-(3,4-Dichlorophenyl)isoxazol-5-yl |
| 2-n-Propoxyprop-2-yl | 3-(2,6-Dichlorophenyl)isoxazol-5-yl |
| 2-n-Propoxyprop-2-yl | 3-(3-Nitrophenyl)isoxazol-5-yl |
| 2-n-Propoxyprop-2-yl | 3-(2-Methoxyphenyl)isoxazol-5-yl |
| 2-n-Propoxyprop-2-yl | 3-(4-Trifluoromethylphenyl)isoxazol-5-yl |
| 2-n-Propoxyprop-2-yl | 3-(3-Trifluoromethylphenyl)isoxazol-5-yl |
| 2-n-Propoxyprop-2-yl | 3-(4-Bromophenyl)isoxazol-5-yl |
| 2-n-Propoxyprop-2-yl | 3-(3-Chlorophenyl)isoxazol-5-yl |
| 2-n-Propoxyprop-2-yl | 3-(2-Chlorophenyl)isoxazol-5-yl |
| 2-n-Propoxyprop-2-yl | 3-(3-Fluorophenyl)isoxazol-5-yl |
| 2-n-Propoxyprop-2-yl | 3-(3-Phenoxyphenyl)isoxazol-5-yl |
| 2-n-Propoxyprop-2-yl | 3-(2,6-Difluorophenyl)isoxazol-5-yl |
| 2-n-Propoxyprop-2-yl | 3-Trifluoromethylisoxazol-5-yl |
| 2-n-Propoxyprop-2-yl | 3-(2-Naphthyl)isoxazol-5-yl |
| 2-n-Propoxyprop-2-yl | 3-(1-Naphthyl)isoxazol-5-yl |
| 2-n-Propoxyprop-2-yl | 3-tert-Butyl-5-phenylisoxazol-4-yl |
| 2-n-Propoxyprop-2-yl | 5-Methylisoxazol-4-yl |
| 2-n-Propoxyprop-2-yl | 4-Ethoxycarbonylisoxazol-5-yl |
| 2-n-Propoxyprop-2-yl | 5-Cyclopropylisoxazol-3-yl |
| 2-n-Propoxyprop-2-yl | 4-Chloro-3-(4-bromophenyl)isoxazol-5-yl |
| 2-n-Propoxyprop-2-yl | 4-Chloro-3-(3-chlorophenyl)isoxazol-5-yl |
| 2-n-Propoxyprop-2-yl | 4-Chloro-3-(3-fluorophenyl)isoxazol-5-yl |
| 2-n-Propoxyprop-2-yl | 4-Chloro-3-(2-chlorophenyl)isoxazol-5-yl |
| 2-n-Propoxyprop-2-yl | 2-Phenyloxazol-4-yl |
| 2-n-Propoxyprop-2-yl | 2-(4-Fluorophenyl)oxazol-4-yl |
| 2-n-Propoxyprop-2-yl | 2-(4-Chlorophenyl)oxazol-4-yl |
| 2-n-Propoxyprop-2-yl | 2-(4-Bromophenyl)oxazol-4-yl |
| 2-n-Propoxyprop-2-yl | 2-(3-Chlorophenyl)oxazol-4-yl |
| 2-n-Propoxyprop-2-yl | 2-(4-Methylphenyl)oxazol-4-yl |
| 2-n-Propoxyprop-2-yl | 2-tert-Butyloxazol-4-yl |
| 2-n-Propoxyprop-2-yl | 2-(2,4-Dichlorophenyl)oxazol-4-yl |
| 2-n-Propoxyprop-2-yl | 2-(4-Methoxyphenyl)oxazol-4-yl |
| 2-n-Propoxyprop-2-yl | 2-(4-Chlorophenyl)-5-bromooxazol-4-yl |
| 2-n-Propoxyprop-2-yl | 2-Cyclopropyloxazol-4-yl |
| 2-n-Propoxyprop-2-yl | 2-Isopropyloxazol-4-yl |
| 2-n-Propoxyprop-2-yl | 2-tert-Butyloxazol-4-yl |
| 2-n-Propoxyprop-2-yl | 2-tert-Butyloxazol-5-y |
| 2-n-Propoxyprop-2-yl | 2-Benzyloxazol-4-yl |
| 2-n-Propoxyprop-2-yl | 2-Methylthiazol-4-yl |
| 2-n-Propoxyprop-2-yl | 2-Isopropylthiazol-4-yl |
| 2-n-Propoxyprop-2-yl | 2-Cyclopropylthiazol-4-yl |
| 2-n-Propoxyprop-2-yl | 4-(4-Methoxyphenyl)thiazol-2-yl |
| 2-n-Propoxyprop-2-yl | 2-Acetamidothiazol-4-yl |
| 2-n-Propoxyprop-2-yl | 2-Phenylthiazol-4-yl |
| 2-n-Propoxyprop-2-yl | 2-(2-Chlorophenyl)thiazol-4-yl |
| 2-n-Propoxyprop-2-yl | 2-(4-Chlorophenyl)thiazol-4-yl |
| 2-n-Propoxyprop-2-yl | 2-(2,4-Dichlorophenyl)thiazol-4-yl |
| 2-n-Propoxyprop-2-yl | 2-(2,6-Dichlorophenyl)thiazol-4-yl |
| 2-n-Propoxyprop-2-yl | 2-(3-Fluorophenyl)thiazol-4-yl |
| 2-n-Propoxyprop-2-yl | 2-(3-Chlorophenyl)thiazol-4-yl |
| 2-n-Propoxyprop-2-yl | 2-(4-Trifluoromethylphenyl)thiazol-4-yl |
| 2-n-Propoxyprop-2-yl | 2-(3-Methylphenyl)thiazol-4-yl |
| 2-n-Propoxyprop-2-yl | 2-(4-Methoxyphenyl)thiazol-4-yl |
| 2-n-Propoxyprop-2-yl | 2-Methylthiazol-4-yl |
| 2-n-Propoxyprop-2-yl | 2-(4-Fluorophenyl)thiazol-4-yl |
| 2-n-Propoxyprop-2-yl | 2-Methyl-1,3,4-thiadiazol-5-yl |
| 2-n-Propoxyprop-2-yl | 2-Phenyl-1,3,4-thiadiazol-5-yl |
| 2-n-Propoxyprop-2-yl | 2-Cyclopropyl-1,3,4-thiadiazol-5-yl |
| 2-n-Propoxyprop-2-yl | 2-Isopropyl-1,3,4-thiadiazol-5-yl |
| 2-n-Propoxyprop-2-yl | 2-Phenoxymethyl-1,3,4-thiadiazol-5-yl |
| 2-n-Propoxyprop-2-yl | 2-(4-Chlorophenyl)-1,3,4-thiadiazol-5-yl |
| 2-n-Propoxyprop-2-yl | 2-Phenyl-1,3,4-oxadiazol-5-yl |
| 2-n-Propoxyprop-2-yl | 2-(4-Methoxyphenyl)-1,3,4-oxadiazol-5-yl |
| 2-n-Propoxyprop-2-yl | 2-(2-Methylphenyl)-1,3,4-oxadiazol-5-yl |
| 2-n-Propoxyprop-2-yl | 2-(4-Methylphenyl)-1,3,4-oxadiazol-5-yl |
| 2-n-Propoxyprop-2-yl | 2-(4-Cyanophenyl)-1,3,4-oxadiazol-5-yl |
| 2-n-Propoxyprop-2-yl | 2-(4-Nitrophenyl)-1,3,4-oxadiazol-5-yl |
| 2-n-Propoxyprop-2-yl | 2-(3-Nitrophenyl)-1,3,4-oxadiazol-5-yl |
| 2-n-Propoxyprop-2-yl | 2-(2-Chlorophenyl)-1,3,4-oxadiazol-5-yl |
| 2-n-Propoxyprop-2-yl | 2-(2,4-Dichlorophenyl)1,3,4-oxadiazol-5-yl |
| 2-n-Propoxyprop-2-yl | 2-Ethyl-1,3,4-oxadiazol-5-yl |
| 2-n-Propoxyprop-2-yl | 2-Isopropyl-1,3,4-oxadiazol-5-yl |
| 2-n-Propoxyprop-2-yl | 2-Cyclopropyl-1,3,4-oxadiazol-5-yl |
| 2-n-Propoxyprop-2-yl | 3-(4-Chlorophenyl)-1,2,4-oxadiazol-5-yl |
| 2-n-Propoxyprop-2-yl | 3-(4-Fluorophenyl)-1,2,4-oxadiazol-5-yl |
| 2-n-Propoxyprop-2-yl | 3-n-Propyl-1,2,4-oxadiazol-5-yl |
| 2-n-Propoxyprop-2-yl | 3-Ethyl-1,2,4-oxadiazol-5-yl |
| 2-n-Propoxyprop-2-yl | 3-Methyl-1,2,4-oxadiazol-5-yl |
| 2-n-Propoxyprop-2-yl | 3-Isopropyl-1,2,4-oxadiazol-5-yl |
| 2-n-Propoxyprop-2-yl | 3-tert-Butylpropyl-1,2,4-oxadiazol-5-yl |
| 2-n-Propoxyprop-2-yl | 3-Cyclopropyl-1,2,4-oxadiazol-5-yl |
| 2-n-Propoxyprop-2-yl | 3-Cyclohexyl-1,2,4-oxadiazol-5-yl |
| 2-n-Propoxyprop-2-yl | 5-Isopropyl-1,2,4-oxadiazol-3-yl |
| 2-n-Propoxyprop-2-yl | 5-(4-Chlorophenyl)-1,2,4-oxadiazol-3-yl |

TABLE A-continued

| R³ | R² |
|---|---|
| 2-n-Propoxyprop-2-yl | 3-Carbomethoxy-1,2,4-oxadiazol-5-yl |
| 2-n-Propoxyprop-2-yl | 5-Chloro-1,2,3-thiadiazol-4-yl |
| 2-n-Propoxyprop-2-yl | 5-Methyl-1,2,3-thiadiazol-4-yl |
| 2-n-Propoxyprop-2-yl | 4-Methyl-1,2,3-thiadiazol-5-yl |
| 2-n-Propoxyprop-2-yl | 5-Chloro-1,2,4-thiadiazol-3-yl |
| 2-n-Propoxyprop-2-yl | Benzimidazol-2-yl |
| 2-n-Propoxyprop-2-yl | Benzoxazol-2-yl |
| 2-n-Propoxyprop-2-yl | Benzthiophen-3-yl |
| 2-n-Propoxyprop-2-yl | Benzofuran-2-yl |
| 2-n-Propoxyprop-2-yl | 5-Chlorobenzofuran-2-yl |
| 2-n-Propoxyprop-2-yl | 5-Chlorobenzoxazol-2-yl |
| 2-n-Propoxyprop-2-yl | 1-Methylpyrazol-3-yl |
| 2-n-Propoxyprop-2-yl | 1-(4-Methylphenyl)pyrazol-4-yl |
| 2-n-Propoxyprop-2-yl | 1,3-Dimethylpyrazol-5-yl |
| 2-n-Propoxyprop-2-yl | 1-Phenyl-3-ethoxypyrazol-5-yl |
| 2-n-Propoxyprop-2-yl | 1-Phenyl-3-methylpyrazol-5-yl |
| 2-n-Propoxyprop-2-yl | 3-Cyclopropyl-1-methyl-1,2,4-triazol-5-yl |
| 2-n-Propoxyprop-2-yl | 3-Cyclohexyl-1-methyl-1,2,4-triazol-5-yl |
| 2-n-Propoxyprop-2-yl | 1,3-Dimethyl-1,2,4-triazol-5-yl |
| 2-n-Propoxyprop-2-yl | 5-Phenyl-1,2,4-triazol-3-yl |
| 2-Isopropoxyprop-2-yl | Phenyl |
| 2-Isopropoxyprop-2-yl | 2-Chlorophenyl |
| 2-Isopropoxyprop-2-yl | 3-Chlorophenyl |
| 2-Isopropoxyprop-2-yl | 4-Chlorophenyl |
| 2-Isopropoxyprop-2-yl | 2,6-Dichlorophenyl |
| 2-Isopropoxyprop-2-yl | 2,4-Dichlorophenyl |
| 2-Isopropoxyprop-2-yl | 2-Methylphenyl |
| 2-Isopropoxyprop-2-yl | 3-Methylphenyl |
| 2-Isopropoxyprop-2-yl | 4-Methylphenyl |
| 2-Isopropoxyprop-2-yl | 2,5-Dimethylphenyl |
| 2-Isopropoxyprop-2-yl | 2,4,6-Trimethylphenyl |
| 2-Isopropoxyprop-2-yl | 3-Methoxyphenyl |
| 2-Isopropoxyprop-2-yl | 4-Methoxyphenyl |
| 2-Isopropoxyprop-2-yl | 2-Nitrophenyl |
| 2-Isopropoxyprop-2-yl | 3-Nitrophenyl |
| 2-Isopropoxyprop-2-yl | 4-Nitrophenyl |
| 2-Isopropoxyprop-2-yl | 2-Bromophenyl |
| 2-Isopropoxyprop-2-yl | 4-Bromophenyl |
| 2-Isopropoxyprop-2-yl | 4-Cyanophenyl |
| 2-Isopropoxyprop-2-yl | 4-Dimethylaminophenyl |
| 2-Isopropoxyprop-2-yl | 4-Carbomethoxyphenyl |
| 2-Isopropoxyprop-2-yl | 2-Methoxy-5-nitrophenyl |
| 2-Isopropoxyprop-2-yl | 2-Trifluoromethylphenyl |
| 2-Isopropoxyprop-2-yl | 4-Trifluoromethylphenyl |
| 2-Isopropoxyprop-2-yl | 4-tert-Butylphenyl |
| 2-Isopropoxyprop-2-yl | 2-Chloro-6-nitrophenyl |
| 2-Isopropoxyprop-2-yl | 2-Fluorophenyl |
| 2-Isopropoxyprop-2-yl | 4-Fluorophenyl |
| 2-Isopropoxyprop-2-yl | 2,3,4,5,6-Pentafluorophenyl |
| 2-Isopropoxyprop-2-yl | 2-Chloro-3-isopropylphenyl |
| 2-Isopropoxyprop-2-yl | 2,6-Difluorophenyl |
| 2-Isopropoxyprop-2-yl | 2-Chloro-3-trifluoromethylphenyl |
| 2-Isopropoxyprop-2-yl | 2-Biphenyl |
| 2-Isopropoxyprop-2-yl | 3-Biphenyl |
| 2-Isopropoxyprop-2-yl | 4-Biphenyl |
| 2-Isopropoxyprop-2-yl | 4'-Chlorobiphenyl-4-yl |
| 2-Isopropoxyprop-2-yl | 3-Phenoxyphenyl |
| 2-Isopropoxyprop-2-yl | 3,4-Methylenedioxyphenyl |
| 2-Isopropoxyprop-2-yl | 1-Naphthyl |
| 2-Isopropoxyprop-2-yl | 2-Naphthyl |
| 2-Isopropoxyprop-2-yl | 9-Anthracenyl |
| 2-Isopropoxyprop-2-yl | 2-Furyl |
| 2-Isopropoxyprop-2-yl | 4-Isopropylfuran-2-yl |
| 2-Isopropoxyprop-2-yl | 5-Carboxymethylfuran-2-yl |
| 2-Isopropoxyprop-2-yl | 5-Methylfuran-2-yl |
| 2-Isopropoxyprop-2-yl | 5-Trifluoromethylfuran-2-yl |
| 2-Isopropoxyprop-2-yl | 3-Furyl |
| 2-Isopropoxyprop-2-yl | 2-Thienyl |
| 2-Isopropoxyprop-2-yl | 5-Chlorothien-2-yl |
| 2-Isopropoxyprop-2-yl | 3-Thienyl |
| 2-Isopropoxyprop-2-yl | 5-Bromothien-2-yl |
| 2-Isopropoxyprop-2-yl | Benzothiophen-3-yl |
| 2-Isopropoxyprop-2-yl | 2-Pyrrolyl |
| 2-Isopropoxyprop-2-yl | 1-Phenylpyrrol-2-yl |
| 2-Isopropoxyprop-2-yl | 3-Pyrrolyl |
| 2-Isopropoxyprop-2-yl | Isoxazol-5-yl |
| 2-Isopropoxyprop-2-yl | Isoxazol-3-yl |
| 2-Isopropoxyprop-2-yl | 3-Phenylisoxazol-5-yl |
| 2-Isopropoxyprop-2-yl | 3-Methylisoxazol-5-yl |
| 2-Isopropoxyprop-2-yl | 4-Chloro-3-methylisoxazol-5-yl |
| 2-Isopropoxyprop-2-yl | 4-Chloro-3-isopropylisoxazol-5-yl |
| 2-Isopropoxyprop-2-yl | 4-Chloro-3-sec-butylisoxazol-5-yl |
| 2-Isopropoxyprop-2-yl | 4-Chloro-3-tert-butylisoxazol-5-yl |
| 2-Isopropoxyprop-2-yl | 4-Chloro-3-cyclohexylisoxazol-5-yl |
| 2-Isopropoxyprop-2-yl | 4-Chloro-3-phenylisoxazol-5-yl |
| 2-Isopropoxyprop-2-yl | 4-Chloro-3-(4-methylphenyl)-isoxazol-5-yl |
| 2-Isopropoxyprop-2-yl | 4-Chloro-3-(4-chlorophenyl)isoxazol-5-yl |
| 2-Isopropoxyprop-2-yl | 4-Chloro-3-(4-fluorophenyl)isoxazol-5-yl |
| 2-Isopropoxyprop-2-yl | 4-Chloro-3-(4-trifluoromethylphenyl)-isoxazol-5-yl |
| 2-Isopropoxyprop-2-yl | 4-Chloro-3-(2,6-difluorophenyl)-isoxazol-5-yl |
| 2-Isopropoxyprop-2-yl | 4-Chloro-3-phenylisoxazol-5-yl |
| 2-Isopropoxyprop-2-yl | 3,5-Dimethylisoxazol-4-yl |
| 2-Isopropoxyprop-2-yl | 3-Carboxyethylisoxazol-5-yl |
| 2-Isopropoxyprop-2-yl | 3-(3,4-Dichlorophenyl)isoxazol-5-yl |
| 2-Isopropoxyprop-2-yl | 3-(3-Nitrophenyl)isoxazol-5-yl |
| 2-Isopropoxyprop-2-yl | 3-(4-Chlorophenyl)isoxazol-5-yl |
| 2-Isopropoxyprop-2-yl | 3-(4-Fluorophenyl)isoxazol-5-yl |
| 2-Isopropoxyprop-2-yl | 3-(3,4-Difluorophenyl)isoxazol-5-yl |
| 2-Isopropoxyprop-2-yl | 3-Phenylisoxazol-5-yl |
| 2-Isopropoxyprop-2-yl | 3-Methoxymethylisoxazol-5-yl |
| 2-Isopropoxyprop-2-yl | 3-Methylisoxazol-5-yl |
| 2-Isopropoxyprop-2-yl | 3-Ethylisoxazol-5-yl |
| 2-Isopropoxyprop-2-yl | 3-n-Propylisoxazol-5-yl |
| 2-Isopropoxyprop-2-yl | 3-n-Butylisoxazol-5-yl |
| 2-Isopropoxyprop-2-yl | 3-Isopropylisoxazol-5-yl |
| 2-Isopropoxyprop-2-yl | 3-Isobutylisoxazol-5-yl |
| 2-Isopropoxyprop-2-yl | 3-tert-Butylisoxazol-5-yl |
| 2-Isopropoxyprop-2-yl | 3-sec-Butylisoxazol-5-yl |
| 2-Isopropoxyprop-2-yl | 3-Methoxyisoxazol-5-yl |
| 2-Isopropoxyprop-2-yl | 3-Cyclopropylisoxazol-5-yl |
| 2-Isopropoxyprop-2-yl | 3-Cyclopropylisoxazol-4-yl |
| 2-Isopropoxyprop-2-yl | 3-Cyclohexylisoxazol-5-yl |
| 2-Isopropoxyprop-2-yl | 3-(3-Methylphenyl)isoxazol-5-yl |
| 2-Isopropoxyprop-2-yl | 3-(3,4-Dichlorophenyl)isoxazol-5-yl |
| 2-Isopropoxyprop-2-yl | 3-(2,6-Dichlorophenyl)isoxazol-5-yl |
| 2-Isopropoxyprop-2-yl | 3-(3-Nitrophenyl)isoxazol-5-yl |
| 2-Isopropoxyprop-2-yl | 3-(2-Methoxyphenyl)isoxazol-5-yl |
| 2-Isopropoxyprop-2-yl | 3-(4-Trifluoromethylphenyl)isoxazol-5-yl |
| 2-Isopropoxyprop-2-yl | 3-(3-Trifluoromethylphenyl)isoxazol-5-yl |
| 2-Isopropoxyprop-2-yl | 3-(4-Bromophenyl)isoxazol-5-yl |
| 2-Isopropoxyprop-2-yl | 3-(3-Chlorophenyl)isoxazol-5-yl |
| 2-Isopropoxyprop-2-yl | 3-(2-Chlorophenyl)isoxazol-5-yl |
| 2-Isopropoxyprop-2-yl | 3-(3-Fluorophenyl)isoxazol-5-yl |
| 2-Isopropoxyprop-2-yl | 3-(3-Phenoxyphenyl)isoxazol-5-yl |
| 2-Isopropoxyprop-2-yl | 3-(2,6-Difluorophenyl)isoxazol-5-yl |
| 2-Isopropoxyprop-2-yl | 3-Trifluoromethylisoxazol-5-yl |
| 2-Isopropoxyprop-2-yl | 3-(2-Naphthyl)isoxazol-5-yl |
| 2-Isopropoxyprop-2-yl | 3-(1-Naphthyl)isoxazol-5-yl |
| 2-Isopropoxyprop-2-yl | 3-tert-Butyl-5-phenylisoxazol-4-yl |
| 2-Isopropoxyprop-2-yl | 5-Methylisoxazol-4-yl |
| 2-Isopropoxyprop-2-yl | 4-Ethoxycarbonylisoxazol-5-yl |
| 2-Isopropoxyprop-2-yl | 5-Cyclopropylisoxazol-3-yl |
| 2-Isopropoxyprop-2-yl | 4-Chloro-3-(4-bromophenyl)isoxazol-5-yl |
| 2-Isopropoxyprop-2-yl | 4-Chloro-3-(3-chlorophenyl)isoxazol-5-yl |
| 2-Isopropoxyprop-2-yl | 4-Chloro-3-(3-fluorophenyl)isoxazol-5-yl |
| 2-Isopropoxyprop-2-yl | 4-Chloro-3-(2-chlorophenyl)isoxazol-5-yl |
| 2-Isopropoxyprop-2-yl | 2-Phenyloxazol-4-yl |
| 2-Isopropoxyprop-2-yl | 2-(4-Fluorophenyl)oxazol-4-yl |

TABLE A-continued $R^1R^2CH-ON=C(CN)-R^3$  $R^1 = H$  I

| $R^3$ | $R^2$ |
|---|---|
| 2-Isopropoxyprop-2-yl | 2-(4-Chlorophenyl)oxazol-4-yl |
| 2-Isopropoxyprop-2-yl | 2-(4-Bromophenyl)oxazol-4-yl |
| 2-Isopropoxyprop-2-yl | 2-(3-Chlorophenyl)oxazol-4-yl |
| 2-Isopropoxyprop-2-yl | 2-(4-Methylphenyl)oxazol-4-yl |
| 2-Isopropoxyprop-2-yl | 2-tert-Butyloxazol-4-yl |
| 2-Isopropoxyprop-2-yl | 2-(2,4-Dichlorophenyl)oxazol-4-yl |
| 2-Isopropoxyprop-2-yl | 2-(4-Methoxyphenyl)oxazol-4-yl |
| 2-Isopropoxyprop-2-yl | 2-(4-Chlorophenyl)-5-bromooxazol-4-yl |
| 2-Isopropoxyprop-2-yl | 2-Cyclopropyloxazol-4-yl |
| 2-Isopropoxyprop-2-yl | 2-Isopropyloxazol-4-yl |
| 2-Isopropoxyprop-2-yl | 2-tert-Butyloxazol-4-yl |
| 2-Isopropoxyprop-2-yl | 2-tert-Butyloxazol-5-y |
| 2-Isopropoxyprop-2-yl | 2-Benzyloxazol-4-yl |
| 2-Isopropoxyprop-2-yl | 2-Methylthiazol-4-yl |
| 2-Isopropoxyprop-2-yl | 2-Isopropylthiazol-4-yl |
| 2-Isopropoxyprop-2-yl | 2-Cyclopropylthiazol-4-yl |
| 2-Isopropoxyprop-2-yl | 4-(4-Methoxyphenyl)thiazol-2-yl |
| 2-Isopropoxyprop-2-yl | 2-Acetamidothiazol-4-yl |
| 2-Isopropoxyprop-2-yl | 2-Phenylthiazol-4-yl |
| 2-Isopropoxyprop-2-yl | 2-(2-Chlorophenyl)thiazol-4-yl |
| 2-Isopropoxyprop-2-yl | 2-(4-Chlorophenyl)thiazol-4-yl |
| 2-Isopropoxyprop-2-yl | 2-(2,4-Dichlorophenyl)thiazol-4-yl |
| 2-Isopropoxyprop-2-yl | 2-(2,6-Dichlorophenyl)thiazol-4-yl |
| 2-Isopropoxyprop-2-yl | 2-(3-Fluorophenyl)thiazol-4-yl |
| 2-Isopropoxyprop-2-yl | 2-(3-Chlorophenyl)thiazol-4-yl |
| 2-Isopropoxyprop-2-yl | 2-(4-Trifluoromethylphenyl)thiazol-4-yl |
| 2-Isopropoxyprop-2-yl | 2-(3-Methylphenyl)thiazol-4-yl |
| 2-Isopropoxyprop-2-yl | 2-(4-Methoxyphenyl)thiazol-4-yl |
| 2-Isopropoxyprop-2-yl | 2-Methylthiazol-4-yl |
| 2-Isopropoxyprop-2-yl | 2-(4-Fluorophenyl)thiazol-4-yl |
| 2-Isopropoxyprop-2-yl | 2-Methyl-1,3,4-thiadiazol-5-yl |
| 2-Isopropoxyprop-2-yl | 2-Phenyl-1,3,4-thiadiazol-5-yl |
| 2-Isopropoxyprop-2-yl | 2-Cyclopropyl-1,3,4-thiadiazol-5-yl |
| 2-Isopropoxyprop-2-yl | 2-Isopropyl-1,3,4-thiadiazol-5-yl |
| 2-Isopropoxyprop-2-yl | 2-Phenoxymethyl-1,3,4-thiadiazol-5-yl |
| 2-Isopropoxyprop-2-yl | 2-(4-Chlorophenyl)-1,3,4-thiadiazol-5-yl |
| 2-Isopropoxyprop-2-yl | 2-Phenyl-1,3,4-oxadiazol-5-yl |
| 2-Isopropoxyprop-2-yl | 2-(4-Methoxyphenyl)-1,3,4-oxadiazol-5-yl |
| 2-Isopropoxyprop-2-yl | 2-(2-Methylphenyl)-1,3,4-oxadiazol-5-yl |
| 2-Isopropoxyprop-2-yl | 2-(4-Methylphenyl)-1,3,4-oxadiazol-5-yl |
| 2-Isopropoxyprop-2-yl | 2-(4-Cyanophenyl)-1,3,4-oxadiazol-5-yl |
| 2-Isopropoxyprop-2-yl | 2-(4-Nitrophenyl)-1,3,4-oxadiazol-5-yl |
| 2-Isopropoxyprop-2-yl | 2-(3-Nitrophenyl)-1,3,4-oxadiazol-5-yl |
| 2-Isopropoxyprop-2-yl | 2-(2-Chlorophenyl)-1,3,4-oxadiazol-5-yl |
| 2-Isopropoxyprop-2-yl | 2-(2,4-Dichlorophenyl)1,3,4-oxadiazol-5-yl |
| 2-Isopropoxyprop-2-yl | 2-Ethyl-1,3,4-oxadiazol-5-yl |
| 2-Isopropoxyprop-2-yl | 2-Isopropyl-1,3,4-oxadiazol-5-yl |
| 2-Isopropoxyprop-2-yl | 2-Cyclopropyl-1,3,4-oxadiazol-5-yl |
| 2-Isopropoxyprop-2-yl | 3-(4-Chlorophenyl)-1,2,4-oxadiazol-5-yl |
| 2-Isopropoxyprop-2-yl | 3-(4-Fluorophenyl)-1,2,4-oxadiazol-5-yl |
| 2-Isopropoxyprop-2-yl | 3-n-Propyl-1,2,4-oxadiazol-5-yl |
| 2-Isopropoxyprop-2-yl | 3-Ethyl-1,2,4-oxadiazol-5-yl |
| 2-Isopropoxyprop-2-yl | 3-Methyl-1,2,4-oxadiazol-5-yl |
| 2-Isopropoxyprop-2-yl | 3-Isopropyl-1,2,4-oxadiazol-5-yl |
| 2-Isopropoxyprop-2-yl | 3-tert-Butylpropyl-1,2,4-oxadiazol-5-yl |
| 2-Isopropoxyprop-2-yl | 3-Cyclopropyl-1,2,4-oxadiazol-5-yl |
| 2-Isopropoxyprop-2-yl | 3-Cyclohexyl-1,2,4-oxadiazol-5-yl |
| 2-Isopropoxyprop-2-yl | 5-Isopropyl-1,2,4-oxadiazol-3-yl |
| 2-Isopropoxyprop-2-yl | 5-(4-Chlorophenyl)-1,2,4-oxadiazol-3-yl |
| 2-Isopropoxyprop-2-yl | 3-Carbomethoxy-1,2,4-oxadiazol-5-yl |
| 2-Isopropoxyprop-2-yl | 5-Chloro-1,2,3-thiadiazol-4-yl |
| 2-Isopropoxyprop-2-yl | 5-Methyl-1,2,3-thiadiazol-4-yl |
| 2-Isopropoxyprop-2-yl | 4-Methyl-1,2,3-thiadiazol-5-yl |
| 2-Isopropoxyprop-2-yl | 5-Chloro-1,2,4-thiadiazol-3-yl |
| 2-Isopropoxyprop-2-yl | Benzimidazol-2-yl |
| 2-Isopropoxyprop-2-yl | Benzoxazol-2-yl |
| 2-Isopropoxyprop-2-yl | Benzothiophen-3-yl |
| 2-Isopropoxyprop-2-yl | Benzofuran-2-yl |
| 2-Isopropoxyprop-2-yl | 5-Chlorobenzofuran-2-yl |
| 2-Isopropoxyprop-2-yl | 5-Chlorobenzoxazol-2-yl |
| 2-Isopropoxyprop-2-yl | 1-Methylpyrazol-3-yl |
| 2-Isopropoxyprop-2-yl | 1-(4-Methylphenyl)pyrazol-4-yl |
| 2-Isopropoxyprop-2-yl | 1,3-Dimethylpyrazol-5-yl |
| 2-Isopropoxyprop-2-yl | 1-Phenyl-3-ethoxypyrazol-5-yl |
| 2-Isopropoxyprop-2-yl | 1-Phenyl-3-methylpyrazol-5-yl |
| 2-Isopropoxyprop-2-yl | 3-Cyclopropyl-1-methyl-1,2,4-triazol-5-yl |
| 2-Isopropoxyprop-2-yl | 3-Cyclohexyl-1-methyl-1,2,4-triazol-5-yl |
| 2-Isopropoxyprop-2-yl | 1,3-Dimethyl-1,2,4-triazol-5-yl |
| 2-Isopropoxyprop-2-yl | 5-Phenyl-1,2,4-triazol-3-yl |
| 2-Methylthioprop-2-yl | Phenyl |
| 2-Methylthioprop-2-yl | 2-Chlorophenyl |
| 2-Methylthioprop-2-yl | 3-Chlorophenyl |
| 2-Methylthioprop-2-yl | 4-Chlorophenyl |
| 2-Methylthioprop-2-yl | 2,6-Dichlorophenyl |
| 2-Methylthioprop-2-yl | 2,4-Dichlorophenyl |
| 2-Methylthioprop-2-yl | 2-Methylphenyl |
| 2-Methylthioprop-2-yl | 3-Methylphenyl |
| 2-Methylthioprop-2-yl | 4-Methylphenyl |
| 2-Methylthioprop-2-yl | 2,5-Dimethylphenyl |
| 2-Methylthioprop-2-yl | 2,4,6-Trimethylphenyl |
| 2-Methylthioprop-2-yl | 3-Methoxyphenyl |
| 2-Methylthioprop-2-yl | 4-Methoxyphenyl |
| 2-Methylthioprop-2-yl | 2-Nitrophenyl |
| 2-Methylthioprop-2-yl | 3-Nitrophenyl |
| 2-Methylthioprop-2-yl | 4-Nitrophenyl |
| 2-Methylthioprop-2-yl | 2-Bromophenyl |
| 2-Methylthioprop-2-yl | 4-Bromophenyl |
| 2-Methylthioprop-2-yl | 4-Cyanophenyl |
| 2-Methylthioprop-2-yl | 4-Dimethylaminophenyl |
| 2-Methylthioprop-2-yl | 4-Carbomethoxyphenyl |
| 2-Methylthioprop-2-yl | 2-Methoxy-5-nitrophenyl |
| 2-Methylthioprop-2-yl | 2-Trifluoromethylphenyl |
| 2-Methylthioprop-2-yl | 4-Trifluoromethylphenyl |
| 2-Methylthioprop-2-yl | 4-tert-Butylphenyl |
| 2-Methylthioprop-2-yl | 2-Chloro-6-nitrophenyl |
| 2-Methylthioprop-2-yl | 2-Fluorophenyl |
| 2-Methylthioprop-2-yl | 4-Fluorophenyl |
| 2-Methylthioprop-2-yl | 2,3,4,5,6-Pentafluorophenyl |
| 2-Methylthioprop-2-yl | 2-Chloro-3-isopropylphenyl |
| 2-Methylthioprop-2-yl | 2,6-Difluorophenyl |
| 2-Methylthioprop-2-yl | 2-Chloro-3-trifluoromethylphenyl |
| 2-Methylthioprop-2-yl | 2-Biphenyl |
| 2-Methylthioprop-2-yl | 3-Biphenyl |
| 2-Methylthioprop-2-yl | 4-Biphenyl |
| 2-Methylthioprop-2-yl | 4'-Chlorobiphenyl-4-yl |
| 2-Methylthioprop-2-yl | 3-Phenoxyphenyl |
| 2-Methylthioprop-2-yl | 3,4-Methylenedioxyphenyl |
| 2-Methylthioprop-2-yl | 1-Naphthyl |
| 2-Methylthioprop-2-yl | 2-Naphthyl |
| 2-Methylthioprop-2-yl | 9-Anthracenyl |
| 2-Methylthioprop-2-yl | 2-Furyl |
| 2-Methylthioprop-2-yl | 4-Isopropylfuran-2-yl |
| 2-Methylthioprop-2-yl | 5-Carboxymethylfuran-2-yl |
| 2-Methylthioprop-2-yl | 5-Methylfuran-2-yl |
| 2-Methylthioprop-2-yl | 5-Trifluoromethylfuran-2-yl |
| 2-Methylthioprop-2-yl | 3-Furyl |
| 2-Methylthioprop-2-yl | 2-Thienyl |
| 2-Methylthioprop-2-yl | 5-Chlorothien-2-yl |
| 2-Methylthioprop-2-yl | 3-Thienyl |
| 2-Methylthioprop-2-yl | 5-Bromothien-3-yl |
| 2-Methylthioprop-2-yl | Benzothiophen-3-yl |
| 2-Methylthioprop-2-yl | 2-Pyrrolyl |
| 2-Methylthioprop-2-yl | 1-Phenylpyrrol-2-yl |
| 2-Methylthioprop-2-yl | 3-Pyrrolyl |
| 2-Methylthioprop-2-yl | Isoxazol-5-yl |
| 2-Methylthioprop-2-yl | Isoxazol-3-yl |
| 2-Methylthioprop-2-yl | 3-Phenylisoxazol-5-yl |
| 2-Methylthioprop-2-yl | 3-Methylisoxazol-5-yl |
| 2-Methylthioprop-2-yl | 4-Chloro-3-methylisoxazol-5-yl |
| 2-Methylthioprop-2-yl | 4-Chloro-3-isopropylisoxazol-5-yl |
| 2-Methylthioprop-2-yl | 4-Chloro-3-sec-butylisoxazol-5-yl |
| 2-Methylthioprop-2-yl | 4-Chloro-3-tert-butylisoxazol-5-yl |
| 2-Methylthioprop-2-yl | 4-Chloro-3-cyclohexylisoxazol-5-yl |
| 2-Methylthioprop-2-yl | 4-Chloro-3-phenylisoxazol-5-yl |

TABLE A-continued

| | $R^1R^2CH-ON=C(CN)-R^3$ | $R^1 = H$ | I |
|---|---|---|---|

| $R^3$ | $R^2$ |
|---|---|
| 2-Methylthioprop-2-yl | 4-Chloro-3-(4-methylphenyl)isoxazol-5-yl |
| 2-Methylthioprop-2-yl | 4-Chloro-3-(4-chlorophenyl)-isoxazol-5-yl |
| 2-Methylthioprop-2-yl | 4-Chloro-3-(4-fluorophenyl)-isoxazol-5-yl |
| 2-Methylthioprop-2-yl | 4-Chloro-3-(4-trifluoromethylphenyl)-isoxazol-5-yl |
| 2-Methylthioprop-2-yl | 4-Chloro-3-(2,6-difluorophenyl)-isoxazol-5-yl |
| 2-Methylthioprop-2-yl | 4-Chloro-3-phenylisoxazol-5-yl |
| 2-Methylthioprop-2-yl | 3,5-Dimethylisoxazol-4-yl |
| 2-Methylthioprop-2-yl | 3-Carboxyethylisoxazol-5-yl |
| 2-Methylthioprop-2-yl | 3-(3,4-Dichlorophenyl)isoxazol-5-yl |
| 2-Methylthioprop-2-yl | 3-(3-Nitrophenyl)isoxazol-5-yl |
| 2-Methylthioprop-2-yl | 3-(4-Chlorophenyl)isoxazol-5-yl |
| 2-Methylthioprop-2-yl | 3-(4-Fluorophenyl)isoxazol-5-yl |
| 2-Methylthioprop-2-yl | 3-(3,4-Difluorophenyl)isoxazol-5-yl |
| 2-Methylthioprop-2-yl | 3-Phenylisoxazol-5-yl |
| 2-Methylthioprop-2-yl | 3-Methoxymethylisoxazol-5-yl |
| 2-Methylthioprop-2-yl | 3-Methylisoxazol-5-yl |
| 2-Methylthioprop-2-yl | 3-Ethylisoxazol-5-yl |
| 2-Methylthiaprop-2-yl | 3-n-Propylisoxazol-5-yl |
| 2-Methylthioprop-2-yl | 3-n-Butylisoxazol-5-yl |
| 2-Methylthioprop-2-yl | 3-Isopropylisoxazol-5-yl |
| 2-Methylthioprop-2-yl | 3-Isobutylisoxazol-5-yl |
| 2-Methylthioprop-2-yl | 3-tert-Butylisoxazol-5-yl |
| 2-Methylthioprop-2-yl | 3-sec-Butylisoxazol-5-yl |
| 2-Methylthioprop-2-yl | 3-Methoxyisoxazol-5-yl |
| 2-Methylthioprop-2-yl | 3-Cyclopropylisoxazol-5-yl |
| 2-Methylthioprop-2-yl | 3-Cyclopropylisoxazol-4-yl |
| 2-Methylthioprop-2-yl | 3-Cyclohexylisoxazol-5-yl |
| 2-Methylthioprop-2-yl | 3-(3-Methylphenyl)isoxazol-5-yl |
| 2-Methylthioprop-2-yl | 3-(3,4-Dichlorophenyl)isoxazol-5-yl |
| 2-Methylthioprop-2-yl | 3-(2,6-Dichlorophenyl)isoxazol-5-yl |
| 2-Methylthioprop-2-yl | 3-(3-Nitrophenyl)isoxazol-5-yl |
| 2-Methylthioprop-2-yl | 3-(2-Methoxyphenyl)isoxazol-5-yl |
| 2-Methylthioprop-2-yl | 3-(4-Trifluoromethylphenyl)isoxazol-5-yl |
| 2-Methylthioprop-2-yl | 3-(3-Trifluoromethylphenyl)isoxazol-5-yl |
| 2-Methylthioprop-2-yl | 3-(4-Bromophenyl)isoxazol-5-yl |
| 2-Methylthioprop-2-yl | 3-(3-Chlorophenyl)isoxazol-5-yl |
| 2-Methylthioprop-2-yl | 3-(2-Chlorophenyl)isoxazol-5-yl |
| 2-Methylthioprop-2-yl | 3-(3-Fluorophenyl)isoxazol-5-yl |
| 2-Methylthioprop-2-yl | 3-(3-Phenoxyphenyl)isoxazol-5-yl |
| 2-Methylthioprop-2-yl | 3-(2,6-Difluorophenyl)isoxazol-5-yl |
| 2-Methylthioprop-2-yl | 3-Trifluoromethylisoxazol-5-yl |
| 2-Methylthioprop-2-yl | 3-(2-Naphthyl)isoxazol-5-yl |
| 2-Methylthioprop-2-yl | 3-(1-Naphthyl)isoxazol-5-yl |
| 2-Methylthioprop-2-yl | 3-tert-Butyl-5-phenylisoxazol-4-yl |
| 2-Methylthioprop-2-yl | 5-Methylisoxazol-4-yl |
| 2-Methylthioprop-2-yl | 4-Ethoxycarbonylisoxazol-5-yl |
| 2-Methylthioprop-2-yl | 5-Cyclopropylisoxazol-3-yl |
| 2-Methylthioprop-2-yl | 4-Chloro-3-(4-bromophenyl)isoxazol-5-yl |
| 2-Methylthioprop-2-yl | 4-Chloro-3-(3-chlorophenyl)isoxazol-5-yl |
| 2-Methylthioprop-2-yl | 4-Chloro-3-(3-fluorophenyl)isoxazol-5-yl |
| 2-Methylthioprop-2-yl | 4-Chloro-3-(2-chlorophenyl)isoxazol-5-yl |
| 2-Methylthioprop-2-yl | 2-Phenyloxazol-4-yl |
| 2-Methylthioprop-2-yl | 2-(4-Fluorophenyl)oxazol-4-yl |
| 2-Methylthioprop-2-yl | 2-(4-Chlorophenyl)oxazol-4-yl |
| 2-Methylthioprop-2-yl | 2-(4-Bromophenyl)oxazol-4-yl |
| 2-Methylthioprop-2-yl | 2-(3-Chlorophenyl)oxazol-4-yl |
| 2-Methylthioprop-2-yl | 2-(4-Methylphenyl)oxazol-4-yl |
| 2-Methylthioprop-2-yl | 2-tert-Butyloxazol-4-yl |
| 2-Methylthioprop-2-yl | 2-(2,4-Dichlorophenyl)oxazol-4-yl |
| 2-Methylthioprop-2-yl | 2-(4-Methoxyphenyl)oxazol-4-yl |
| 2-Methylthioprop-2-yl | 2-(4-Chlorophenyl)-5-bromooxazol-4-yl |
| 2-Methylthioprop-2-yl | 2-Cyclopropyloxazol-4-yl |
| 2-Methylthioprop-2-yl | 2-Isopropyloxazol-4-yl |
| 2-Methylthioprop-2-yl | 2-tert-Butyloxazol-4-yl |
| 2-Methylthioprop-2-yl | 2-tert-Butyloxazol-5-yl |
| 2-Methylthioprop-2-yl | 2-Benzyloxazol-4-yl |
| 2-Methylthioprop-2-yl | 2-Methylthiazol-4-yl |
| 2-Methylthioprop-2-yl | 2-Isopropylthiazol-4-yl |
| 2-Methylthioprop-2-yl | 2-Cyclopropylthiazol-4-yl |
| 2-Methylthioprop-2-yl | 4-(4-Methoxyphenyl)thiazol-2-yl |
| 2-Methylthioprop-2-yl | 2-Acetamidothiazol-4-yl |
| 2-Methylthioprop-2-yl | 2-Phenylthiazol-4-yl |
| 2-Methylthioprop-2-yl | 2-(2-Chlorophenyl)thiazol-4-yl |
| 2-Methylthioprop-2-yl | 2-(4-Chlorophenyl)thiazol-4-yl |
| 2-Methylthioprop-2-yl | 2-(2,4-Dichlorophenyl)thiazol-4-yl |
| 2-Methylthioprop-2-yl | 2-(2,6-Dichlorophenyl)thiazol-4-yl |
| 2-Methylthioprop-2-yl | 2-(3-Fluorophenyl)thiazol-4-yl |
| 2-Methylthioprop-2-yl | 2-(3-Chlorophenyl)thiazol-4-yl |
| 2-Methylthioprop-2-yl | 2-(4-Trifluoromethylphenyl)thiazol-4-yl |
| 2-Methylthioprop-2-yl | 2-(3-Methylphenyl)thiazol-4-yl |
| 2-Methylthioprop-2-yl | 2-(4-Methoxyphenyl)thiazol-4-yl |
| 2-Methylthioprop-2-yl | 2-Methylthiazol-4-yl |
| 2-Methylthioprop-2-yl | 2-(4-Fluorophenyl)thiazol-4-yl |
| 2-Methylthioprop-2-yl | 2-Methyl-1,3,4-thiadiazol-5-yl |
| 2-Methylthioprop-2-yl | 2-Phenyl-1,3,4-thiadiazol-5-yl |
| 2-Methylthioprop-2-yl | 2-Cyclopropyl-1,3,4-thiadiazol-5-yl |
| 2-Methylthioprop-2-yl | 2-Isopropyl-1,3,4-thiadiazol-5-yl |
| 2-Methylthioprop-2-yl | 2-Phenoxymethyl-1,3,4-thiadiazol-5-yl |
| 2-Methylthioprop-2-yl | 2-(4-Chlorophenyl)-1,3,4-thiadiazol-5-yl |
| 2-Methylthioprop-2-yl | 2-Phenyl-1,3,4-oxadiazol-5-yl |
| 2-Methylthioprop-2-yl | 2-(4-Methoxyphenyl)-1,3,4-oxadiazol-5-yl |
| 2-Methylthioprop-2-yl | 2-(2-Methylphenyl)-1,3,4-oxadiazol-5-yl |
| 2-Methylthioprop-2-yl | 2-(4-Methylphenyl)-1,3,4-oxadiazol-5-yl |
| 2-Methylthioprop-2-yl | 2-(4-Cyanophenyl)-1,3,4-oxadiazol-5-yl |
| 2-Methylthioprop-2-yl | 2-(4-Nitrophenyl)-1,3,4-oxadiazol-5-yl |
| 2-Methylthioprop-2-yl | 2-(3-Nitrophenyl)-1,3,4-oxadiazol-5-yl |
| 2-Methylthioprop-2-yl | 2-(2-Chlorophenyl)-1,3,4-oxadiazol-5-yl |
| 2-Methylihioprop-2-yl | 2-(2,4-Dichlorophenyl)-1,3,4-oxadiazol-5-yl |
| 2-Methylthioprop-2-yl | 2-Ethyl-1,3,4-oxadiazol-5-yl |
| 2-Methylthioprop-2-yl | 2-Isopropyl-1,3,4-oxadiazol-5-yl |
| 2-Methylthioprop-2-yl | 2-Cyclopropyl-1,3,4-oxadiazol-5-yl |
| 2-Methylthioprop-2-yl | 3-(4-Chlorophenyl)-1,2,4-oxadiazol-5-yl |
| 2-Methylthioprop-2-yl | 3-(4-Fluorophenyl)-1,2,4-oxadiazol-5-yl |
| 2-Methylthioprop-2-yl | 3-n-Propyl-1,2,4-oxadiazol-5-yl |
| 2-Methylthioprop-2-yl | 3-Ethyl-1,2,4-oxadiazol-5-yl |
| 2-Methylthioprop-2-yl | 3-Methyl-1,2,4-oxadiazol-5-yl |
| 2-Methylthioprop-2-yl | 3-Isopropyl-1,2,4-oxadiazol-5-yl |
| 2-Methylthioprop-2-yl | 3-tert-Butylpropyl-1,2,4-oxadiazol-5-yl |
| 2-Methylthioprop-2-yl | 3-Cyclopropyl-1,2,4-oxadiazol-5-yl |
| 2-Methylthioprop-2-yl | 3-Cyclohexyl-1,2,4-oxadiazol-5-yl |
| 2-Methylthioprop-2-yl | 5-Isopropyl-1,2,4-oxadiazol-3-yl |
| 2-Methylthioprop-2-yl | 5-(4-Chlorophenyl)-1,2,4-oxadiazol-3-yl |
| 2-Methylthioprop-2-yl | 3-Carbomethoxy-1,2,4-oxadiazol-5-yl |
| 2-Methylthioprop-2-yl | 5-Chloro-1,2,3-thiadiazol-4-yl |
| 2-Methylthioprop-2-yl | 5-Methyl-1,2,3-thiadiazol-4-yl |
| 2-Methylthioprop-2-yl | 4-Methyl-1,2,3-thiadiazol-5-yl |
| 2-Methylthioprop-2-yl | 5-Chloro-1,2,4-thiadiazol-3-yl |
| 2-Methylthioprop-2-yl | Benzimidazol-2-yl |
| 2-Methylthioprop-2-yl | Benzoxazol-2-yl |
| 2-Methylthioprop-2-yl | Benzothiophen-3-yl |
| 2-Methylthioprop-2-yl | Benzofuran-2-yl |
| 2-Methylthioprop-2-yl | 5-Chlorobenzofuran-2-yl |
| 2-Methylthioprop-2-yl | 5-Chlorobenzoxazol-2-yl |
| 2-Methylthioprop-2-yl | 1-Methylpyrazol-3-yl |
| 2-Methylthioprop-2-yl | 1-(4-Methylphenyl)pyrazol-4-yl |
| 2-Methylthioprop-2-yl | 1,3-Dimethylpyrazol-5-yl |
| 2-Methylthioprop-2-yl | 1-Phenyl-3-ethoxypyrazol-5-yl |
| 2-Methylthioprop-2-yl | 1-Phenyl-3-methylpyrazol-5-yl |
| 2-Methylthioprop-2-yl | 3-Cyclopropyl-1-methyl-1,2,4-triazol-5-yl |
| 2-Methylthioprop-2-yl | 3-Cyclohexyl-1-methyl-1,2,4-triazol-5-yl |
| 2-Methylthioprop-2-yl | 1,3-Dimethyl-1,2,4-triazol-5-yl |
| 2-Methylthioprop-2-yl | 5-Phenyl-1,2,4-triazol-3-yl |
| 2-Ethylthioprop-2-yl | Phenyl |
| 2-Ethylthioprop-2-yl | 2-Chlorophenyl |

TABLE A-continued $R^1R^2CH-ON=C(CN)-R^3$  $R^1 = H$  I

| $R^3$ | $R^2$ |
|---|---|
| 2-Ethylthioprop-2-yl | 3-Chlorophenyl |
| 2-Ethylthioprop-2-yl | 4-Chlorophenyl |
| 2-Ethylthioprop-2-yl | 2,6-Dichlorophenyl |
| 2-Ethylthioprop-2-yl | 2,4-Dichlorophenyl |
| 2-Ethylthioprop-2-yl | 2-Methylphenyl |
| 2-Ethylthioprop-2-yl | 3-Methylphenyl |
| 2-Ethylthioprop-2-yl | 4-Methylphenyl |
| 2-Ethylthioprop-2-yl | 2,5-Dimethylphenyl |
| 2-Ethylthioprop-2-yl | 2,4,6-Trimethylphenyl |
| 2-Ethylthioprop-2-yl | 3-Methoxyphenyl |
| 2-Ethylthioprop-2-yl | 4-Methoxyphenyl |
| 2-Ethylthioprop-2-yl | 2-Nitrophenyl |
| 2-Ethylthioprop-2-yl | 3-Nitrophenyl |
| 2-Ethylthioprop-2-yl | 4-Nitrophenyl |
| 2-Ethylthioprop-2-yl | 2-Bromophenyl |
| 2-Ethylthioprop-2-yl | 4-Bromophenyl |
| 2-Ethylthioprop-2-yl | 4-Cyanophenyl |
| 2-Ethylthioprop-2-yl | 4-Dimethylaminophenyl |
| 2-Ethylthioprop-2-yl | 4-Carbomethoxyphenyl |
| 2-Ethylthioprop-2-yl | 2-Methoxy-5-nitrophenyl |
| 2-Ethylthioprop-2-yl | 2-Trifluoromethylphenyl |
| 2-Ethylthioprop-2-yl | 4-Trifluoromethylphenyl |
| 2-Ethylthioprop-2-yl | 4-tert-Butylphenyl |
| 2-Ethylthioprop-2-yl | 2-Chloro-6-nitrophenyl |
| 2-Ethylthioprop-2-yl | 2-Fluorophenyl |
| 2-Ethylthioprop-2-yl | 4-Fluorophenyl |
| 2-Ethylthioprop-2-yl | 2,3,4,5,6-Pentafluorophenyl |
| 2-Ethylthioprop-2-yl | 2-Chloro-3-isopropylphenyl |
| 2-Ethylthioprop-2-yl | 2,6-Difluorophenyl |
| 2-Ethylthioprop-2-yl | 2-Chloro-3-trifluoromethylphenyl |
| 2-Ethylthioprop-2-yl | 2-Biphenyl |
| 2-Ethylthioprop-2-yl | 3-Biphenyl |
| 2-Ethylthioprop-2-yl | 4-Biphenyl |
| 2-Ethylthioprop-2-yl | 4'-Chlorobiphenyl-4-yl |
| 2-Ethylthioprop-2-yl | 3-Phenoxyphenyl |
| 2-Ethylthioprop-2-yl | 3,4-Methylenedioxyphenyl |
| 2-Ethylthioprop-2-yl | 1-Naphthyl |
| 2-Ethylthioprop-2-yl | 2-Naphthyl |
| 2-Ethylthioprop-2-yl | 9-Anthracenyl |
| 2-Ethylthioprop-2-yl | 2-Furyl |
| 2-Ethylthioprop-2-yl | 4-Isopropylfuran-2-yl |
| 2-Ethylthioprop-2-yl | 5-Carboxymethylfuran-2-yl |
| 2-Ethylthioprop-2-yl | 5-Methylfuran-2-yl |
| 2-Ethylthioprop-2-yl | 5-Trifluoromethylfuran-2-yl |
| 2-Ethylthioprop-2-yl | 3-Furyl |
| 2-Ethylthioprop-2-yl | 2-Thienyl |
| 2-Ethylthioprop-2-yl | 5-Chlorothien-2-yl |
| 2-Ethylthioprop-2-yl | 3-Thienyl |
| 2-Ethylthioprop-2-yl | 5-Bromothien-3-yl |
| 2-Ethylthioprop-2-yl | Benzothiophen-3-yl |
| 2-Ethylthioprop-2-yl | 2-Pyrrolyl |
| 2-Ethylthioprop-2-yl | 1-Phenylpyrrol-2-yl |
| 2-Ethylthioprop-2-yl | 3-Pyrrolyl |
| 2-Ethylthioprop-2-yl | Isoxazol-5-yl |
| 2-Ethylthioprop-2-yl | Isoxazol-3-yl |
| 2-Ethylthioprop-2-yl | 3-Phenylisoxazol-5-yl |
| 2-Ethylthioprop-2-yl | 3-Methylisoxazol-5-yl |
| 2-Ethylthioprop-2-yl | 4-Chloro-3-methylisoxazol-5-yl |
| 2-Ethylthioprop-2-yl | 4-Chloro-3-isopropylisoxazol-5-yl |
| 2-Ethylthioprop-2-yl | 4-Chloro-3-sec-butylisoxazol-5-yl |
| 2-Ethylthioprop-2-yl | 4-Chloro-3-tert-butylisoxazol-5-yl |
| 2-Ethylthioprop-2-yl | 4-Chloro-3-cyclohexylisoxazol-5-yl |
| 2-Ethylthioprop-2-yl | 4-Chloro-3-phenylisoxazol-5-yl |
| 2-Ethylthioprop-2-yl | 4-Chloro-3-(4-methylphenyl)isoxazol-5-yl |
| 2-Ethylthioprop-2-yl | 4-Chloro-3-(4-chlorophenyl)-isoxazol-5-yl |
| 2-Ethylthioprop-2-yl | 4-Chloro-3-(4-fluorophenyl)-isoxazol-5-yl |
| 2-Ethylthioprop-2-yl | 4-Chloro-3-(4-trifluoromethylphenyl)-isoxazol-5-yl |
| 2-Ethylthioprop-2-yl | 4-Chloro-3-(2,6-difluorophenyl)-isoxazol-5-yl |
| 2-Ethylthioprop-2-yl | 4-Chloro-3-phenylisoxazol-5-yl |
| 2-Ethylthioprop-2-yl | 3,5-Dimethylisoxazol-4-yl |
| 2-Ethylthioprop-2-yl | 3-Carboxyethylisoxazol-5-yl |
| 2-Ethylthioprop-2-yl | 3-(3,4-Dichlorophenyl)isoxazol-5-yl |
| 2-Ethylthioprop-2-yl | 3-(3-Nitrophenyl)isoxazol-5-yl |
| 2-Ethylthioprop-2-yl | 3-(4-Chlorophenyl)isoxazol-5-yl |
| 2-Ethylthioprop-2-yl | 3-(4-Fluorophenyl)isoxazol-5-yl |
| 2-Ethylthioprop-2-yl | 3-(3,4-Difluorophenyl)isoxazol-5-yl |
| 2-Ethylthioprop-2-yl | 3-Phenylisoxazol-5-yl |
| 2-Ethylthioprop-2-yl | 3-Methoxymethylisoxazol-5-yl |
| 2-Ethylthioprop-2-yl | 3-Methylisoxazol-5-yl |
| 2-Ethylthioprop-2-yl | 3-Ethylisoxazol-5-yl |
| 2-Ethylthioprop-2-yl | 3-n-Propylisoxazol-5-yl |
| 2-Ethylthioprop-2-yl | 3-n-Butylisoxazol-5-yl |
| 2-Ethylthioprop-2-yl | 3-Isopropylisoxazol-5-yl |
| 2-Ethylthioprop-2-yl | 3-Isobutylisoxazol-5-yl |
| 2-Ethylthioprop-2-yl | 3-tert-Butylisoxazol-5-yl |
| 2-Ethylthioprop-2-yl | 3-sec-Butylisoxazol-5-yl |
| 2-Ethylthioprop-2-yl | 3-Methoxyisoxazol-5-yl |
| 2-Ethylthioprop-2-yl | 3-Cyclopropylisoxazol-5-yl |
| 2-Ethylthioprop-2-yl | 3-Cyclopropylisoxazol-4-yl |
| 2-Ethylthioprop-2-yl | 3-Cyclohexylisoxazol-5-yl |
| 2-Ethylthioprop-2-yl | 3-(3-Methylphenyl)isoxazol-5-yl |
| 2-Ethylthioprop-2-yl | 3-(3,4-Dichlorophenyl)isoxazol-5-yl |
| 2-Ethylthioprop-2-yl | 3-(2,6-Dichlorophenyl)isoxazol-5-yl |
| 2-Ethylthioprop-2-yl | 3-(3-Nitrophenyl)isoxazol-5-yl |
| 2-Ethylthioprop-2-yl | 3-(2-Methoxyphenyl)isoxazol-5-yl |
| 2-Ethylthioprop-2-yl | 3-(4-Trifluoromethylphenyl)isoxazol-5-yl |
| 2-Ethylthioprop-2-yl | 3-(3-Trifluoromethylphenyl)isoxazol-5-yl |
| 2-Ethylthioprop-2-yl | 3-(4-Bromophenyl)isoxazol-5-yl |
| 2-Ethylthioprop-2-yl | 3-(3-Chlorophenyl)isoxazol-5-yl |
| 2-Ethylthioprop-2-yl | 3-(2-Chlorophenyl)isoxazol-5-yl |
| 2-Ethylthioprop-2-yl | 3-(3-Fluorophenyl)isoxazol-5-yl |
| 2-Ethylthioprop-2-yl | 3-(3-Phenoxyphenyl)isoxazol-5-yl |
| 2-Ethylthioprop-2-yl | 3-(2,6-Difluorophenyl)isoxazol-5-yl |
| 2-Ethylthioprop-2-yl | 3-Trifluoromethylisoxazol-5-yl |
| 2-Ethylthioprop-2-yl | 3-(2-Naphthyl)isoxazol-5-yl |
| 2-Ethylthioprop-2-yl | 3-(1-Naphthyl)isoxazol-5-yl |
| 2-Ethylthioprop-2-yl | 3-tert-Butyl-5-phenylisoxazol-4-yl |
| 2-Ethylthioprop-2-yl | 5-Methylisoxazol-4-yl |
| 2-Ethylthioprop-2-yl | 4-Ethoxycarbonylisoxazol-5-yl |
| 2-Ethylthioprop-2-yl | 5-Cyclopropylisoxazol-3-yl |
| 2-Ethylthioprop-2-yl | 4-Chloro-3-(4-bromophenyl)isoxazol-5-yl |
| 2-Ethylthioprop-2-yl | 4-Chloro-3-(3-chlorophenyl)isoxazol-5-yl |
| 2-Ethylthioprop-2-yl | 4-Chloro-3-(3-fluorophenyl)isoxazol-5-yl |
| 2-Ethylthioprop-2-yl | 4-Chloro-3-(2-chlorophenyl)isoxazol-5-yl |
| 2-Ethylthioprop-2-yl | 2-Phenyloxazol-4-yl |
| 2-Ethylthioprop-2-yl | 2-(4-Fluorophenyl)oxazol-4-yl |
| 2-Ethylthioprop-2-yl | 2-(4-Chlorophenyl)oxazol-4-yl |
| 2-Ethylthioprop-2-yl | 2-(4-Bromophenyl)oxazol-4-yl |
| 2-Ethylthioprop-2-yl | 2-(3-Chlorophenyl)oxazol-4-yl |
| 2-Ethylthioprop-2-yl | 2-(4-Methylphenyl)oxazol-4-yl |
| 2-Ethylthioprop-2-yl | 2-tert-Butyloxazol-4-yl |
| 2-Ethylthioprop-2-yl | 2-(2,4-Dichlorophenyl)oxazol-4-yl |
| 2-Ethylthioprop-2-yl | 2-(4-Methoxyphenyl)oxazol-4-yl |
| 2-Ethylthioprop-2-yl | 2-(4-Chlorophenyl)-5-bromooxazol-4-yl |
| 2-Ethylthioprop-2-yl | 2-Cyclopropyloxazol-4-yl |
| 2-Ethylthioprop-2-yl | 2-Isopropyloxazol-4-yl |
| 2-Ethylthioprop-2-yl | 2-tert-Butyloxazol-4-yl |
| 2-Ethylthioprop-2-yl | 2-tert-Butyloxazol-5-y |
| 2-Ethylthioprop-2-yl | 2-Benzyloxazol-4-yl |
| 2-Ethylthioprop-2-yl | 2-Methylthiazol-4-yl |
| 2-Ethylthioprop-2-yl | 2-Isopropylthiazol-4-yl |
| 2-Ethylthioprop-2-yl | 2-Cyclopropylthiazol-4-yl |
| 2-Ethylthioprop-2-yl | 4-(4-Methoxyphenyl)thiazol-2-yl |
| 2-Ethylthioprop-2-yl | 2-Acetamidothiazol-4-yl |
| 2-Ethylthioprop-2-yl | 2-Phenylthiazol-4-yl |
| 2-Ethylthioprop-2-yl | 2-(2-Chlorophenyl)thiazol-4-yl |
| 2-Ethylthioprop-2-yl | 2-(4-Chlorophenyl)thiazol-4-yl |
| 2-Ethylthioprop-2-yl | 2-(2,4-Dichlorophenyl)thiazol-4-yl |
| 2-Ethylthioprop-2-yl | 2-(2,6-Dichlorophenyl)thiazol-4-yl |
| 2-Ethylthioprop-2-yl | 2-(3-Fluorophenyl)thiazol-4-yl |

TABLE A-continued

| | R¹R²CH—ON=C(CN)—R³ | R¹ = H | I |
|---|---|---|---|

| R³ | R² |
|---|---|
| 2-Ethylthioprop-2-yl | 2-(3-Chlorophenyl)thiazol-4-yl |
| 2-Ethylthioprop-2-yl | 2-(4-Trifluoromethylphenyl)thiazol-4-yl |
| 2-Ethylthioprop-2-yl | 2-(3-Methylphenyl)thiazol-4-yl |
| 2-Ethylthioprop-2-yl | 2-(4-Methoxyphenyl)thiazol-4-yl |
| 2-Ethylthioprop-2-yl | 2-Methylthiazol-4-yl |
| 2-Ethylthioprop-2-yl | 2-(4-Fluorophenyl)thiazol-4-yl |
| 2-Ethylthioprop-2-yl | 2-Methyl-1,3,4-thiadiazol-5-yl |
| 2-Ethylthioprop-2-yl | 2-Phenyl-1,3,4-thiadiazol-5-yl |
| 2-Ethylthioprop-2-yl | 2-Cyclopropyl-1,3,4-thiadiazol-5-yl |
| 2-Ethylthioprop-2-yl | 2-Isopropyl-1,3,4-thiadiazol-5-yl |
| 2-Ethylthioprop-2-yl | 2-Phenoxymethyl-1,3,4-thiadiazol-5-yl |
| 2-Ethylthioprop-2-yl | 2-(4-Chlorophenyl)-1,3,4-thiadiazol-5-yl |
| 2-Ethylthioprop-2-yl | 2-Phenyl-1,3,4-oxadiazol-5-yl |
| 2-Ethylthioprop-2-yl | 2-(4-Methoxyphenyl)-1,3,4-oxadiazol-5-yl |
| 2-Ethylthioprop-2-yl | 2-(2-Methylphenyl)-1,3,4-oxadiazol-5-yl |
| 2-Ethylthioprop-2-yl | 2-(4-Methylphenyl)-1,3,4-oxadiazol-5-yl |
| 2-Ethylthioprop-2-yl | 2-(4-Cyanophenyl)-1,3,4-oxadiazol-5-yl |
| 2-Ethylthioprop-2-yl | 2-(4-Nitrophenyl)1,3,4-oxadiazol-5-yl |
| 2-Ethylthioprop-2-yl | 2-(3-Nitrophenyl)1,3,4-oxadiazol-5-yl |
| 2-Ethylthioprop-2-yl | 2-(2-Chlorophenyl)-1,3,4-oxadiazol-5-yl |
| 2-Ethylthioprop-2-yl | 2-(2,4-Dichlorophenyl)1,3,4-oxadiazol-5-yl |
| 2-Ethylthioprop-2-yl | 2-Ethyl-1,3,4-oxadiazol-5-yl |
| 2-Ethylthioprop-2-yl | 2-Isopropyl-1,3,4-oxadiazol-5-yl |
| 2-Ethylthioprop-2-yl | 2-Cyclopropyl-1,3,4-oxadiazol-5-yl |
| 2-Ethylthioprop-2-yl | 3-(4-Chlorophenyl)-1,2,4-oxadiazol-5-yl |
| 2-Ethylthioprop-2-yl | 3-(4-Fluorophenyl)-1,2,4-oxadiazol-5-yl |
| 2-Ethylthioprop-2-yl | 3-n-Propyl-1,2,4-oxadiazol-5-yl |
| 2-Ethylthioprop-2-yl | 3-Ethyl-1,2,4-oxadiazol-5-yl |
| 2-Ethylthioprop-2-yl | 3-Methyl-1,2,4-oxadiazol-5-yl |
| 2-Ethylthioprop-2-yl | 3-Isopropyl-1,2,4-oxadiazol-5-yl |
| 2-Ethylthioprop-2-yl | 3-tert-Butylpropyl-1,2,4-oxadiazol-5-yl |
| 2-Ethylthioprop-2-yl | 3-Cyclopropyl-1,2,4-oxadiazol-5-yl |
| 2-Ethylthioprop-2-yl | 3-Cyclohoxyl-1,2,4-oxadiazol-5-yl |
| 2-Ethylthioprop-2-yl | 5-Isopropyl-1,2,4-oxadiazol-3-yl |
| 2-Ethylthioprop-2-yl | 5-(4-Chlorophenyl)-1,2,4-oxadiazol-3-yl |
| 2-Ethylthioprop-2-yl | 3-Carbomethoxy-1,2,4-oxadiazol-5-yl |
| 2-Ethylthioprop-2-yl | 5-Chloro-1,2,3-thiadiazol-4-yl |
| 2-Ethylthioprop-2-yl | 5-Methyl-1,2,3-thiadiazol-4-yl |
| 2-Ethylthioprop-2-yl | 4-Methyl-1,2,3-thiadiazol-5-yl |
| 2-Ethylthioprop-2-yl | 5-Chloro-1,2,4-thiadiazol-3-yl |
| 2-Ethylthioprop-2-yl | Benzimidazol-2-yl |
| 2-Ethylthioprop-2-yl | Benzoxazol-2-yl |
| 2-Ethylthioprop-2-yl | Benzthiophen-3-yl |
| 2-Ethylthioprop-2-yl | Benzofuran-2-yl |
| 2-Ethylthioprop-2-yl | 5-Chlorobenzofuran-2-yl |
| 2-Ethylthioprop-2-yl | 5-Chlorobenzoxazol-2-yl |
| 2-Ethylthioprop-2-yl | 1-Methylpyrazol-3-yl |
| 2-Ethylthioprop-2-yl | 1-(4-Methylphenyl)pyrazol-4-yl |
| 2-Ethylthioprop-2-yl | 1,3-Dimethylpyrazol-5-yl |
| 2-Ethylthioprop-2-yl | 1-Phenyl-3-ethoxypyrazol-5-yl |
| 2-Ethylthioprop-2-yl | 1-Phenyl-3-methylpyrazol-5-yl |
| 2-Ethylthioprop-2-yl | 3-Cyclopropyl-1-methyl-1,2,4-triazol-5-yl |
| 2-Ethylthioprop-2-yl | 3-Cyclohexyl-1-methyl-1,2,4-triazol-5-yl |
| 2-Ethylthioprop-2-yl | 1,3-Dimethyl-1,2,4-triazol-5-yl |
| 2-Ethylthioprop-2-yl | 5-Phenyl-1,2,4-triazol-3-yl |
| 2-n-Propylthioprop-2-yl | Phenyl |
| 2-n-Propylthioprop-2-yl | 2-Chlorophenyl |
| 2-n-Propylthioprop-2-yl | 3-Chlorophenyl |
| 2-n-Propylthioprop-2-yl | 4-Chlorophenyl |
| 2-n-Propylthioprop-2-yl | 2,6-Dichlorophenyl |
| 2-n-Propylthioprop-2-yl | 2,4-Dichlorophenyl |
| 2-n-Propylthioprop-2-yl | 2-Methylphenyl |
| 2-n-Propylthioprop-2-yl | 3-Methylphenyl |
| 2-n-Propylthioprop-2-yl | 4-Methylphenyl |
| 2-n-Propylthioprop-2-yl | 2,5-Dimethylphenyl |
| 2-n-Propylthioprop-2-yl | 2,4,6-Trimethylphenyl |
| 2-n-Propylthioprop-2-yl | 3-Methoxyphenyl |
| 2-n-Propylthioprop-2-yl | 4-Methoxyphenyl |
| 2-n-Propylthioprop-2-yl | 2-Nitrophenyl |
| 2-n-Propylthioprop-2-yl | 3-Nitrophenyl |
| 2-n-Propylthioprop-2-yl | 4-Nitrophenyl |
| 2-n-Propylthioprop-2-yl | 2-Bromophenyl |
| 2-n-Propylthioprop-2-yl | 4-Bromophenyl |
| 2-n-Propylthioprop-2-yl | 4-Cyanophenyl |
| 2-n-Propylthioprop-2-yl | 4-Dimethylaminophenyl |
| 2-n-Propylthioprop-2-yl | 4-Carbomethoxyphenyl |
| 2-n-Propylthioprop-2-yl | 2-Methoxy-5-nitrophenyl |
| 2-n-Propylthioprop-2-yl | 2-Trifluoromethylphenyl |
| 2-n-Propylthioprop-2-yl | 4-Trifluoromethylphenyl |
| 2-n-Propylthioprop-2-yl | 4-tert-Butylphenyl |
| 2-n-Propylthioprop-2-yl | 2-Chloro-6-nitrophenyl |
| 2-n-Propylthioprop-2-yl | 2-Fluorophenyl |
| 2-n-Propylthioprop-2-yl | 4-Fluorophenyl |
| 2-n-Propylthioprop-2-yl | 2,3,4,5,6-Pentafluorophenyl |
| 2-n-Propylthioprop-2-yl | 2-Chloro-3-isopropylphenyl |
| 2-n-Propylthioprop-2-yl | 2,6-Difluorophenyl |
| 2-n-Propylthioprop-2-yl | 2-Chloro-3-trifluoromethylphenyl |
| 2-n-Propylthioprop-2-yl | 2-Biphenyl |
| 2-n-Propylthioprop-2-yl | 3-Biphenyl |
| 2-n-Propylthioprop-2-yl | 4-Biphenyl |
| 2-n-Propylthioprop-2-yl | 4'-Chlorobiphenyl-4-yl |
| 2-n-Propylthioprop-2-yl | 3-Phenoxyphenyl |
| 2-n-Propylthioprop-2-yl | 3,4-Methylenedioxyphenyl |
| 2-n-Propylthioprop-2-yl | 1-Naphthyl |
| 2-n-Propylthioprop-2-yl | 2-Naphthyl |
| 2-n-Propylthioprop-2-yl | 9-Anthracenyl |
| 2-n-Propylthioprop-2-yl | 2-Furyl |
| 2-n-Propylthioprop-2-yl | 4-Isopropylfuran-2-yl |
| 2-n-Propylthioprop-2-yl | 5-Carboxymethylfuran-2-yl |
| 2-n-Propylthioprop-2-yl | 5-Methylfuran-2-yl |
| 2-n-Propylthioprop-2-yl | 5-Trifluoromethylfuran-2-yl |
| 2-n-Propylthioprop-2-yl | 3-Furyl |
| 2-n-Propylthioprop-2-yl | 2-Thienyl |
| 2-n-Propylthioprop-2-yl | 5-Chlorothien-2-yl |
| 2-n-Propylthioprop-2-yl | 3-Thienyl |
| 2-n-Propylthioprop-2-yl | 5-Bromothien-3-yl |
| 2-n-Propylthioprop-2-yl | Benzothiophen-3-yl |
| 2-n-Propylthioprop-2-yl | 2-Pyrrolyl |
| 2-n-Propylthioprop-2-yl | 1-Phenylpyrrol-2-yl |
| 2-n-Propylthioprop-2-yl | 3-Pyrrolyl |
| 2-n-Propylthioprop-2-yl | Isoxazol-5-yl |
| 2-n-Propylthioprop-2-yl | Isoxazol-3-yl |
| 2-n-Propylthioprop-2-yl | 3-Phenylisoxazol-5-yl |
| 2-n-Propylthioprop-2-yl | 3-Methylisoxazol-5-yl |
| 2-n-Propylthioprop-2-yl | 4-Chloro-3-methylisoxazol-5-yl |
| 2-n-Propylthioprop-2-yl | 4-Chloro-3-isopropylisoxazol-5-yl |
| 2-n-Propylthioprop-2-yl | 4-Chloro-3-sec-butylisoxazol-5-yl |
| 2-n-Propylthioprop-2-yl | 4-Chloro-3-tert-butylisoxazol-5-yl |
| 2-n-Propylthioprop-2-yl | 4-Chloro-3-cyclohexylisoxazol-5-yl |
| 2-n-Propylthioprop-2-yl | 4-Chloro-3-phenylisoxazol-5-yl |
| 2-n-Propylthioprop-2-yl | 4-Chloro-3-(4-methylphenyl)isoxazol-5-yl |
| 2-n-Propylthioprop-2-yl | 4-Chloro-3-(4-chlorophenyl)-isoxazol-5-yl |
| 2-n-Propylthioprop-2-yl | 4-Chloro-3-(4-fluorophenyl)-isoxazol-5-yl |
| 2-n-Propylthioprop-2-yl | 4-Chloro-3-(4-trifluoromethylphenyl)-isoxazol-5-yl |
| 2-n-Propylthioprop-2-yl | 4-Chloro-3-(2,6-difluorophenyl)-isoxazol-5-yl |
| 2-n-Propylthioprop-2-yl | 4-Chloro-3-phenylisoxazol-5-yl |
| 2-n-Propylthioprop-2-yl | 3,5-Dimethylisoxazol-4-yl |
| 2-n-Propylthioprop-2-yl | 3-Carboxyethylisoxazol-5-yl |
| 2-n-Propylthioprop-2-yl | 3-(3,4-Dichlorophenyl)isoxazol-5-yl |
| 2-n-Propylthioprop-2-yl | 3-(3-Nitrophenyl)isoxazol-5-yl |
| 2-n-Propylthioprop-2-yl | 3-(4-Chlorophenyl)isoxazol-5-yl |
| 2-n-Propylthioprop-2-yl | 3-(4-Fluorophenyl)isoxazol-5-yl |
| 2-n-Propylthioprop-2-yl | 3-(3,4-Difluorophenyl)isoxazol-5-yl |
| 2-n-Propylthioprop-2-yl | 3-Phenylisoxazol-5-yl |
| 2-n-Propylthioprop-2-yl | 3-Methoxymethylisoxazol-5-yl |
| 2-n-Propylthioprop-2-yl | 3-Methylisoxazol-5-yl |
| 2-n-Propylthioprop-2-yl | 3-Ethylisoxazol-5-yl |
| 2-n-Propylthioprop-2-yl | 3-n-Propylisoxazol-5-yl |
| 2-n-Propylthioprop-2-yl | 3-n-Butylisoxazol-5-yl |

TABLE A-continued $R^1R^2CH-ON=C(CN)-R^3 \quad R^1 = H \quad I$

| $R^3$ | $R^2$ |
|---|---|
| 2-n-Propylthioprop-2-yl | 3-Isopropylisoxazol-5-yl |
| 2-n-Propylthioprop-2-yl | 3-Isobutylisoxazol-5-yl |
| 2-n-Propylthioprop-2-yl | 3-tert-Butylisoxazol-5-yl |
| 2-n-Propylthioprop-2-yl | 3-sec-Butylisoxazol-5-yl |
| 2-n-Propylthioprop-2-yl | 3-Methoxyisoxazol-5-yl |
| 2-n-Propylthioprop-2-yl | 3-Cyclopropylisoxazol-5-yl |
| 2-n-Propylthioprop-2-yl | 3-Cyclopropylisoxazol-4-yl |
| 2-n-Propylthioprop-2-yl | 3-Cyclohexylisoxazol-5-yl |
| 2-n-Propylthioprop-2-yl | 3-(3-Methylphenyl)isoxazol-5-yl |
| 2-n-Propylthioprop-2-yl | 3-(3,4-Dichlorophenyl)isoxazol-5-yl |
| 2-n-Propylthioprop-2-yl | 3-(2,6-Dichlorophenyl)isoxazol-5-yl |
| 2-n-Propylthioprop-2-yl | 3-(3-Nitrophenyl)isoxazol-5-yl |
| 2-n-Propylthioprop-2-yl | 3-(2-Methoxyphenyl)isoxazol-5-yl |
| 2-n-Propylthioprop-2-yl | 3-(4-Trifluoromethylphenyl)isoxazol-5-yl |
| 2-n-Propylthioprop-2-yl | 3-(3-Trifluoromethylphenyl)isoxazol-5-yl |
| 2-n-Propylthioprop-2-yl | 3-(4-Bromophenyl)isoxazol-5-yl |
| 2-n-Propylthioprop-2-yl | 3-(3-Chlorophenyl)isoxazol-5-yl |
| 2-n-Propylthioprop-2-yl | 3-(2-Chlorophenyl)isoxazol-5-yl |
| 2-n-Propylthioprop-2-yl | 3-(3-Fluorophenyl)isoxazol-5-yl |
| 2-n-Propylthioprop-2-yl | 3-(3-Phenoxyphenyl)isoxazol-5-yl |
| 2-n-Propylthioprop-2-yl | 3-(2,6-Difluorophenyl)isoxazol-5-yl |
| 2-n-Propylthioprop-2-yl | 3-Trifluoromethylisoxazol-5-yl |
| 2-n-Propylthioprop-2-yl | 3-(2-Naphthyl)isoxazol-5-yl |
| 2-n-Propylthioprop-2-yl | 3-(1-Naphthyl)isoxazol-5-yl |
| 2-n-Propylthioprop-2-yl | 3-tert-Butyl-5-phenylisoxazol-4-yl |
| 2-n-Propylthioprop-2-yl | 5-Methylisoxazol-4-yl |
| 2-n-Propylthioprop-2-yl | 4-Ethoxycarbonylisoxazol-5-yl |
| 2-n-Propylthioprop-2-yl | 5-Cyclopropylisoxazol-3-yl |
| 2-n-Propylthioprop-2-yl | 4-Chloro-3-(4-bromophenyl)isoxazol-5-yl |
| 2-n-Propylthioprop-2-yl | 4-Chloro-3-(3-chlorophenyl)isoxazol-5-yl |
| 2-n-Propylthioprop-2-yl | 4-Chloro-3-(3-fluorophenyl)isoxazol-5-yl |
| 2-n-Propylthioprop-2-yl | 4-Chloro-3-(2-chlorophenyl)isoxazol-5-yl |
| 2-n-Propylthioprop-2-yl | 2-Phenyloxazol-4-yl |
| 2-n-Propylthioprop-2-yl | 2-(4-Fluorophenyl)oxazol-4-yl |
| 2-n-Propylthioprop-2-yl | 2-(4-Chlorophenyl)oxazol-4-yl |
| 2-n-Propylthioprop-2-yl | 2-(4-Bromophenyl)oxazol-4-yl |
| 2-n-Propylthioprop-2-yl | 2-(3-Chlorophenyl)oxazol-4-yl |
| 2-n-Propylthioprop-2-yl | 2-(4-Methylphenyl)oxazol-4-yl |
| 2-n-Propylthioprop-2-yl | 2-tert-Butyloxazol-4-yl |
| 2-n-Propylthioprop-2-yl | 2-(2,4-Dichlorophenyl)oxazol-4-yl |
| 2-n-Propylthioprop-2-yl | 2-(4-Methoxyphenyl)oxazol-4-yl |
| 2-n-Propylthioprop-2-yl | 2-(4-Chlorophenyl)-5-bromooxazol-4-yl |
| 2-n-Propylthioprop-2-yl | 2-Cyclopropyloxazol-4-yl |
| 2-n-Propylthioprop-2-yl | 2-Isopropyloxazol-4-yl |
| 2-n-Propylthioprop-2-yl | 2-tert-Butyloxazol-4-yl |
| 2-n-Propylthioprop-2-yl | 2-tert-Butyloxazol-5-y |
| 2-n-Propylthioprop-2-yl | 2-Benzyloxazol-4-yl |
| 2-n-Propylthioprop-2-yl | 2-Methylthiazol-4-yl |
| 2-n-Propylthioprop-2-yl | 2-Isopropylthiazol-4-yl |
| 2-n-Propylthioprop-2-yl | 2-Cyclopropylthiazol-4-yl |
| 2-n-Propylthioprop-2-yl | 4-(4-Methoxyphenyl)thiazol-2-yl |
| 2-n-Propylthioprop-2-yl | 2-Acetamidothiazol-4-yl |
| 2-n-Propylthioprop-2-yl | 2-Phenylthiazol-4-yl |
| 2-n-Propylthioprop-2-yl | 2-(2-Chlorophenyl)thiazol-4-yl |
| 2-n-Propylthioprop-2-yl | 2-(4-Chlorophenyl)thiazol-4-yl |
| 2-n-Propylthioprop-2-yl | 2-(2,4-Dichlorophenyl)thiazol-4-yl |
| 2-n-Propylthioprop-2-yl | 2-(2,6-Dichlorophenyl)thiazol-4-yl |
| 2-n-Propylthioprop-2-yl | 2-(3-Fluorophenyl)thiazol-4-yl |
| 2-n-Propylthioprop-2-yl | 2-(3-Chlorophenyl)thiazol-4-yl |
| 2-n-Propylthioprop-2-yl | 2-(4-Trifluoromethylphenyl)thiazol-4-yl |
| 2-n-Propylthioprop-2-yl | 2-(3-Methylphenyl)thiazol-4-yl |
| 2-n-Propylthioprop-2-yl | 2-(4-Methoxyphenyl)thiazol-4-yl |
| 2-n-Propylthioprop-2-yl | 2-Methylthiazol-4-yl |
| 2-n-Propylthioprop-2-yl | 2-(4-Fluorophenyl)thiazol-4-yl |
| 2-n-Propylthioprop-2-yl | 2-Methyl-1,3,4-thiadiazol-5-yl |
| 2-n-Propylthioprop-2-yl | 2-Phenyl-1,3,4-thiadiazol-5-yl |
| 2-n-Propylthioprop-2-yl | 2-Cyclopropyl-1,3,4-thiadiazol-5-yl |
| 2-n-Propylthioprop-2-yl | 2-Isopropyl-1,3,4-thiadiazol-5-yl |
| 2-n-Propylthioprop-2-yl | 2-Phenoxymethyl-1,3,4-thiadiazol-5-yl |
| 2-n-Propylthioprop-2-yl | 2-(4-Chlorophenyl)-1,3,4-thiadiazol-5-yl |
| 2-n-Propylthioprop-2-yl | 2-Phenyl-1,3,4-oxadiazol-5-yl |
| 2-n-Propylthioprop-2-yl | 2-(4-Methoxyphenyl)-1,3,4-oxadiazol-5-yl |
| 2-n-Propylthioprop-2-yl | 2-(2-Methylphenyl)-1,3,4-oxadiazol-5-yl |
| 2-n-Propylthioprop-2-yl | 2-(4-Methylphenyl)-1,3,4-oxadiazol-5-yl |
| 2-n-Propylthioprop-2-yl | 2-(4-Cyanophenyl)-1,3,4-oxadiazol-5-yl |
| 2-n-Propylthioprop-2-yl | 2-(4-Nitrophenyl)-1,3,4-oxadiazol-5-yl |
| 2-n-Propylthioprop-2-yl | 2-(3-Nitrophenyl)-1,3,4-oxadiazol-5-yl |
| 2-n-Propylthioprop-2-yl | 2-(2-Chlorophenyl)-1,3,4-oxadiazol-5-yl |
| 2-n-Propylthioprop-2-yl | 2-(2,4-Dichlorophenyl)-1,3,4-oxadiazol-5-yl |
| 2-n-Propylthioprop-2-yl | 2-Ethyl-1,3,4-oxadiazol-5-yl |
| 2-n-Propylthioprop-2-yl | 2-Isopropyl-1,3,4-oxadiazol-5-yl |
| 2-n-Propylthioprop-2-yl | 2-Cyclopropyl-1,3,4-oxadiazol-5-yl |
| 2-n-Propylthioprop-2-yl | 3-(4-Chlorophenyl)-1,2,4-oxadiazol-5-yl |
| 2-n-Propylthioprop-2-yl | 3-(4-Fluorophenyl)-1,2,4-oxadiazol-5-yl |
| 2-n-Propylthioprop-2-yl | 3-n-Propyl-1,2,4-oxadiazol-5-yl |
| 2-n-Propylthioprop-2-yl | 3-Ethyl-1,2,4-oxadiazol-5-yl |
| 2-n-Propylthioprop-2-yl | 3-Methyl-1,2,4-oxadiazol-5-yl |
| 2-n-Propylthioprop-2-yl | 3-Isopropyl-1,2,4-oxadiazol-5-yl |
| 2-n-Propylthioprop-2-yl | 3-tert-Butylpropyl-1,2,4-oxadiazol-5-yl |
| 2-n-Propylthioprop-2-yl | 3-Cyclopropyl-1,2,4-oxadiazol-5-yl |
| 2-n-Propylthioprop-2-yl | 3-Cyclohexyl-1,2,4-oxadiazol-5-yl |
| 2-n-Propylthioprop-2-yl | 5-Isopropyl-1,2,4-oxadiazol-3-yl |
| 2-n-Propylthioprop-2-yl | 5-(4-Chlorophenyl)-1,2,4-oxadiazol-3-yl |
| 2-n-Propylthioprop-2-yl | 3-Carbomethoxy-1,2,4-oxadiazol-5-yl |
| 2-n-Propylthioprop-2-yl | 5-Chloro-1,2,3-thiadiazol-4-yl |
| 2-n-Propylthioprop-2-yl | 5-Methyl-1,2,3-thiadiazol-4-yl |
| 2-n-Propylthioprop-2-yl | 4-Methyl-1,2,3-thiadiazol-5-yl |
| 2-n-Propylthioprop-2-yl | 5-Chloro-1,2,4-thiadiazol-3-yl |
| 2-n-Propylthioprop-2-yl | Benzimidazol-2-yl |
| 2-n-Propylthioprop-2-yl | Benzoxazol-2-yl |
| 2-n-Propylthioprop-2-yl | Benzthiophen-3-yl |
| 2-n-Propylthioprop-2-yl | Benzofuran-2-yl |
| 2-n-Propylthioprop-2-yl | 5-Chlorobenzofuran-2-yl |
| 2-n-Propylthioprop-2-yl | 5-Chlorobenzoxazol-2-yl |
| 2-n-Propylthioprop-2-yl | 1-Methylpyrazol-3-yl |
| 2-n-Propylthioprop-2-yl | 1-(4-Methylphenyl)pyrazol-4-yl |
| 2-n-Propylthioprop-2-yl | 1,3-Dimethylpyrazol-5-yl |
| 2-n-Propylthioprop-2-yl | 1-Phenyl-3-ethoxypyrazol-5-yl |
| 2-n-Propylthioprop-2-yl | 1-Phenyl-3-methylpyrazol-5-yl |
| 2-n-Propylthioprop-2-yl | 3-Cyclopropyl-1-methyl-1,2,4-triazol-5-yl |
| 2-n-Propylthioprop-2-yl | 3-Cyclohexyl-1-methyl-1,2,4-triazol-5-yl |
| 2-n-Propylthioprop-2-yl | 1,3-Dimethyl-1,2,4-triazol-5-yl |
| 2-n-Propylthioprop-2-yl | 5-Phenyl-1,2,4-triazol-3-yl |
| 2-Isopropylthioprop-2-yl | Phenyl |
| 2-Isopropylthioprop-2-yl | 2-Chlorophenyl |
| 2-Isopropylthioprop-2-yl | 3-Chlorophenyl |
| 2-Isopropylthioprop-2-yl | 4-Chlorophenyl |
| 2-Isopropylthioprop-2-yl | 2,6-Dichlorophenyl |
| 2-Isopropylthioprop-2-yl | 2,4-Dichlorophenyl |
| 2-Isopropylthioprop-2-yl | 2-Methylphenyl |
| 2-Isopropylthioprop-2-yl | 3-Methylphenyl |
| 2-Isopropylthioprop-2-yl | 4-Methylphenyl |
| 2-Isopropylthioprop-2-yl | 2,5-Dimethylphenyl |
| 2-Isopropylthioprop-2-yl | 2,4,6-Trimethylphenyl |
| 2-Isopropylthioprop-2-yl | 3-Methoxyphenyl |
| 2-Isopropylthioprop-2-yl | 4-Methoxyphenyl |
| 2-Isopropylthioprop-2-yl | 2-Nitrophenyl |
| 2-Isopropylthioprop-2-yl | 3-Nitrophenyl |
| 2-Isopropylthioprop-2-yl | 4-Nitrophenyl |
| 2-Isopropylthioprop-2-yl | 2-Bromophenyl |
| 2-Isopropylthioprop-2-yl | 4-Bromophenyl |
| 2-Isopropylthioprop-2-yl | 4-Cyanophenyl |
| 2-Isopropylthioprop-2-yl | 4-Dimethylaminophenyl |
| 2-Isopropylthioprop-2-yl | 4-Carbomethoxyphenyl |
| 2-Isopropylthioprop-2-yl | 2-Methoxy-5-nitrophenyl |
| 2-Isopropylthioprop-2-yl | 2-Trifluoromethylphenyl |
| 2-Isopropylthioprop-2-yl | 4-Trifluoromethylphenyl |
| 2-Isopropylthioprop-2-yl | 4-tert-Butylphenyl |
| 2-Isopropylthioprop-2-yl | 2-Chloro-6-nitrophenyl |

TABLE A-continued

| R³ | R² |
|---|---|
| | R¹R²CH—ON=C(CN)—R³   R¹ = H   I |
| 2-Isopropylthioprop-2-yl | 2-Fluorophenyl |
| 2-Isopropylthioprop-2-yl | 4-Fluorophenyl |
| 2-Isopropylthioprop-2-yl | 2,3,4,5,6-Pentafluorophenyl |
| 2-Isopropylthioprop-2-yl | 2-Chloro-3-isopropylphenyl |
| 2-Isopropylthioprop-2-yl | 2,6-Difluorophenyl |
| 2-Isopropylthioprop-2-yl | 2-Chloro-3-trifluoromethylphenyl |
| 2-Isopropylthioprop-2-yl | 2-Biphenyl |
| 2-Isopropylthioprop-2-yl | 3-Biphenyl |
| 2-Isopropylthioprop-2-yl | 4-Biphenyl |
| 2-Isopropylthioprop-2-yl | 4'-Chlorobiphenyl-4-yl |
| 2-Isopropylthioprop-2-yl | 3-Phenoxyphenyl |
| 2-Isopropylthioprop-2-yl | 3,4-Methylenedioxyphenyl |
| 2-Isopropylthioprop-2-yl | 1-Naphthyl |
| 2-Isopropylthioprop-2-yl | 2-Naphthyl |
| 2-Isopropylthioprop-2-yl | 9-Anthracenyl |
| 2-Isopropylthioprop-2-yl | 2-Furyl |
| 2-Isopropylthioprop-2-yl | 4-Isopropylfuran-2-yl |
| 2-Isopropylthioprop-2-yl | 5-Carboxymethyl-furan-2-yl |
| 2-Isopropylthioprop-2-yl | 5-Methylfuran-2-yl |
| 2-Isopropylthioprop-2-yl | 5-Trifluoromethylfuran-2-yl |
| 2-Isopropylthioprop-2-yl | 3-Furyl |
| 2-Isopropylthioprop-2-yl | 2-Thienyl |
| 2-Isopropylthioprop-2-yl | 5-Chlorothien-2-yl |
| 2-Isopropylthioprop-2-yl | 3-Thienyl |
| 2-Isopropylthioprop-2-yl | 5-Bromothien-3-yl |
| 2-Isopropylthioprop-2-yl | Benzothiophen-3-yl |
| 2-Isopropylthioprop-2-yl | 2-Pyrrolyl |
| 2-Isopropylthioprop-2-yl | 1-Phenylpyrrol-2-yl |
| 2-Isopropylthioprop-2-yl | 3-Pyrrolyl |
| 2-Isopropylthioprop-2-yl | Isoxazol-5-yl |
| 2-Isopropylthioprop-2-yl | Isoxazol-3-yl |
| 2-Isopropylthioprop-2-yl | 3-Phenylisoxazol-5-yl |
| 2-Isopropylthioprop-2-yl | 3-Methylisoxazol-5-yl |
| 2-Isopropylthioprop-2-yl | 4-Chloro-3-methylisoxazol-5-yl |
| 2-Isopropylthioprop-2-yl | 4-Chloro-3-isopropylisoxazol-5-yl |
| 2-Isopropylthioprop-2-yl | 4-Chloro-3-sec-butylisoxazol-5-yl |
| 2-Isopropylthioprop-2-yl | 4-Chloro-3-tert-butylisoxazol-5-yl |
| 2-Isopropylthioprop-2-yl | 4-Chloro-3-cyclohexylisoxazol-5-yl |
| 2-Isopropylthioprop-2-yl | 4-Chloro-3-phenylisoxazol-5-yl |
| 2-Isopropylthioprop-2-yl | 4-Chloro-3-(4-methylphenyl)isoxazol-5-yl |
| 2-Isopropylthioprop-2-yl | 4-Chloro-3-(4-chlorophenyl)isoxazol-5-yl |
| 2-Isopropylthioprop-2-yl | 4-Chloro-3-(4-fluorophenyl)isoxazol-5-yl |
| 2-Isopropylthioprop-2-yl | 4-Chloro-3-(4-trifluoromethylphenyl)-isoxazol-5-yl |
| 2-Isopropylthioprop-2-yl | 4-Chloro-3-(2,6-difluorophenyl)-isoxazol-5-yl |
| 2-Isopropylthioprop-2-yl | 4-Chloro-3-phenylisoxazol-5-yl |
| 2-Isopropylthioprop-2-yl | 3,5-Dimethylisoxazol-4-yl |
| 2-Isopropylthioprop-2-yl | 3-Carboxyethylisoxazol-5-yl |
| 2-Isopropylthioprop-2-yl | 3-(3,4-Dichlorophenyl)isoxazol-5-yl |
| 2-Isopropylthioprop-2-yl | 3-(3-Nitrophenyl)isoxazol-5-yl |
| 2-Isopropylthioprop-2-yl | 3-(4-Chlorophenyl)isoxazol-5-yl |
| 2-Isopropylthioprop-2-yl | 3-(4-Fluorophenyl)isoxazol-5-yl |
| 2-Isopropylthioprop-2-yl | 3-(3,4-Difluorophenyl)isoxazol-5-yl |
| 2-Isopropylthioprop-2-yl | 3-Phenylisoxazol-5-yl |
| 2-Isopropylthioprop-2-yl | 3-Methoxymethylisoxazol-5-yl |
| 2-Isopropylthioprop-2-yl | 3-Methylisoxazol-5-yl |
| 2-Isopropylthioprop-2-yl | 3-Ethylisoxazol-5-yl |
| 2-Isopropylthioprop-2-yl | 3-n-Propylisoxazol-5-yl |
| 2-Isopropylthioprop-2-yl | 3-n-Butylisoxazol-5-yl |
| 2-Isopropylthioprop-2-yl | 3-Isopropylisoxazol-5-yl |
| 2-Isopropylthioprop-2-yl | 3-Isobutylisoxazol-5-yl |
| 2-Isopropylthioprop-2-yl | 3-tert-Butylisoxazol-5-yl |
| 2-Isopropylthioprop-2-yl | 3-sec-Butylisoxazol-5-yl |
| 2-Isopropylthioprop-2-yl | 3-Methoxyisoxazol-5-yl |
| 2-Isopropylthioprop-2-yl | 3-Cyclopropylisoxazol-5-yl |
| 2-Isopropylthioprop-2-yl | 3-Cyclopropylisoxazol-4-yl |
| 2-Isopropylthioprop-2-yl | 3-Cyclohexylisoxazol-5-yl |
| 2-Isopropylthioprop-2-yl | 3-(3-Methylphenyl)isoxazol-5-yl |
| 2-Isopropylthioprop-2-yl | 3-(3,4-Dichlorophenyl)isoxazol-5-yl |
| 2-Isopropylthioprop-2-yl | 3-(2,6-Dichlorophenyl)isoxazol-5-yl |
| 2-Isopropylthioprop-2-yl | 3-(3-Nitrophenyl)isoxazol-5-yl |
| 2-Isopropylthioprop-2-yl | 3-(2-Methoxyphenyl)isoxazol-5-yl |
| 2-Isopropylthioprop-2-yl | 3-(4-Trifluoromethylphenyl)isoxazol-5-yl |
| 2-Isopropylthioprop-2-yl | 3-(3-Trifluoromethylphenyl)isoxazol-5-yl |
| 2-Isopropylthioprop-2-yl | 3-(4-Bromophenyl)isoxazol-5-yl |
| 2-Isopropylthioprop-2-yl | 3-(3-Chlorophenyl)isoxazol-5-yl |
| 2-Isopropylthioprop-2-yl | 3-(2-Chlorophenyl)isoxazol-5-yl |
| 2-Isopropylthioprop-2-yl | 3-(3-Fluorophenyl)isoxazol-5-yl |
| 2-Isopropylthioprop-2-yl | 3-(3-Phenoxyphenyl)isoxazol-5-yl |
| 2-Isopropylthioprop-2-yl | 3-(2,6-Difluorophenyl)isoxazol-5-yl |
| 2-Isopropylthioprop-2-yl | 3-Trifluoromethylisoxazol-5-yl |
| 2-Isopropylthioprop-2-yl | 3-(2-Naphthyl)isoxazol-5-yl |
| 2-Isopropylthioprop-2-yl | 3-(1-Naphthyl)isoxazol-5-yl |
| 2-Isopropylthioprop-2-yl | 3-tert-Butyl-5-phenylisoxazol-4-yl |
| 2-Isopropylthioprop-2-yl | 5-Methylisoxazol-4-yl |
| 2-Isopropylthioprop-2-yl | 4-Ethoxycarbonylisoxazol-5-yl |
| 2-Isopropylthioprop-2-yl | 5-Cyclopropylisoxazol-3-yl |
| 2-Isopropylthioprop-2-yl | 4-Chloro-3-(4-bromophenyl)isoxazol-5-yl |
| 2-Isopropylthioprop-2-yl | 4-Chloro-3-(3-chlorophenyl)isoxazol-5-yl |
| 2-Isopropylthioprop-2-yl | 4-Chloro-3-(3-fluorophenyl)isoxazol-5-yl |
| 2-Isopropylthioprop-2-yl | 4-Chloro-3-(2-chlorophenyl)isoxazol-5-yl |
| 2-Isopropylthioprop-2-yl | 2-Phenyloxazol-4-yl |
| 2-Isopropylthioprop-2-yl | 2-(4-Fluorophenyl)oxazol-4-yl |
| 2-Isopropylthioprop-2-yl | 2-(4-Chlorophenyl)oxazol-4-yl |
| 2-Isopropylthioprop-2-yl | 2-(4-Bromophenyl)oxazol-4-yl |
| 2-Isopropylthioprop-2-yl | 2-(3-Chlorophenyl)oxazol-4-yl |
| 2-Isopropylthioprop-2-yl | 2-(4-Methylphenyl)oxazol-4-yl |
| 2-Isopropylthioprop-2-yl | 2-tert-Butyloxazol-4-yl |
| 2-Isopropylthioprop-2-yl | 2-(2,4-Dichlorophenyl)oxazol-4-yl |
| 2-Isopropylthioprop-2-yl | 2-(4-Methoxyphenyl)oxazol-4-yl |
| 2-Isopropylthioprop-2-yl | 2-(4-Chlorophenyl)-5-bromooxazol-4-yl |
| 2-Isopropylthioprop-2-yl | 2-Cyclopropyloxazol-4-yl |
| 2-Isopropylthioprop-2-yl | 2-Isopropyloxazol-4-yl |
| 2-Isopropylthioprop-2-yl | 2-tert-Butyloxazol-4-yl |
| 2-Isopropylthioprop-2-yl | 2-tert-Butyloxazol-5-y |
| 2-Isopropylthioprop-2-yl | 2-Benzyloxazol-4-yl |
| 2-Isopropylthioprop-2-yl | 2-Methylthiazol-4-yl |
| 2-Isopropylthioprop-2-yl | 2-Isopropylthiazol-4-yl |
| 2-Isopropylthioprop-2-yl | 2-Cyclopropylthiazol-4-yl |
| 2-Isopropylthioprop-2-yl | 4-(4-Methoxyphenyl)thiazol-2-yl |
| 2-Isopropylthioprop-2-yl | 2-Acetamidothiazol-4-yl |
| 2-Isopropylthioprop-2-yl | 2-Phenylthiazol-4-yl |
| 2-Isopropylthioprop-2-yl | 2-(2-Chlorophenyl)thiazol-4-yl |
| 2-Isopropylthioprop-2-yl | 2-(4-Chlorophenyl)thiazol-4-yl |
| 2-Isopropylthioprop-2-yl | 2-(2,4-Dichlorophenyl)thiazol-4-yl |
| 2-Isopropylthioprop-2-yl | 2-(2,6-Dichlorophenyl)thiazol-4-yl |
| 2-Isopropylthioprop-2-yl | 2-(3-Fluorophenyl)thiazol-4-yl |
| 2-Isopropylthioprop-2-yl | 2-(3-Chlorophenyl)thiazol-4-yl |
| 2-Isopropylthioprop-2-yl | 2-(4-Trifluoromethylphenyl)thiazol-4-yl |
| 2-Isopropylthioprop-2-yl | 2-(3-Methylphenyl)thiazol-4-yl |
| 2-Isopropylthioprop-2-yl | 2-(4-Methoxyphenyl)thiazol-4-yl |
| 2-Isopropylthioprop-2-yl | 2-Methylthiazol-4-yl |
| 2-Isopropylthioprop-2-yl | 2-(4-Fluorophenyl)thiazol-4-yl |
| 2-Isopropylthioprop-2-yl | 2-Methyl-1,3,4-thiadiazol-5-yl |
| 2-Isopropylthioprop-2-yl | 2-Phenyl-1,3,4-thiadiazol-5-yl |
| 2-Isopropylthioprop-2-yl | 2-Cyclopropyl-1,3,4-thiadiazol-5-yl |
| 2-Isopropylthioprop-2-yl | 2-Isopropyl-1,3,4-thiadiazol-5-yl |
| 2-Isopropylthioprop-2-yl | 2-Phenoxymethyl-1,3,4-thiadiazol-5-yl |
| 2-Isopropylthioprop-2-yl | 2-(4-Chlorophenyl)-1,3,4-thiadiazol-5-yl |
| 2-Isopropylthioprop-2-yl | 2-Phenyl-1,3,4-oxadiazol-5-yl |
| 2-Isopropylthioprop-2-yl | 2-(4-Methoxyphenyl)-1,3,4-oxadiazol-5-yl |
| 2-Isopropylthioprop-2-yl | 2-(2-Methylphenyl)-1,3,4-oxadiazol-5-yl |
| 2-Isopropylthioprop-2-yl | 2-(4-Methylphenyl)-1,3,4-oxadiazol-5-yl |
| 2-Isopropylthioprop-2-yl | 2-(4-Cyanophenyl)-1,3,4-oxadiazol-5-yl |
| 2-Isopropylthioprop-2-yl | 2-(4-Nitrophenyl)-1,3,4-oxadiazol-5-yl |
| 2-Isopropylthioprop-2-yl | 2-(3-Nitrophenyl)-1,3,4-oxadiazol-5-yl |
| 2-Isopropylthioprop-2-yl | 2-(2-Chlorophenyl)-1,3,4-oxadiazol-5-yl |
| 2-Isopropylthioprop-2-yl | 2-(2,4-Dichlorophenyl)1,3,4-oxadiazol-5-yl |

TABLE A-continued $R^1R^2CH—ON=C(CN)—R^3$   $R^1 = H$   I

| R³ | R² |
|---|---|
| 2-Isopropylthioprop-2-yl | 2-Ethyl-1,3,4-oxadiazol-5-yl |
| 2-Isopropylthioprop-2-yl | 2-Isopropyl-1,3,4-oxadiazol-5-yl |
| 2-Isopropylthioprop-2-yl | 2-Cyclopropyl-1,3,4-oxadiazol-5-yl |
| 2-Isopropylthioprop-2-yl | 3-(4-Chlorophenyl)-1,2,4-oxadiazol-5-yl |
| 2-Isopropylthioprop-2-yl | 3-(4-Fluorophenyl)-1,2,4-oxadiazol-5-yl |
| 2-Isopropylthioprop-2-yl | 3-n-Propyl-1,2,4-oxadiazol-5-yl |
| 2-Isopropylthioprop-2-yl | 3-Ethyl-1,2,4-oxadiazol-5-yl |
| 2-isopropylthioprop-2-yl | 3-Methyl-1,2,4-oxadiazol-5-yl |
| 2-Isopropylthioprop-2-yl | 3-Isopropyl-1,2,4-oxadiazol-5-yl |
| 2-Isopropylthioprop-2-yl | 3-tert-Butylpropyl-1,2,4-oxadiazol-5-yl |
| 2-Isopropylthioprop-2-yl | 3-Cyclopropyl-1,2,4-oxadiazol-5-yl |
| 2-Isopropylthioprop-2-yl | 3-Cyclohexyl-1,2,4-oxadiazol-5-yl |
| 2-Isopropylthioprop-2-yl | 5-Isopropyl-1,2,4-oxadiazol-3-yl |
| 2-Isopropylthioprop-2-yl | 5-(4-Chlorophenyl)-1,2,4-oxadiazol-3-yl |
| 2-Isopropylthioprop-2-yl | 3-Carbomethoxy-1,2,4-oxadiazol-5-yl |
| 2-Isopropylthioprop-2-yl | 5-Chloro-1,2,3-thiadiazol-4-yl |
| 2-Isopropylthioprop-2-yl | 5-Methyl-1,2,3-thiadiazol-4-yl |
| 2-Isopropylthioprop-2-yl | 4-Methyl-1,2,3-thiadiazol-5-yl |
| 2-Isopropylthioprop-2-yl | 5-Chloro-1,2,4-thiadiazol-3-yl |
| 2-Isopropylthioprop-2-yl | Benzimidazol-2-yl |
| 2-Isopropylthioprop-2-yl | Benzoxazol-2-yl |
| 2-Isopropylthioprop-2-yl | Benzthiophen-3-yl |
| 2-Isopropylthioprop-2-yl | Benzofuran-2-yl |
| 2-Isopropylthioprop-2-yl | 5-Chlorobenzofuran-2-yl |
| 2-Isopropylthioprop-2-yl | 5-Chlorobenzoxazol-2-yl |
| 2-Isopropylthioprop-2-yl | 1-Methylpyrazol-3-yl |
| 2-Isopropylthioprop-2-yl | 1-(4-Methylphenyl)pyrazol-4-yl |
| 2-Isopropylthioprop-2-yl | 1,3-Dimethylpyrazol-5-yl |
| 2-Isopropylthioprop-2-yl | 1-Phenyl-3-ethoxypyrazol-5-yl |
| 2-Isopropylthioprop-2-yl | 1-Phenyl-3-methylpyrazol-5-yl |
| 2-Isopropylthioprop-2-yl | 3-Cyclopropyl-1-methyl-1,2,4-triazol-5-yl |
| 2-Isopropylthioprop-2-yl | 3-Cyclohexyl-1-methyl-1,2,4-triazol-5-yl |
| 2-Isopropylthioprop-2-yl | 1,3-Dimethyl-1,2,4-triazol-5-yl |
| 2-Isopropylthioprop-2-yl | 5-Phenyl-1,2,4-triazol-3-yl |
| Isopropyl | Phenyl |
| Isopropyl | 2-Chlorophenyl |
| Isopropyl | 3-Chlorophenyl |
| Isopropyl | 4-Chlorophenyl |
| Isopropyl | 2,6-Dichlorophenyl |
| Isopropyl | 2,4-Dichlorophenyl |
| Isopropyl | 2-Methylphenyl |
| Isopropyl | 3-Methylphenyl |
| Isopropyl | 4-Methylphenyl |
| Isopropyl | 2,5-Dimethylphenyl |
| Isopropyl | 2,4,6-Trimethylphenyl |
| Isopropyl | 3-Methoxyphenyl |
| Isopropyl | 4-Methoxyphenyl |
| Isopropyl | 2-Nitrophenyl |
| Isopropyl | 3-Nitrophenyl |
| Isopropyl | 4-Nitrophenyl |
| Isopropyl | 2-Bromophenyl |
| Isopropyl | 4-Bromophenyl |
| Isopropyl | 4-Cyanophenyl |
| Isopropyl | 4-Dimethylaminophenyl |
| Isopropyl | 4-Carbomethoxyphenyl |
| Isopropyl | 2-Methoxy-5-nitrophenyl |
| Isopropyl | 2-Trifluoromethylphenyl |
| Isopropyl | 4-Trifluoromethylphenyl |
| Isopropyl | 4-tert-Butylphenyl |
| Isopropyl | 2-Chloro-6-nitrophenyl |
| Isopropyl | 2-Fluorophenyl |
| Isopropyl | 4-Fluorophenyl |
| Isopropyl | 2,3,4,5,6-Pentafluorophenyl |
| Isopropyl | 2-Chloro-3-isopropylphenyl |
| Isopropyl | 2,6-Difluorophenyl |
| Isopropyl | 2-Chloro-3-trifluoromethylphenyl |
| Isopropyl | 2-Biphenyl |
| Isopropyl | 3-Biphenyl |
| Isopropyl | 4-Biphenyl |
| Isopropyl | 4'-Chlorobiphenyl-4-yl |
| Isopropyl | 3-Phenoxyphenyl |
| Isopropyl | 3,4-Methylenedioxyphenyl |
| Isopropyl | 1-Naphthyl |
| Isopropyl | 2-Naphthyl |
| Isopropyl | 9-Anthracenyl |
| Isopropyl | 2-Furyl |
| Isopropyl | 4-Isopropylfuran-2-yl |
| Isopropyl | 5-Carboxymethylfuran-2-yl |
| Isopropyl | 5-Methylfuran-2-yl |
| Isopropyl | 5-Trifluoromethylfuran-2-yl |
| Isopropyl | 3-Furyl |
| Isopropyl | 2-Thienyl |
| Isopropyl | 5-Chlorothien-2-yl |
| Isopropyl | 3-Thienyl |
| Isopropyl | 5-Bromothien-3-yl |
| Isopropyl | Benzothiophen-3-yl |
| Isopropyl | 2-Pyrrolyl |
| Isopropyl | 1-Phenylpyrrol-2-yl |
| Isopropyl | 3-Pyrrolyl |
| Isopropyl | Isoxazol-5-yl |
| Isopropyl | Isoxazol-3-yl |
| Isopropyl | 3-Phenylisoxazol-5-yl |
| Isopropyl | 3-Methylisoxazol-5-yl |
| Isopropyl | 4-Chloro-3-methylisoxazol-5-yl |
| Isopropyl | 4-Chloro-3-isopropylisoxazol-5-yl |
| Isopropyl | 4-Chloro-3-sec-butylisoxazol-5-yl |
| Isopropyl | 4-Chloro-3-tert-butylisoxazol-5-yl |
| Isopropyl | 4-Chloro-3-cyclohexylisoxazol-5-yl |
| Isopropyl | 4-Chloro-3-phenylisoxazol-5-yl |
| Isopropyl | 4-Chloro-3-(4-methylphenyl)isoxazol-5-yl |
| Isopropyl | 4-Chloro-3-(4-chlorophenyl)-isoxazol-5-yl |
| Isopropyl | 4-Chloro-3-(4-fluorophenyl)isoxazol-5-yl |
| Isopropyl | 4-Chloro-3-(4-trifluoromethylphenyl)-isoxazol-5-yl |
| Isopropyl | 4-Chloro-3-(2,6-difluorophenyl)-isoxazol-5-yl |
| Isopropyl | 4-Chloro-3-phenylisoxazol-5-yl |
| Isopropyl | 3,5-Dimethylisoxazol-4-yl |
| Isopropyl | 3-Carboxyethylisoxazol-5-yl |
| Isopropyl | 3-(3,4-Dichlorophenyl)isoxazol-5-yl |
| Isopropyl | 3-(3-Nitrophenyl)isoxazol-5-yl |
| Isopropyl | 3-(4-Chlorophenyl)isoxazol-5-yl |
| Isopropyl | 3-(4-Fluorophenyl)isoxazol-5-yl |
| Isopropyl | 3-(3,4-Difluorophenyl)isoxazol-5-yl |
| Isopropyl | 3-Phenylisoxazol-5-yl |
| Isopropyl | 3-Methoxymethylisoxazol-5-yl |
| Isopropyl | 3-Methylisoxazol-5-yl |
| Isopropyl | 3-Ethylisoxazol-5-yl |
| Isopropyl | 3-n-Propylisoxazol-5-yl |
| Isopropyl | 3-n-Butylisoxazol-5-yl |
| Isopropyl | 3-Isopropylisoxazol-5-yl |
| Isopropyl | 3-Isobutylisoxazol-5-yl |
| Isopropyl | 3-tert-Butylisoxazol-5-yl |
| Isopropyl | 3-sec-Butylisoxazol-5-yl |
| Isopropyl | 3-Methoxyisoxazol-5-yl |
| Isopropyl | 3-Cyclopropylisoxazol-5-yl |
| Isopropyl | 3-Cyclopropylisoxazol-4-yl |
| Isopropyl | 3-Cyclohexylisoxazol-5-yl |
| Isopropyl | 3-(3-Methylphenyl)isoxazol-5-yl |
| Isopropyl | 3-(3,4-Dichlorophenyl)isoxazol-5-yl |
| Isopropyl | 3-(2,6-Dichlorophenyl)isoxazol-5-yl |
| Isopropyl | 3-(3-Nitrophenyl)isoxazol-5-yl |
| Isopropyl | 3-(2-Methoxyphenyl)isoxazol-5-yl |
| Isopropyl | 3-(4-Trifluoromethylphenyl)isoxazol-5-yl |
| Isopropyl | 3-(3-Trifluoromethylphenyl)isoxazol-5-yl |
| Isopropyl | 3-(4-Bromophenyl)isoxazol-5-yl |
| Isopropyl | 3-(3-Chlorophenyl)isoxazol-5-yl |
| Isopropyl | 3-(2-Chlorophenyl)isoxazol-5-yl |
| Isopropyl | 3-(3-Fluorophenyl)isoxazol-5-yl |
| Isopropyl | 3-(3-Phenoxyphenyl)isoxazol-5-yl |
| Isopropyl | 3-(2,6-Difluorophenyl)isoxazol-5-yl |
| Isopropyl | 3-Trifluoromethylisoxazol-5-yl |
| Isopropyl | 3-(2-Naphthyl)isoxazol-5-yl |

TABLE A-continued

| | $R^1R^2CH-ON=C(CN)-R^3$ $R^1 = H$ | I |
|---|---|---|
| $R^3$ | $R^2$ | |
| Isopropyl | 3-(1-Naphthyl)isoxazol-5-yl | |
| Isopropyl | 3-tert-Butyl-5-phenylisoxazol-4-yl | |
| Isopropyl | 5-Methylisoxazol-4-yl | |
| Isopropyl | 4-Ethoxycarbonylisoxazol-5-yl | |
| Isopropyl | 5-Cyclopropylisoxazol-3-yl | |
| Isopropyl | 4-Chloro-3-(4-bromophenyl)isoxazol-5-yl | |
| Isopropyl | 4-Chloro-3-(3-chlorophenyl)isoxazol-5-yl | |
| Isopropyl | 4-Chloro-3-(3-fluorophenyl)isoxazol-5-yl | |
| Isopropyl | 4-Chloro-3-(2-chlorophenyl)isoxazol-5-yl | |
| Isopropyl | 2-Phenyloxazol-4-yl | |
| Isopropyl | 2-(4-Fluorophenyl)oxazol-4-yl | |
| Isopropyl | 2-(4-Chlorophenyl)oxazol-4-yl | |
| Isopropyl | 2-(4-Bromophenyl)oxazol-4-yl | |
| Isopropyl | 2-(3-Chlorophenyl)oxazol-4-yl | |
| Isopropyl | 2-(4-Methylphenyl)oxazol-4-yl | |
| Isopropyl | 2-tert-Butyloxazol-4-yl | |
| Isopropyl | 2-(2,4-Dichlorophenyl)oxazol-4-yl | |
| Isopropyl | 2-(4-Methoxyphenyl)oxazol-4-yl | |
| Isopropyl | 2-(4-Chlorophenyl)-5-bromooxazol-4-yl | |
| Isopropyl | 2-Cyclopropyloxazol-4-yl | |
| Isopropyl | 2-Isopropyloxazol-4-yl | |
| Isopropyl | 2-tert-Butyloxazol-4-yl | |
| Isopropyl | 2-tert-Butyloxazol-5-y | |
| Isopropyl | 2-Benzyloxazol-4-yl | |
| Isopropyl | 2-Methylthiazol-4-yl | |
| Isopropyl | 2-Isopropylthiazol-4-yl | |
| Isopropyl | 2-Cyclopropylthiazol-4-yl | |
| Isopropyl | 4-(4-Methoxyphenyl)thiazol-2-yl | |
| Isopropyl | 2-Acetamidothiazol-4-yl | |
| Isopropyl | 2-Phenylthiazol-4-yl | |
| Isopropyl | 2-(2-Chlorophenyl)thiazol-4-yl | |
| Isopropyl | 2-(4-Chlorophenyl)thiazol-4-yl | |
| Isopropyl | 2-(2,4-Dichlorophenyl)thiazol-4-yl | |
| Isopropyl | 2-(2,6-Dichlorophenyl)thiazol-4-yl | |
| Isopropyl | 2-(3-Fluorophenyl)thiazol-4-yl | |
| Isopropyl | 2-(3-Chlorophenyl)thiazol-4-yl | |
| Isopropyl | 2-(4-Trifluoromethylphenyl)thiazol-4-yl | |
| Isopropyl | 2-(3-Methylphenyl)thiazol-4-yl | |
| Isopropyl | 2-(4-Methoxyphenyl)thiazol-4-yl | |
| Isopropyl | 2-Methylthiazol-4-yl | |
| Isopropyl | 2-(4-Fluorophenyl)thiazol-4-yl | |
| Isopropyl | 2-Methyl-1,3,4-thiadiazol-5-yl | |
| Isopropyl | 2-Phenyl-1,3,4-thiadiazol-5-yl | |
| Isopropyl | 2-Cyclopropyl-1,3,4-thiadiazol-5-yl | |
| Isopropyl | 2-Isopropyl-1,3,4-thiadiazol-5-yl | |
| Isopropyl | 2-Phenoxymethyl-1,3,4-thiadiazol-5-yl | |
| Isopropyl | 2-(4-Chlorophenyl)-1,3,4-thiadiazol-5-yl | |
| Isopropyl | 2-Phenyl-1,3,4-oxadiazol-5-yl | |
| Isopropyl | 2-(4-Methoxyphenyl)-1,3,4-oxadiazol-5-yl | |
| Isopropyl | 2-(2-Methylphenyl)-1,3,4-oxadiazol-5-yl | |
| Isopropyl | 2-(4-Methylphenyl)-1,3,4-oxadiazol-5-yl | |
| Isopropyl | 2-(4-Cyanophenyl)-1,3,4-oxadiazol-5-yl | |
| Isopropyl | 2-(4-Nitrophenyl)-1,3,4-oxadiazol-5-yl | |
| Isopropyl | 2-(3-Nitrophenyl)-1,3,4-oxadiazol-5-yl | |
| Isopropyl | 2-(2-Chlorophenyl)1,3,4-oxadiazol-5-yl | |
| Isopropyl | 2-(2,4-Dichlorophenyl)-1,3,4-oxadiazol-5-yl | |
| Isopropyl | 2-Ethyl-1,3,4-oxadiazol-5-yl | |
| Isopropyl | 2-Isopropyl-1,3,4-oxadiazol-5-yl | |
| Isopropyl | 2-Cyclopropyl-1,3,4-oxadiazol-5-yl | |
| Isopropyl | 3-(4-Chlorophenyl)-1,2,4-oxadiazol-5-yl | |
| Isopropyl | 3-(4-Fluorophenyl)-1,2,4-oxadiazol-5-yl | |
| Isopropyl | 3-n-Propyl-1,2,4-oxadiazol-5-yl | |
| Isopropyl | 3-Ethyl-1,2,4-oxadiazol-5-yl | |
| Isopropyl | 3-Methyl-1,2,4-oxadiazol-5-yl | |
| Isopropyl | 3-Isopropyl-1,2,4-oxadiazol-5-yl | |
| Isopropyl | 3-tert-Butylpropyl-1,2,4-oxadiazol-5-yl | |
| Isopropyl | 3-Cyclopropyl-1,2,4-oxadiazol-5-yl | |
| Isopropyl | 3-Cyclohexyl-1,2,4-oxadiazol-5-yl | |
| Isopropyl | 5-Isopropyl-1,2,4-oxadiazol-3-yl | |
| Isopropyl | 5-(4-Chlorophenyl)-1,2,4-oxadiazol-3-yl | |
| Isopropyl | 3-Carbomethoxy-1,2,4-oxadiazol-5-yl | |
| Isopropyl | 5-Chloro-1,2,3-thiadiazol-4-yl | |
| Isopropyl | 5-Methyl-1,2,3-thiadiazol-4-yl | |
| Isopropyl | 4-Methyl-1,2,3-thiadiazol-5-yl | |
| Isopropyl | 5-Chloro-1,2,4-thiadiazol-3-yl | |
| Isopropyl | Benzimidazol-2-yl | |
| Isopropyl | Benzoxazol-2-yl | |
| Isopropyl | Benzthiophen-3-yl | |
| Isopropyl | Benzofuran-2-yl | |
| Isopropyl | 5-Chlorobenzofuran-2-yl | |
| Isopropyl | 5-Chlorobenzoxazol-2-yl | |
| Isopropyl | 1-Methylpyrazol-3-yl | |
| Isopropyl | 1-(4-Methylphenyl)pyrazol-4-yl | |
| Isopropyl | 1,3-Dimethylpyrazol-5-yl | |
| Isopropyl | 1-Phenyl-3-ethoxypyrazol-5-yl | |
| Isopropyl | 1-Phenyl-3-methylpyrazol-5-yl | |
| Isopropyl | 3-Cyclopropyl-1-methyl-1,2,4-triazol-5-yl | |
| Isopropyl | 3-Cyclohexyl-1-methyl-1,2,4-triazol-5-yl | |
| Isopropyl | 1,3-Dimethyl-1,2,4-triazol-5-yl | |
| Isopropyl | 5-Phenyl-1,2,4-triazol-3-yl | |
| Cyclopropyl | Phenyl | |
| Cyclopropyl | 2-Chlorophenyl | |
| Cyclopropyl | 3-Chlorophenyl | |
| Cyclopropyl | 4-Chlorophenyl | |
| Cyclopropyl | 2,6-Dichlorophenyl | |
| Cyclopropyl | 2,4-Dichlorophenyl | |
| Cyclopropyl | 2-Methylphenyl | |
| Cyclopropyl | 3-Methylphenyl | |
| Cyclopropyl | 4-Methylphenyl | |
| Cyclopropyl | 2,5-Dimethylphenyl | |
| Cyclopropyl | 2,4,6-Trimethylphenyl | |
| Cyclopropyl | 3-Methoxyphenyl | |
| Cyclopropyl | 4-Methoxyphenyl | |
| Cyclopropyl | 2-Nitrophenyl | |
| Cyclopropyl | 3-Nitrophenyl | |
| Cyclopropyl | 4-Nitrophenyl | |
| Cyclopropyl | 2-Bromophenyl | |
| Cyclopropyl | 4-Bromophenyl | |
| Cyclopropyl | 4-Cyanophenyl | |
| Cyclopropyl | 4-Dimethylaminophenyl | |
| Cyclopropyl | 4-Carbomethoxyphenyl | |
| Cyclopropyl | 2-Methoxy-5-nitrophenyl | |
| Cyclopropyl | 2-Trifluoromethylphenyl | |
| Cyclopropyl | 4-Trifluoromethylphenyl | |
| Cyclopropyl | 4-tert-Butylphenyl | |
| Cyclopropyl | 2-Chloro-6-nitrophenyl | |
| Cyclopropyl | 2-Fluorophenyl | |
| Cyclopropyl | 4-Fluorophenyl | |
| Cyclopropyl | 2,3,4,5,6-Pentafluorophenyl | |
| Cyclopropyl | 2-Chloro-3-isopropylphenyl | |
| Cyclopropyl | 2,6-Difluorophenyl | |
| Cyclopropyl | 2-Chloro-3-trifluoromethylphenyl | |
| Cyclopropyl | 2-Biphenyl | |
| Cyclopropyl | 3-Biphenyl | |
| Cyclopropyl | 4-Biphenyl | |
| Cyclopropyl | 4'-Chlorobiphenyl-4-yl | |
| Cyclopropyl | 3-Phenoxyphenyl | |
| Cyclopropyl | 3,4-Methylenedioxyphenyl | |
| Cyclopropyl | 1-Naphthyl | |
| Cyclopropyl | 2-Naphthyl | |
| Cyclopropyl | 9-Anthracenyl | |
| Cyclopropyl | 2-Furyl | |
| Cyclopropyl | 4-Isopropylfuran-2-yl | |
| Cyclopropyl | 5-Carboxymethylfuran-2-yl | |
| Cyclopropyl | 5-Methylfuran-2-yl | |
| Cyclopropyl | 5-Trifluoromethylfuran-2-yl | |
| Cyclopropyl | 3-Furyl | |
| Cyclopropyl | 2-Thienyl | |
| Cyclopropyl | 5-Chlorothien-2-yl | |
| Cyclopropyl | 3-Thienyl | |
| Cyclopropyl | 5-Bromothien-3-yl | |
| Cyclopropyl | Benzothiophen-3-yl | |

TABLE A-continued $R^1R^2CH-ON=C(CN)-R^3 \quad R^1 = H \quad I$

| $R^3$ | $R^2$ |
|---|---|
| Cyclopropyl | 2-Pyrrolyl |
| Cyclopropyl | 1-Phenylpyrrol-2-yl |
| Cyclopropyl | 3-Pyrrolyl |
| Cyclopropyl | Isoxazol-5-yl |
| Cyclopropyl | Isoxazol-3-yl |
| Cyclopropyl | 3-Phenylisoxazol-5-yl |
| Cyclopropyl | 3-Methylisoxazol-5-yl |
| Cyclopropyl | 4-Chloro-3-methylisoxazol-5-yl |
| Cyclopropyl | 4-Chloro-3-isopropylisoxazol-5-yl |
| Cyclopropyl | 4-Chloro-3-sec-butylisoxazol-5-yl |
| Cyclopropyl | 4-Chloro-3-tert-butylisoxazol-5-yl |
| Cyclopropyl | 4-Chloro-3-cyclohexylisoxazol-5-yl |
| Cyclopropyl | 4-Chloro-3-phenylisoxazol-5-yl |
| Cyclopropyl | 4-Chloro-3-(4-methylphenyl)isoxazol-5-yl |
| Cyclopropyl | 4-Chloro-3-(4-chlorophenyl)isoxazol-5-yl |
| Cyclopropyl | 4-Chloro-3-(4-fluorophenyl)isoxazol-5-yl |
| Cyclopropyl | 4-Chloro-3-(4-trifluoromethylphenyl)-isoxazol-5-yl |
| Cyclopropyl | 4-Chloro-3-(2,6-difluorophenyl)-isoxazol-5-yl |
| Cyclopropyl | 4-Chloro-3-phenylisoxazol-5-yl |
| Cyclopropyl | 3,5-Dimethylisoxazol-4-yl |
| Cyclopropyl | 3-Carboxyethylisoxazol-5-yl |
| Cyclopropyl | 3-(3,4-Dichlorophenyl)isoxazol-5-yl |
| Cyclopropyl | 3-(3-Nitrophenyl)isoxazol-5-yl |
| Cyclopropyl | 3-(4-Chlorophenyl)isoxazol-5-yl |
| Cyclopropyl | 3-(4-Fluorophenyl)isoxazol-5-yl |
| Cyclopropyl | 3-(3,4-Difluorophenyl)isoxazol-5-yl |
| Cyclopropyl | 3-Phenylisoxazol-5-yl |
| Cyclopropyl | 3-Methoxymethylisoxazol-5-yl |
| Cyclopropyl | 3-Methylisoxazol-5-yl |
| Cyclopropyl | 3-Ethylisoxazol-5-yl |
| Cyclopropyl | 3-n-Propylisoxazol-5-yl |
| Cyclopropyl | 3-n-Butylisoxazol-5-yl |
| Cyclopropyl | 3-Isopropylisoxazol-5-yl |
| Cyclopropyl | 3-Isobutylisoxazol-5-yl |
| Cyclopropyl | 3-tert-Butylisoxazol-5-yl |
| Cyclopropyl | 3-sec-Butylisoxazol-5-yl |
| Cyclopropyl | 3-Methoxyisoxazol-5-yl |
| Cyclopropyl | 3-Cyclopropylisoxazol-5-yl |
| Cyclopropyl | 3-Cyclopropylisoxazol-4-yl |
| Cyclopropyl | 3-Cyclohexylisoxazol-5-yl |
| Cyclopropyl | 3-(3-Methylphenyl)isoxazol-5-yl |
| Cyclopropyl | 3-(3,4-Dichlorophenyl)isoxazol-5-yl |
| Cyclopropyl | 3-(2,6-Dichlorophenyl)isoxazol-5-yl |
| Cyclopropyl | 3-(3-Nitrophenyl)isoxazol-5-yl |
| Cyclopropyl | 3-(2-Methoxyphenyl)isoxazol-5-yl |
| Cyclopropyl | 3-(4-Trifluoromethylphenyl)isoxazol-5-yl |
| Cyclopropyl | 3-(3-Trifluoromethylphenyl)isoxazol-5-yl |
| Cyclopropyl | 3-(4-Bromophenyl)isoxazol-5-yl |
| Cyclopropyl | 3-(3-Chlorophenyl)isoxazol-5-yl |
| Cyclopropyl | 3-(2-Chlorophenyl)isoxazol-5-yl |
| Cyclopropyl | 3-(3-Fluorophenyl)isoxazol-5-yl |
| Cyclopropyl | 3-(3-Phenoxyphenyl)isoxazol-5-yl |
| Cyclopropyl | 3-(2,6-Difluorophenyl)isoxazol-5-yl |
| Cyclopropyl | 3-Trifluoromethylisoxazol-5-yl |
| Cyclopropyl | 3-(2-Naphthyl)isoxazol-5-yl |
| Cyclopropyl | 3-(1-Naphthyl)isoxazol-3-yl |
| Cyclopropyl | 3-tert-Butyl-5-phenylisoxazol-4-yl |
| Cyclopropyl | 5-Methylisoxazol-4-yl |
| Cyclopropyl | 4-Ethoxycarbonylisoxazol-5-yl |
| Cyclopropyl | 5-Cyclopropylisoxazol-3-yl |
| Cyclopropyl | 4-Chloro-3-(4-bromophenyl)isoxazol-5-yl |
| Cyclopropyl | 4-Chloro-3-(3-chlorophenyl)isoxazol-5-yl |
| Cyclopropyl | 4-Chloro-3-(3-fluorophenyl)isoxazol-5-yl |
| Cyclopropyl | 4-Chloro-3-(2-chlorophenyl)isoxazol-5-yl |
| Cyclopropyl | 2-Phenyloxazol-4-yl |
| Cyclopropyl | 2-(4-Fluorophenyl)oxazol-4-yl |
| Cyclopropyl | 2-(4-Chlorophenyl)oxazol-4-yl |
| Cyclopropyl | 2-(4-Bromophenyl)oxazol-4-yl |
| Cyclopropyl | 2-(3-Chlorophenyl)oxazol-4-yl |
| Cyclopropyl | 2-(4-Methylphenyl)oxazol-4-yl |
| Cyclopropyl | 2-tert-Butyloxazol-4-yl |
| Cyclopropyl | 2-(2,4-Dichlorophenyl)oxazol-4-yl |
| Cyclopropyl | 2-(4-Methoxyphenyl)oxazol-4-yl |
| Cyclopropyl | 2-(4-Chlorophenyl)-5-bromooxazol-4-yl |
| Cyclopropyl | 2-Cyclopropyloxazol-4-yl |
| Cyclopropyl | 2-Isopropyloxazol-4-yl |
| Cyclopropyl | 2-tert-Butyloxazol-4-yl |
| Cyclopropyl | 2-tert-Butyloxazol-5-y |
| Cyclopropyl | 2-Benzyloxazol-4-yl |
| Cyclopropyl | 2-Methylthiazol-4-yl |
| Cyclopropyl | 2-Isopropylthiazol-4-yl |
| Cyclopropyl | 2-Cyclopropylthiazol-4-yl |
| Cyclopropyl | 4-(4-Methoxyphenyl)thiazol-2-yl |
| Cyclopropyl | 2-Acetamidothiazol-4-yl |
| Cyclopropyl | 2-Phenylthiazol-4-yl |
| Cyclopropyl | 2-(2-Chlorophenyl)thiazol-4-yl |
| Cyclopropyl | 2-(4-Chlorophenyl)thiazol-4-yl |
| Cyclopropyl | 2-(2,4-Dichlorophenyl)thiazol-4-yl |
| Cyclopropyl | 2-(2,6-Dichlorophenyl)thiazol-4-yl |
| Cyclopropyl | 2-(3-Fluorophenyl)thiazol-4-yl |
| Cyclopropyl | 2-(3-Chlorophenyl)thiazol-4-yl |
| Cyclopropyl | 2-(4-Trifluoromethylphenyl)thiazol-4-yl |
| Cyclopropyl | 2-(3-Methylphenyl)thiazol-4-yl |
| Cyclopropyl | 2-(4-Methoxyphenyl)thiazol-4-yl |
| Cyclopropyl | 2-Methylthiazol-4-yl |
| Cyclopropyl | 2-(4-Fluorophenyl)thiazol-4-yl |
| Cyclopropyl | 2-Methyl-1,3,4-thiadiazol-5-yl |
| Cyclopropyl | 2-Phenyl-1,3,4-thiadiazol-5-yl |
| Cyclopropyl | 2-Cyclopropyl-1,3,4-thiadiazol-5-yl |
| Cyclopropyl | 2-Isopropyl-1,3,4-thiadiazol-5-yl |
| Cyclopropyl | 2-Phenoxymethyl-1,3,4-thiadiazol-5-yl |
| Cyclopropyl | 2-(4-Chlorophenyl)-1,3,4-thiadiazol-5-yl |
| Cyclopropyl | 2-Phenyl-1,3,4-oxadiazol-5-yl |
| Cyclopropyl | 2-(4-Methoxyphenyl)-1,3,4-oxadiazol-5-yl |
| Cyclopropyl | 2-(2-Methylphenyl)-1,3,4-oxadiazol-5-yl |
| Cyclopropyl | 2-(4-Methylphenyl)-1,3,4-oxadiazol-5-yl |
| Cyclopropyl | 2-(4-Cyanophenyl)-1,3,4-oxadiazol-5-yl |
| Cyclopropyl | 2-(4-Nitrophenyl)-1,3,4-oxadiazol-5-yl |
| Cyclopropyl | 2-(3-Nitrophenyl)-1,3,4-oxadiazol-5-yl |
| Cyclopropyl | 2-(2-Chlorophenyl)-1,3,4-oxadiazol-5-yl |
| Cyclopropyl | 2-(2,4-Dichlorophenyl)1,3,4-oxadiazol-5-yl |
| Cyclopropyl | 2-Ethyl-1,3,4-oxadiazol-5-yl |
| Cyclopropyl | 2-Isopropyl-1,3,4-oxadiazol-5-yl |
| Cyclopropyl | 2-Cyclopropyl-1,3,4-oxadiazol-5-yl |
| Cyclopropyl | 3-(4-Chlorophenyl)-1,2,4-oxadiazol-5-yl |
| Cyclopropyl | 3-(4-Fluorophenyl)-1,2,4-oxadiazol-5-yl |
| Cyclopropyl | 3-n-Propyl-1,2,4-oxadiazol-5-yl |
| Cyclopropyl | 3-Ethyl-1,2,4-oxadiazol-5-yl |
| Cyclopropyl | 3-Methyl-1,2,4-oxadiazol-5-yl |
| Cyclopropyl | 3-Isopropyl-1,2,4-oxadiazol-5-yl |
| Cyclopropyl | 3-tert-Butylpropyl-1,2,4-oxadiazol-5-yl |
| Cyclopropyl | 3-Cyclopropyl-1,2,4-oxadiazol-5-yl |
| Cyclopropyl | 3-Cyclohexyl-1,2,4-oxadiazol-5-yl |
| Cyclopropyl | 5-Isopropyl-1,2,4-oxadiazol-3-yl |
| Cyclopropyl | 5-(4-Chlorophenyl)-1,2,4-oxadiazol-3-yl |
| Cyclopropyl | 3-Carbomethoxy-1,2,4-oxadiazol-5-yl |
| Cyclopropyl | 5-Chloro-1,2,3-thiadiazol-4-yl |
| Cyclopropyl | 5-Methyl-1,2,3-thiadiazol-4-yl |
| Cyclopropyl | 4-Methyl-1,2,3-thiadiazol-5-yl |
| Cyclopropyl | 5-Chloro-1,2,4-thiadiazol-3-yl |
| Cyclopropyl | Benzimidazol-2-yl |
| Cyclopropyl | Benzoxazol-2-yl |
| Cyclopropyl | Benzthiophen-3-yl |
| Cyclopropyl | Benzofuran-2-yl |
| Cyclopropyl | 5-Chlorobenzofuran-2-yl |
| Cyclopropyl | 5-Chlorobenzoxazol-2-yl |

TABLE A-continued

R¹R²CH—ON=C(CN)—R³    R¹ = H    I

| R³ | R² |
|---|---|
| Cyclopropyl | 1-Methylpyrazol-3-yl |
| Cyclopropyl | 1-(4-Methylphenyl)pyrazol-4-yl |
| Cyclopropyl | 1,3-Dimethylpyrazol-5-yl |
| Cyclopropyl | 1-Phenyl-3-ethoxypyrazol-5-yl |
| Cyclopropyl | 1-Phenyl-3-methylpyrazol-5-yl |
| Cyclopropyl | 3-Cyclopropyl-1-methyl-1,2,4-triazol-5-yl |
| Cyclopropyl | 3-Cyclohexyl-1-methyl-1,2,4-triazol-5-yl |
| Cyclopropyl | 1,3-Dimethyl-1,2,4-triazol-5-yl |
| Cyclopropyl | 5-Phenyl-1,2,4-triazol-3-yl |
| 2-Tetrahydropyranyl | Phenyl |
| 2-Tetrahydropyranyl | 2-Chlorophenyl |
| 2-Tetrahydropyranyl | 3-Chlorophenyl |
| 2-Tetrahydropyranyl | 4-Chlorophenyl |
| 2-Tetrahydropyranyl | 2,6-Dichlorophenyl |
| 2-Tetrahydropyranyl | 2,4-Dichlorophenyl |
| 2-Tetrahydropyranyl | 2-Methylphenyl |
| 2-Tetrahydropyranyl | 3-Methylphenyl |
| 2-Tetrahydropyranyl | 4-Methylphenyl |
| 2-Tetrahydropyranyl | 2,5-Dimethylphenyl |
| 2-Tetrahydropyranyl | 2,4,6-Trimethylphenyl |
| 2-Tetrahydropyranyl | 3-Methoxyphenyl |
| 2-Tetrahydropyranyl | 4-Methoxyphenyl |
| 2-Tetrahydropyranyl | 2-Nitrophenyl |
| 2-Tetrahydropyranyl | 3-Nitrophenyl |
| 2-Tetrahydropyranyl | 4-Nitrophenyl |
| 2-Tetrahydropyranyl | 2-Bromophenyl |
| 2-Tetrahydropyranyl | 4-Bromophenyl |
| 2-Tetrahydropyranyl | 4-Cyanophenyl |
| 2-Tetrahydropyranyl | 4-Dimethylaminophenyl |
| 2-Tetrahydropyranyl | 4-Carbomethoxyphenyl |
| 2-Tetrahydropyranyl | 2-Methoxy-5-nitrophenyl |
| 2-Tetrahydropyranyl | 2-Trifluoromethylphenyl |
| 2-Tetrahydropyranyl | 4-Trifluoromethylphenyl |
| 2-Tetrahydropyranyl | 4-tert-Butylphenyl |
| 2-Tetrahydropyranyl | 2-Chloro-6-nitrophenyl |
| 2-Tetrahydropyranyl | 2-Fluorophenyl |
| 2-Tetrahydropyranyl | 4-Fluorophenyl |
| 2-Tetrahydropyranyl | 2,3,4,5,6-Pentafluorophenyl |
| 2-Tetrahydropyranyl | 2-Chloro-3-isopropylphenyl |
| 2-Tetrahydropyranyl | 2,6-Difluorophenyl |
| 2-Tetrahydropyranyl | 2-Chloro-3-trifluoromethylphenyl |
| 2-Tetrahydropyranyl | 2-Biphenyl |
| 2-Tetrahydropyranyl | 3-Biphenyl |
| 2-Tetrahydropyranyl | 4-Biphenyl |
| 2-Tetrahydropyranyl | 4'-Chlorobiphenyl-4-yl |
| 2-Tetrahydropyranyl | 3-Phenoxyphenyl |
| 2-Tetrahydropyranyl | 3,4-Methylenedioxyphenyl |
| 2-Tetrahydropyranyl | 1-Naphthyl |
| 2-Tetrahydropyranyl | 2-Naphthyl |
| 2-Tetrahydropyranyl | 9-Anthracenyl |
| 2-Tetrahydropyranyl | 2-Furyl |
| 2-Tetrahydropyranyl | 4-Isopropylfuran-2-yl |
| 2-Tetrahydropyranyl | 5-Carboxymethylfuran-2-yl |
| 2-Tetrahydropyranyl | 5-Methylfuran-2-yl |
| 2-Tetrahydropyranyl | 5-Trifluoromethylfuran-2-yl |
| 2-Tetrahydropyranyl | 3-Furyl |
| 2-Tetrahydropyranyl | 2-Thienyl |
| 2-Tetrahydropyranyl | 5-Chlorothien-2-yl |
| 2-Tetrahydropyranyl | 3-Thienyl |
| 2-Tetrahydropyranyl | 5-Bromothien-3-yl |
| 2-Tetrahydropyranyl | Benzothiophen-3-yl |
| 2-Tetrahydropyranyl | 2-Pyrrolyl |
| 2-Tetrahydropyranyl | 1-Phenylpyrrol-2-yl |
| 2-Tetrahydropyranyl | 3-Pyrrolyl |
| 2-Tetrahydropyranyl | Isoxazol-5-yl |
| 2-Tetrahydropyranyl | Isoxazol-3-yl |
| 2-Tetrahydropyranyl | 3-Phenylisoxazol-5-yl |
| 2-Tetrahydropyranyl | 3-Methylisoxazol-5-yl |
| 2-Tetrahydropyranyl | 4-Chloro-3-methylisoxazol-5-yl |
| 2-Tetrahydropyranyl | 4-Chloro-3-isopropylisoxazol-5-yl |
| 2-Tetrahydropyranyl | 4-Chloro-3-sec-butylisoxazol-5-yl |
| 2-Tetrahydropyranyl | 4-Chloro-3-tert-butylisoxazol-5-yl |
| 2-Tetrahydropyranyl | 4-Chloro-3-cyclohexylisoxazol-5-yl |
| 2-Tetrahydropyranyl | 4-Chloro-3-phenylisoxazol-5-yl |
| 2-Tetrahydropyranyl | 4-Chloro-3-(4-methylphenyl)isoxazol-5-yl |
| 2-Tetrahydropyranyl | 4-Chloro-3-(4-chlorophenyl)isoxazol-5-yl |
| 2-Tetrahydropyranyl | 4-Chloro-3-(4-fluorophenyl)isoxazol-5-yl |
| 2-Tetrahydropyranyl | 4-Chloro-3-(4-trifluoromethylphenyl)-isoxazol-5-yl |
| 2-Tetrahydropyranyl | 4-Chloro-3-(2,6-difluorophenyl)-isoxazol-5-yl |
| 2-Tetrahydropyranyl | 4-Chloro-3-phenylisoxazol-5-yl |
| 2-Tetrahydropyranyl | 3,5-Dimethylisoxazol-4-yl |
| 2-Tetrahydropyranyl | 3-Carboxyethylisoxazol-5-yl |
| 2-Tetrahydropyranyl | 3-(3,4-Dichlorophenyl)isoxazol-5-yl |
| 2-Tetrahydropyranyl | 3-(3-Nitrophenyl)isoxazol-5-yl |
| 2-Tetrahydropyranyl | 3-(4-Chlorophenyl)isoxazol-5-yl |
| 2-Tetrahydropyranyl | 3-(4-Fluorophenyl)isoxazol-5-yl |
| 2-Tetrahydropyranyl | 3-(3,4-Difluorophenyl)isoxazol-5-yl |
| 2-Tetrahydropyranyl | 3-Phenylisoxazol-5-yl |
| 2-Tetrahydropyranyl | 3-Methoxymethylisoxazol-5-yl |
| 2-Tetrahydropyranyl | 3-Methylisoxazol-5-yl |
| 2-Tetrahydropyranyl | 3-Ethylisoxazol-5-yl |
| 2-Tetrahydropyranyl | 3-n-Propylisoxazol-5-yl |
| 2-Tetrahydropyranyl | 3-n-Butylisoxazol-5-yl |
| 2-Tetrahydropyranyl | 3-Isopropylisoxazol-5-yl |
| 2-Tetrahydropyranyl | 3-Isobutylisoxazol-5-yl |
| 2-Tetrahydropyranyl | 3-tert-Butylisoxazol-5-yl |
| 2-Tetrahydropyranyl | 3-sec-Butylisoxazol-5-yl |
| 2-Tetrahydropyranyl | 3-Methoxyisoxazol-5-yl |
| 2-Tetrahydropyranyl | 3-Cyclopropylisoxazol-5-yl |
| 2-Tetrahydropyranyl | 3-Cyclopropylisoxazol-4-yl |
| 2-Tetrahydropyranyl | 3-Cyclohexylisoxazol-5-yl |
| 2-Tetrahydropyranyl | 3-(3-Methylphenyl)isoxazol-5-yl |
| 2-Tetrahydropyranyl | 3-(3,4-Dichlorophenyl)isoxazol-5-yl |
| 2-Tetrahydropyranyl | 3-(2,6-Dichlorophenyl)isoxazol-5-yl |
| 2-Tetrahydropyranyl | 3-(3-Nitrophenyl)isoxazol-5-yl |
| 2-Tetrahydropyranyl | 3-(2-Methoxyphenyl)isoxazol-5-yl |
| 2-Tetrahydropyranyl | 3-(4-Trifluoromethylphenyl)isoxazol-5-yl |
| 2-Tetrahydropyranyl | 3-(3-Trifluoromethylphenyl)isoxazol-5-yl |
| 2-Tetrahydropyranyl | 3-(4-Bromophenyl)isoxazol-5-yl |
| 2-Tetrahydropyranyl | 3-(3-Chlorophenyl)isoxazol-5-yl |
| 2-Tetrahydropyranyl | 3-(2-Chlorophenyl)isoxazol-5-yl |
| 2-Tetrahydropyranyl | 3-(3-Fluorophenyl)isoxazol-5-yl |
| 2-Tetrahydropyranyl | 3-(3-Phenoxyphenyl)isoxazol-5-yl |
| 2-Tetrahydropyranyl | 3-(2,6-Difluorophenyl)isoxazol-5-yl |
| 2-Tetrahydropyranyl | 3-Trifluoromethylisoxazol-5-yl |
| 2-Tetrahydropyranyl | 3-(2-Naphthyl)isoxazol-5-yl |
| 2-Tetrahydropyranyl | 3-(1-Naphthyl)isoxazol-5-yl |
| 2-Tetrahydropyranyl | 3-tert-Butyl-5-phenylisoxazol-4-yl |
| 2-Tetrahydropyranyl | 5-Methylisoxtzol-4-yl |
| 2-Tetrahydropyranyl | 4-Ethoxycarbonylisoxazol-5-yl |
| 2-Tetrahydropyranyl | 5-Cyclopropylisoxazol-3-yl |
| 2-Tetrahydropyranyl | 4-Chloro-3-(4-bromophenyl)isoxazol-5-yl |
| 2-Tetrahydropyranyl | 4-Chloro-3-(3-chlorophenyl)isoxazol-5-yl |
| 2-Tetrahydropyranyl | 4-Chloro-3-(3-fluorophenyl)isoxazol-5-yl |
| 2-Tetrahydropyranyl | 4-Chloro-3-(2-chlorophenyl)isoxazol-5-yl |
| 2-Tetrahydropyranyl | 2-Phenyloxazol-4-yl |
| 2-Tetrahydropyranyl | 2-(4-Fluorophenyl)oxazol-4-yl |
| 2-Tetrahydropyranyl | 2-(4-Chlorophenyl)oxazol-4-yl |
| 2-Tetrahydropyranyl | 2-(4-Bromophenyl)oxazol-4-yl |
| 2-Tetrahydropyranyl | 2-(3-Chlorophenyl)oxazol-4-yl |
| 2-Tetrahydropyranyl | 2-(4-Methylphenyl)oxazol-4-yl |
| 2-Tetrahydropyranyl | 2-tert-Butyloxazol-4-yl |
| 2-Tetrahydropyranyl | 2-(2,4-Dichlorophenyl)oxazol-4-yl |
| 2-Tetrahydropyranyl | 2-(4-Methoxyphenyl)oxazol-4-yl |
| 2-Tetrahydropyranyl | 2-(4-Chlorophenyl)-5-bromooxazol-4-yl |
| 2-Tetrahydropyranyl | 2-Cyclopropyloxazol-4-yl |
| 2-Tetrahydropyranyl | 2-Isopropyloxazol-4-yl |
| 2-Tetrahydropyranyl | 2-tert-Butyloxazol-4-yl |

TABLE A-continued $R^1R^2CH—ON═C(CN)—R^3$    $R^1 = H$    I

| $R^3$ | $R^2$ |
|---|---|
| 2-Tetrahydropyranyl | 2-tert-Butyloxazol-5-y |
| 2-Tetrahydropyranyl | 2-Benzyloxazol-4-yl |
| 2-Tetrahydropyranyl | 2-Methylthiazol-4-yl |
| 2-Tetrahydropyranyl | 2-Isopropylthiazol-4-yl |
| 2-Tetrahydropyranyl | 2-Cyclopropylthiazol-4-yl |
| 2-Tetrahydropyranyl | 4-(4-Methoxyphenyl)thiazol-2-yl |
| 2-Tetrahydropyranyl | 2-Acetamidothiazol-4-yl |
| 2-Tetrahydropyranyl | 2-Phenylthiazol-4-yl |
| 2-Tetrahydropyranyl | 2-(2-Chlorophenyl)thiazol-4-yl |
| 2-Tetrahydropyranyl | 2-(4-Chlorophenyl)thiazol-4-yl |
| 2-Tetrahydropyranyl | 2-(2,4-Dichlorophenyl)thiazol-4-yl |
| 2-Tetrahydropyranyl | 2-(2,6-Dichlorophenyl)thiazol-4-yl |
| 2-Tetrahydropyranyl | 2-(3-Fluorophenyl)thiazol-4-yl |
| 2-Tetrahydropyranyl | 2-(3-Chlorophenyl)thiazol-4-yl |
| 2-Tetrahydropyranyl | 2-(4-Trifluoromethylphenyl)thiazol-4-yl |
| 2-Tetrahydropyranyl | 2-(3-Methylphenyl)thiazol-4-yl |
| 2-Tetrahydropyranyl | 2-(4-Methoxyphenyl)thiazol-4-yl |
| 2-Tetrahydropyranyl | 2-Methylthiazol-4-yl |
| 2-Tetrahydropyranyl | 2-(4-Fluorophenyl)thiazol-4-yl |
| 2-Tetrahydropyranyl | 2-Methyl-1,3,4-thiadiazol-5-yl |
| 2-Tetrahydropyranyl | 2-Phenyl-1,3,4-thiadiazol-5-yl |
| 2-Tetrahydropyranyl | 2-Cyclopropyl-1,3,4-thiadiazol-5-yl |
| 2-Tetrahydropyranyl | 2-Isopropyl-1,3,4-thiadiazol-5-yl |
| 2-Tetrahydropyranyl | 2-Phenoxymethyl-1,3,4-thiadiazol-5-yl |
| 2-Tetrahydropyranyl | 2-(4-Chlorophenyl)-1,3,4-thiaiiazol-5-yl |
| 2-Tetrahydropyranyl | 2-Phenyl-1,3,4-oxadiazol-5-yl |
| 2-Tetrahydropyranyl | 2-(4-Methoxyphenyl)-1,3,4-oxadiazol-5-yl |
| 2-Tetrahydropyranyl | 2-(2-Methylphenyl)-1,3,4-oxadiazol-5-yl |
| 2-Tetrahydropyranyl | 2-(4-Methylphenyl)-1,3,4-oxadiazol-5-yl |
| 2-Tetrahydropyranyl | 2-(4-Cyanophenyl)-1,3,4-oxadiazol-5-yl |
| 2-Tetrahydropyranyl | 2-(4-Nitrophenyl)-1,3,4-oxadiazol-5-yl |
| 2-Tetrahydropyranyl | 2-(3-Nitrophenyl)-1,3,4-oxadiazol-5-yl |
| 2-Tetrahydropyranyl | 2-(2-Chlorophenyl)-1,3,4-oxadiazol-5-yl |
| 2-Tetrahydropyranyl | 2-(2,4-Dichlorophenyl)-1,3,4-oxadiazol-5-yl |
| 2-Tetrahydropyranyl | 2-Ethyl-1,3,4-oxadiazol-5-yl |
| 2-Tetrahydropyranyl | 2-Isopropyl-1,3,4-oxadiazol-5-yl |
| 2-Tetrahydropyranyl | 2-Cyclopropyl-1,3,4-oxadiazol-5-yl |
| 2-Tetrahydropyranyl | 3-(4-Chlorophenyl)-1,2,4-oxadiazol-5-yl |
| 2-Tetrahydropyranyl | 3-(4-Fluorophenyl)-1,2,4-oxadiazol-5-yl |
| 2-Tetrahydropyranyl | 3-n-Propyl-1,2,4-oxadiazol-5-yl |
| 2-Tetrahydropyranyl | 3-Ethyl-1,2,4-oxadiazol-5-yl |
| 2-Tetrahydropyranyl | 3-Methyl-1,2,4-oxadiazol-5-yl |
| 2-Tetrahydropyranyl | 3-Isopropyl-1,2,4-oxadiazol-5-yl |
| 2-Tetrahydropyranyl | 3-tert-Butylpropyl-1,2,4-oxadiazol-5-yl |
| 2-Tetrahydropyranyl | 3-Cyclopropyl-1,2,4-oxadiazol-5-yl |
| 2-Tetrahydropyranyl | 3-Cyclohexyl-1,2,4-oxadiazol-5-yl |
| 2-Tetrahydropyranyl | 5-Isopropyl-1,2,4-oxadiazol-3-yl |
| 2-Tetrahydropyranyl | 5-(4-Chlorophenyl)-1,2,4-oxadiazol-3-yl |
| 2-Tetrahydropyranyl | 3-Carbomethoxy-1,2,4-oxadiazol-5-yl |
| 2-Tetrahydropyranyl | 5-Chloro-1,2,3-thiadiazol-4-yl |
| 2-Tetrahydropyranyl | 5-Methyl-1,2,3-thiadiazol-4-yl |
| 2-Tetrahydropyranyl | 4-Methyl-1,2,3-thiadiazol-5-yl |
| 2-Tetrahydropyranyl | 5-Chloro-1,2,4-thiadiazol-3-yl |
| 2-Tetrahydropyranyl | Benzimidazol-2-yl |
| 2-Tetrahydropyranyl | Benzoxazol-2-yl |
| 2-Tetrahydropyranyl | Benzthiophen-3-yl |
| 2-Tetrahydropyranyl | Benzofuran-2-yl |
| 2-Tetrahydropyranyl | 5-Chlorobenzofuran-2-yl |
| 2-Tetrahydropyranyl | 5-Chlorobenzoxazol-2-yl |
| 2-Tetrahydropyranyl | 1-Methylpyrazol-3-yl |
| 2-Tetrahydropyranyl | 1-(4-Methylphenyl)pyrazol-4-yl |
| 2-Tetrahydropyranyl | 1,3-Dimethylpyrazol-5-yl |
| 2-Tetrahydropyranyl | 1-Phenyl-3-ethoxypyrazol-5-yl |
| 2-Tetrahydropyranyl | 1-Phenyl-3-methylpyrazol-5-yl |
| 2-Tetrahydropyranyl | 3-Cyclopropyl-1-methyl-1,2,4-triazol-5-yl |
| 2-Tetrahydropyranyl | 3-Cyclohexyl-1-methyl-1,2,4-triazol-5-yl |
| 2-Tetrahydropyranyl | 1,3-Dimethyl-1,2,4-triazol-5-yl |
| 2-Tetrahydropyranyl | 5-Phenyl-1,2,4-triazol-3-yl |

TABLE B $R^1R^2CH—ON═C(CN)-R^3$    $R^1 = H$    I

| $R^3$ | $R^2$ |
|---|---|
| 2-n-Butoxyprop-2-yl | 2-Chloro-3-isopropylphenyl |
| 2-n-Butoxyprop-2-yl | 2,6-Difluorophenyl |
| 2-n-Butoxyprop-2-yl | 2-Chloro-3-trifluoromethylphenyl |
| 2-n-Butoxyprop-2-yl | 3-Phenylisoxazol-5-yl |
| 2-n-Butoxyprop-2-yl | 3-Methylisoxazol-5-y |
| 2-n-Butoxyprop-2-yl | 4-Chloro-3-methylisoxazol-5-yl |
| 2-n-Butoxyprop-2-yl | 4-Chloro-3-isopropylisoxazol-5-yl |
| 2-n-Butoxyprop-2-yl | 4-Chloro-3-sec-butylisoxazol-5-yl |
| 2-n-Butoxyprop-2-yl | 4-Chloro-3-tert-butylisoxazol-5-yl |
| 2-n-Butoxyprop-2-yl | 4-Chloro-3-cyclohexylisoxazol-5-yi |
| 2-n-Butoxyprop-2-yl | 4-Chloro-3-phenylisoxazol-5-yl |
| 2-n-Butoxyprop-2-yl | 4-Chloro-3-(4-methylphenyl)-isoxazol-5-yl |
| 2-n-Butoxyprop-2-yl | 4-Chloro-3-(4-chlorophenyl)isoxazol-5-yl |
| 2-n-Butoxyprop-2-yl | 4-Chloro-3-(4-fluorophenyl)isoxazol-5-yl |
| 2-n-Butoxyprop-2-yl | 4-Chloro-3-(4-trifluoromethylphenyl)-isoxazol-5-yl |
| 2-n-Butoxyprop-2-yl | 4-Chloro-3-(2,6-difluorophenyl)-isoxazol-5-yl |
| 2-n-Butoxyprop-2-yl | 2-Phenyloxazol-4-yl |
| 2-n-Butoxyprop-2-yl | 2-(4-Fluorophenyl)oxazol-4-yl |
| 2-n-Butoxyprop-2-yl | 2-(4-Chlorophenyl)oxazol-4-yl |
| 2-n-Butoxyprop-2-yl | 2-(4-Bromophenyl)oxazol-4-yl |
| 2-n-Butoxyprop-2-yl | 2-(3-Chlorophenyl)oxazol-4-yl |
| 2-n-Butoxyprop-2-yl | 2-(4-Methylphenyl)oxazol-4-yl |
| 2-n-Butoxyprop-2-yl | 2-tert-Butyloxazol-4-yl |
| 2-n-Butoxyprop-2-yl | 2-(2,4-Dichlorophenyl)oxazol-4-yl |
| 2-n-Butoxyprop-2-yl | 2-(4-Methoxyphenyl)oxazol-4-yl |
| 2-n-Butoxyprop-2-yl | 2-(4-Chlorophenyl)-5-bromooxazol-4-yl |
| 2-Isobutoxyprop-2-yl | 2-Chloro-3-isopropylphenyl |
| 2-Isobutoxyprop-2-yl | 2,6-Difluorophenyl |
| 2-Isobutoxyprop-2-yl | 2-Chloro-3-trifluoromethylphenyl |
| 2-Isobutoxyprop-2-yl | 3-Phenylisoxazol-5-yl |
| 2-Isobutoxyprop-2-yl | 3-Methylisoxazol-5-yl |
| 2-Isobutoxyprop-2-yl | 4-Chloro-3-methylisoxazol-5-yl |
| 2-Isobutoxyprop-2-yl | 4-Chloro-3-isopropylisoxazol-5-yl |
| 2-Isobutoxyprop-2-yl | 4-Chloro-3-sec-butylisoxazol-5-yl |
| 2-Isobutoxyprop-2-yl | 4-Chloro-3-tert-butylisoxazol-5-yl |
| 2-Isobutoxyprop-2-yl | 4-Chloro-3-cyclohexylisoxazol-5-yl |
| 2-Isobutoxyprop-2-yl | 4-Chloro-3-phenylisoxazol-5-yl |
| 2-Isobutoxyprop-2-yl | 4-Chloro-3-(4-methylphenyl)isoxazol-5-yl |
| 2-Isobutoxyprop-2-yl | 4-Chloro-3-(4-chlorophenyl)isoxazol-5-yl |
| 2-Isobutoxyprop-2-yl | 4-Chloro-3-(4-fluorophenyl)isoxazol-5-yl |
| 2-Isobutoxyprop-2-yl | 4-Chloro-3-(4-trifluoromethylphenyl)-isoxazol-5-yl |
| 2-Isobutoxyprop-2-yl | 4-Chloro-3-(2,6-difluorophenyl)-isoxazol-5-yl |
| 2-Isobutoxyprop-2-yl | 2-Phenyloxazol-4-yl |
| 2-Isobutoxyprop-2-yl | 2-(4-Fluorophenyl)oxazol-4-yl |
| 2-Isobutoxyprop-2-yl | 2-(4-Chlorophenyl)oxazol-4-yl |
| 2-Isobutoxyprop-2-yl | 2-(4-Bromophenyl)oxazol-4-yl |
| 2-Isobutoxyprop-2-yl | 2-(3-Chlorophenyl)oxazol-4-yi |
| 2-Isobutoxyprop-2-yl | 2-(4-Methylphenyl)oxazol-4-yl |
| 2-Isobutoxyprop-2-yl | 2-tert-Butyloxazol-4-yl |
| 2-Isobutoxyprop-2-yl | 2-(2,4-Dichlorophenyl)oxazol-4-yl |
| 2-Isobutoxyprop-2-yl | 2-(4-Methoxyphenyl)oxazol-4-yl |
| 2-Isobutoxyprop-2-yl | 2-(4-Chlorophenyl)-5-bromooxazol-4-yl |
| 2-sec-Butoxyprop-2-yl | 2-Chloro-3-isopropylphenyl |
| 2-sec-Butoxyprop-2-yl | 2,6-Difluoiophenyl |
| 2-sec-Butoxyprop-2-yl | 2-Chloro-3-trifluoromethylphenyl |
| 2-sec-Butoxyprop-2-yl | 3-Phenylisoxazol-5-yl |
| 2-sec-Butoxyprop-2-yl | 3-Methylisoxazol-5-yl |
| 2-sec-Butoxyprop-2-yl | 4-Chloro-3-methylisoxazol-5-yl |
| 2-sec-Butoxyprop-2-yl | 4-Chloro-3-isopropylisoxazol-5-yl |
| 2-sec-Butoxyprop-2-yl | 4-Chloro-3-sec-butylisoxazol-5-yl |
| 2-sec-Butoxyprop-2-yl | 4-Chloro-3-tert-butylisoxazol-5-yl |
| 2-sec-Butoxyprop-2-yl | 4-Chloro-3-cyclohexylisoxazol-5-yl |
| 2-sec-Butoxyprop-2-yl | 4-Chloro-3-phenylisoxazol-5-yl |
| 2-sec-Butoxyprop-2-yl | 4-Chloro-3-(4-methylphenyl)isoxazol-5-yl |

TABLE B-continued

| $R^3$ | $R^2$ |
|---|---|
| 2-sec-Butoxyprop-2-yl | 4-Chloro-3-(4-chlorophenyl)isoxazol-5-yl |
| 2-sec-Butoxyprop-2-yl | 4-Chloro-3-(4-fluorophenyl)isoxazol-5-yl |
| 2-sec-Butoxyprop-2-yl | 4-Chloro-3-(4-trifluoromethylphenyl)-isoxazol-5-yl |
| 2-sec-Butoxyprop-2-yl | 4-Chloro-3-(2,6-difluorophenyl)-isoxazol-5-yl |
| 2-sec-Butoxyprop-2-yl | 2-Phenyloxazol-4-yl |
| 2-sec-Butoxyprop-2-yl | 2-(4-Fluorophenyl)oxazol-4-yl |
| 2-sec-Butoxyprop-2-yl | 2-(4-Chlorophenyl)oxazol-4-yl |
| 2-sec-Butoxyprop-2-yl | 2-(4-Bromophenyl)oxazol-4-yl |
| 2-sec-Butoxyprop-2-yl | 2-(3-Chlorophenyl)oxazol-4-yl |
| 2-sec-Butoxyprop-2-yl | 2-(4-Methylphenyl)oxazol-4-yl |
| 2-sec-Butoxyprop-2-yl | 2-tert-Butyloxazol-4-yl |
| 2-sec-Butoxyprop-2-yl | 2-(2,4-Dichlorophenyl)oxazol-4-yl |
| 2-sec-Butoxyprop-2-yl | 2-(4-Methoxyphenyl)oxazol-4-yl |
| 2-sec-Butoxyprop-2-yl | 2-(4-Chlorophenyl)-5-bromooxazol-4-yl |
| 2-tert-Butoxyprop-2-yl | 2-Chloro-3-isopropylphenyl |
| 2-tert-Butoxyprop-2-yl | 2,6-Difluorophenyl |
| 2-tert-Butoxyprop-2-yl | 2-Chloro-3-trifluoromethylphenyl |
| 2-tert-Butoxyprop-2-yl | 3-Phenylisoxazol-5-yl |
| 2-tert-Butoxyprop-2-yl | 3-Methylisoxazol-5-yl |
| 2-tert-Butoxyprop-2-yl | 4-Chloro-3-methylisoxazol-5-yl |
| 2-tert-Butoxyprop-2-yl | 4-Chloro-3-isopropylisoxazol-5-yl |
| 2-tert-Butoxyprop-2-yl | 4-Chloro-3-sec-butylisoxazol-5-yl |
| 2-tert-Butoxyprop-2-yl | 4-Chloro-3-tert-butylisoxazol-5-yl |
| 2-tert-Butoxyprop-2-yl | 4-Chloro-3-cyclohexylisoxazol-5-yl |
| 2-tert-Butoxyprop-2-yl | 4-Chloro-3-phenylisoxazol-5-yl |
| 2-tert-Butoxyprop-2-yl | 4-Chloro-3-(4-methylphenyl)isoxazol-5-yl |
| 2-tert-Butoxyprop-2-yl | 4-Chloro-3-(4-chlorophenyl)isoxazol-5-yl |
| 2-tert-Butoxyprop-2-yl | 4-Chloro-3-(4-fluorophenyl)isoxazol-5-yl |
| 2-tert-Butoxyprop-2-yl | 4-Chloro-3-(4-trifluoromethylphenyl)-isoxazol-5-yl |
| 2-tert-Butoxyprop-2-yl | 4-Chloro-3-(2,6-difluorophenyl)-isoxazol-5-yl |
| 2-tert-Butoxyprop-2-yl | 2-Phenyloxazol-4-yl |
| 2-tert-Butoxyprop-2-yl | 2-(4-Fluorophenyl)oxazol-4-yl |
| 2-tert-Butoxyprop-2-yl | 2-(4-Chlorophenyl)oxazol-4-yl |
| 2-tert-Butoxyprop-2-yl | 2-(4-Bromophenyl)oxazol-4-yl |
| 2-tert-Butoxyprop-2-yl | 2-(3-Chlorophenyl)oxazol-4-yl |
| 2-tert-Butoxyprop-2-yl | 2-(4-Methylphenyl)oxazol-4-yl |
| 2-tert-Butoxyprop-2-yl | 2-tert-Butyloxazol-4-yl |
| 2-tert-Butoxyprop-2-yl | 2-(2,4-Dichlorophenyl)oxazol-4-yl |
| 2-tert-Butoxyprop-2-yl | 2-(4-Methoxyphenyl)oxazol-4-yl |
| 2-tert-Butoxyprop-2-yl | 2-(4-Chlorophenyl)-5-bromooxazol-4-yl |
| 2-n-Butylthioprop-2-yl | 2-Chloro-3-isopropylphenyl |
| 2-n-Butylthioprop-2-yl | 2,6-Difluorophenyl |
| 2-n-Butylthioprop-2-yl | 2-Chloro-3-trifluoromethylphenyl |
| 2-n-Butylthioprop-2-yl | 3-Phenylisoxazol-5-yl |
| 2-n-Butylthioprop-2-yl | 3-Methylisoxazol-5-yl |
| 2-n-Butylthioprop-2-yl | 4-Chloro-3-methylisoxazol-5-yl |
| 2-n-Butylthioprop-2-yl | 4-Chloro-3-isopropylisoxazol-5-yl |
| 2-n-Butylthioprop-2-yl | 4-Chloro-3-sec-butylisoxazol-5-yl |
| 2-n-Butylthioprop-2-yl | 4-Chloro-3-tert-butylisoxazol-5-yl |
| 2-n-Butylthioprop-2-yl | 4-Chloro-3-cyclohexylisoxazol-5-yl |
| 2-n-Butylthioprop-2-yl | 4-Chloro-3-phenylisoxazol-5-yl |
| 2-n-Butylthioprop-2-yl | 4-Chloro-3-(4-methylphenyl)isoxazol-5-yl |
| 2-n-Butylthioprop-2-yl | 4-Chloro-3-(4-chlorophenyl)isoxazol-5-yl |
| 2-n-Butylthioprop-2-yl | 4-Chloro-3-(4-fluorophenyl)isoxazol-5-yl |
| 2-n-Butylthioprop-2-yl | 4-Chloro-3-(4-trifluoromethylphenyl)-isoxazol-5-yl |
| 2-n-Butylthioprop-2-yl | 4-Chloro-3-(2,6-difluorophenyl)-isoxazol-5-yl |
| 2-n-Butylthioprop-2-yl | 2-Phenyloxazol-4-yl |
| 2-n-Butylthioprop-2-yl | 2-(4-Fluorophenyl)oxazol-4-yl |
| 2-n-Butylthioprop-2-yl | 2-(4-Chlorophenyl)oxazol-4-yl |
| 2-n-Butylthioprop-2-yl | 2-(4-Bromophenyl)oxazol-4-yl |
| 2-n-Butylthioprop-2-yl | 2-(3-Chlorophenyl)oxazol-4-yl |
| 2-n-Butylthioprop-2-yl | 2-(4-Methylphenyl)oxazol-4-yl |
| 2-n-Butylthioprop-2-yl | 2-tert-Butyloxazol-4-yl |
| 2-n-Butylthioprop-2-yl | 2-(2,4-Dichlorophenyl)oxazol-4-yl |
| 2-n-Butylthioprop-2-yl | 2-(4-Methoxyphenyl)oxazol-4-yi |
| 2-n-Butylthioprop-2-yl | 2-(4-Chlorophenyl)-5-bromooxazol-4-yl |
| 2-Isobutylthioprop-2-yl | 2-Chloro-3-isopropylphonyl |
| 2-Isobutylthioprop-2-yl | 2,6-Difluorophenyl |
| 2-Isobutylthioprop-2-yl | 2-Chloro-3-trifluoromethylphenyl |
| 2-Isobutylthioprop-2-yl | 3-Phenylisoxazol-5-yl |
| 2-Isobutylthioprop-2-yl | 3-Methylisoxazol-5-yl |
| 2-Isobutylthioprop-2-yl | 4-Chloro-3-methylisoxazol-5-yl |
| 2-Isobutylthioprop-2-yl | 4-Chloro-3-isopropylisoxazol-5-yl |
| 2-Isobutylthioprop-2-yl | 4-Chloro-3-sec-butylisoxazol-5-yl |
| 2-Isobutylthioprop-2-yl | 4-Chloro-3-tert-butylisoxazol-5-yl |
| 2-Isobutylthioprop-2-yl | 4-Chloro-3 cyclohexylisoxazol-5-yi |
| 2-Isobutylthioprop-2-yl | 4-Chloro-3-phenylisoxazol-5-yl |
| 2-Isobutylthioprop-2-yl | 4-Chloro-3-(4-methylphenyl)isoxazol-5-yl |
| 2-Isobutylthioprop-2-yl | 4-Chloro-3-(4-chlorophenyl)isoxazol-5-yl |
| 2-Isobutylthioprop-2-yl | 4-Chloro-3-(4-fluorophenyl)isoxazol-5-yl |
| 2-Isobutylthioprop-2-yl | 4-Chloro-3-(4-trifluoromethylphenyl)-isoxazol-5-yl |
| 2-Isobutylthioprop-2-yl | 4-Chloro-3-(2,6-difluorophenyl)-isoxazol-5-yl |
| 2-Isobutylthioprop-2-yl | 2-Phenyloxazol-4-yl |
| 2-Isobutylthioprop-2-yl | 2-(4-Fluorophenyl)oxazol-4-yl |
| 2-Isobutylthioprop-2-yl | 2-(4-Chlorophenyl)oxazol-4-yl |
| 2-Isobutylthioprop-2-yl | 2-(4-Bromophenyl)oxazol-4-yl |
| 2-Isobutylthioprop-2-yl | 2-(3-Chlorophenyl)oxazol-4-yl |
| 2-Isobutylthioprop-2-yl | 2-(4-Methylphenyl)oxazol-4-yl |
| 2-Isobutylthioprop-2-yl | 2-tert-Butyloxazol-4-yl |
| 2-Isobutylthioprop-2-yl | 2-(2,4-Dichlorophenyl)oxazol-4-yl |
| 2-Isobutylthioprop-2-yl | 2-(4-Methoxyphenyl)oxazol-4-yl |
| 2-Isobutylthioprop-2-yl | 2-(4-Chlorophenyl)-5-bromooxazol-4-yl |
| 2-sec-Butylthioprop-2-yl | 2-Chloro-3-isopropylphenyl |
| 2-sec-Butylthioprop-2-yl | 2,6-Difluorophenyl |
| 2-sec-Butylthioprop-2-yl | 2-Chloro-3-trifluoromethylphenyl |
| 2-sec-Butylthioprop-2-yl | 3-Phenylisoxazol-5-yl |
| 2-sec-Butylthioprop-2-yl | 3-Methylisoxazol-5-yl |
| 2-sec-Butylthioprop-2-yl | 4-Chloro-3-mothylisoxazol-5-yl |
| 2-sec-Butylthioprop-2-yl | 4-Chloro-3-isopropylisoxazol-5-yl |
| 2-sec-Butylthioprop-2-yl | 4-Chloro-3-sec-butylisoxazol-5-yl |
| 2-sec-Butylthioprop-2-yl | 4-Chloro-3-tert-butylisoxazol-5-yl |
| 2-sec-Butylthioprop-2-yl | 4-Chloro-3-cyclohexylisoxazol-5-yl |
| 2-sec-Butylthioprop-2-yl | 4-Chloro-3-phenylisoxazol-5-yl |
| 2-sec-Butylthioprop-2-yl | 4-Chloro-3-(4-methylphenyl)isoxazol-5-yl |
| 2-sec-Butylthioprop-2-yl | 4-Chloro-3-(4-chlorophenyl)isoxazol-5-yl |
| 2-sec-Butylthioprop-2-yl | 4-Chloro-3-(4-fluorophenyl)isoxazol-5-yl |
| 2-sec-Butylthioprop-2-yl | 4-Chloro-3-(4-trifluoromethylphenyl)-isoxazol-5-yl |
| 2-sec-Butylthioprop-2-yl | 4-Chloro-3-(2,6-difluorophenyl)-isoxazol-5-yl |
| 2-sec-Butylthioprop-2-yl | 2-Phenyloxazol-4-yl |
| 2-sec-Butylthioprop-2-yl | 2-(4-Fluorophenyl)oxazol-4-yl |
| 2-sec-Butylthioprop-2-yl | 2-(4-Chlorophenyl)oxazol-4-yl |
| 2-sec-Butylthioprop-2-yl | 2-(4-Bromophenyl)oxazol-4-yl |
| 2-sec-Butylthioprop-2-yl | 2-(3-Chlorophenyl)oxazol-4-yl |
| 2-sec-Butylthioprop-2-yl | 2-(4-Methylphenyl)oxazol-4-yl |
| 2-sec-Butylthioprop-2-yl | 2-tert-Butyloxazol-4-yl |
| 2-sec-Butylthioprop-2-yl | 2-(2,4-Dichlorophenyl)oxazol-4-yl |
| 2-sec-Butylthioprop-2-yl | 2-(4-Methoxyphenyl)oxazol-4-yl |
| 2-sec-Butylthioprop-2-yl | 2-(4-Chlorophenyl)-5-bromooxazol-4-yl |
| 2-tert-Butylthioprop-2-yl | 2-Chloro-3-isopropylphenyl |
| 2-tert-Butylthiprop-2-yl | 2,6-Difluorophenyl |
| 2-tert-Butylthiprop-2-yl | 2-Chloro-3-trifluoromethylphenyl |
| 2-tert-Butylthiprop-2-yl | 3-Phenylisoxazol-5-yl |

TABLE B-continued $R^1R^2CH-ON=C(CN)-R^3$  $R^1 = H$  I

| R³ | R² |
|---|---|
| 2-tert-Butylthiprop-2-yl | 3-Methylisoxazol-5-yl |
| 2-tert-Butylthiprop-2-yl | 4-Chloro-3-methylisoxazol-5-yl |
| 2-tert-Butylthiprop-2-yl | 4-Chloro-3-isopropylisoxazol-5-yl |
| 2-tert-Butylthiprop-2-yl | 4-Chloro-3-sec-butylisoxazol-5-yl |
| 2-tert-Butylthiprop-2-yl | 4-Chloro-3-tert-butylisoxazol-5-yl |
| 2-tert-Butylthiprop-2-yl | 4-Chloro-3-cyclohexylisoxazol-5-yl |
| 2-tert-Butylthiprop-2-yl | 4-Chloro-3-phenylisoxazol-5-yl |
| 2-tert-Butylthiprop-2-yl | 4-Chloro-3-(4-methylphenyl)isoxazol-5-yl |
| 2-tert-Butylthiprop-2-yl | 4-Chloro-3-(4-chlorophenyl)isoxazol-5-yl |
| 2-tert-Butylthiprop-2-yl | 4-Chloro-3-(4-fluorophenyl)isoxazol-5-yl |
| 2-tert-Butylthiprop-2-yl | 4-Chloro-3-(4-trifluoromethylphenyl)-isoxazol-5-yl |
| 2-tert-Butylthiprop-2-yl | 4-Chloro-3-(2,6-difluorophenyl)-isoxazol-5-yl |
| 2-tert-Butylthiprop-2-yl | 2-Phenyloxazol-4-yl |
| 2-tert-Butylthiprop-2-yl | 2-(4-Fluorophenyl)oxazol-4-yl |
| 2-tert-Butylthiprop-2-yl | 2-(4-Chlorophenyl)oxazol-4-yl |
| 2-tert-Butylthiprop-2-yl | 2-(4-Bromophenyl)oxazol-4-yl |
| 2-tert-Butylthiprop-2-yl | 2-(3-Chlorophenyl)oxazol-4-yl |
| 2-tert-Butylthiprop-2-yl | 2-(4-Methylphenyl)oxazol-4-yl |
| 2-tert-Butylthiprop-2-yl | 2-tert-Butyloxazol-4-yl |
| 2-tert-Butylthiprop-2-yl | 2-(2,4-Dichlorophenyl)oxazol-4-yl |
| 2-tert-Butylthiprop-2-yl | 2-(4-Methoxyphenyl)oxazol-4-yl |
| 2-tert-Butylthiprop-2-yl | 2-(4-Chlorophenyl)-5-bromooxazol-4-yl |
| 2,2-Dichlorocyclopropyl | 2-Chloro-3-isopropylphenyl |
| 2,2-Dichlorocyclopropyl | 2,6-Difluorophenyl |
| 2,2-Dichlorocyclopropyl | 2-Chloro-3-trifluoromethylphenyl |
| 2,2-Dichlorocyclopropyl | 3-Phenylisoxazol-5-yl |
| 2,2-Dichlorocyclopropyl | 3-Methylisoxazol-5-yl |
| 2,2-Dichlorocyclopropyl | 4-Chloro-3-methylisoxazol-5-yl |
| 2,2-Dichlorocyclopropyl | 4-Chloro-3-isopropylisoxazol-5-yl |
| 2,2-Dichlorocyclopropyl | 4-Chloro-3-sec-butylisoxazol-5-yl |
| 2,2-Dichlorocyclopropyl | 4-Chloro-3-tert-butylisoxazol-5-yl |
| 2,2-Dichlorocyclopropyl | 4-Chloro-3-cyclohexylisoxazol-5-yl |
| 2,2-Dichlorocyclopropyl | 4-Chloro-3-phenylisoxazol-5-yl |
| 2,2-Dichlorocyclopropyl | 4-Chloro-3-(4-methylphenyl)isoxazol-5-yl |
| 2,2-Dichlorocyclopropyl | 4-Chloro-3-(4-chlorophenyl)isoxazol-5-yl |
| 2,2-Dichlorocyclopropyl | 4-Chloro-3-(4-fluorophenyl)isoxazol-5-yl |
| 2,2-Dichlorocyclopropyl | 4-Chloro-3-(4-trifluoromethylphenyl)-isoxazol-5-yl |
| 2,2-Dichlorocyclopropyl | 4-Chloro-3-(2,6-difluorophenyl)-isoxazol-5-yl |
| 2,2-Dichlorocyclopropyl | 2-Phenyloxazol-4-yl |
| 2,2-Dichlorocyclopropyl | 2-(4-Fluorophenyl)oxazol-4-yl |
| 2,2-Dichlorocyclopropyl | 2-(4-Chlorophenyl)oxazol-4-yl |
| 2,2-Dichlorocyclopropyl | 2-(4-Bromophenyl)oxazol-4-yl |
| 2,2-Dichlorocyclopropyl | 2-(3-Chlorophenyl)oxazol-4-yl |
| 2,2-Dichlorocyclopropyl | 2-(4-Methylphenyl)oxazol-4-yl |
| 2,2-Dichlorocyclopropyl | 2-tert-Butyloxazol-4-yl |
| 2,2-Dichlorocyclopropyl | 2-(2,4-Dichlorophenyl)oxazol-4-yl |
| 2,2-Dichlorocyclopropyl | 2-(4-Methoxyphenyl)oxazol-4-yl |
| 2,2-Dichlorocyclopropyl | 2-(4-Chlorophenyl)-5-bromooxazol-4-yl |
| 2-Tetrahydrofuranyl | 2-Chloro-3-isopropylphenyl |
| 2-Tetrahydrofuranyl | 2,6-Difluorophenyl |
| 2-Tetrahydrofuranyl | 2-Chloro-3-trifluoromethylphenyl |
| 2-Tetrahydrofuranyl | 3-Phenylisoxazol-5-yl |
| 2-Tetrahydrofuranyl | 3-Methylisoxazol-5-yl |
| 2-Tetrahydrofuranyl | 4-Chloro-3-methylisoxazol-5-yl |
| 2-Tetrahydrofuranyl | 4-Chloro-3-isopropylisoxazol-5-yl |
| 2-Tetrahydrofuranyl | 4-Chloro-3-sec-butylisoxazol-5-yl |
| 2-Tetrahydrofuranyl | 4-Chloro-3-tert-butylisoxazol-5-yl |
| 2-Tetrahydrofuranyl | 4-Chloro-3-cyclohexylisoxazol-5-yl |
| 2-Tetrahydrofuranyl | 4-Chloro-3-phenylisoxazol-5-yl |
| 2-Tetrahydrofuranyl | 4-Chloro-3-(4-methylphenyl)isoxazol-5-yl |
| 2-Tetrahydrofuranyl | 4-Chloro-3-(4-chlorophenyl)isoxazol-5-yl |
| 2-Tetrahydrofuranyl | 4-Chloro-3-(4-fluorophenyl)isoxazol-5-yl |
| 2-Tetrahydrofuranyl | 4-Chloro-3-(4-trifluoromethylphenyl)-isoxazol-5-yl |
| 2-Tetrahydrofuranyl | 4-Chloro-3-(2,6-difluorophenyl)-isoxazol-5-yl |
| 2-Tetrahydrofuranyl | 2-Phenyloxazol-4-yl |
| 2-Tetrahydrofuranyl | 2-(4-Fluorophenyl)oxazol-4-yl |
| 2-Tetrahydrofuranyl | 2-(4-Chlorophenyl)oxazol-4-yl |
| 2-Tetrahydrofuranyl | 2-(4-Bromophenyl)oxazol-4-yl |
| 2-Tetrahydrofuranyl | 2-(3-Chlorophenyl)oxazol-4-yl |
| 2-Tetrahydrofuranyl | 2-(4-Methylphenyl)oxazol-4-yl |
| 2-Tetrahydrofuranyl | 2-tert-Butyloxazol-4-yl |
| 2-Tetrahydrofuranyl | 2-(2,4-Dichlorophenyl)oxazol-4-yl |
| 2-Tetrahydrofuranyl | 2-(4-Methoxyphenyl)oxazol-4-yl |
| 2-Tetrahydrofuranyl | 2-(4-Chlorophenyl)-5-bromooxazol-4-yl |
| 2-Tetrahydrofuranyl | 2-Chloro-3-isopropylphenyl |
| 2-Tetrahydrofuranyl | 2,6-Difluorophenyl |
| 2-Tetrahydrofuranyl | 2-Chloro-3-trifluoromethylphenyl |
| 2-Tetrahydrofuranyl | 3-Phenylisoxazol-5-yl |
| 2-Tetrahydrofuranyl | 3-Methylisoxazol-5-yl |
| 2-Tetrahydrofuranyl | 4-Chloro-3-methylisoxazol-5-yl |
| 2-Tetrahydrofuranyl | 4-Chloro-3-isopropylisoxazol-5-yl |
| 2-Tetrahydrofuranyl | 4-Chloro-3-sec-butylisoxazol-5-yl |
| 2-Tetrahydrofuranyl | 4-Chloro-3-tert-butylisoxazol-5-yl |
| 2-Tetrahydrofuranyl | 4-Chloro-3-cyclohexylisoxazol-5-yl |
| 2-Tetrahydrofuranyl | 4-Chloro-3-phenylisoxazol-5-yl |
| 2-Tetrahydrofuranyl | 4-Chloro-3-(4-methylphenyl)isoxazol-5-yl |
| 2-Tetrahydrofuranyl | 4-Chloro-3-(4-chlorophenyl)isoxazol-5-yl |
| 2-Tetrahydrofuranyl | 4-Chloro-3-(4-fluorophenyl)isoxazol-5-yl |
| 2-Tetrahydrofuranyl | 4-Chloro-3-(4-trifluoromethylphenyl)-isoxazol-5-yl |
| 2-Tetrahydrofuranyl | 4-Chloro-3-(2,6-difluorophenyl)-isoxazol-5-yl |
| 2-Tetrahydrofuranyl | 2-Phenyloxazol-4-yl |
| 2-Tetrahydrofuranyl | 2-(4-Fluorophenyl)oxazol-4-yl |
| 2-Tetrahydrofuranyl | 2-(4-Chlorophenyl)oxazol-4-yl |
| 2-Tetrahydrofuranyl | 2-(4-Bromophenyl)oxazol-4-yl |
| 2-Tetrahydrofuranyl | 2-(3-Chlorophenyl)oxazol-4-yl |
| 2-Tetrahydrofuranyl | 2-(4-Methylphenyl)oxazol-4-yl |
| 2-Tetrahydrofuranyl | 2-tert-Butyloxazol-4-yl |
| 2-Tetrahydrofuranyl | 2-(2,4-Dichlorophenyl)oxazol-4-yl |
| 2-Tetrahydrofuranyl | 2-(4-Methoxyphenyl)oxazol-4-yl |
| 2-Tetrahydrofuranyl | 2-(4-Chlorophenyl)-5-bromooxazol-4-yl |
| 2-Methyltetrahydropyran-2-yl | 2-Chloro-3-isopropylphenyl |
| 2-Methyltetrahydropyran-2-yl | 2,6-Difluorophenyl |
| 2-Methyltetrahydropyran-2-yl | 2-Chloro-3-trifluoromethylphenyl |
| 2-Methyltetrahydropyran-2-yl | 3-Phenylisoxazol-5-yl |
| 2-Methyltetrahydropyran-2-yl | 3-Methylisoxazol-5-yl |
| 2-Methyltetrahydropyran-2-yl | 4-Chloro-3-methylisoxazol-5-yl |
| 2-Methyltetrahydropyran-2-yl | 4-Chloro-3-isopropylisoxazol-5-yl |

TABLE B-continued

| R¹R²CH—ON═C(CN)-R³ | R¹ = H | I |
|---|---|---|

| R³ | R² |
|---|---|
| 2-Methyltetrahydropyran-2-yl | 4-Chloro-3-sec-butylisoxazol-5-yl |
| 2-Methyltetrahydropyran-2-yl | 4-Chloro-3-tert-butylisoxazol-5-yl |
| 2-Methyltetrahydropyran-2-yl | 4-Chloro-3-cyclohexylisoxazol-5-yl |
| 2-Methyltetrahydropyran-2-yl | 4-Chloro-3-phenylisoxazol-5-yl |
| 2-Methyltetrahydropyran-2-yl | 4-Chloro-3-(4-methylphenyl)isoxazol-5-yl |
| 2-Methyltetrahydropyran-2-yl | 4-Chloro-3-(4-chlorophenyl)isoxazol-5-yl |
| 2-Methyltetrahydropyran-2-yl | 4-Chloro-3-(4-fluorophenyl)isoxazol-5-yl |
| 2-Methyltetrahydropyran-2-yl | 4-Chloro-3-(4-trifluoromethylphenyl)isoxazol-5-yl |
| 2-Methyltetrahydropyran-2-yl | 4-Chloro-3-(2,6-difluorophenyl)isoxazol-5-yl |
| 2-Methyltetrahydropyran-2-yl | 2-Phenyloxazol-4-yl |
| 2-Methyltetrahydropyran-2-yl | 2-(4-Fluorophenyl)oxazol-4-yl |
| 2-Methyltetrahydropyran-2-yl | 2-(4-Chlorophenyl)oxazol-4-yl |
| 2-Methyltetrahydropyran-2-yl | 2-(4-Bromophenyl)oxazol-4-yl |
| 2-Methyltetrahydropyran-2-yl | 2-(3-Chlorophenyl)oxazol-4-yl |
| 2-Methyltetrahydropyran-2-yl | 2-(4-Methylphenyl)oxazol-4-yl |
| 2-Methyltetrahydropyran-2-yl | 2-tert-Butyloxazol-4-yl |
| 2-Methyltetrahydropyran-2-yl | 2-(2,4-Dichlorophenyl)oxazol-4-yl |
| 2-Methyltetrahydropyran-2-yl | 2-(4-Methoxyphenyl)oxazol-4-yl |
| 2-Methyltetrahydropyran-2-yl | 2-(4-Chlorophenyl)-5-bromooxazol-4-yl |
| 2-Methyltetrahydropyran-3-yl | 2-Chloro-3-isopropylphenyl |
| 4-Methyltetrahydropyran-3-yl | 2,6-Difluorophenyl |
| 4-Methyltetrahydropyran-3-yl | 2-Chloro-3-trifluoromethylphenyl |
| 4-Methyltetrahydropyran-3-yl | 3-Phenylisoxazol-5-yl |
| 4-Methyltetrahydropyran-3-yl | 3-Methylisoxazol-5-yl |
| 4-Methyltetrahydropyran-3-yl | 4-Chloro-3-methylisoxazol-5-yl |
| 4-Methyltetrahydropyran-3-yl | 4-Chloro-3-isopropylisoxazol-5-yl |
| 4-Methyltetrahydropyran-3-yl | 4-Chloro-3-sec-butylisoxazol-5-yl |
| 4-Methyltetrahydropyran-3-yl | 4-Chloro-3-tert-butylisoxazol-5-yl |
| 4-Methyltetrahydropyran-3-yl | 4-Chloro-3-cyclohexylisoxazol-5-yl |
| 4-Methyltetrahydropyran-3-yl | 4-Chloro-3-phenylisoxazol-5-yl |
| 4-Methyltetrahydropyran-3-yl | 4-Chloro-3-(4-methylphenyl)isoxazol-5-yl |
| 4-Methyltetrahydropyran-3-yl | 4-Chloro-3-(4-chlorophenyl)isoxazol-5-yl |
| 4-Methyltetrahydropyran-3-yl | 4-Chloro-3-(4-fluorophenyl)isoxazol-5-yl |
| 4-Methyltetrahydropyran-3-yl | 4-Chloro-3-(4-trifluoromethylphenyl)oxazol-5-yl |
| 4-Methyltetrahydropyran-3-yl | 4-Chloro-3-(2,6-difluorophenyl)isoxazol-5-yl |
| 4-Methyltetrahydropyran-3-yl | 2-Phenyloxazol-4-yl |
| 4-Methyltetrahydropyran-3-yl | 2-(4-Fluorophenyl)oxazol-4-yl |
| 4-Methyltetrahydropyran-3-yl | 2-(4-Chlorophenyl)oxazol-4-yl |
| 4-Methyltetrahydropyran-3-yl | 2-(4-Bromophenyl)oxazol-4-yl |
| 4-Methyltetrahydropyran-3-yl | 2-(3-Chlorophenyl)oxazol-4-yl |
| 4-Methyltetrahydropyran-3-yl | 2-(4-Methylphenyl)oxazol-4-yl |
| 4-Methyltetrahydropyran-3-yl | 2-tert-Butyloxazol-4-yl |
| 4-Methyltetrahydropyran-3-yl | 2-(2,4-Dichlorophenyl)oxazol-4-yl |
| 4-Methyltetrahydropyran-3-yl | 2-(4-Methoxyphenyl)oxazol-4-yl |
| 4-Methyltetrahydropyran-3-yl | 2-(4-Chlorophenyl)-5-bromooxazol-4-yl |
| Methyl | 2-Chloro-3-isopropylphenyl |
| Methyl | 2,6-Difluorophenyl |
| Methyl | 2-Chloro-3-trifluoromethylphenyl |
| Methyl | 3-Phenylisoxazol-5-yl |
| Methyl | 3-Methylisoxazol-5-yl |
| Methyl | 4-Chloro-3-methylisoxazol-5-yl |
| Methyl | 4-Chloro-3-isopropylisoxazol-5-yl |
| Methyl | 4-Chloro-3-sec-butylisoxazol-5-yl |
| Methyl | 4-Chloro-3-tert-butylisoxazol-5-yl |
| Methyl | 4-Chloro-3-cyclohexylisoxazol-5-yl |
| Methyl | 4-Chloro-3-phenylisoxazol-5-yl |
| Methyl | 4-Chloro-3-(4-methylphenyl)isoxazol-5-yl |
| Methyl | 4-Chloro-3-(4-chlorophenyl)isoxazol-5-yl |
| Methyl | 4-Chloro-3-(4-fluorophenyl)isoxazol-5-yl |
| Methyl | 4-Chloro-3-(4-trifluoromethylphenyl)isoxazol-5-yl |
| Methyl | 4-Chloro-3-(2,6-difluorophenyl)isoxazol-5-yl |
| Methyl | 2-Phenyloxazol-4-yl |
| Methyl | 2-(4-Fluorophenyl)oxazol-4-yl |
| Methyl | 2-(4-Chlorophenyl)oxazol-4-yl |
| Methyl | 2-(4-Bromophenyl)oxazol-4-yl |
| Methyl | 2-(3-Chlorophenyl)oxazol-4-yl |
| Methyl | 2-(4-Methylphenyl)oxazol-4-yl |
| Methyl | 2-tert-Butyloxazol-4-yl |
| Methyl | 2-(2,4-Dichlorophenyl)oxazol-4-yl |
| Methyl | 2-(4-Methoxyphenyl)oxazol-4-yl |
| Methyl | 2-(4-Chlorophenyl)-5-bromooxazol-4-yl |
| Ethyl | 2-Chloro-3-isopropylphenyl |
| Ethyl | 2,6-Difluorophenyl |
| Ethyl | 2-Chloro-3-trifluoromethylphenyl |
| Ethyl | 3-Phenylisoxazol-5-yl |
| Ethyl | 3-Methylisoxazol-5-yl |
| Ethyl | 4-Chloro-3-methylisoxazol-5-yl |
| Ethyl | 4-Chloro-3-isopropylisoxazol-5-yl |
| Ethyl | 4-Chloro-3-sec-butylisoxazol-5-yl |
| Ethyl | 4-Chloro-3-tert-butylisoxazol-5-yl |
| Ethyl | 4-Chloro-3-cyclohoxyisoxazol-5-yl |
| Ethyl | 4-Chloro-3-phenylisoxazol-5-yl |
| Ethyl | 4-Chloro-3-(4-methylphenyl)isoxazol-5-yl |
| Ethyl | 4-Chloro-3-(4-chlorophenyl)isoxazol-5-yl |
| Ethyl | 4-Chloro-3-(4-fluorophenyl)isoxazol-5-yl |
| Ethyl | 4-Chloro-3-(4-trifluoromethylphenyl)isoxazol-5-yl |
| Ethyl | 4-Chloro-3-(2,6-difluorophenyl)isoxazol-5-yl |
| Ethyl | 2-Phenyloxazol-4-yl |
| Ethyl | 2-(4-Fluorophenyl)oxazol-4-yl |
| Ethyl | 2-(4-Chlorophenyl)oxazol-4-yl |
| Ethyl | 2-(4-Bromophenyl)oxazol-4-yl |
| Ethyl | 2-(3-Chlorophenyl)oxazol-4-yl |
| Ethyl | 2-(4-Methylphenyl)oxazol-4-yl |
| Ethyl | 2-tert-Butyloxazol-4-yl |

TABLE B-continued

| R¹R²CH—ON=C(CN)-R³ | R¹ = H | I |
|---|---|---|

| R³ | R² |
|---|---|
| Ethyl | 2-(2,4-Dichlorophenyl)oxazol-4-yl |
| Ethyl | 2-(4-Methoxyphenyl)oxazol-4-yl |
| Ethyl | 2-(4-Chlorophenyl)-5-bromooxazol-4-yl |
| n-Propyl | 2-Chloro-3-isopropylphenyl |
| n-Propyl | 2,6-Difluorophenyl |
| n-Propyl | 2-Chloro-3-trifluoromethylphenyl |
| n-Propyl | 3-Phenylisoxazol-5-yl |
| n-Propyl | 3-Methylisoxazol-5-yl |
| n-Propyl | 4-Chloro-3-methylisoxazol-5-yl |
| n-Propyl | 4-Chloro-3-isopropylisoxazol-5-yl |
| n-Propyl | 4-Chloro-3-sec-butylisoxazol-5-yl |
| n-Propyl | 4-Chloro-3-tert-butylisoxazol-5-yl |
| n-Propyl | 4-Chloro-3-cyclohexylisoxazol-5-yl |
| n-Propyl | 4-Chloro-3-phenylisoxazol-5-yl |
| n-Propyl | 4-Chloro-3-(4-methylphenyl)isoxazol-5-yl |
| n-Propyl | 4-Chloro-3-(4-chlorophenyl)isoxazol-5-yl |
| n-Propyl | 4-Chloro-3-(4-fluorophenyl)isoxazol-5-yl |
| n-Propyl | 4-Chloro-3-(4-trifluoromethylphenyl)isoxazol-5-yl |
| n-Propyl | 4-Chloro-3-(2,6-difluorophenyl)isoxazol-5-yl |
| n-Propyl | 2-Phenyloxazol-4-yl |
| n-Propyl | 2-(4-Fluorophenyl)oxazol-4-yl |
| n-Propyl | 2-(4-Chlorophenyl)oxazol-4-yl |
| n-Propyl | 2-(4-Bromophenyl)oxazol-4-yl |
| n-Propyl | 2-(3-Chlorophenyl)oxazol-4-yl |
| n-Propyl | 2-(4-Methylphenyl)oxazol-4-yl |
| n-Propyl | 2-tert-Butyloxazol-4-yl |
| n-Propyl | 2-(2,4-Dichlorophenyl)oxazol-4-yl |
| n-Propyl | 2-(4-Methoxyphenyl)oxazol-4-yl |
| n-Propyl | 2-(4-Chlorophenyl)-5-bromooxazol-4-yl |
| n-Butyl | 2-Chloro-3-isopropylphenyl |
| n-Butyl | 2,6-Difluorophenyl |
| n-Butyl | 2-Chloro-3-trifluoromethylphenyl |
| n-Butyl | 3-Phenylisoxazol-5-yl |
| n-Butyl | 3-Methylisoxazol-5-yl |
| n-Butyl | 4-Chloro-3-methylisoxazol-5-yl |
| n-Butyl | 4-Chloro-3-isopropylisoxazol-5-yl |
| n-Butyl | 4-Chloro-3-sec-butylisoxazol-5-yl |
| n-Butyl | 4-Chloro-3-tert-butylisoxazol-5-yl |
| n-Butyl | 4-Chloro-3-cyclohexylisoxazol-5-yl |
| n-Butyl | 4-Chloro-3-phenylisoxazol-5-yl |
| n-Butyl | 4-Chloro-3-(4-methylphenyl)isoxazol-5-yl |
| n-Butyl | 4-Chloro-3-(4-chlorophenyl)isoxazol-5-yl |
| n-Butyl | 4-Chloro-3-(4-fluorophenyl)isoxazol-5-yl |
| n-Butyl | 4-Chloro-3-(4-trifluoromethylphenyl)isoxazol-5-yl |
| n-Butyl | 4-Chloro-3-(2,6-difluorophenyl)isoxazol-5-yl |
| n-Butyl | 2-Phenyloxazol-4-yl |
| n-Butyl | 2-(4-Fluorophenyl)oxazol-4-yl |
| n-Butyl | 2-(4-Chlorophenyl)oxazol-4-yl |
| n-Butyl | 2-(4-Bromophenyl)oxazol-4-yl |
| n-Butyl | 2-(3-Chlorophenyl)oxazol-4-yl |
| n-Butyl | 2-(4-Methylphenyl)oxazol-4-yl |
| n-Butyl | 2-tert-Butyloxazol-4-yl |
| n-Butyl | 2-(2,4-Dichlorophenyl)oxazol-4-yl |
| n-Butyl | 2-(4-Methoxyphenyl)oxazol-4-yl |
| n-Butyl | 2-(4-Chlorophenyl)-5-bromooxazol-4-yl |
| sec-Butyl | 2-Chloro-3-isopropylphenyl |
| sec-Butyl | 2,6-Difluorophenyl |
| sec-Butyl | 2-Chloro-3-trifluoromethylphenyl |
| sec-Butyl | 3-Phenylisoxazol-5-yl |
| sec-Butyl | 3-Methylisoxazol-5-yl |
| sec-Butyl | 4-Chloro-3-methylisoxazol-5-yl |
| sec-Butyl | 4-Chloro-3-isopropylisoxazol-5-yl |
| sec-Butyl | 4-Chloro-3-sec-butylisoxazol-5-yl |
| sec-Butyl | 4-Chloro-3-tert-butylisoxazol-5-yl |
| sec-Butyl | 4-Chloro-3-cyclohexylisoxazol-5-yl |
| sec-Butyl | 4-Chloro-3-phenylisoxazol-5-yl |
| sec-Butyl | 4-Chloro-3-(4-methylphenyl)isoxazol-5-yl |
| sec-Butyl | 4-Chloro-3-(4-chlorophenyl)isoxazol-5-yl |
| sec-Butyl | 4-Chloro-3-(4-fluorophenyl)isoxazol-5-yl |
| sec-Butyl | 4-Chloro-3-(4-trifluoromethylphenyl)isoxazol-5-yl |
| sec-Butyl | 4-Chloro-3-(2,6-difluorophenyl)isoxazol-5-yl |
| sec-Butyl | 2-Phenyloxazol-4-yl |
| sec-Butyl | 2-(4-Fluorophenyl)oxazol-4-yl |
| sec-Butyl | 2-(4-Chlorophenyl)oxazol-4-yl |
| sec-Butyl | 2-(4-Bromophenyl)oxazol-4-yl |
| sec-Butyl | 2-(3-Chlorophenyl)oxazol-4-yl |
| sec-Butyl | 2-(4-Methylphenyl)oxazol-4-yl |
| sec-Butyl | 2-tert-Butyloxazol-4-yl |
| sec-Butyl | 2-(2,4-Dichlorophenyl)oxazol-4-yl |
| sec-Butyl | 2-(4-Methoxyphenyl)oxazol-4-yl |
| sec-Butyl | 2-(4-Chlorophenyl)-5-bromooxazol-4-yl |
| Isobutyl | 2-Chloro-3-isopropylphenyl |
| Isobutyl | 2,6-Difluorophenyl |
| Isobutyl | 2-Chloro-3-trifluoromethylphenyl |
| Isobutyl | 3-Phenylisoxazol-5-yl |
| Isobutyl | 3-Methylisoxazol-5-yl |
| Isobutyl | 4-Chloro-3-methylisoxazol-5-yl |
| Isobutyl | 4-Chloro-3-isopropylisoxazol-5-yl |
| Isobutyl | 4-Chloro-3-sec-butylisoxazol-5-yl |
| Isobutyl | 4-Chloro-3-tert-butylisoxazol-5-yl |
| Isobutyl | 4-Chloro-3-cyclohoxylisoxazol-5-yl |
| Isobutyl | 4-Chloro-3-phenylisoxazol-5-yl |
| Isobutyl | 4-Chloro-3-(4-methylphenyl)isoxazol-5-yl |
| Isobutyl | 4-Chloro-3-(4-Chlorophenyl)isoxazol-5-yl |
| Isobutyl | 4-Chloro-3-(4-fluorophenyl)isoxazol-5-yl |
| Isobutyl | 4-Chloro-3-(4-trifluoromethylphenyl)isoxazol-5-yl |
| Isobutyl | 4-Chloro-3-(2,6-difluorophenyl)isoxazol-5-yl |
| Isobutyl | 2-Phenyloxazol-4-yl |
| Isobutyl | 2-(4-Fluorophenyl)oxazol-4-yl |
| Isobutyl | 2-(4-Chlorophenyl)oxazol-4-yl |
| Isobutyl | 2-(4-Bromophenyl)oxazol-4-yl |
| Isobutyl | 2-(3-Chlorophenyl)oxazol-4-yl |
| Isobutyl | 2-(4-Methylphenyl)oxazol-4-yl |
| Isobutyl | 2-tert-Butyloxazol-4-yl |
| Isobutyl | 2-(2,4-Dichlorophenyl)oxazol-4-yl |
| Isobutyl | 2-(4-Methoxyphenyl)oxazol-4-yl |
| Isobutyl | 2-(4-Chlorophenyl)-5-bromooxazol-4-yl |
| 1,1-Dimethylpropyl | 2-Chloro-3-isopropylphenyl |
| 1,1-Dimethylpropyl | 2,6-Difluorophenyl |
| 1,1-Dimethylpropyl | 2-Chloro-3-trifluoromethylphenyl |
| 1,1-Dimethylpropyl | 3-Phenylisoxazol-5-yl |
| 1,1-Dimethylpropyl | 3-Methylisoxazol-5-yl |
| 1,1-Dimethylpropyl | 4-Chloro-3-methylisoxazol-5-yl |
| 1,1-Dimethylpropyl | 4-Chloro-3-isopropylisoxazol-5-yl |
| 1,1-Dimethylpropyl | 4-Chloro-3-sec-butylisoxazol-5-yl |
| 1,1-Dimethylpropyl | 4-Chloro-3-tert-butylisoxazol-5-yl |
| 1,1-Dimethylpropyl | 4-Chloro-3-cyclohexylisoxazol-5-yl |
| 1,1-Dimethylpropyl | 4-Chloro-3-phenylisoxazol-5-yl |
| 1,1-Dimethylpropyl | 4-Chloro-3-(4-methylphenyl)isoxazol-5-yl |
| 1,1-Dimethylpropyl | 4-Chloro-3-(4-chlorophenyl)isoxazol-5-yl |
| 1,1-Dimethylpropyl | 4-Chloro-3-(4-fluorophenyl)isoxazol-5-yl |
| 1,1-Dimethylpropyl | 4-Chloro-3-(4-trifluoromethylphenyl)isoxazol-5-yl |
| 1,1-Dimethylpropyl | 4-Chloro-3-(2,6-difluorophenyl)isoxazol-5-yl |
| 1,1-Dimethylpropyl | 2-Phenyloxazol-4-yl |
| 1,1-Dimethylpropyl | 2-(4-Fluorophenyl)oxazol-4-yl |

TABLE B-continued

| | R¹R²CH—ON=C(CN)-R³ | R¹ = H | I |
|---|---|---|---|
| R³ | R² | | |

| R³ | R² |
|---|---|
| 1,1-Dimethylpropyl | 2-(4-Chlorophenyl)oxazol-4-yl |
| 1,1-Dimethylpropyl | 2-(4-Bromophenyl)oxazol-4-yl |
| 1,1-Dimethylpropyl | 2-(3-Chlorophenyl)oxazol-4-yl |
| 1,1-Dimethylpropyl | 2-(4-Methylphenyl)oxazol-4-yl |
| 1,1-Dimethylpropyl | 2-tert-Butyloxazol-4-yl |
| 1,1-Dimethylpropyl | 2-(2,4-Dichlorophenyl)oxazol-4-yl |
| 1,1-Dimethylpropyl | 2-(4-Methoxyphenyl)oxazol-4-yl |
| 1,1-Dimethylpropyl | 2-(4-Chlorophenyl)-5-bromooxazol-4-yl |
| 1,1,2-Trimethylpropyl | 2-Chloro-3-isopropylphenyl |
| 1,1,2-Trimethylpropyl | 2,6-Difluorophenyl |
| 1,1,2-Trimethylpropyl | 2-Chloro-3-trifluoromethylphenyl |
| 1,1,2-Trimethylpropyl | 3-Phenylisoxazol-5-yl |
| 1,1,2-Trimethylpropyl | 3-Methylisoxazol-5-yl |
| 1,1,2-Trimethylpropyl | 4-Chloro-3-methylisoxazol-5-yl |
| 1,1,2-Trimethylpropyl | 4-Chloro-3-isopropylisoxazol-5-yl |
| 1,1,2-Trimethylpropyl | 4-Chloro-3-sec-butylisoxazol-5-yl |
| 1,1,2-Trimethylpropyl | 4-Chloro-3-tert-butylisoxazol-5-yl |
| 1,1,2-Trimethylpropyl | 4-Chloro-3-cyclohexylisoxazol-5-yl |
| 1,1,2-Trimethylpropyl | 4-Chloro-3-phenylisoxazol-5-yl |
| 1,1,2-Trimethylpropyl | 4-Chloro-3-(4-methylphenyl)isoxazol-5-yl |
| 1,1,2-Trimethylpropyl | 4-Chloro-3-(4-chlorophenyl)isoxazol-5-yl |
| 1,1,2-Trimethylpropyl | 4-Chloro-3-(4-fluorophenyl)isoxazol-5-yl |
| 1,1,2-Trimethylpropyl | 4-Chloro-3-(4-trifluoromethylphenyl)-isoxazol-5-yl |
| 1,1,2-Trimethylpropyl | 4-Chloro-3-(2,6-difluorophenyl)-isoxazol-5-yl |
| 1,1,2-Trimethylpropyl | 2-Phenyloxazol-4-yl |
| 1,1,2-Trimethylpropyl | 2-(4-Fluorophenyl)oxazol-4-yl |
| 1,1,2-Trimethylpropyl | 2-(4-Chlorophenyl)oxazol-4-yl |
| 1,1,2-Trimethylpropyl | 2-(4-Bromophenyl)oxazol-4-yl |
| 1,1,2-Trimethylpropyl | 2-(3-Chlorophenyl)oxazol-4-yi |
| 1,1,2-Trimethylpropyl | 2-(4-Methylphenyl)oxazol-4-yl |
| 1,1,2-Trimethylpropyl | 2-tert-Butyloxazol-4-yl |
| 1,1,2-Trimethylpropyl | 2-(2,4-Dichlorophenyl)oxazol-4-yl |
| 1,1,2-Trimethylpropyl | 2-(4-Methoxyphenyl)oxazol-4-yl |
| 1,1,2-Trimethylpropyl | 2-(4-Chlorophenyl)-5-bromooxazol-4-yl |
| tert-Butyl | 2-Chloro-3-isopropylphenyl |
| tert-Butyl | 2,6-Difluorophenyl |
| tert-Butyl | 2-Chloro-3-trifluoromethylphenyl |
| tert-Butyl | 3-Phenylisoxazol-5-yl |
| tert-Butyl | 3-Methylisoxazol-5-yl |
| tert-Butyl | 4-Chloro-3-methylisoxazol-5-yl |
| tert-Butyl | 4-Chloro-3-isopropylisoxazol-5-yl |
| tert-Butyl | 4-Chloro-3-sec-butylisoxazol-5-yl |
| tert-Butyl | 4-Chloro-3-tert-butylisoxazol-5-yl |
| tert-Butyl | 4-Chloro-3-cyclohoxylisoxazol-5-yl |
| tert-Butyl | 4-Chloro-3-phenylisoxazol-5-yl |
| tert-Butyl | 4-Chloro-3-(4-methylphenyl)isoxazol-5-yl |
| tert-Butyl | 4-Chloro-3-(4-chlorophenyl)isoxazol-5-yl |
| tert-Butyl | 4-Chloro-3-(4-fluorophenyl)isoxazol-5-yl |
| tert-Butyl | 4-Chloro-3-(4-trifluoromethylphenyl)-isoxazol-5-yl |
| tert-Butyl | 4-Chloro-3-(2,6-difluorophenyl)-isoxazol-5-yl |
| tert-Butyl | 2-Phenyloxazol-4-yl |
| tert-Butyl | 2-(4-Fluorophenyl)oxazol-4-yl |
| tert-Butyl | 2-(4-Chlorophenyl)oxazol-4-yl |
| tert-Butyl | 2-(4-Bromophenyl)oxazol-4-yl |
| tert-Butyl | 2-(3-Chlorophenyl)oxazol-4-yl |
| tert-Butyl | 2-(4-Methylphenyl)oxazol-4-yl |
| tert-Butyl | 2-tert-Butyloxazol-4-yl |
| tert-Butyl | 2-(2,4-Dichlorophenyl)oxazol-4-yl |
| tert-Butyl | 2-(4-Methoxyphenyl)oxazol-4-yl |
| tert-Butyl | 2-(4-Chlorophenyl)-5-bromooxazol-4-yl |
| 1,1,2,2-Tetramethyl-propyl | 2-Chloro-3-isopropylphenyl |
| 1,1,2,2-Tetramethyl-propyl | 2,6-Difluorophenyl |
| 1,1,2,2-Tetramethyl-propyl | 2-Chloro-3-trifluoromethylphenyl |
| 1,1,2,2-Tetramethyl-propyl | 3-Phenylisoxazol-5-yl |
| 1,1,2,2-Tetramethyl-propyl | 3-Methylisoxazol-5-yl |
| 1,1,2,2-Tetramethyl-propyl | 4-Chloro-3-methylisoxazol-5-yl |
| 1,1,2,2-Tetramethyl-propyl | 4-Chloro-3-isopropylisoxazol-5-yl |
| 1,1,2,2-Tetramethyl-propyl | 4-Chloro-3-sec-butylisoxazol-5-yl |
| 1,1,2,2-Tetramethyl-propyl | 4-Chloro-3-tert-butylisoxazol-5-yl |
| 1,1,2,2-Tetramethyl-propyl | 4-Chloro-3-cyclohexylisoxazol-5-yl |
| 1,1,2,2-Tetramethyl-propyl | 4-Chloro-3-phenylisoxazol-5-yl |
| 1,1,2,2-Tetramethyl-propyl | 4-Chloro-3-(4-methylphenyl)isoxazol-5-yl |
| 1,1,2,2-Tetramethyl-propyl | 4-Chloro-3-(4-chlorophenyl)isoxazol-5-yl |
| 1,1,2,2-Tetramethyl-propyl | 4-Chloro-3-(4-fluorophenyl)isoxazol-5-yl |
| 1,1,2,2-Tetramethyl-propyl | 4-Chloro-3-(4-trifluoromethylphenyl)-isoxazol-5-yl |
| 1,1,2,2-Tetramethyl-propyl | 4-Chloro-3-(2,6-difluorophenyl)-isoxazol-5-yl |
| 1,1,2,2-Tetramethyl-propyl | 2-Phenyloxazol-4-yl |
| 1,1,2,2-Tetramethyl-propyl | 2-(4-Fluorophenyl)oxazol-4-yl |
| 1,1,2,2-Tetramethyl-propyl | 2-(4-Chlorophenyl)oxazol-4-yl |
| 1,1,2,2-Tetramethyl-propyl | 2-(4-Bromophenyl)oxazol-4-yl |
| 1,1,2,2-Tetramethyl-propyl | 2-(3-Chlorophenyl)oxazol-4-yl |
| 1,1,2,2-Tetramethyl-propyl | 2-(4-Methylphenyl)oxazol-4-yl |
| 1,1,2,2-Tetramethyl-propyl | 2-tert-Butyloxazol-4-yl |
| 1,1,2,2-Tetramethyl-propyl | 2-(2,4-Dichlorophenyl)oxazol-4-yl |
| 1,1,2,2-Tetramethyl-propyl | 2-(4-Methoxyphenyl)oxazol-4-yl |
| 1,1,2,2-Tetramethyl-propyl | 2-(4-Chlorophenyl)-5-bromooxazol-4-yl |
| 1-Chloro-1-methylethyl | 2-Chloro-3-isopropylphenyl |
| 1-Chloro-1-methylethyl | 2,6-Difluorophenyl |
| 1-Chloro-1-methylethyl | 2-Chloro-3-trifluoromethylphenyl |
| 1-Chloro-1-methylethyl | 3-Phenylisoxazol-5-yl |
| 1-Chloro-1-methylethyl | 3-Methylisoxazol-5-yl |
| 1-Chloro-1-methylethyl | 4-Chloro-3-methylisoxazol-5-yl |
| 1-Chloro-1-methylethyl | 4-Chloro-3-isopropylisoxazol-5-yl |
| 1-Chloro-1-methylethyl | 4-Chloro-3-sec-butylisoxazol-5-yl |
| 1-Chloro-1-methylethyl | 4-Chloro-3-tert-butylisoxazol 5-yl |
| 1-Chloro-1-methylethyl | 4-Chloro-3-cyclohexylisoxazol-5-yl |
| 1-Chloro-1-methylethyl | 4-Chloro-3-phenylisoxazol-5-yl |
| 1-Chloro-1-methylethyl | 4-Chloro-3-(4-methylphenyl)isoxazol-5-yl |
| 1-Chloro-1-methylethyl | 4-Chloro-3-(4-chlorophenyl)isoxazol-5-yl |
| 1-Chloro-1-methylethyl | 4-Chloro-3-(4-fluorophenyl)isoxazol-5-yl |
| 1-Chloro-1-methylethyl | 4-Chloro-3-(4-trifluoromethylphenyl)-isoxazol-5-yl |
| 1-Chloro-1-methylethyl | 4-Chloro-3-(2,6-difluorophenyl)-isoxazol-5-yl |
| 1-Chloro-1-methylethyl | 2-Phenyloxazol-4-yl |
| 1-Chloro-1-methylethyl | 2-(4-Fluorophenyl)oxazol-4-yl |
| 1-Chloro-1-methylethyl | 2-(4-Chlorophenyl)oxazol-4-yl |
| 1-Chloro-1-methylethyl | 2-(4-Bromophenyl)oxazol-4-yl |
| 1-Chloro-1-methylethyl | 2-(3-Chlorophenyl)oxazol-4-yl |
| 1-Chloro-1-methylethyl | 2-(4-Methylphenyl)oxazol-4-yl |
| 1-Chloro-1-methylethyl | 2-tert-Butyloxazol-4-yl |

TABLE B-continued $R^1R^2CH—ON=C(CN)-R^3$    $R^1 = H$    I

| R³ | R² |
|---|---|
| 1-Chloro-1-methylethyl | 2-(2,4-Dichlorophenyl)oxazol-4-yl |
| 1-Chloro-1-methylethyl | 2-(4-Methoxyphenyl)oxazol-4-yl |
| 1-Chloro-1-methylethyl | 2-(4-Chlorophenyl)-5-bromooxazol-4-yl |
| 2-Chloro-1,1-dimethylethyl | 2-Chloro-3-isopropylphenyl |
| 2-Chloro-1,1-dimethylethyl | 2,6-Difluorophenyl |
| 2-Chloro-1,1-dimethylethyl | 2-Chloro-3-trifluoromethylphenyl |
| 2-Chloro-1,1-dimethylethyl | 3-Phenylisoxazol-5-yl |
| 2-Chloro-1,1-dimethylethyl | 3-Methylisoxazol-5-yl |
| 2-Chloro-1,1-dimethylethyl | 4-Chloro-3-methylisoxazol-5-yl |
| 2-Chloro-1,1-dimethylethyl | 4-Chloro-3-isopropylisoxazol-5-yl |
| 2-Chloro-1,1-dimethylethyl | 4-Chloro-3-sec-butylisoxazol-5-yl |
| 2-Chloro-1,1-dimethylethyl | 4-Chloro-3-tert-butylisoxazol-5-yl |
| 2-Chloro-1,1-dimethylethyl | 4-Chloro-3-cyclohexylisoxazol-5-yl |
| 2-Chloro-1,1-dimethylethyl | 4-Chloro-3-phenylisoxazol-5-yl |
| 2-Chloro-1,1-dimethylethyl | 4-Chloro-3-(4-methylphenyl)isoxazol-5-yl |
| 2-Chloro-1,1-dimethylethyl | 4-Chloro-3-(4-chlorophenyl)isoxazol-5-yl |
| 2-Chloro-1,1-dimethylethyl | 4-Chloro-3-(4-fluorophenyl)isoxazol-5-yl |
| 2-Chloro-1,1-dimethylethyl | 4-Chloro-3-(4-trifluoromethylphenyl)isoxazol-5-yl |
| 2-Chloro-1,1-dimethylethyl | 4-Chloro-3-(2,6-difluorophenyl)isoxazol-5-yl |
| 2-Chloro-1,1-dimethylethyl | 2-Phenyloxazol-4-yl |
| 2-Chloro-1,1-dimethylethyl | 2-(4-Fluorophenyl)oxazol-4-yl |
| 2-Chloro-1,1-dimethylethyl | 2-(4-Chlorophenyl)oxazol-4-yl |
| 2-Chloro-1,1-dimethylethyl | 2-(4-Bromophenyl)oxazol-4-yl |
| 2-Chloro-1,1-dimethylethyl | 2-(3-Chlorophenyl)oxazol-4-yl |
| 2-Chloro-1,1-dimethylethyl | 2-(4-Methylphenyl)oxazol-4-yl |
| 2-Chloro-1,1-dimethylethyl | 2-tert-Butyloxazol-4-yl |
| 2-Chloro-1,1-dimethylethyl | 2-(2,4-Dichlorophenyl)oxazol-4-yl |
| 2-Chloro-1,1-dimethylethyl | 2-(4-Methoxyphenyl)oxazol-4-yl |
| 2-Chloro-1,1-dimethylethyl | 2-(4-Chlorophenyl)-5-bromooxazol-4-yl |
| 1-Methoxymethyl | 2-Chloro-3-isopropylphenyl |
| 1-Methoxymethyl | 2,6-Difluorophenyl |
| 1-Methoxymethyl | 2-Chloro-3-trifluoromethylphenyl |
| 1-Methoxymethyl | 3-Phenylisoxazol-5-yl |
| 1-Methoxymethyl | 3-Methylisoxazol-5-yl |
| 1-Methoxymethyl | 4-Chloro-3-methylisoxazol-5-yl |
| 1-Methoxymethyl | 4-Chloro-3-isopropylisoxazol-5-yl |
| 1-Methoxymethyl | 4-Chloro-3-sec-butylisoxazol-5-yl |
| 1-Methoxymethyl | 4-Chloro-3-tert-butylisoxazol-5-yl |
| 1-Methoxymethyl | 4-Chloro-3-cyclohexylisoxazol-5-yl |
| 1-Methoxymethyl | 4-Chloro-3-phenylisoxazol-5-yl |
| 1-Methoxymethyl | 4-Chloro-3-(4-methylphenyl)isoxazol-5-yl |
| 1-Methoxymethyl | 4-Chloro-3-(4-chlorophenyl)isoxazol-5-yl |
| 1-Methoxymethyl | 4-Chloro-3-(4-fluorophenyl)isoxazol-5-yl |
| 1-Methoxymethyl | 4-Chloro-3-(4-trifluoromethylphenyl)isoxazol-5-yl |
| 1-Methoxymethyl | 4-Chloro-3-(2,6-difluorophenyl)isoxazol-5-yl |
| 1-Methoxymethyl | 2-Phenyloxazol-4-yl |
| 1-Methoxymethyl | 2-(4-Fluorophenyl)oxazol-4-yl |
| 1-Methoxymethyl | 2-(4-Chlorophenyl)oxazol-4-yl |
| 1-Methoxymethyl | 2-(4-Bromophenyl)oxazol-4-yl |
| 1-Methoxymethyl | 2-(3-Chlorophenyl)oxazol-4-yl |
| 1-Methoxymethyl | 2-(4-Methylphenyl)oxazol-4-yl |
| 1-Methoxymethyl | 2-tert-Butyloxazol-4-yl |
| 1-Methoxymethyl | 2-(2,4-Dichlorophenyl)oxazol-4-yl |
| 1-Methoxymethyl | 2-(4-Methoxyphenyl)oxazol-4-yl |
| 1-Methoxymethyl | 2-(4-Chlorophenyl)-5-bromooxazol-4-yl |
| 1-Methoxyethyl | 2-Chloro-3-isopropylphenyl |
| 1-Methoxyethyl | 2,6-Difluorophenyl |
| 1-Methoxyethyl | 2-Chloro-3-trifluoromethylphenyl |
| 1-Methoxyethyl | 3-Phenylisoxazol-5-yl |
| 1-Methoxyethyl | 3-Methylisoxazol-5-yl |
| 1-Methoxyethyl | 4-Chloro-3-methylisoxazol-5-yl |
| 1-Methoxyethyl | 4-Chloro-3-isopropylisoxazol-5-yl |
| 1-Methoxyethyl | 4-Chloro-3-sec-butylisoxazol-5-yl |
| 1-Methoxyethyl | 4-Chloro-3-tert-butylisoxazol-5-yl |
| 1-Methoxyethyl | 4-Chloro-3-cyclohexylisoxazol-5-yl |
| 1-Methoxyethyl | 4-Chloro-3-phenylisoxazol-5-yl |
| 1-Methoxyethyl | 4-Chloro-3-(4-methylphenyl)isoxazol-5-yl |
| 1-Methoxyethyl | 4-Chloro-3-(4-chlorophenyl)isoxazol-5-yl |
| 1-Methoxyethyl | 4-Chloro-3-(4-fluorophenyl)isoxazol-5-yl |
| 1-Methoxyethyl | 4-Chloro-3-(4-trifluoromethylphenyl)isoxazol-5-yl |
| 1-Methoxyethyl | 4-Chloro-3-(2,6-difluorophenyl)isoxazol-5-yl |
| 1-Methoxyethyl | 2-Phenyloxazol-4-yl |
| 1-Methoxyethyl | 2-(4-Fluorophenyl)oxazol-4-yi |
| 1-Methoxyethyl | 2-(4-Chlorophenyl)oxazol-4-yl |
| 1-Methoxyethyl | 2-(4-Bromophenyl)oxazol-4-yl |
| 1-Methoxyethyl | 2-(3-Chlorophenyl)oxazol-4-yl |
| 1-Methoxyethyl | 2-(4-Methylphenyl)oxazol-4-yl |
| 1-Methoxyethyl | 2-tert-Butyloxazol-4-yl |
| 1-Methoxyethyl | 2-(2,4-Dichlorophenyl)oxazol-4-yl |
| 1-Methoxyethyl | 2-(4-Methoxyphenyl)oxazol-4-yl |
| 1-Methoxyethyl | 2-(4-Chlorophenyl)-5-bromooxazol-4-yi |
| n-Propoxymethyl | 2-Chloro-3-isopropylphenyl |
| n-Propoxymethyl | 2,6-Difluorophenyl |
| n-Propoxymethyl | 2-Chloro-3-trifluoromethylphenyl |
| n-Propoxymethyl | 3-Phenylisoxazol-5-yl |
| n-Propoxymethyl | 3-Methylisoxazol-5-yl |
| n-Propoxymethyl | 4-Chloro-3-methylisoxazol-5-yl |
| n-Propoxymethyl | 4-Chloro-3-isopropylisoxazol-5-yl |
| n-Propoxymethyl | 4-Chloro-3-sec-butylisoxazol-5-yl |
| n-Propoxymethyl | 4-Chloro-3-tert-butylisoxazol-5-yl |
| n-Propoxymethyl | 4-Chloro-3-cyclohexylisoxazol-5-yl |
| n-Propoxymethyl | 4-Chloro-3-phenylisoxazol-5-yl |
| n-Propoxymethyl | 4-Chloro-3-(4-methylphenyl)isoxazol-5-yl |
| n-Propoxymethyl | 4-Chloro-3-(4-chlorophenyl)isoxazol-5-yl |
| n-Propoxymethyl | 4-Chloro-3-(4-fluorophenyl)isoxazol-5-yl |
| n-Propoxymethyl | 4-Chloro-3-(4-trifluoromethylphenyl)isoxazol-5-yl |
| n-Propoxymethyl | 4-Chloro-3-(2,6-difluorophenyl)isoxazol-5-yl |
| n-Propoxymethyl | 2-Phenyloxazol-4-yl |
| n-Propoxymethyl | 2-(4-Fluorophenyl)oxazol-4-yl |
| n-Propoxymethyl | 2-(4-Chlorophenyl)oxazol-4-yl |
| n-Propoxymethyl | 2-(4-Bromophenyl)oxazol-4-yl |
| n-Propoxymethyl | 2-(3-Chlorophenyl)oxazol-4-yl |
| n-Propoxymethyl | 2-(4-Methylphenyl)oxazol-4-yl |
| n-Propoxymethyl | 2-tert-Butyloxazol-4-yl |
| n-Propoxymethyl | 2-(2,4-Dichlorophenyl)oxazol-4-yl |
| n-Propoxymethyl | 2-(4-Methoxyphenyl)oxazol-4-yl |
| n-Propoxymethyl | 2-(4-Chlorophenyl)-5-bromooxazol-4-yl |
| Isopropoxymethyl | 2-Chloro-3-isopropylphenyl |
| Isopropoxymethyl | 2,6-Difluorophenyl |

TABLE B-continued

| | R¹R²CH—ON=C(CN)-R³ | R¹ = H | I |
|---|---|---|---|
| R³ | R² | | |

| R³ | R² |
|---|---|
| Isopropoxymethyl | 2-Chloro-3-trifluoromethylphenyl |
| Isopropoxymethyl | 3-Phenylisoxazol-5-yl |
| Isopropoxymethyl | 3-Methylisoxazol-5-yl |
| Isopropoxymethyl | 4-Chloro-3-methylisoxazol-5-yl |
| Isopropoxymethyl | 4-Chloro-3-isopropylisoxazol-5-yl |
| Isopropoxymethyl | 4-Chloro-3-sec-butylisoxazol-5-yl |
| Isopropoxymethyl | 4-Chloro-3-tert-butylisoxazol-5-yl |
| Isopropoxymethyl | 4-Chloro-3-cyclohexylisoxazol-5-yl |
| Isopropoxymethyl | 4-Chloro-3-phenylisoxazol-5-yl |
| Isopropoxymethyl | 4-Chloro-3-(4-methylphenyl)isoxazol-5-yl |
| Isopropoxymethyl | 4-Chloro-3-(4-chlorophenyl)isoxazol-5-yl |
| Isopropoxymethyl | 4-Chloro-3-(4-fluorophenyl)isoxazol-5-yl |
| Isopropoxymethyl | 4-Chloro-3-(4-trifluoromethylphenyl)-isoxazol-5-yl |
| Isopropoxymethyl | 4-Chloro-3-(2,6-difluorophenyl)-isoxazol-5-yl |
| Isopropoxymethyl | 2-Phenyloxazol-4-yl |
| Isopropoxymethyl | 2-(4-Fluorophenyl)oxazol-4-yl |
| Isopropoxymethyl | 2-(4-Chlorophenyl)oxazol-4-yl |
| Isopropoxymethyl | 2-(4-Bromophenyl)oxazol-4-yl |
| Isopropoxymethyl | 2-(3-Chlorophenyl)oxazol-4-yl |
| Isopropoxymethyl | 2-(4-Methylphenyl)oxazol-4-yl |
| Isopropoxymethyl | 2-tert-Butyloxazol-4-yl |
| Isopropoxymethyl | 2-(2,4-Dichlorophenyl)oxazol-4-yl |
| Isopropoxymethyl | 2-(4-Methoxyphenyl)oxazol-4-yl |
| Isopropoxymethyl | 2-(4-Chlorophenyl)-5-bromooxazol-4-yl |
| tert-Butoxymethyl | 2-Chloro-3-isopropylphenyl |
| tert-Butoxymethyl | 2,6-Difluorophenyl |
| tert-Butoxymethyl | 2-Chloro-3-trifluoromethylphenyl |
| tert-Butoxymethyl | 3-Phenylisoxazol-5-yl |
| tert-Butoxymethyl | 3-Methylisoxazol-5-yl |
| tert-Butoxymethyl | 4-Chloro-3-methylisoxazol-5-yl |
| tert-Butoxymethyl | 4-Chloro-3-isopropylisoxazol-5-yl |
| tert-Butoxymethyl | 4-Chloro-3-sec-butylisoxazol-5-yl |
| tert-Butoxymethyl | 4-Chloro-3-tert-butylisoxazol-5-yl |
| tert-Butoxymethyl | 4-Chloro-3-cyclohexylisoxazol-5-yl |
| tert-Butoxymethyl | 4-Chloro-3-phenylisoxazol-5-yl |
| tert-Butoxymethyl | 4-Chloro-3-(4-methylphenyl)isoxazol-5-yl |
| tert-Butoxymethyl | 4-Chloro-3-(4-chlorophenyl)isoxazol-5-yl |
| tert-Butoxymethyl | 4-Chloro-3-(4-fluorophenyl)isoxazol-5-yl |
| tert-Butoxymethyl | 4-Chloro-3-(4-trifluoromethylphenyl)-isoxazol-5-yl |
| tert-Butoxymethyl | 4-Chloro-3-(2,6-difluorophenyl)-isoxazol-5-yl |
| tert-Butoxymethyl | 2-Phenyloxazol-4-yl |
| tert-Butoxymethyl | 2-(4-Fluorophenyl)oxazol-4-yl |
| tert-Butoxymethyl | 2-(4-Chlorophenyl)oxazol-4-yl |
| tert-Butoxymethyl | 2-(4-Bromophenyl)oxazol-4-yl |
| tert-Butoxymethyl | 2-(3-Chlorophenyl)oxazol-4-yl |
| tert-Butoxymethyl | 2-(4-Methylphenyl)oxazol-4-yl |
| tert-Butoxymethyl | 2-tert-Butyloxazol-4-yl |
| tert-Butoxymethyl | 2-(2,4-Dichlorophenyl)oxazol-4-yl |
| tert-Butoxymethyl | 2-(4-Methoxyphenyl)oxazol-4-yl |
| tert-Butoxymethyl | 2-(4-Chlorophenyl)-5-bromooxazol-4-yl |
| 1-Bromo-1-methylethyl | 2-Chloro-3-isopropylphenyl |
| 1-Bromo-1-methylethyl | 2,6-Difluorophenyl |
| 1-Bromo-1-methylethyl | 2-Chloro-3-trifluoromethylphenyl |
| 1-Bromo-1-methylethyl | 3-Phenylisoxazol-5-yl |
| 1-Bromo-1-methylethyl | 3-Methylisoxazol-5-yl |
| 1-Bromo-1-methylethyl | 4-Chloro-3-methylisoxazol-5-yl |
| 1-Bromo-1-methylethyl | 4-Chloro-3-isopropylisoxazol-5-yl |
| 1-Bromo-1-methylethyl | 4-Chloro-3-sec-butylisoxazol-5-yl |
| 1-Bromo-1-methylethyl | 4-Chloro-3-tert-butylisoxazol-5-yl |
| 1-Bromo-1-methylethyl | 4-Chloro-3-cyclohexylisoxazol-5-yl |
| 1-Bromo-1-methylethyl | 4-Chloro-3-phenylisoxazol-5-yl |
| 1-Bromo-1-methylethyl | 4-Chloro-3-(4-methylphenyl)isoxazol-5-yl |
| 1-Bromo-1-methylethyl | 4-Chloro-3-(4-chlorophenyl)isoxazol-5-yl |
| 1-Bromo-1-methylethyl | 4-Chloro-3-(4-fluorophenyl)isoxazol-5-yl |
| 1-Bromo-1-methylethyl | 4-Chloro-3-(4-trifluoromethylphenyl)-isoxazol-5-yl |
| 1-Bromo-1-methylethyl | 4-Chloro-3-(2,6-difluorophenyl)-isoxazol-5-yl |
| 1-Bromo-1-methylethyl | 2-Phenyloxazol-4-yl |
| 1-Bromo-1-methylethyl | 2-(4-Fluorophenyl)oxazol-4-yl |
| 1-Bromo-1-methylethyl | 2-(4-Chlorophenyl)oxazol-4-yl |
| 1-Bromo-1-mathylethyl | 2-(4-Bromophenyl)oxazol-4-yl |
| 1-Bromo-1-methylethyl | 2-(3-Chlorophenyl)oxazol-4-yl |
| 1-Bromo-1-methylethyl | 2-(4-Methylphenyl)oxazol-4-yl |
| 1-Bromo-1-methylethyl | 2-tert-Butyloxazol-4-yl |
| 1-Bromo-1-methylethyl | 2-(2,4-Dichlorophenyl)oxazol-4-yl |
| 1-Bromo-1-methylethyl | 2-(4-Methoxyphenyl)oxazol-4-yl |
| 1-Bromo-1-methylethyl | 2-(4-Chlorophenyl)-5-bromooxazol-4-yl |
| 1-Methoxy-1-methylethyl | 2-Chloro-3-isopropylphenyl |
| 1-Methoxy-1-methylethyl | 2,6-Difluorophenyl |
| 1-Methoxy-1-methylethyl | 2-Chloro-3-trifluoromethylphenyl |
| 1-Methoxy-1-methylethyl | 3-Phenylisoxazol-5-yl |
| 1-Methoxy-1-methylethyl | 3-Methylisoxazol-5-yl |
| 1-Methoxy-1-methylethyl | 4-Chloro-3-methylisoxazol-5-yl |
| 1-Methoxy-1-methylethyl | 4-Chloro-3-isopropylisoxazol-5-yl |
| 1-Methoxy-1-methylethyl | 4-Chloro-3-sec-butylisoxazol-5-yl |
| 1-Methoxy-1-methylethyl | 4-Chloro-3-tert-butylisoxazol-5-yl |
| 1-Methoxy-1-methylethyl | 4-Chloro-3-cyclohexylisoxazol-5-yl |
| 1-Methoxy-1-methylethyl | 4-Chloro-3-phenylisoxazol-5-yl |
| 1-Methoxy-1-methylethyl | 4-Chloro-3-(4-methylphenyl)isoxazol-5-yl |
| 1-Methoxy-1-methylethyl | 4-Chloro-3-(4-chlorophenyl)isoxazol-5-yl |
| 1-Methoxy-1-methylethyl | 4-Chloro-3-(4-fluorophenyl)isoxazol-5-yl |
| 1-Methoxy-1-methylethyl | 4-Chloro-3-(4-trifluoromethylphenyl)-isoxazol-5-yl |
| 1-Methoxy-1-methylethyl | 4-Chloro-3-(2,6-difluorophenyl)-isoxazol-5-yl |
| 1-Methoxy-1-methylethyl | 2-Phenyloxazol-4-yl |
| 1-Methoxy-1-methylethyl | 2-(4-Fluorophenyl)oxazol-4-yl |
| 1-Methoxy-1-methylethyl | 2-(4-Chlorophenyl)oxazol-4-yl |
| 1-Methoxy-1-methylethyl | 2-(4-Bromophenyl)oxazol-4-yl |
| 1-Methoxy-1-methylethyl | 2-(3-Chlorophenyl)oxazol-4-yl |
| 1-Methoxy-1-methylethyl | 2-(4-Methylphenyl)oxazol-4-yl |
| 1-Methoxy-1-methylethyl | 2-tert-Butyloxazol-4-yl |
| 1-Methoxy-1-methylethyl | 2-(2,4-Dichlorophenyl)oxazol-4-yl |
| 1-Methoxy-1-methylethyl | 2-(4-Methoxyphenyl)oxazol-4-yl |
| 1-Methoxy-1-methylethyl | 2-(4-Chlorophenyl)-5-bromoexazol-4-yl |
| Methylthiomethyl | 2-Chloro-3-isopropylphenyl |
| Methylthiomethyl | 2,6-Difluorophenyl |
| Methylthiomethyl | 2-Chloro-3-trifluoromethylphenyl |
| Methylthiomethyl | 3-Phenylisoxazol-5-yl |
| Methylthiomethyl | 3-Methylisoxazol-5-yl |
| Methylthiomethyl | 4-Chloro-3-methylisoxazol-5-yl |
| Methylthiomethyl | 4-Chloro-3-isopropylisoxazol-5-yl |
| Methylthiomethyl | 4-Chloro-3-sec-butylisoxazol-5-yl |
| Methylthiomethyl | 4-Chloro-3-tert-butylisoxazol-5-yl |
| Methylthiomethyl | 4-Chloro-3-cyclohexylisoxazol-5-yl |
| Methylthiomethyl | 4-Chloro-3-phenylisoxazol-5-yl |
| Methylthiomethyl | 4-Chloro-3-(4-methylphenyl)isoxazol-5-yl |
| Methylthiomethyl | 4-Chloro-3-(4-chlorophenyl)isoxazol-5-yl |
| Methylthiomethyl | 4-Chloro-3-(4-fluorophenyl)isoxazol-5-yl |
| Methylthiomethyl | 4-Chloro-3-(4-trifluoromethylphenyl)-isoxazol-5-yl |
| Methylthiomethyl | 4-Chloro-3-(2,6-difluorophenyl)-isoxazol-5-yl |
| Methylthiomethyl | 2-Phenyloxazol-4-yl |
| Methylthiomethyl | 2-(4-Fluorophenyl)oxazol-4-yl |
| Methylthiomethyl | 2-(4-Chlorophenyl)oxazol-4-yl |
| Methylthiomethyl | 2-(4-Bromophenyl)oxazol-4-yl |
| Methylthiomethyl | 2-(3-Chlorophenyl)oxazol-4-yl |
| Methylthiomethyl | 2-(4-Methylphenyl)oxazol-4-yl |
| Methylthiomethyl | 2-tert-Butyloxazol-4-yl |

TABLE B-continued $R^1R^2CH-ON=C(CN)-R^3 \qquad R^1 = H \qquad I$

| $R^3$ | $R^2$ |
|---|---|
| Methylthiomethyl | 2-(2,4-Dichlorophenyl)oxazol-4-yl |
| Methylthiomethyl | 2-(4-Methoxyphenyl)oxazol-4-yl |
| Methylthiomethyl | 2-(4-Chlorophenyl)-5-bromooxazol-4-yl |
| 2-tert-Butylthiomethyl | 2-Chloro-3-isopropylphenyl |
| 2-tert-Butylthiomethyl | 2,6-Difluorophenyl |
| 2-tert-Butylthiomethyl | 2-Chloro-3-trifluoromethylphenyl |
| 2-tert-Butylthiomethyl | 3-Phenylisoxazol-5-yl |
| 2-tert-Butylthiomethyl | 3-Methylisoxazol-5-yl |
| 2-tert-Butylthiomethyl | 4-Chloro-3-methylisoxazol-5-yl |
| 2-tert-Butylthiomethyl | 4-Chloro-3-isopropylisoxazol-5-yl |
| 2-tert-Butylthiomethyl | 4-Chloro-3-sec-butylisoxazol-5-yl |
| 2-tert-Butylthiomethyl | 4-Chloro-3-tert-butylisoxazol-5-yl |
| 2-tert-Butylthiomethyl | 4-Chloro-3-cyclohexylisoxazol-5-yl |
| 2-tert-Butylthiomethyl | 4-Chloro-3-phenylisoxazol-5-yl |
| 2-tert-Butylthiomethyl | 4-Chloro-3-(4-methylphenyl)isoxazol-5-yl |
| 2-tert-Butylthiomethyl | 4-Chloro-3-(4-chlorophenyl)isoxazol-5-yl |
| 2-tert-Butylthiomethyl | 4-Chloro-3-(4-fluorophenyl)isoxazol-5-yl |
| 2-tert-Butylthiomethyl | 4-Chloro-3-(4-trifluoromethylphenyl)-isoxazol-5-yl |
| 2-tert-Butylthiomethyl | 4-Chloro-3-(2,6-difluorophenyl)-isoxazol-5-yl |
| 2-tert-Butylthiomethyl | 2-Phonyloxazol-4-yl |
| 2-tert-Butylthiomethyl | 2-(4-Fluorophenyl)oxazol-4-yl |
| 2-tert-Butylthiomethyl | 2-(4-Chlorophenyl)oxazol-4-yl |
| 2-tert-Butylthiomethyl | 2-(4-Bromophenyl)oxazol-4-yl |
| 2-tert-Butylthiomethyl | 2-(3-Chlorophenyl)oxazol-4-yl |
| 2-tert-Butylthiomethyl | 2-(4-Methylphenyl)oxazol-4-yl |
| 2-tert-Butylthiomethyl | 2-tert-Butyloxazol-4-yl |
| 2-tert-Butylthiomethyl | 2-(2,4-Dichlorophenyl)oxazol-4-yl |
| 2-tert-Butylthiomethyl | 2-(4-Methoxyphenyl)oxazol-4-yl |
| 2-tert-Butylthiomethyl | 2-(4-Chlorophenyl)-5-bromooxazol-4-yl |
| n-Hexyl | 2-Chloro-3-isopropylphenyl |
| n-Hexyl | 2,6-Difluorophenyl |
| n-Hexyl | 2-Chloro-3-trifluoromethylphenyl |
| n-Hexyl | 3-Phenylisoxazol-5-yl |
| n-Hexyl | 3-Methylisoxazol-5-yl |
| n-Hexyl | 4-Chloro-3-methylisoxazol-5-yl |
| n-Hexyl | 4-Chloro-3-isopropylisoxazol-5-yl |
| n-Hexyl | 4-Chloro-3-sec-butylisoxazol-5-yl |
| n-Hexyl | 4-Chloro-3-tert-butylisoxazol-5-yl |
| n-Hexyl | 4-Chloro-3-cyclohexylisoxazol-5-yl |
| n-Hexyl | 4-Chloro-3-phenylisoxazol-5-yl |
| n-Hexyl | 4-Chloro-3-(4-methylphenyl)isoxazol-5-yl |
| n-Hexyl | 4-Chloro-3-(4-chlorophenyl)isoxazol-5-yl |
| n-Hexyl | 4-Chloro-3-(4-fluorophenyl)isoxazol-5-yl |
| n-Hexyl | 4-Chloro-3-(4-trifluoromethylphenyl)-isoxazol-5-yl |
| n-Hexyl | 4-Chloro-3-(2,6-difluorophenyl)-isoxazol-5-yl |
| n-Hexyl | 2-Phenyloxazol-4-yl |
| n-Hexyl | 2-(4-Fluorophenyl)oxazol-4-yl |
| n-Hexyl | 2-(4-Chlorophenyl)oxazol-4-yl |
| n-Hexyl | 2-(4-Bromophenyl)oxazol-4-yl |
| n-Hexyl | 2-(3-Chlorophenyl)oxazol-4-yl |
| n-Hexyl | 2-(4-Methylphenyl)oxazol-4-yl |
| n-Hexyl | 2-tert-Butyloxazol-4-yl |
| n-Hexyl | 2-(2,4-Dichlorophenyl)oxazol-4-yl |
| n-Hexyl | 2-(4-Methoxyphenyl)oxazol-4-yl |
| n-Hexyl | 2-(4-Chlorophenyl)-5-bromooxazol-4-yl |
| n-Decyl | 2-Chloro-3-isopropylphenyl |
| n-Decyl | 2,6-Difluorophenyl |
| n-Decyl | 2-Chloro-3-trifluoro-methylphenyl |
| n-Decyl | 3-Phenylisoxazol-5-yl |
| n-Decyl | 3-Methylisoxazol-5-yl |
| n-Decyl | 4-Chloro-3-methylisoxazol-5-yl |
| n-Decyl | 4-Chloro-3-isopropylisoxazol-5-yl |
| n-Decyl | 4-Chloro-3-sec-butylisoxazol-5-yl |
| n-Decyl | 4-Chloro-3-tert-butylisoxazol-5-yl |
| n-Decyl | 4-Chloro-3-cyclohexylisoxazol-5-yl |
| n-Decyl | 4-Chloro-3-phenylisoxazol-5-yl |
| n-Decyl | 4-Chloro-3-(4-methylphenyl)isoxazol-5-yl |
| n-Decyl | 4-Chloro-3-(4-chlorophenyl)isoxazol-5-yl |
| n-Decyl | 4-Chloro-3-(4-fluorophenyl)isoxazol-5-yl |
| n-Decyl | 4-Chloro-3-(4-trifluoromethylphenyl)-isoxazol-5-yl |
| n-Decyl | 4-Chloro-3-(2,6-difluorophenyl)-isoxazol-5-yl |
| n-Decyl | 2-Phenyloxazol-4-yl |
| n-Decyl | 2-(4-Fluorophenyl)oxazol-4-yl |
| n-Decyl | 2-(4-Chlorophenyl)oxazol-4-yl |
| n-Decyl | 2-(4-Bromophenyl)oxazol-4-yl |
| n-Decyl | 2-(3-Chlorophenyl)oxazol-4-yl |
| n-Decyl | 2-(4-Methylphenyl)oxazol-4-yl |
| n-Decyl | 2-tert-Butyloxazol-4-yl |
| n-Decyl | 2-(2,4-Dichlorophenyl)oxazol-4-yl |
| n-Decyl | 2-(4-Methoxyphenyl)oxazol-4-yl |
| n-Decyl | 2-(4-Chlorophenyl)-5-bromooxazol-4-yl |
| Cyclohexyl | 2-Chloro-3-isopropylphenyl |
| Cyclohexyl | 2,6-Difluorophenyl |
| Cyclohexyl | 2-Chloro-3-trifluoromethylphenyl |
| Cyclohexyl | 3-Phenylisoxazol-5-yl |
| Cyclohexyl | 3-Methylisoxazol-5-yl |
| Cyclohexyl | 4-Chloro-3-methylisoxazol-5-yl |
| Cyclohexyl | 4-Chloro-3-isopropylisoxazol-5-yl |
| Cyclohexyl | 4-Chloro-3-sec-butylisoxazol-5-yl |
| Cyclohexyl | 4-Chloro-3-tert-butylisoxazol-5-yl |
| Cyclohexyl | 4-Chloro-3-cyclohexylisoxazol-5-yl |
| Cyclohexyl | 4-Chloro-3-phenylisoxazol-5-yl |
| Cyclohexyl | 4-Chloro-3-(4-methylphenyl)isoxazol-5-yl |
| Cyclohexyl | 4-Chloro-3-(4-chlorophenyl)isoxazol-5-yl |
| Cyclohexyl | 4-Chloro-3-(4-fluorophenyl)isoxazol-5-yl |
| Cyclohexyl | 4-Chloro-3-(4-trifluoromethylphenyl)-isoxazol-5-yl |
| Cyclohexyl | 4-Chloro-3-(2,6-difluorophenyl)-isoxazol-5-yl |
| Cyclohexyl | 2-Phenyloxazol-4-yl |
| Cyclohexyl | 2-(4-Fluorophenyl)oxazol-4-yl |
| Cyclohexyl | 2-(4-Chlorophenyl)oxazol-4-yl |
| Cyclohexyl | 2-(4-Bromophenyl)oxazol-4-yl |
| Cyclohexyl | 2-(3-Chlorophenyl)oxazol-4-yl |
| Cyclohexyl | 2-(4-Methylphenyl)oxazol-4-yl |
| Cyclohexyl | 2-tert-Butyloxazol-4-yl |
| Cyclohexyl | 2-(2,4-Dichlorophenyl)oxazol-4-yl |
| Cyclohexyl | 2-(4-Methoxyphenyl)oxazol-4-yl |
| Cyclohexyl | 2-(4-Chlorophenyl)-5-bromooxazol-4-yl |
| Phenylthiomethyl | 2-Chloro-3-isopropylphenyl |
| Phenylthiomethyl | 2,6-Difluorophenyl |
| Phenylthiomethyl | 2-Chloro-3-trifluoromethylphenyl |
| Phenylthiomethyl | 3-Phenylisoxazol-5-yl |
| Phenylthiomethyl | 3-Methylisoxazol-5-yl |
| Phenylthiomethyl | 4-Chloro-3-methylisoxazol-5-yl |
| Phenylthiomethyl | 4-Chloro-3-isopropylisoxazol-5-yl |
| Phenylthiomethyl | 4-Chloro-3-sec-butylisoxazol-5-yl |
| Phenylthiomethyl | 4-Chloro-3-tert-butylisoxazol-5-yl |
| Phenylthiomethyl | 4-Chloro-3-cyclohexylisoxazol-5-yl |
| Phenylthiomethyl | 4-Chloro-3-phenylisoxazol-5-yl |
| Phenylthiomethyl | 4-Chloro-3-(4-methylphenyl)isoxazol-5-yl |
| Phenylthiomethyl | 4-Chloro-3-(4-chlorophenyl)isoxazol-5-yl |
| Phenylthiomethyl | 4-Chloro-3-(4-fluorophenyl)isoxazol-5-yl |
| Phenylthiomethyl | 4-Chloro-3-(4-trifluoromethylphenyl)-isoxazol-5-yl |
| Phenylthiomethyl | 4-Chloro-3-(2,6-difluorophenyl)-isoxazol-5-yl |
| Phenylthiomethyl | 2-Phenyloxazol-4-yl |
| Phenylthiomethyl | 2-(4-Fluorophenyl)oxazol-4-yl |

TABLE B-continued

| | R¹R²CH—ON=C(CN)-R³ R¹ = H I | |
|---|---|---|
| R³ | R² | |
| Phenylthiomethyl | 2-(4-Chlorophenyl)oxazol-4-yl | |
| Phenylthiomethyl | 2-Bromophenyl)oxazol-4-yl | |
| Phenylthiomethyl | 2-(3-Chlorophenyl)oxazol-4-yl | |
| Phenylthiomethyl | 2-(4-Methylphenyl)oxazol-4-yl | |
| Phenylthiomethyl | 2-tert-Butyloxazol-4-yl | |
| Phenylthiomethyl | 2-(2,4-Dichlorophenyl)oxazol-4-yl | |
| Phenylthiomethyl | 2-(4-Methoxyphenyl)oxazol-4-yl | |
| Phenylthiomethyl | 2-(4-Chlorophenyl)-5-bromooxazol-4-yl | |
| Ethynyl | 2-Chloro-3-isopropylphenyl | |
| Ethynyl | 2,6-Difluorophenyl | |
| Ethynyl | 2-Chloro-3-trifluoromethylphenyl | |
| Ethynyl | 3-Phenylisoxazol-5-yl | |
| Ethynyl | 3-Methylisoxazol-5-y | |
| Ethynyl | 4-Chloro-3-methylisoxazol-5-yl | |
| Ethynyl | 4-Chloro-3-isopropylisoxazol-5-yl | |
| Ethynyl | 4-Chloro-3-sec-butylisoxazol-5-yl | |
| Ethynyl | 4-Chloro-3-tert-butylisoxazol-5-yl | |
| Ethynyl | 4-Chloro-3-cyclohexylisoxazol-5-yl | |
| Ethynyl | 4-Chloro-3-phenylisoxazol-5-yl | |
| Ethynyl | 4-Chloro-3-(4-methylphenyl)isoxazol-5-yl | |
| Ethynyl | 4-Chloro-3-(4-chlorophenyl)isoxazol-5-yl | |
| Ethynyl | 4-Chloro-3-(4-fluorophenyl)isoxazol-5-yl | |
| Ethynyl | 4-Chloro-3-(4-trifluoromethylphenyl)-isoxazol-5-yl | |
| Ethynyl | 4-Chloro-3-(2,6-difluorophenyl)-isoxazol-5-yl | |
| Ethynyl | 2-Phenyloxazol-4-yl | |
| Ethynyl | 2-(4-Fluorophenyl)oxazol-4-yl | |
| Ethynyl | 2-(4-Chlorophenyl)oxazol-4-yl | |
| Ethynyl | 2-(4-Bromophenyl)oxazol-4-yl | |
| Ethynyl | 2-(3-Chlorophenyl)oxazol-4-yl | |
| Ethynyl | 2-(4-Methylphenyl)oxazol-4-yl | |
| Ethynyl | 2-tert-Butyloxazol-4-yl | |
| Ethynyl | 2-(2,4-Dichlorophenyl)oxazol-4-yl | |
| Ethynyl | 2-(4-Methoxyphenyl)oxazol-4-yl | |
| Ethynyl | 2-(4-Chlorophenyl)-5-bromooxazol-4-yl | |
| 1-Propynyl | 2-Chloro-3-isopropylphenyl | |
| 1-Propynyl | 2,6-Difluorophenyl | |
| 1-Propynyl | 2-Chloro-3-trifluoromethylphenyl | |
| 1-Propynyl | 3-Phenylisoxazol-5-yl | |
| 1-Propynyl | 3-Methylisoxazol-5-yl | |
| 1-Propynyl | 4-Chloro-3-methylisoxazol-5-yl | |
| 1-Propynyl | 4-Chloro-3-isopropylisoxazol-5-yl | |
| 1-Propynyl | 4-Chloro-3-sec-butylisoxazol-5-yl | |
| 1-Propynyl | 4-Chloro-3-tert-butylisoxazol-5-yl | |
| 1-Propynyl | 4-Chloro-3-cyclohexylisoxazol-5-yl | |
| 1-Propynyl | 4-Chloro-3-phenylisoxazol-5-yl | |
| 1-Propynyl | 4-Chloro-3-(4-methylphenyl)isoxazol-5-yl | |
| 1-Propynyl | 4-Chloro-3-(4-chlorophenyl)isoxazol-5-yl | |
| 1-Propynyl | 4-Chloro-3-(4-fluorophenyl)isoxazol-5-yl | |
| 1-Propynyl | 4-Chloro-3-(4-trifluoromethylphenyl)-isoxazol-5-yl | |
| 1-Propynyl | 4-Chloro-3-(2,6-difluorophenyl)-isoxazol-5-yl | |
| 1-Propynyl | 2-Phenyloxazol-4-yl | |
| 1-Propynyl | 2-(4-Fluorophenyl)oxazol-4-yl | |
| 1-Propynyl | 2-(4-Chlorophenyl)oxazol-4-yl | |
| 1-Propynyl | 2-(4-Bromophenyl)oxazol-4-yl | |
| 1-Propynyl | 2-(3-Chlorophenyl)oxazol-4-yl | |
| 1-Propynyl | 2-(4-Methylphenyl)oxazol-4-yl | |
| 1-Propynyl | 2-tert-Butyloxazol-4-yl | |
| 1-Propynyl | 2-(2,4-Dichlorophenyl)oxazol-4-yl | |
| 1-Propynyl | 2-(4-Methoxyphenyl)oxazol-4-yl | |
| 1-Propynyl | 2-(4-Chlorophenyl)-5-bromooxazol-4-yl | |
| Benzyl | 2-Chloro-3-isopropylphenyl | |
| Benzyl | 2,6-Difluorophenyl | |
| Benzyl | 2-Chloro-3-trifluoromethylphenyl | |
| Benzyl | 3-Phenylisoxazol-5-yl | |
| Benzyl | 3-Methylisoxazol-5-yl | |
| Benzyl | 4-Chloro-3-methylisoxazol-5-yl | |
| Benzyl | 4-Chloro-3-isopropylisoxazol-5-yl | |
| Benzyl | 4-Chloro-3-sec-butylisoxazol-5-yl | |
| Benzyl | 4-Chloro-3-tert-butylisoxazol-5-yl | |
| Benzyl | 4-Chloro-3-cyclohexylisoxazol-5-yl | |
| Benzyl | 4-Chloro-3-phenylisoxazol-5-yl | |
| Benzyl | 4-Chloro-3-(4-methylphenyl)isoxazol-5-yl | |
| Benzyl | 4-Chloro-3-(4-chlorophenyl)isoxazol-5-yl | |
| Benzyl | 4-Chloro-3-(4-fluorophenyl)isoxazol-5-yl | |
| Benzyl | 4-Chloro-3-(4-trifluoromethylphenyl)-isoxazol-5-yl | |
| Benzyl | 4-Chloro-3-(2,6-difluorophenyl)-isoxazol-5-yl | |
| Benzyl | 2-Phenyloxazol-4-yl | |
| Benzyl | 2-(4-Fluorophenyl)oxazol-4-yl | |
| Benzyl | 2-(4-Chlorophenyl)oxazol-4-yl | |
| Benzyl | 2-(4-Bromophenyl)oxazol-4-yl | |
| Benzyl | 2-(3-Chlorophenyl)oxazol-4-yl | |
| Benzyl | 2-(4-Methylphenyl)oxazol-4-yl | |
| Benzyl | 2-tert-Butyloxazol-4-yl | |
| Benzyl | 2-(2,4-Dichlorophenyl)oxazol-4-yl | |
| Benzyl | 2-(4-Methoxyphenyl)oxazol-4-yl | |
| Benzyl | 2-(4-Chlorophenyl)-5-bromooxazol-4-yl | |
| 2-Methylbenzyl | 2-Chloro-3-isopropylphenyl | |
| 2-Methylbenzyl | 2,6-Difluorophenyl | |
| 2-Methylbenzyl | 2-Chloro-3-trifluoromethylphenyl | |
| 2-Methylbenzyl | 3-Phenylisoxazol-5-yl | |
| 2-Methylbenzyl | 3-Methylisoxazol-5-yl | |
| 2-Methylbenzyl | 4-Chloro-3-methylisoxazol-5-yl | |
| 2-Methylbenzyl | 4-Chloro-3-isopropylisoxazol-5-yl | |
| 2-Methylbenzyl | 4-Chloro-3-sec-butylisoxazol-5-yl | |
| 2-Methylbenzyl | 4-Chloro-3-tert-butylisoxazol-5-yl | |
| 2-Methylbenzyl | 4-Chloro-3-cyclohexylisoxazol-5-yl | |
| 2-Methylbenzyl | 4-Chloro-3-phenylisoxazol-5-yl | |
| 2-Methylbenzyl | 4-Chloro-3-(4-methylphenyl)isoxazol-5-yl | |
| 2-Methylbenzyl | 4-Chloro-3-(4-chlorophenyl)isoxazol-5-yl | |
| 2-Methylbenzyl | 4-Chloro-3-(4-fluorophenyl)isoxazol-5-yl | |
| 2-Methylbenzyl | 4-Chloro-3-(4-trifluoromethylphenyl)-isoxazol-5-yl | |
| 2-Methylbenzyl | 4-Chloro-3-(2,6-difluorophenyl)-isoxazol-5-yl | |
| 2-Methylbenzyl | 2-Phenyloxazol-4-yl | |
| 2-Methylbenzyl | 2-(4-Fluorophenyl)oxazol-4-yl | |
| 2-Methylbenzyl | 2-(4-Chlorophenyl)oxazol-4-yl | |
| 2-Methylbenzyl | 2-(4-Bromophenyl)oxazol-4-yl | |
| 2-Methylbenzyl | 2-(3-Chlorophenyl)oxazol-4-yl | |
| 2-Methylbenzyl | 2-(4-Methylphenyl)oxazol-4-yl | |
| 2-Methylbenzyl | 2-tert-Butyloxazol-4-yl | |
| 2-Methylbenzyl | 2-(2,4-Dichlorophenyl)oxazol-4-yl | |
| 2-Methylbenzyl | 2-(4-Methoxyphenyl)oxazol-4-yl | |
| 3-Methylbenzyl | 2-(4-Chlorophenyl)-5-bromooxazol-4-yl | |
| 3-Methylbenzyl | 2-Chloro-3-isopropylphenyl | |
| 3-Methylbenzyl | 2,6-Difluorophenyl | |
| 3-Methylbenzyl | 2-Chloro-3-trifluoromethylphenyl | |
| 3-Methylbenzyl | 3-Phenylisoxazol-5-yl | |
| 3-Methylbenzyl | 3-Methylisoxazol-5-yl | |
| 3-Methylbenzyl | 4-Chloro-3-methylisoxazol-5-yl | |
| 3-Methylbenzyl | 4-Chloro-3-isopropylisoxazol-5-yl | |
| 3-Methylbenzyl | 4-Chloro-3-sec-butylisoxazol-5-yl | |
| 3-Methylbenzyl | 4-Chloro-3-tert-butylisoxazol-5-yl | |
| 3-Methylbenzyl | 4-Chloro-3-cyclohexylisoxazol-5-yl | |
| 3-Methylbenzyl | 4-Chloro-3-phenylisoxazol-5-yl | |
| 3-Methylbenzyl | 4-Chloro-3-(4-methylphenyl)isoxazol-5-yl | |
| 3-Methylbenzyl | 4-Chloro-3-(4-chlorophenyl)isoxazol-5-yl | |
| 3-Methylbenzyl | 4-Chloro-3-(4-fluorophenyl)isoxazol-5-yl | |
| 3-Methylbenzyl | 4-Chloro-3-(4-trifluoromethylphenyl)- | |

TABLE B-continued $R^1R^2CH-ON=C(CN)-R^3 \quad R^1 = H \quad I$

| R³ | R² |
|---|---|
| | isoxazol-5-yl |
| 3-Methylbenzyl | 4-Chloro-3-(2,6-difluorophenyl)-isoxazol-5-yl |
| 3-Methylbenzyl | 2-Phenyloxazol-4-yl |
| 3-Methylbenzyl | 2-(4-Fluorophenyl)oxazol-4-yl |
| 3-Methylbenzyl | 2-(4-Chlorophenyl)oxazol-4-yl |
| 3-Methylbenzyl | 2-(4-Bromophenyl)oxazol-4-yl |
| 3-Methylbenzyl | 2-(3-Chlorophenyl)oxazol-4-yl |
| 3-Methylbenzyl | 2-(4-Methylphenyl)oxazol-4-yl |
| 3-Methylbenzyl | 2-tert-Butyloxazol-4-yl |
| 3-Methylbenzyl | 2-(2,4-Dichlorophenyl)oxazol-4-yl |
| 3-Methylbenzyl | 2-(4-Methoxyphenyl)oxazol-4-yl |
| 3-Methylbenzyl | 2-(4-Chlorophenyl)-5-bromooxazol-4-yl |
| 4-Methylbenzyl | 2-Chloro-3-isopropylphenyl |
| 4-Methylbenzyl | 2,6-Difluorophenyl |
| 4-Methylbenzyl | 2-Chloro-3-trifluoromethylphenyl |
| 4-Methylbenzyl | 3-Phenylisoxazol-5-yl |
| 4-Methylbenzyl | 3-Methylisoxazol-5-yl |
| 4-Methylbenzyl | 4-Chloro-3-methylisoxazol-5-yl |
| 4-Methylbenzyl | 4-Chloro-3-isopropylisoxazol-5-yl |
| 4-Methylbenzyl | 4-Chloro-3-sec-butylisoxazol-5-yl |
| 4-Methylbenzyl | 4-Chloro-3-tert-butylisoxazol-5-yl |
| 4-Methylbenzyl | 4-Chloro-3-cyclohexylisoxazol-5-yl |
| 4-Methylbenzyl | 4-Chloro-3-phenylisoxazol-5-yl |
| 4-Methylbenzyl | 4-Chloro-3-(4-methylphenyl)isoxazol-5-yl |
| 4-Methylbenzyl | 4-Chloro-3-(4-chlorophenyl)isoxazol-5-yl |
| 4-Methylbenzyl | 4-Chloro-3-(4-fluorophenyl)isoxazol-5-yl |
| 4-Methylbenzyl | 4-Chloro-3-(4-trifluoromethylphenyl)-isoxazol-5-yl |
| 4-Methylbenzyl | 4-Chloro-3-(2,6-difluorophenyl)-isoxazol-5-yl |
| 4-Methylbenzyl | 2-Phenyloxazol-4-yl |
| 4-Methylbenzyl | 2-(4-Fluorophenyl)oxazol-4-yl |
| 4-Methylbenzyl | 2-(4-Chlorophenyl)oxazol-4-yl |
| 4-Methylbenzyl | 2-(4-Bromophenyl)oxazol-4-yl |
| 4-Methylbenzyl | 2-(3-Chlorophenyl)oxazol-4-yl |
| 4-Methylbenzyl | 2-(4-Methylphenyl)oxazol-4-yl |
| 4-Methylbenzyl | 2-tert-Butyloxazol-4-yl |
| 4-Methylbenzyl | 2-(2,4-Dichlorophenyl)oxazol-4-yl |
| 4-Methylbenzyl | 2-(4-Methoxyphenyl)oxazol-4-yl |
| 4-Methylbenzyl | 2-(4-Chlorophenyl)-5-bromooxazol-4-yl |
| 4-tert-Butylbenzyl | 2-Chloro-3-isopropylphenyl |
| 4-tert-Butylbenzyl | 2,6-Difluorophenyl |
| 4-tert-Butylbenzyl | 2-Chloro-3-trifluoromethylphenyl |
| 4-tert-Butylbenzyl | 3-Phenylisoxazol-5-yl |
| 4-tert-Butylbenzyl | 3-Methylisoxazol-5-yl |
| 4-tert-Butylbenzyl | 4-Chloro-3-methylisoxazol-5-yl |
| 4-tert-Butylbenzyl | 4-Chloro-3-isopropylisoxazol-5-yl |
| 4-tert-Butylbenzyl | 4-Chloro-3-sec-butylisoxazol-5-yl |
| 4-tert-Butylbenzyl | 4-Chloro-3-tert-butylisoxazol-5-yl |
| 4-tert-Butylbenzyl | 4-Chloro-3-cyclohexylisoxazol-5-yl |
| 4-tert-Butylbenzyl | 4-Chloro-3-phenylisoxazol-5-yl |
| 4-tert-Butylbenzyl | 4-Chloro-3-(4-methylphenyl)isoxazol-5-yl |
| 4-tert-Butylbenzyl | 4-Chloro-3-(4-chlorophenyl)isoxazol-5-yl |
| 4-tert-Butylbenzyl | 4-Chloro-3-(4-fluorophenyl)isoxazol-5-yl |
| 4-tert-Butylbenzyl | 4-Chloro-3-(4-trifluoromethylphenyl)-isoxazol-5-yl |
| 4-tert-Butylbenzyl | 4-Chloro-3-(2,6-difluorophenyl)-isoxazol-5-yl |
| 4-tert-Butylbenzyl | 2-Phenyloxazol-4-yl |
| 4-tert-Butylbenzyl | 2-(4-Fluorophenyl)oxazol-4-yl |
| 4-tert-Butylbenzyl | 2-(4-Chlorophenyl)oxazol-4-yl |
| 4-tert-Butylbenzyl | 2-(4-Bromophenyl)oxazol-4-yl |
| 4-tert-Butylbenzyl | 2-(3-Chlorophenyl)oxazol-4-yl |
| 4-tert-Butylbenzyl | 2-(4-Methylphenyl)oxazol-4-yl |
| 4-tert-Butylbenzyl | 2-tert-Butyloxazol-4-yl |
| 4-tert-Butylbenzyl | 2-(2,4-Dichlorophenyl)oxazol-4-yl |
| 4-tert-Butylbenzyl | 2-(4-Methoxyphenyl)oxazol-4-yl |
| 4-tert-Butylbenzyl | 2-(4-Chlorophenyl)-5-bromooxazol-4-yl |
| 2-Chlorobenzyl | 2-Chloro-3-isopropylphenyl |
| 2-Chlorobenzyl | 2,6-Difluorophenyl |
| 2-Chlorobenzyl | 2-Chloro-3-trifluoromethylphenyl |
| 2-Chlorobenzyl | 3-Phenylisoxazol-5-yl |
| 2-Chlorobenzyl | 3-Methylisoxazol-5-yl |
| 2-Chlorobenzyl | 4-Chloro-3-methylisoxazol-5-yl |
| 2-Chlorobenzyl | 4-Chloro-3-isopropylisoxazol-5-yl |
| 2-Chlorobenzyl | 4-Chloro-3-sec-butylisoxazol-5-yl |
| 2-Chlorobenzyl | 4-Chloro-3-tert-butylisoxazol-5-yl |
| 2-Chlorobenzyl | 4-Chloro-3-cyclohoxylisoxazol-5-yl |
| 2-Chlorobenzyl | 4-Chloro-3-phenylisoxazol-5-yl |
| 2-Chlorobenzyl | 4-Chloro-3-(4-methylphenyl)isoxazol-5-yl |
| 2-Chlorobenzyl | 4-Chloro-3-(4-chlorophenyl)isoxazol-5-yl |
| 2-Chlorobenzyl | 4-Chloro-3-(4-fluorophenyl)isoxazol-5-yl |
| 2-Chlorobenzyl | 4-Chloro-3-(4-trifluoromethylphenyl)-isoxazol-5-yl |
| 2-Chlorobenzyl | 4-Chloro-3-(2,6-difluorophenyl)-isoxazol-5-yl |
| 2-Chlorobenzyl | 2-Phenyloxazol-4-yl |
| 2-Chlorobenzyl | 2-(4-Fluorophenyl)oxazol-4-yl |
| 2-Chlorobenzyl | 2-(4-Chlorophenyl)oxazol-4-yl |
| 2-Chlorobenzyl | 2-(4-Bromophenyl)oxazol-4-yl |
| 2-Chlorobenzyl | 2-(3-Chlorophenyl)oxazol-4-yl |
| 2-Chlorobenzyl | 2-(4-Methylphenyl)oxazol-4-yl |
| 2-Chlorobenzyl | 2-tert-Butyloxazol-4-yl |
| 2-Chlorobenzyl | 2-(2,4-Dichlorophenyl)oxazol-4-yl |
| 2-Chlorobenzyl | 2-(4-Methoxyphenyl)oxazol-4-yl |
| 2-Chlorobenzyl | 2-(4-Chlorophenyl)-5-bromooxazol-4-yl |
| 3-Chlorobenzyl | 2-Chloro-3-isopropylphenyl |
| 3-Chlorobenzyl | 2,6-Difluorophenyl |
| 3-Chlorobenzyl | 2-Chloro-3-trifluoromethylphenyl |
| 3-Chlorobenzyl | 3-Phenylisoxazol-5-yl |
| 3-Chlorobenzyl | 3-Methylisoxazol-5-yl |
| 3-Chlorobenzyl | 4-Chloro-3-methylisoxazol-5-yl |
| 3-Chlorobenzyl | 4-Chloro-3-isopropylisoxazol-5-yl |
| 3-Chlorobenzyl | 4-Chloro-3-sec-butylisoxazol-5-yl |
| 3-Chlorobenzyl | 4-Chloro-3-tert-butylisoxazol-5-yl |
| 3-Chlorobenzyl | 4-Chloro-3-cyclohexylisoxazol-5-yl |
| 3-Chlorobenzyl | 4-Chloro-3-phenylisoxazol-5-yl |
| 3-Chlorobenzyl | 4-Chloro-3-(4-methylphenyl)isoxazol-5-yl |
| 3-Chlorobenzyl | 4-Chloro-3-(4-chlorophenyl)isoxazol-5-yl |
| 3-Chlorobenzyl | 4-Chloro-3-(4-fluorophenyl)isoxazol-5-yl |
| 3-Chlorobenzyl | 4-Chloro-3-(4-trifluoromethylphenyl)-isoxazol-5-yl |
| 3-Chlorobenzyl | 4-Chloro-3-(2,6-difluorophenyl)-isoxazol-5-yl |
| 3-Chlorobenzyl | 2-Phenyloxazol-4-yl |
| 3-Chlorobenzyl | 2-(4-Fluorophenyl)oxazol-4-yl |
| 3-Chlorobenzyl | 2-(4-Chlorophenyl)oxazol-4-yl |
| 3-Chlorobenzyl | 2-(4-Bromophenyl)oxazol-4-yl |
| 3-Chlorobenzyl | 2-(3-Chlorophenyl)oxazol-4-yl |
| 3-Chlorobenzyl | 2-(4-Methylphenyl)oxazol-4-yl |
| 3-Chlorobenzyl | 2-tert-Butyloxazol-4-yl |
| 3-Chlorobenzyl | 2-(2,4-Dichlorophenyl)oxazol-4-yl |
| 3-Chlorobenzyl | 2-(4-Methoxyphenyl)oxazol-4-yl |
| 3-Chlorobenzyl | 2-(4-Chlorophenyl)-5-bromooxazol-4-yl |
| 4-Chlorogenzyl | 2-Chloro-3-isopropylphenyl |
| 4-Chlorobenzyl | 2,6-Difluorophenyl |
| 4-Chlorobenzyl | 2-Chloro-3-trifluoromethylphenyl |
| 4-Chlorobenzyl | 3-Phenylisoxazol-5-yl |
| 4-Chlorobenzyl | 3-Methylisoxazol-5-y |
| 4-Chlorobenzyl | 4-Chloro-3-methylisoxazol-5-yl |
| 4-Chlorobenzyl | 4-Chloro-3-isopropylisoxazol-5-yl |
| 4-Chlorobenzyl | 4-Chloro-3-sec-butylisoxazol-5-yl |
| 4-Chlorobenzyl | 4-Chloro-3-tert-butylisoxazol-5-yl |
| 4-Chlorobenzyl | 4-Chloro-3-cyclohexylisoxazol-5-yl |
| 4-Chlorobenzyl | 4-Chloro-3-phenylisoxazol-5-yl |
| 4-Chlorobenzyl | 4-Chloro-3-(4-methylphenyl)isoxazol-5-yl |

TABLE B-continued

| | $R^1R^2CH—ON=C(CN)-R^3$ $R^1 = H$ | I |
|---|---|---|
| $R^3$ | $R^2$ | |

| $R^3$ | $R^2$ |
|---|---|
| 4-Chlorobenzyl | 4-Chloro-3-(4-chlorophenyl)isoxazol-5-yl |
| 4-Chlorobenzyl | 4-Chloro-3-(4-fluorophenyl)isoxazol-5-yl |
| 4-Chlorobenzyl | 4-Chloro-3-(4-trifluoromethylphenyl)isoxazol-5-yl |
| 4-Chlorobenzyl | 4-Chloro-3-(2,6-difluorophenyl)isoxazol-5-yl |
| 4-Chlorobenzyl | 2-Phenyloxazol-4-yl |
| 4-Chlorobenzyl | 2-(4-Fluorophenyl)oxazol-4-yl |
| 4-Chlorobenzyl | 2-(4-Chlorophenyl)oxazol-4-yl |
| 4-Chlorobenzyl | 2-(4-Bromophenyl)oxazol-4-yl |
| 4-Chlorobenzyl | 2-(3-Chlorophenyl)oxazol-4-yl |
| 4-Chlorobenzyl | 2-(4-Methylphenyl)oxazol-4-yl |
| 4-Chlorobenzyl | 2-tert-Butyloxazol-4-yl |
| 4-Chlorobenzyl | 2-(2,4-Dichlorophenyl)oxazol-4-yl |
| 4-Chlorobenzyl | 2-(4-Methoxyphenyl)oxazol-4-yl |
| 4-Chlorobenzyl | 2-(4-Chlorophenyl)-5-bromooxazol-4-yl |
| 2,4-Dichlorobenzyl | 2-Chloro-3-isopropylphenyl |
| 2,4-Dichlorobenzyl | 2,6-Difluorophenyl |
| 2,4-Dichlorobenzyl | 2-Chloro-3-trifluoromethylphenyl |
| 2,4-Dichlorobenzyl | 3-Phenylisoxazol-5-yl |
| 2,4-Dichlorobenzyl | 3-Methylisoxazol-5-yl |
| 2,4-Dichlorobenzyl | 4-Chloro-3-methylisoxazol-5-yl |
| 2,4-Dichlorobenzyl | 4-Chloro-3-isopropylisoxazol-5-yl |
| 2,4-Dichlorobenzyl | 4-Chloro-3-sec-butylisoxazol-5-yl |
| 2,4-Dichlorobenzyl | 4-Chloro-3-tert-butylisoxazol-5-yl |
| 2,4-Dichlorobenzyl | 4-Chloro-3-cyclohexylisoxazol-5-yl |
| 2,4-Dichlorobenzyl | 4-Chloro-3-phenylisoxazol-5-yl |
| 2,4-Dichlorobenzyl | 4-Chloro-3-(4-methylphenyl)isoxazol-5-yl |
| 2,4-Dichlorobenzyl | 4-Chloro-3-(4-chlorophenyl)isoxazol-5-yl |
| 2,4-Dichlorobenzyl | 4-Chloro-3-(4-fluorophenyl)isoxazol-5-yl |
| 2,4-Dichlorobenzyl | 4-Chloro-3-(4-trifluoromethylphenyl)isoxazol-5-yl |
| 2,4-Dichlorobenzyl | 4-Chloro-3-(2,6-difluorophenyl)isoxazol-5-yl |
| 2,4-Dichlorobenzyl | 2-Phenyloxazol-4-yl |
| 2,4-Dichlorobenzyl | 2-(4-Fluorophenyl)oxazol-4-yl |
| 2,4-Dichlorobenzyl | 2-(4-Chlorophenyl)oxazol-4-yl |
| 2,4-Dichlorobenzyl | 2-(4-Bromophenyl)oxazol-4-yl |
| 2,4-Dichlorobenzyl | 2-(3-Chlorophenyl)oxazol-4-yl |
| 2,4-Dichlorobenzyl | 2-(4-Methylphenyl)oxazol-4-yl |
| 2,4-Dichlorobenzyl | 2-tert-Butyloxazol-4-yl |
| 2,4-Dichlorobenzyl | 2-(2,4-Dichlorophenyl)oxazol-4-yl |
| 2,4-Dichlorobenzyl | 2-(4-Methoxyphenyl)oxazol-4-yl |
| 2,4-Dichlorobenzyl | 2-(4-Chlorophenyl)-5-bromooxazol-4-yl |
| 2,4,6-Trichlorobenzyl | 2-Chloro-3-isopropylphenyl |
| 2,4,6-Trichlorobenzyl | 2,6-Difluorophenyl |
| 2,4,6-Trichlorobenzyl | 2-Chloro-3-trifluoromethylphenyl |
| 2,4,6-Trichlorobenzyl | 3-Phenylisoxazol-5-yl |
| 2,4,6-Trichlorobenzyl | 3-Methylisoxazol-5-yl |
| 2,4,6-Trichlorobenzyl | 4-Chloro-3-methylisoxazol-5-yl |
| 2,4,6-Trichlorobenzyl | 4-Chloro-3-isopropylisoxazol-5-yl |
| 2,4,6-Trichlorobenzyl | 4-Chloro-3-sec-butylisoxazol-5-yl |
| 2,4,6-Trichlorobenzyl | 4-Chloro-3-tert-butylisoxazol-5-yl |
| 2,4,6-Trichlorobenzyl | 4-Chloro-3-cyclohexylisoxazol-5-yl |
| 2,4,6-Trichlorobenzyl | 4-Chloro-3-phenylisoxazol-5-yl |
| 2,4,6-Trichlorobenzyl | 4-Chloro-3-(4-methylphenyl)isoxazol-5-yl |
| 2,4,6-Trichlorobenzyl | 4-Chloro-3-(4-chlorophenyl)isoxazol-5-yl |
| 2,4,6-Trichlorobenzyl | 4-Chloro-3-(4-fluorophenyl)isoxazol-5-yl |
| 2,4,6-Trichlorobenzyl | 4-Chloro-3-(4-trifluoromethylphenyl)isoxazol-5-yl |
| 2,4,6-Trichlorobenzyl | 4-Chloro-3-(2,6-difluorophenyl)isoxazol-5-yl |
| 2,4,6-Trichlorobenzyl | 2-Phenyloxazol-4-yl |
| 2,4,6-Trichlorobenzyl | 2-(4-Fluorophenyl)oxazol-4-yl |
| 2,4,6-Trichlorobenzyl | 2-(4-Chlorophenyl)oxazol-4-yl |
| 2,4,6-Trichlorobenzyl | 2-(4-Bromophenyl)oxazol-4-yl |
| 2,4,6-Trichlorobenzyl | 2-(3-Chlorophenyl)oxazol-4-yl |
| 2,4,6-Trichlorobenzyl | 2-(4-Methylphenyl)oxazol-4-yl |
| 2,4,6-Trichlorobenzyl | 2-tert-Butyloxazol-4-yl |
| 2,4,6-Trichlorobenzyl | 2-(2,4-Dichlorophenyl)oxazol-4-yl |
| 2,4,6-Trichlorobenzyl | 2-(4-Methoxyphenyl)oxazol-4-yl |
| 2,4,6-Trichlorobenzyl | 2-(4-Chlorophenyl)-5-bromooxazol-4-yl |
| 2-Trifluoromethylbenzyl | 2-Chloro-3-isopropylphenyl |
| 2-Trifluoromethylbenzyl | 2,6-Difluorophenyl |
| 2-Trifluoromethylbenzyl | 2-Chloro-3-trifluoromethylphenyl |
| 2-Trifluoromethylbenzyl | 3-Phenylisoxazol-5-yl |
| 2-Trifluoromethylbenzyl | 3-Methylisoxazol-5-y |
| 2-Trifluoromethylbenzyl | 4-Chloro-3-methylisoxazol-5-yl |
| 2-Trifluoromethylbenzyl | 4-Chloro-3-isopropylisoxazol-5-yl |
| 2-Trifluoromethylbenzyl | 4-Chloro-3-sec-butylisoxazol-5-yl |
| 2-Trifluoromethylbenzyl | 4-Chloro-3-tert-butylisoxazol-5-yl |
| 2-Trifluoromethylbenzyl | 4-Chloro-3-cyclohexylisoxazol-5-yl |
| 2-Trifluoromethylbenzyl | 4-Chloro-3-phenylisoxazol-5-yl |
| 2-Trifluoromethylbenzyl | 4-Chloro-3-(4-methylphenyl)isoxazol-5-yl |
| 2-Trifluoromethylbenzyl | 4-Chloro-3-(4-chlorophenyl)isoxazol-5-yl |
| 2-Trifluoromethylbenzyl | 4-Chloro-3-(4-fluorophenyl)isoxazol-5-yl |
| 2-Trifluoromethylbenzyl | 4-Chloro-3-(4-trifluoromethylphenyl)isoxazol-5-yl |
| 2-Trifluoromethylbenzyl | 4-Chloro-3-(2,6-difluorophenyl)isoxazol-5-yl |
| 2-Trifluoromethylbenzyl | 2-Phenyloxazol-4-yl |
| 2-Trifluoromethylbenzyl | 2-(4-Fluorophenyl)oxazol-4-yl |
| 2-Trifluoromethylbenzyl | 2-(4-Chlorophenyl)oxazol-4-yl |
| 2-Trifluoromethylbenzyl | 2-(4-Bromophenyl)oxazol-4-yl |
| 2-Trifluoromethylbenzyl | 2-(3-Chlorophenyl)oxazol-4-yl |
| 2-Trifluoromethylbenzyl | 2-(4-Methylphenyl)oxazol-4-yl |
| 2-Trifluoromethylbenzyl | 2-tert-Butyloxazol-4-yl |
| 2-Trifluoromethylbenzyl | 2-(2,4-Dichlorophenyl)oxazol-4-yl |
| 2-Trifluoromethylbenzyl | 2-(4-Methoxyphenyl)oxazol-4-yl |
| 2-Trifluoromethylbenzyl | 2-(4-Chlorophenyl)-5-bromooxazol-4-yl |
| 3-Trifluoromethylbenzyl | 2-Chloro-3-isopropylphenyl |
| 3-Trifluoromethylbenzyl | 2,6-Difluorophenyl |
| 3-Trifluoromethylbenzyl | 2-Chloro-3-trifluoromethylphenyl |
| 3-Trifluoromethylbenzyl | 3-Phenylisoxazol-5-yl |
| 3-Trifluoromethylbenzyl | 3-Methylisoxazol-5-yl |
| 3-Trifluoromethylbenzyl | 4-Chloro-3-methylisoxazol-5-yl |
| 3-Trifluoromethylbenzyl | 4-Chloro-3-isopropylisoxazol-5-yl |
| 3-Trifluoromethylbenzyl | 4-Chloro-3-sec-butylisoxazol-5-yl |
| 3-Trifluoromethylbenzyl | 4-Chloro-3-tert-butylisoxazol-5-yl |
| 3-Trifluoromethylbenzyl | 4-Chloro-3-cyclohexylisoxazol-5-yl |
| 3-Trifluoromethylbenzyl | 4-Chloro-3-phenylisoxazol-5-yl |
| 3-Trifluoromethylbenzyl | 4-Chloro-3-(4-methylphenyl)isoxazol-5-yl |
| 3-Trifluoromethylbenzyl | 4-Chloro-3-(4-chlorophenyl)isoxazol-5-yl |
| 3-Trifluoromethylbenzyl | 4-Chloro-3-(4-fluorophenyl)isoxazol-5-yl |
| 3-Trifluoromethylbenzyl | 4-Chloro-3-(4-trifluoromethylphenyl)isoxazol-5-yl |
| 3-Trifluoromethylbenzyl | 4-Chloro-3-(2,6-difluorophenyl)isoxazol-5-yl |
| 3-Trifluoromethylbenzyl | 2-Phenyloxazol-4-yl |
| 3-Trifluoromethylbenzyl | 2-(4-Fluorophenyl)oxazol-4-yl |
| 3-Trifluoromethylbenzyl | 2-(4-Chlorophenyl)oxazol-4-yl |
| 3-Trifluoromethylbenzyl | 2-(4-Bromophenyl)oxazol-4-yl |
| 3-Trifluoromethylbenzyl | 2-(3-Chlorophenyl)oxazol-4-yl |
| 3-Trifluoromethylbenzyl | 2-(4-Methylphenyl)oxazol-4-yl |
| 3-Trifluoromethylbenzyl | 2-tert-Butyloxazol-4-yl |
| 3-Trifluoromethylbenzyl | 2-(2,4-Dichlorophenyl)oxazol-4-yl |
| 3-Trifluoromethylbenzyl | 2-(4-Methoxyphenyl)oxazol-4-yl |
| 3-Trifluoromethylbenzyl | 2-(4-Chlorophenyl)-5-bromooxazol-4-yl |
| 4-Trifluoromethylbenzyl | 2-Chloro-3-isopropylphenyl |
| 4-Trifluoromethylbenzyl | 2,6-Difluorophenyl |
| 4-Trifluoromethylbenzyl | 2-Chloro-3-trifluoromethylphenyl |
| 4-Trifluoromethylbenzyl | 3-Phenylisoxazol-5-yl |
| 4-Trifluoromethylbenzyl | 3-Methylisoxazol-5-yl |
| 4-Trifluoromethylbenzyl | 4-Chloro-3-methylisoxazol-5-yl |
| 4-Trifluoromethylbenzyl | 4-Chloro-3-isopropylisoxazol-5-yl |
| 4-Trifluoromethylbenzyl | 4-Chloro-3-sec-butylisoxazol-5-yl |

TABLE B-continued

| R³ | R² |
|---|---|
| 4-Trifluoromethylbenzyl | 4-Chloro-3-tert-butylisoxazol-5-yl |
| 4-Trifluoromethylbenzyl | 4-Chloro-3-cyclohexylisoxazol-5-yl |
| 4-Trifluoromethylbenzyl | 4-Chloro-3-phenylisoxazol-5-yl |
| 4-Trifluoromethylbenzyl | 4-Chloro-3-(4-methylphenyl)isoxazol-5-yl |
| 4-Trifluoromethylbenzyl | 4-Chloro-3-(4-chlorophenyl)isoxazol-5-yl |
| 4-Trifluoromethylbenzyl | 4-Chloro-3-(4-fluorophenyl)isoxazol-5-yl |
| 4-Trifluoromethylbenzyl | 4-Chloro-3-(4-trifluoromethylphenyl)-isoxazol-5-yl |
| 4-Trifluoromethylbenzyl | 4-Chloro-3-(2,6-difluorophenyl)-isoxazol-5-yl |
| 4-Trifluoromethylbenzyl | 2-Phenyloxazol-4-yl |
| 4-Trifluoromethylbenzyl | 2-(4-Fluorophenyl)oxazol-4-yl |
| 4-Trifluoromethylbenzyl | 2-(4-Chlorophenyl)oxazol-4-yl |
| 4-Trifluoromethylbenzyl | 2-(4-Bromophenyl)oxazol-4-yl |
| 4-Trifluoromethylbenzyl | 2-(3-Chlorophenyl)oxazol-4-yl |
| 4-Trifluoromethylbenzyl | 2-(4-Methylphenyl)oxazol-4-yl |
| 4-Trifluoromethylbenzyl | 2-tert-Butyloxazol-4-yl |
| 4-Trifluoromethylbenzyl | 2-(2,4-Dichlorophenyl)oxazol-4-yl |
| 4-Trifluoromethylbenzyl | 2-(4-Methoxyphenyl)oxazol-4-yl |
| 4-Trifluoromethylbenzyl | 2-(4-Chlorophenyl)-5-bromooxazol-4-yl |
| 2-Methoxybenzyl | 2-Chloro-3-isopropylphenyl |
| 2-Methoxybenzyl | 2,6-Difluorophenyl |
| 2-Methoxybenzyl | 2-Chloro-3-trifluoromethylphenyl |
| 2-Methoxybenzyl | 3-Phenylisoxazol-5-yl |
| 2-Methoxybenzyl | 3-Methylisoxazol-5-yl |
| 2-Methoxybenzyl | 4-Chloro-3-methylisoxazol-5-yl |
| 2-Methoxybenzyl | 4-Chloro-3-isopropylisoxazol-5-yl |
| 2-Methoxybenzyl | 4-Chloro-3-sec-butylisoxazol-5-yl |
| 2-Methoxybenzyl | 4-Chloro-3-tert-butylisoxazol-5-yl |
| 2-Methoxybenzyl | 4-Chloro-3-cyclohexylisoxazol-5-yl |
| 2-Methoxybenzyl | 4-Chloro-3-phenylisoxazol-5-yl |
| 2-Methoxybenzyl | 4-Chloro-3-(4-methylphenyl)isoxazol-5-yl |
| 2-Methoxybenzyl | 4-Chloro-3-(4-chlorophenyl)isoxazol-5-yl |
| 2-Methoxybenzyl | 4-Chloro-3-(4-fluorophenyl)isoxazol-5-yl |
| 2-Methoxybenzyl | 4-Chloro-3-(4-trifluoromethylphenyl)-isoxazol-5-yl |
| 2-Methoxybenzyl | 4-Chloro-3-(2,6-difluorophenyl)-isoxazol-5-yl |
| 2-Methoxybenzyl | 2-Phenyloxazol-4-yl |
| 2-Methoxybenzyl | 2-(4-Fluorophenyl)oxazol-4-yl |
| 2-Methoxybenzyl | 2-(4-Chlorophenyl)oxazol-4-yl |
| 2-Methoxybenzyl | 2-(4-Bromophenyl)oxazol-4-yl |
| 2-Methoxybenzyl | 2-(3-Chlorophenyl)oxazol-4-yl |
| 2-Methoxybenzyl | 2-(4-Methylphenyl)oxazol-4-yl |
| 2-Methoxybenzyl | 2-tert-Butyloxazol-4-yl |
| 2-Methoxybenzyl | 2-(2,4-Dichlorophenyl)oxazol-4-yl |
| 2-Methoxybenzyl | 2-(4-Methoxyphenyl)oxazol-4-yl |
| 2-Methoxybenzyl | 2-(4-Chlorophenyl)-5-bromooxazol-4-yl |
| 4-Phenoxybenzyl | 2-Chloro-3-isopropylphenyl |
| 4-Phenoxybenzyl | 2,6-Difluorophenyl |
| 4-Phenoxybenzyl | 2-Chloro-3-trifluoromethylphenyl |
| 4-Phenoxybenzyl | 3-Phenylisoxazol-5-yl |
| 4-Phenoxybenzyl | 3-Methylisoxazol-5-yl |
| 4-Phenoxybenzyl | 4-Chloro-3-methylisoxazol-5-yl |
| 4-Phenoxybenzyl | 4-Chloro-3-isopropylisoxazol-5-yl |
| 4-Phenoxybenzyl | 4-Chloro-3-sec-butylisoxazol-5-yl |
| 4-Phenoxybenzyl | 4-Chloro-3-tert-butylisoxazol-5-yl |
| 4-Phenoxybenzyl | 4-Chloro-3-cyclohexylisoxazol-5-yl |
| 4-Phenoxybenzyl | 4-Chloro-3-phenylisoxazol-5-yl |
| 4-Phenoxybenzyl | 4-Chloro-3-(4-methylphenyl)isoxazol-5-yl |
| 4-Phenoxybenzyl | 4-Chloro-3-(4-chlorophenyl)isoxazol-5-yl |
| 4-Phenoxybenzyl | 4-Chloro-3-(4-fluorophenyl)isoxazol-5-yl |
| 4-Phenoxybenzyl | 4-Chloro-3-(4-trifluoromethylphenyl)-isoxazol-5-yl |
| 4-Phenoxybenzyl | 4-Chloro-3-(2,6-difluorophenyl)-isoxazol-5-yl |
| 4-Phenoxybenzyl | 2-Phenyloxazol-4-yl |
| 4-Phenoxybenzyl | 2-(4-Fluorophenyl)oxazol-4-yl |
| 4-Phenoxybenzyl | 2-(4-Chlorophenyl)oxazol-4-yl |
| 4-Phenoxybenzyl | 2-(4-Bromophenyl)oxazol-4-yl |
| 4-Phenoxybenzyl | 2-(3-Chlorophenyl)oxazol-4-yl |
| 4-Phenoxybenzyl | 2-(4-Methylphenyl)oxazol-4-yl |
| 4-Phenoxybenzyl | 2-tert-Butyloxazol-4-yl |
| 4-Phenoxybenzyl | 2-(2,4-Dichlorophenyl)oxazol-4-yl |
| 4-Phenoxybenzyl | 2-(4-Methoxyphenyl)oxazol-4-yl |
| 4-Phenoxybenzyl | 2-(4-Chlorophenyl)-5-bromooxazol-4-yl |
| 1-Phenylpropyl | 2-Chloro-3-isopropylphenyl |
| 1-Phenylpropyl | 2,6-Difluorophenyl |
| 1-Phenylpropyl | 2-Chloro-3-trifluoromethylphenyl |
| 1-Phenylpropyl | 3-Phenylisoxazol-5-yl |
| 1-Phenylpropyl | 3-Methylisoxazol-5-yl |
| 1-Phenylpropyl | 4-Chloro-3-methylisoxazol-5-yl |
| 1-Phenylpropyl | 4-Chloro-3-isopropylisoxazol-5-yl |
| 1-Phenylpropyl | 4-Chloro-3-sec-butylisoxazol-5-yl |
| 1-Phenylpropyl | 4-Chloro-3-tert-butylisoxazol-5-yl |
| 1-Phenylpropyl | 4-Chloro-3-cyclohexylisoxazol-5-yl |
| 1-Phenylpropyl | 4-Chloro-3-phenylisoxazol-5-yl |
| 1-Phenylpropyl | 4-Chloro-3-(4-methylphenyl)isoxazol-5-yl |
| 1-Phenylpropyl | 4-Chloro-3-(4-chlorophenyl)isoxazol-5-yl |
| 1-Phenylpropyl | 4-Chloro-3-(4-fluorophenyl)isoxazol-5-yl |
| 1-Phenylpropyl | 4-Chloro-3-(4-trifluoromethylphenyl)-isoxazol-5-yl |
| 1-Phenylpropyl | 4-Chloro-3-(2,6-difluorophenyl)-isoxazol-5-yl |
| 1-Phenylpropyl | 2-Phenyloxazol-4-yl |
| 1-Phenylpropyl | 2-(4-Fluorophenyl)oxazol-4-yl |
| 1-Phenylpropyl | 2-(4-Chlorophenyl)oxazol-4-yl |
| 1-Phenylpropyl | 2-(4-Bromophenyl)oxazol-4-yl |
| 1-Phenylpropyl | 2-(3-Chlorophenyl)oxazol-4-yl |
| 1-Phenylpropyl | 2-(4-Methylphenyl)oxazol-4-yl |
| 1-Phenylpropyl | 2-tert-Butyloxazol-4-yl |
| 1-Phenylpropyl | 2-(2,4-Dichlorophenyl)oxazol-4-yl |
| 1-Phenylpropyl | 2-(4-Methoxyphenyl)oxazol-4-yl |
| 1-Phenylpropyl | 2-(4-Chlorophenyl)-5-bromooxazol-4-yl |
| 3-Phenylpropyl | 2-Chloro-3-isopropylphenyl |
| 3-Phenylpropyl | 2,6-Difluorophenyl |
| 3-Phenylpropyl | 2-Chloro-3-trifluoromethylphenyl |
| 3-Phenylpropyl | 3-Phenylisoxazol-5-yl |
| 3-Phenylpropyl | 3-Methylisoxazol-5-yl |
| 3-Phenylpropyl | 4-Chloro-3-methylisoxazol-5-yl |
| 3-Phenylpropyl | 4-Chloro-3-isopropylisoxazol-5-yl |
| 3-Phenylpropyl | 4-Chloro-3-sec-butylisoxazol-5-yl |
| 3-Phenylpropyl | 4-Chloro-3-tert-butylisoxazol-5-yl |
| 3-Phenylpropyl | 4-Chloro-3-cyclohexylisoxazol-5-yl |
| 3-Phenylpropyl | 4-Chloro-3-phenylisoxazol-5-yl |
| 3-Phenylpropyl | 4-Chloro-3-(4-methylphenyl)isoxazol-5-yl |
| 3-Phenylpropyl | 4-Chloro-3-(4-Chlorophenyl)isoxazol-5-yl |
| 3-Phenylpropyl | 4-Chloro-3-(4-fluorophenyl)isoxazol-5-yl |
| 3-Phenylpropyl | 4-Chloro-3-(4-trifluoromethylphenyl)-isoxazol-5-yl |
| 3-Phenylpropyl | 4-Chloro-3-(2,6-difluorophenyl)-isoxazol-5-yl |
| 3-Phenylpropyl | 2-Phenyloxazol-4-yl |
| 3-Phenylpropyl | 2-(4-Fluorophenyl)oxazol-4-yl |
| 3-Phenylpropyl | 2-(4-Chlorophenyl)oxazol-4-yl |
| 3-Phenylpropyl | 2-(4-Bromophenyl)oxazol-4-yl |
| 3-Phenylpropyl | 2-(3-Chlorophenyl)oxazol-4-yl |
| 3-Phenylpropyl | 2-(4-Methylphenyl)oxazol-4-yl |
| 3-Phenylpropyl | 2-tert-Butyloxazol-4-yl |
| 3-Phenylpropyl | 2-(2,4-Dichlorophenyl)oxazol-4-yl |
| 3-Phenylpropyl | 2-(4-Methoxyphenyl)oxazol-4-yl |
| 3-Phenylpropyl | 2-(4-Chlorophenyl)-5-bromooxazol-4-yl |
| Oxiranyl | 2-Chloro-3-isopropylphenyl |
| Oxiranyl | 2,6-Difluorophenyl |
| Oxiranyl | 2-Chloro-3-trifluoromethylphenyl |

TABLE B-continued

| R³ | R² |
|---|---|
| | R¹R²CH—ON=C(CN)-R³    R¹ = H    I |

| R³ | R² |
|---|---|
| Oxiranyl | 3-Phenylisoxazol-5-yl |
| Oxiranyl | 3-Methylisoxazol-5-yl |
| Oxiranyl | 4-Chloro-3-methylisoxazol-5-yl |
| Oxiranyl | 4-Chloro-3-isopropylisoxazol-5-yl |
| Oxiranyl | 4-Chloro-3-sec-butylisoxazol-5-yl |
| Oxiranyl | 4-Chloro-3-tert-butylisoxazol-5-yl |
| Oxiranyl | 4-Chloro-3-cyclohexylisoxazol-5-yl |
| Oxiranyl | 4-Chloro-3-phenylisoxazol-5-yl |
| Oxiranyl | 4-Chloro-3-(4-methylphenyl)isoxazol-5-yl |
| Oxiranyl | 4-Chloro-3-(4-chlorophenyl)isoxazol-5-yl |
| Oxiranyl | 4-Chloro-3-(4-fluorophenyl)isoxazol-5-yl |
| Oxiranyl | 4-Chloro-3-(4-trifluoromethylphenyl)-isoxazol-5-yl |
| Oxiranyl | 4-Chloro-3-(2,6-difluorophenyl)-isoxazol-5-yl |
| Oxiranyl | 2-Phenyloxazol-4-yl |
| Oxiranyl | 2-(4-Fluorophenyl)oxazol-4-yl |
| Oxiranyl | 2-(4-Chlorophenyl)oxazol-4-yl |
| Oxiranyl | 2-(4-Bromophenyl)oxazol-4-yl |
| Oxiranyl | 2-(3-Chlorophenyl)oxazol-4-yl |
| Oxiranyl | 2-(4-Methylphenyl)oxazol-4-yl |
| Oxiranyl | 2-tert-Butyloxazol-4-yl |
| Oxiranyl | 2-(2,4-Dichlorophenyl)oxazol-4-yl |
| Oxiranyl | 2-(4-Methoxyphenyl)oxazol-4-yl |
| Oxiranyl | 2-(4-Chlorophenyl)-5-bromooxazol-4-yl |
| Trifluoromethyl | 2-Chloro-3-isopropylphenyl |
| Trifluoromethyl | 2,6-Difluorophenyl |
| Trifluoromethyl | 2-Chloro-3-trifluoromethylphenyl |
| Trifluoromethyl | 3-Phenylisoxazol-5-yl |
| Trifluoromethyl | 3-Methylisoxazol-5-yl |
| Trifluoromethyl | 4-Chloro-3-methylisoxazol-5-yl |
| Trifluoromethyl | 4-Chloro-3-isopropylisoxazol-5-yl |
| Trifluoromethyl | 4-Chloro-3-sec-butylisoxazol-5-yl |
| Trifluoromethyl | 4-Chloro-3-tert-butylisoxazol-5-yl |
| Trifluoromethyl | 4-Chloro-3-cyclohexylisoxazol-5-yl |
| Trifluoromethyl | 4-Chloro-3-phenylisoxazol-5-yl |
| Trifluoromethyl | 4-Chloro-3-(4-methylphenyl)isoxazol-5-yl |
| Trifluoromethyl | 4-Chloro-3-(4-chlorophenyl)isoxazol-5-yl |
| Trifluoromethyl | 4-Chloro-3-(4-fluorophenyl)isoxazol-5-yl |
| Trifluoromethyl | 4-Chloro-3-(4-trifluoromethylphenyl)-isoxazol-5-yl |
| Trifluoromethyl | 4-Chloro-3-(2,6-difluorophenyl)-isoxazol-5-yl |
| Trifluoromethyl | 2-Phenyloxazol-4-yl |
| Trifluoromethyl | 2-(4-Fluorophenyl)oxazol-4-yl |
| Trifluoromethyl | 2-(4-Chlorophenyl)oxazol-4-yl |
| Trifluoromethyl | 2-(4-Bromophenyl)oxazol-4-yl |
| Trifluoromethyl | 2-(3-Chlorophenyl)oxazol-4-yl |
| Trifluoromethyl | 2-(4-Methylphenyl)oxazol-4-yl |
| Trifluoromethyl | 2-tert-Butyloxazol-4-yl |
| Trifluoromethyl | 2-(2,4-Dichlorophenyl)oxazol-4-yl |
| Trifluoromethyl | 2-(4-Methoxyphenyl)oxazol-4-yl |
| Trifluoromethyl | 2-(4-Chlorophenyl)-5-bromooxazol-4-yl |
| 2-Fluoroethyl | 2-Chloro-3-isopropylphenyl |
| 2-Fluoroethyl | 2,6-Difluorophenyl |
| 2-Fluoroethyl | 2-Chloro-3-trifluoromethylphenyl |
| 2-Fluoroethyl | 3-Phenylisoxazol-5-yl |
| 2-Fluoroethyl | 3-Methylisoxazol-5-yl |
| 2-Fluoroethyl | 4-Chloro-3-methylisoxazol-5-yl |
| 2-Fluoroethyl | 4-Chloro-3-isopropylinoxazol-5-yl |
| 2-Fluoroethyl | 4-Chloro-3-sec-butylisoxazol-5-yl |
| 2-Fluoroethyl | 4-Chloro-3-tert-butylisoxazol-5-yl |
| 2-Fluoroethyl | 4-Chloro-3-cyclohexylisoxazol-5-yl |
| 2-Fluoroethyl | 4-Chloro-3-phenylisoxazol-5-yl |
| 2-Fluoroethyl | 4-Chloro-3-(4-methylphenyl)isoxazol-5-yl |
| 2-Fluoroethyl | 4-Chloro-3-(4-chlorophenyl)isoxazol-5-yl |
| 2-Fluoroethyl | 4-Chloro-3-(4-fluorophenyl)isoxazol-5-yl |
| 2-Fluoroethyl | 4-Chloro-3-(4-trifluoromethylphenyl)-isoxazol-5-yl |
| 2-Fluoroethyl | 4-Chloro-3-(2,6-difluorophenyl)-isoxazol-5-yl |
| 2-Fluoroethyl | 2-Phenyloxazol-4-yl |
| 2-Fluoroethyl | 2-(4-Fluorophenyl)oxazol-4-yl |
| 2-Fluoroethyl | 2-(4-Chlorophenyl)oxazol-4-yl |
| 2-Fluoroethyl | 2-(4-Bromophenyl)oxazol-4-yl |
| 2-Fluoroethyl | 2-(3-Chlorophenyl)oxazol-4-yl |
| 2-Fluoroethyl | 2-(4-Methylphenyl)oxazol-4-yl |
| 2-Fluoroethyl | 2-tert-Butyloxazol-4-yl |
| 2-Fluoroethyl | 2-(2,4-Dichlorophenyl)oxazol-4-yl |
| 2-Fluoroethyl | 2-(4-Methoxyphenyl)oxazol-4-yl |
| 2-Fluoroethyl | 2-(4-Chlorophenyl)-5-bromooxazol-4-yl |
| 2,2,2-Trifluoroethyl | 2-Chloro-3-isopropylphenyl |
| 2,2,2-Trifluoroethyl | 2,6-Difluorophenyl |
| 2,2,2-Trifluoroethyl | 2-Chloro-3-trifluoromethylphenyl |
| 2,2,2-Trifluoroethyl | 3-Phenylisoxazol-5-yl |
| 2,2,2-Trifluoroethyl | 3-Methylisoxazol-5-yl |
| 2,2,2-Trifluoroethyl | 4-Chloro-3-methylisoxazol-5-yl |
| 2,2,2-Trifluoroethyl | 4-Chloro-3-isopropylisoxazol-5-yl |
| 2,2,2-Trifluoroethyl | 4-Chloro-3-sec-butylisoxazol-5-yl |
| 2,2,2-Trifluoroethyl | 4-Chloro-3-tert-butylisoxazol-5-yl |
| 2,2,2-Trifluoroethyl | 4-Chloro-3-cyclohexylisoxazol-5-yl |
| 2,2,2-Trifluoroethyl | 4-Chloro-3-phenylisoxazol-5-yl |
| 2,2,2-Trifluoroethyl | 4-Chloro-3-(4-methylphenyl)isoxazol-5-yl |
| 2,2,2-Trifluoroethyl | 4-Chloro-3-(4-chlorophenyl)isoxazol-5-yl |
| 2,2,2-Trifluoroethyl | 4-Chloro-3-(4-fluorophenyl)isoxazol-5-yl |
| 2,2,2-Trifluoroethyl | 4-Chloro-3-(4-trifluoromethylphenyl)-isoxazol-5-yl |
| 2,2,2-Trifluoroethyl | 4-Chloro-3-(2,6-difluorophenyl)-isoxazol-5-yl |
| 2,2,2-Trifluoroethyl | 2-Phenyloxazol-4-yl |
| 2,2,2-Trifluoroethyl | 2-(4-Fluorophenyl)oxazol-4-yl |
| 2,2,2-Trifluoroethyl | 2-(4-Chlorophenyl)oxazol-4-yl |
| 2,2,2-Trifluoroethyl | 2-(4-Bromophenyl)oxazol-4-yl |
| 2,2,2-Trifluoroethyl | 2-(3-Chlorophenyl)oxazol-4-yl |
| 2,2,2-Trifluoroethyl | 2-(4-Methylphenyl)oxazol-4-yl |
| 2,2,2-Trifluoroethyl | 2-tert-Butyloxazol-4-yl |
| 2,2,2-Trifluoroethyl | 2-(2,4-Dichlorophenyl)oxazol-4-yl |
| 2,2,2-Trifluoroethyl | 2-(4-Methoxyphenyl)oxazol-4-yl |
| 2,2,2-Trifluoroethyl | 2-(4-Chlorophenyl)-5-bromooxazol-4-yl |
| Pentafluoroethyl | 2-Chloro-3-isopropylphenyl |
| Pentafluoroethyl | 2,6-Difluorophenyl |
| Pentafluoroethyl | 2-Chloro-3-trifluoromethylphenyl |
| Pentafluoroethyl | 3-Phenylisoxazol-5-yl |
| Pentafluoroethyl | 3-Methylisoxazol-5-yl |
| Pentafluoroethyl | 4-Chloro-3-methylisoxazol-5-yl |
| Pentafluoroethyl | 4-Chloro-3-isopropylisoxazol-5-yl |
| Pentafluoroethyl | 4-Chloro-3-sec-butylisoxazol-5-yl |
| Pentafluoroethyl | 4-Chloro-3-tert-butylisoxazol-5-yl |
| Pentafluoroethyl | 4-Chloro-3-cyclohexylisoxazol-5-yl |
| Pentafluoroethyl | 4-Chloro-3-phenylisoxazol-5-yl |
| Pentafluoroethyl | 4-Chloro-3-(4-methylphenyl)isoxazol-5-yl |
| Pentafluoroethyl | 4-Chloro-3-(4-chlorophenyl)isoxazol-5-yl |
| Pentafluoroethyl | 4-Chloro-3-(4-fluorophenyl)isoxazol-5-yl |
| Pentafluoroethyl | 4-Chloro-3-(4-trifluoromethylphenyl)-isoxazol-5-yl |
| Pentafluoroethyl | 4-Chloro-3-(2,6-difluorophenyl)-isoxazol-5-yl |
| Pentafluoroethyl | 2-Phenyloxazol-4-yl |
| Pentafluoroethyl | 2-(4-Fluorophenyl)oxazol-4-yl |
| Pentafluoroethyl | 2-(4-Chlorophenyl)oxazol-4-yl |
| Pentafluoroethyl | 2-(4-Bromophenyl)oxazol-4-yl |
| Pentafluoroethyl | 2-(3-Chlorophenyl)oxazol-4-yl |
| Pentafluoroethyl | 2-(4-Methylphenyl)oxazol-4-yl |
| Pentafluoroethyl | 2-tert-Butyloxazol-4-yl |
| Pentafluoroethyl | 2-(2,4-Dichlorophenyl)oxazol-4-yl |

TABLE B-continued

| | R¹R²CH—ON=C(CN)-R³ | R¹ = H | I |
|---|---|---|---|
| R³ | R² | | |

| R³ | R² |
|---|---|
| Pentafluoroethyl | 2-(4-Methoxyphenyl)oxazol-4-yl |
| Pentafluoroethyl | 2-(4-Chlorophenyl)-5-bromooxazol-4-yl |
| Chloromethyl | 2-Chloro-3-isopropylphenyl |
| Chloromethyl | 2,6-Difluorophenyl |
| Chloromethyl | 2-Chloro-3-trifluoromethylphenyl |
| Chloromethyl | 3-Phenylisoxazol-5-yl |
| Chloromethyl | 3-Methylisoxazol-5-yl |
| Chloromethyl | 4-Chloro-3-methylisoxazol-5-yl |
| Chloromethyl | 4-Chloro-3-isopropylisoxazol-5-yl |
| Chloromethyl | 4-Chloro-3-sec-butylisoxazol-5-yl |
| Chloromethyl | 4-Chloro-3-tert-butylisoxazol-5-yl |
| Chloromethyl | 4-Chloro-3-cyclohexylisoxazol-5-yl |
| Chloromethyl | 4-Chloro-3-phenylisoxazol-5-yl |
| Chloromethyl | 4-Chloro-3-(4-methylphenyl)isoxazol-5-yl |
| Chloromethyl | 4-Chloro-3-(4-chlorophenyl)isoxazol-5-yl |
| Chloromethyl | 4-Chloro-3-(4-fluorophenyl)isoxazol-5-yl |
| Chloromethyl | 4-Chloro-3-(4-trifluoromethylphenyl)-isoxazol-5-yl |
| Chloromethyl | 4-Chloro-3-(2,6-difluorophenyl)-isoxazol-5-yl |
| Chloromethyl | 2-Phenyloxazol-4-yl |
| Chloromethyl | 2-(4-Fluorophenyl)oxazol-4-yl |
| Chloromethyl | 2-(4-Chlorophenyl)oxazol-4-yl |
| Chloromethyl | 2-(4-Bromophenyl)oxazol-4-yl |
| Chloromethyl | 2-(3-Chlorophenyl)oxazol-4-yl |
| Chloromethyl | 2-(4-Methylphenyl)oxazol-4-yl |
| Chloromethyl | 2-tert-Butyloxazol-4-yl |
| Chloromethyl | 2-(2,4-Dichlorophenyl)oxazol-4-yl |
| Chloromethyl | 2-(4-Methoxyphenyl)oxazol-4-yl |
| Chloromethyl | 2-(4-Chlorophenyl)-5-bromooxazol-4-yl |
| Dichloromethyl | 2-Chloro-3-isopropylphenyl |
| Dichloromethyl | 2,6-Difluorophenyl |
| Dichloromethyl | 2-Chloro-3-trifluoroethylphenyl |
| Dichloromethyl | 3-Phenylisoxazol-5-yl |
| Dichloromethyl | 3-Methylisoxazol-5-yl |
| Dichloromethyl | 4-Chloro-3-methylisoxazol-5-yl |
| Dichloromethyl | 4-Chloro-3-isopropylisoxazol-5-yl |
| Dichloromethyl | 4-Chloro-3-sec-butylisoxazol-5-yl |
| Dichloromethyl | 4-Chloro-3-tert-butylisoxazol-5-yl |
| Dichloromethyl | 4-Chloro-3-cyclohexylisoxazol-5-yl |
| Dichloromethyl | 4-Chloro-3-phenylisoxazol-5-yl |
| Dichloromethyl | 4-Chloro-3-(4-methylphenyl)isoxazol-5-yl |
| Dichloromethyl | 4-Chloro-3-(4-chlorophenyl)isoxazol-5-yl |
| Dichloromethyl | 4-Chloro-3-(4-fluorophenyl)isoxazol-5-yl |
| Dichloromethyl | 4-Chloro-3-(4-trifluoromethylphenyl)-isoxazol-5-yl |
| Dichloromethyl | 4-Chloro-3-(2,6-difluorophenyl)-isoxazol-5-yl |
| Dichloromethyl | 2-Phenyloxazol-4-yl |
| Dichloromethyl | 2-(4-Fluorophenyl)oxazol-4-yl |
| Dichloromethyl | 2-(4-Chlorophenyl)oxazol-4-yi |
| Dichloromethyl | 2-(4-Bromophenyl)oxazol-4-yl |
| Dichloromethyl | 2-(3-Chlorophenyl)oxazol-4-yl |
| Dichloromethyl | 2-(4-Methylphenyl)oxazol-4-yl |
| Dichloromethyl | 2-tert-Butyloxazol-4-yl |
| Dichloromethyl | 2-(2,4-Dichlorophenyl)oxazol-4-yl |
| Dichloromethyl | 2-(4-Methoxyphenyl)oxazol-4-yl |
| Dichloromethyl | 2-(4-Chlorophenyl)-5-bromooxazol-4-yl |
| Trichloromethyl | 2-Chloro-3-isopropylphenyl |
| Trichloromethyl | 2,6-Difluorophenyl |
| Trichloromethyl | 2-Chloro-3-trifluoromethylphenyl |
| Trichloromethyl | 3-Phenylisoxazol-5-yl |
| Trichloromethyl | 3-Methylisoxazol-5-yl |
| Trichloromethyl | 4-Chloro-3-methylisoxazol-5-yl |
| Trichloromethyl | 4-Chloro-3-isopropylisoxazol-5-yl |
| Trichloromethyl | 4-Chloro-3-sec-butylisoxazol-5-yl |
| Trichloromethyl | 4-Chloro-3-tert-butylisoxazol-5-yl |
| Trichloromethyl | 4-Chloro-3-cyclohexylisoxazol-5-yl |
| Trichloromethyl | 4-Chloro-3-phenylisoxazol-5-yl |
| Trichloromethyl | 4-Chloro-3-(4-methylphenyl)isoxazol-5-yl |
| Trichloromethyl | 4-Chloro-3-(4-chlorophenyl)isoxazol-5-yl |
| Trichloromethyl | 4-Chloro-3-(4-fluorophenyl)isoxazol-5-yl |
| Trichloromethyl | 4-Chloro-3-(4-trifluoromethylphenyl)-isoxazol-5-yl |
| Trichloromethyl | 4-Chloro-3-(2,6-difluorophenyl)-isoxazol-5-yl |
| Trichloromethyl | 2-Phenyloxazol-4-yl |
| Trichloromethyl | 2-(4-Fluorophenyl)oxazol-4-yl |
| Trichloromethyl | 2-(4-Chlorophenyl)oxazol-4-yl |
| Trichloromethyl | 2-(4-Bromophenyl)oxazol-4-yl |
| Trichloromethyl | 2-(3-Chlorophenyl)oxazol-4-yl |
| Trichloromethyl | 2-(4-Methylphenyl)oxazol-4-yl |
| Trichloromethyl | 2-tert-Butyloxazol-4-yl |
| Trichloromethyl | 2-(2,4-Dichlorophenyl)oxazol-4-yl |
| Trichloromethyl | 2-(4-Methoxyphenyl)oxazol-4-yl |
| Trichloromethyl | 2-(4-Chlorophenyl)-5-bromooxazol-4-yl |
| 2-Chloroethyl | 2-Chloro-3-isopropylphenyl |
| 2-Chloroethyl | 2,6-Difluorophenyl |
| 2-Chloroethyl | 2-Chloro-3-trifluoromethylphenyl |
| 2-Chloroethyl | 3-Phenylisoxazol-5-yl |
| 2-Chloroethyl | 3-Methylisoxazol-5-yl |
| 2-Chloroethyl | 4-Chloro-3-methylisoxazol-5-yl |
| 2-Chloroethyl | 4-Chloro-3-isopropylisoxazol-5-yl |
| 2-Chloroethyl | 4-Chloro-3-sec-butylisoxazol-5-yl |
| 2-Chloroethyl | 4-Chloro-3-tert-butylisoxazol-5-yl |
| 2-Chloroethyl | 4-Chloro-3-cyclohexylisoxazol-5-yl |
| 2-Chloroethyl | 4-Chloro-3-phenylisoxazol-5-yl |
| 2-Chloroethyl | 4-Chloro-3-(4-methylphenyl)isoxazol-5-yl |
| 2-Chloroethyl | 4-Chloro-3-(4-chlorophenyl)isoxazol-5-yl |
| 2-Chloroethyl | 4-Chloro-3-(4-fluorophenyl)isoxazol-5-yl |
| 2-Chloroethyl | 4-Chloro-3-(4-trifluoromethylphenyl)-isoxazol-5-yl |
| 2-Chloroethyl | 4-Chloro-3-(2,6-difluorophenyl)-isoxazol-5-yl |
| 2-Chloroethyl | 2-Phenyloxazol-4-yl |
| 2-Chloroethyl | 2-(4-Fluorophenyl)oxazol-4-yl |
| 2-Chloroethyl | 2-(4-Chlorophenyl)oxazol-4-yl |
| 2-Chloroethyl | 2-(4-Bromophenyl)oxazol-4-yl |
| 2-Chloroethyl | 2-(3-Chlorophenyl)oxazol-4-yl |
| 2-Chloroethyl | 2-(4-Methylphenyl)oxazol-4-yl |
| 2-Chloroethyl | 2-tert-Butyloxazol-4-yl |
| 2-Chloroethyl | 2-(2,4-Dichlorophenyl)oxazol-4-yl |
| 2-Chloroethyl | 2-(4-Methoxyphenyl)oxazol-4-yl |
| 2-Chloroethyl | 2-(4-Chlorophenyl)-5-bromooxazol-4-yl |
| 2,2,2-Trichloroethyl | 2-Chloro-3-isopropylphenyl |
| 2,2,2-Trichloroethyl | 2,6-Difluorophenyl |
| 2,2,2-Trichloroethyl | 2-Chloro-3-trifluoromethylphenyl |
| 2,2,2-Trichloroethyl | 3-Phenylisoxazol-5-yl |
| 2,2,2-Trichloroethyl | 3-Methylisoxazol-5-y |
| 2,2,2-Trichloroethyl | 4-Chloro-3-methylisoxazol-5-yl |
| 2,2,2-Trichloroethyl | 4-Chloro-3-isopropylisoxazol-5-yl |
| 2,2,2-Trichloroethyl | 4-Chloro-3-sec-butylisoxazol-5-yl |
| 2,2,2-Trichloroethyl | 4-Chloro-3-tert-butylisoxazol-5-yl |
| 2,2,2-Trichloroethyl | 4-Chloro-3-cyclohexylisoxazol-5-yl |
| 2,2,2-Trichloroethyl | 4-Chloro-3-phenylisoxazol-5-yl |
| 2,2,2-Trichloroethyl | 4-Chloro-3-(4-methylphenyl)isoxazol-5-yl |
| 2,2,2-Trichloroethyl | 4-Chloro-3-(4-Chlorophenyl)isoxazol-5-yl |
| 2,2,2-Trichloroethyl | 4-Chloro-3-(4-fluorophenyl)isoxazol-5-yl |
| 2,2,2-Trichloroethyl | 4-Chloro-3-(4-trifluoromethylphenyl)-isoxazol-5-yl |
| 2,2,2-Trichloroethyl | 4-Chloro-3-(2,6-difluorophenyl)-isoxazol-5-yl |
| 2,2,2-Trichloroethyl | 2-Phenyloxazol-4-yl |
| 2,2,2-Trichloroethyl | 2-(4-Fluorophenyl)oxazol-4-yl |
| 2,2,2-Trichloroethyl | 2-(4-Chlorophenyl)oxazol-4-yl |

TABLE B-continued $R^1R^2CH-ON=C(CN)-R^3$  $R^1 = H$  I

| R³ | R² |
|---|---|
| 2,2,2-Trichloroethyl | 2-(4-Bromophenyl)oxazol-4-yl |
| 2,2,2-Trichloroethyl | 2-(3-Chlorophenyl)oxazol-4-yl |
| 2,2,2-Trichloroethyl | 2-(4-Methylphenyl)oxazol-4-yl |
| 2,2,2-Trichloroethyl | 2-tert-Butyloxazol-4-yl |
| 2,2,2-Trichloroethyl | 2-(2,4-Dichlorophenyl)oxazol-4-yl |
| 2,2,2-Trichloroethyl | 2-(4-Methoxyphenyl)oxazol-4-yl |
| 2,2,2-Trichloroethyl | 2-(4-Chlorophenyl)-5-bromooxazol-4-yl |
| Pentachloroethyl | 2-Chloro-3-isopropylphenyl |
| Pentachloroethyl | 2,6-Difluorophenyl |
| Pentachloroethyl | 2-Chloro-3-trifluoromethylphenyl |
| Pentachloroethyl | 3-Phenylisoxazol-5-yl |
| Pentachloroethyl | 3-Methylisoxazol-5-yl |
| Pentachloroethyl | 4-Chloro-3-methylisoxazol-5-yl |
| Pentachloroethyl | 4-Chloro-3-isopropylisoxazol-5-yl |
| Pentachloroethyl | 4-Chloro-3-sec-butylisoxazol-5-yl |
| Pentachloroethyl | 4-Chloro-3-tert-butylisoxazol-5-yl |
| Pentachloroethyl | 4-Chloro-3-cyclohexylisoxazol-5-yl |
| Pentachloroethyl | 4-Chloro-3-phenylisoxazol-5-yl |
| Pentachloroethyl | 4-Chloro-3-(4-methylphenyl)isoxazol-5-yl |
| Pentachloroethyl | 4-Chloro-3-(4-chlorophenyl)isoxazol-5-yl |
| Pentachloroethyl | 4-Chloro-3-(4-fluorophenyl)isoxazol-5-yl |
| Pentachloroethyl | 4-Chloro-3-(4-trifluoromethylphenyl)isoxazol-5-yl |
| Pentachloroethyl | 4-Chloro-3-(2,6-difluorophenyl)isoxazol-5-yl |
| Pentachloroethyl | 2-Phenyloxazol-4-yl |
| Pentachloroethyl | 2-(4-Fluorophenyl)oxazol-4-yl |
| Pentachloroethyl | 2-(4-Chlorophenyl)oxazol-4-yl |
| Pentachloroethyl | 2-(4-Bromophenyl)oxazol-4-yl |
| Pentachloroethyl | 2-(3-Chlorophenyl)oxazol-4-yl |
| Pentachloroethyl | 2-(4-Methylphenyl)oxazol-4-yl |
| Pentachloroethyl | 2-tert-Butyloxazol-4-yl |
| Pentachloroethyl | 2-(2,4-Dichlorophenyl)oxazol-4-yl |
| Pentachloroethyl | 2-(4-Methoxyphenyl)oxazol-4-yl |
| Pentachloroethyl | 2-(4-Chlorophenyl)-5-bromooxazol-4-yl |
| Cyclobutyl | 2-Chloro-3-isopropylphenyl |
| Cyclobutyl | 2,6-Difluorophenyl |
| Cyclobutyl | 2-Chloro-3-trifluoromethylphenyl |
| Cyclobutyl | 3-Phenylisoxazol-5-yl |
| Cyclobutyl | 3-Methylisoxazol-5-yl |
| Cyclobutyl | 4-Chloro-3-methylisoxazol-5-yl |
| Cyclobutyl | 4-Chloro-3-isopropylisoxazol-5-yl |
| Cyclobutyl | 4-Chloro-3-sec-butylisoxazol-5-yl |
| Cyclobutyl | 4-Chloro-3-tert-butylisoxazol-5-yl |
| Cyclobutyl | 4-Chloro-3-cyclohexylisoxazol-5-yl |
| Cyclobutyl | 4-Chloro-3-phenylisoxazol-5-yl |
| Cyclobutyl | 4-Chloro-3-(4-methylphenyl)isoxazol-5-yl |
| Cyclobutyl | 4-Chloro-3-(4-chlorophenyl)isoxazol-5-yl |
| Cyclobutyl | 4-Chloro-3-(4-fluorophenyl)isoxazol-5-yl |
| Cyclobutyl | 4-Chloro-3-(4-trifluoromethylphenyl)isoxazol-5-yl |
| Cyclobutyl | 4-Chloro-3-(2,6-difluorophenyl)isoxazol-5-yl |
| Cyclobutyl | 2-Phenyloxazol-4-yl |
| Cyclobutyl | 2-(4-Fluorophenyl)oxazol-4-yl |
| Cyclobutyl | 2-(4-Chlorophenyl)oxazol-4-yl |
| Cyclobutyl | 2-(4-Bromophenyl)oxazol-4-yl |
| Cyclobutyl | 2-(3-Chlorophenyl)oxazol-4-yl |
| Cyclobutyl | 2-(4-Methylphenyl)oxazol-4-yl |
| Cyclobutyl | 2-tert-Butyloxazol-4-yl |
| Cyclobutyl | 2-(2,4-Dichlorophenyl)oxazol-4-yl |
| Cyclobutyl | 2-(4-Methoxyphenyl)oxazol-4-yl |
| Cyclobutyl | 2-(4-Chlorophenyl)-i-bromooxazol-4-yl |
| Cyclopentyl | 2-Chloro-3-isopropylphenyl |
| Cyclopentyl | 2,6-Difluorophenyl |
| Cyclopentyl | 2-Chloro-3-trifluoromethylphenyl |
| Cyclopentyl | 3-Phenylisoxazol-5-yl |
| Cyclopentyl | 3-Methylisoxazol-5-yl |
| Cyclopentyl | 4-Chloro-3-methylisoxazol-5-yl |
| Cyclopentyl | 4-Chloro-3-isopropylisoxazol-5-yl |
| Cyclopentyl | 4-Chloro-3-sec-butylisoxazol-5-yl |
| Cyclopentyl | 4-Chloro-3-tert-butylisoxazol-5-yl |
| Cyclopentyl | 4-Chloro-3-cyclohexylisoxazol-5-yl |
| Cyclopentyl | 4-Chloro-3-phenylisoxazol-5-yl |
| Cyclopentyl | 4-Chloro-3-(4-methylphenyl)isoxazol-5-yl |
| Cyclopentyl | 4-Chloro-3-(4-chlorophenyl)isoxazol-5-yl |
| Cyclopentyl | 4-Chloro-3-(4-fluorophenyl)isoxazol-5-yl |
| Cyclopentyl | 4-Chloro-3-(4-trifluoromethylphenyl)isoxazol-5-yl |
| Cyclopentyl | 4-Chloro-3-(2,6-difluorophenyl)isoxazol-5-yl |
| Cyclopentyl | 2-Phenyloxazol-4-yl |
| Cyclopentyl | 2-(4-Fluorophenyl)oxazol-4-yl |
| Cyclopentyl | 2-(4-Chlorophenyl)oxazol-4-yl |
| Cyclopentyl | 2-(4-Bromophenyl)oxazol-4-yl |
| Cyclopentyl | 2-(3-Chlorophenyl)oxazol-4-yl |
| Cyclopentyl | 2-(4-Methylphenyl)oxazol-4-yl |
| Cyclopentyl | 2-tert-Butyloxazol-4-yl |
| Cyclopentyl | 2-(2,4-Dichlorophenyl)oxazol-4-yl |
| Cyclopentyl | 2-(4-Methoxyphenyl)oxazol-4-yl |
| Cyclopentyl | 2-(4-Chlorophenyl)-5-bromooxazol-4-yl |
| 1-Methylcyclopropyl | 2-Chloro-3-isopropylphenyl |
| 1-Methylcyclopropyl | 2,6-Difluorophenyl |
| 1-Methylcyclopropyl | 2-Chloro-3-trifluoromethylphenyl |
| 1-Methylcyclopropyl | 3-Phenylisoxazol-5-yl |
| 1-Methylcyclopropyl | 3-Methylisoxazol-5-yl |
| 1-Methylcyclopropyl | 4-Chloro-3-methylisoxazol-5-yl |
| 1-Methylcyclopropyl | 4-Chloro-3-isopropylisoxazol-5-yl |
| 1-Methylcyclopropyl | 4-Chloro-3-sec-butylisoxazol-5-yl |
| 1-Methylcyclopropyl | 4-Chloro-3-tert-butylisoxazol-5-yl |
| 1-Methylcyclopropyl | 4-Chloro-3-cyclohexylisoxazol-5-yl |
| 1-Methylcyclopropyl | 4-Chloro-3-phenylisoxazol-5-yl |
| 1-Methylcyclopropyl | 4-Chloro-3-(4-methylphenyl)isoxazol-5-yl |
| 1-Methylcyclopropyl | 4-Chloro-3-(4-chlorophenyl)isoxazol-5-yl |
| 1-Methylcyclopropyl | 4-Chloro-3-(4-fluorophenyl)isoxazol-5-yl |
| 1-Methylcyclopropyl | 4-Chloro-3-(4-trifluoromethylphenyl)isoxazol-5-yl |
| 1-Methylcyclopropyl | 4-Chloro-3-(2,6-difluorophenyl)isoxazol-5-yl |
| 1-Methylcyclopropyl | 2-Phenyloxazol-4-yl |
| 1-Methylcyclopropyl | 2-(4-Fluorophenyl)oxazol-4-yl |
| 1-Methylcyclopropyl | 2-(4-Chlorophenyl)oxazol-4-yl |
| 1-Methylcyclopropyl | 2-(4-Bromophenyl)oxazol-4-yl |
| 1-Methylcyclopropyl | 2-(3-Chlorophenyl)oxazol-4-yl |
| 1-Methylcyclopropyl | 2-(4-Methylphenyl)oxazol-4-yl |
| 1-Methylcyclopropyl | 2-tert-Butyloxazol-4-yl |
| 1-Methylcyclopropyl | 2-(2,4-Dichlorophenyl)oxazol-4-yl |
| 1-Methylcyclopropyl | 2-(4-Methoxyphenyl)oxazol-4-yl |
| 1-Methylcyclopropyl | 2-(4-Chlorophenyl)-5-bromooxazol-4-yl |
| 2,2-Dimethylcyclopropyl | 2-Chloro-3-isopropylphenyl |
| 2,2-Dimethylcyclopropyl | 2,6-Difluorophenyl |
| 2,2-Dimethylcyclopropyl | 2-Chloro-3-trifluoromethylphenyl |
| 2,2-Dimethylcyclopropyl | 3-Phenylisoxazol-5-yl |
| 2,2-Dimethylcyclopropyl | 3-Methylisoxazol-5-yl |
| 2,2-Dimethylcyclopropyl | 4-Chloro-3-methylisoxazol-5-yl |
| 2,2-Dimethylcyclopropyl | 4-Chloro-3-isopropylisoxazol-5-yl |
| 2,2-Dimethylcyclopropyl | 4-Chloro-3-sec-butylisoxazol-5-yl |
| 2,2-Dimethylcyclopropyl | 4-Chloro-3-tert-butylisoxazol-5-yl |
| 2,2-Dimethylcyclopropyl | 4-Chloro-3-cyclohexylisoxazol-5-yl |
| 2,2-Dimethylcyclopropyl | 4-Chloro-3-phenylisoxazol-5-yl |
| 2,2-Dimethylcyclopropyl | 4-Chloro-3-(4-methylphenyl)isoxazol-5-yl |
| 2,2-Dimethylcyclopropyl | 4-Chloro-3-(4-chlorophenyl)isoxazol-5-yl |
| 2,2-Dimethylcyclopropyl | 4-Chloro-3-(4-fluorophenyl)isoxazol-5-yl |
| 2,2-Dimethylcyclopropyl | 4-Chloro-3-(4-trifluoromethylphenyl)isoxazol-5-yl |

TABLE B-continued $R^1R^2CH-ON=C(CN)-R^3$     $R^1 = H$     I

| $R^3$ | $R^2$ |
|---|---|
| 2,2-Dimethylcyclopropyl | 4-Chloro-3-(2,6-difluorophenyl)isoxazol-5-yl |
| 2,2-Dimethylcyclopropyl | 2-Phenyloxazol-4-yl |
| 2,2-Dimethylcyclopropyl | 2-(4-Fluorophenyl)oxazol-4-yl |
| 2,2-Dimethylcyclopropyl | 2-(4-Chlorophenyl)oxazol-4-yl |
| 2,2-Dimethylcyclopropyl | 2-(4-Bromophenyl)oxazol-4-yl |
| 2,2-Dimethylcyclopropyl | 2-(3-Chlorophenyl)oxazol-4-yl |
| 2,2-Dimethylcyclopropyl | 2-(4-Methylphenyl)oxazol-4-yl |
| 2,2-Dimethylcyclopropyl | 2-tert-Butyloxazol-4-yl |
| 2,2-Dimethylcyclopropyl | 2-(2,4-Dichlorophenyl)oxazol-4-yl |
| 2,2-Dimethylcyclopropyl | 2-(4-Methoxyphenyl)oxazol-4-yl |
| 2,2-Dimethylcyclopropyl | 2-(4-Chlorophenyl)-5-bromooxazol-4-yl |
| 1-Methylcyclohexyl | 2-Chloro-3-isopropylphenyl |
| 1-Methylcyclohexyl | 2,6-Difluorophenyl |
| 1-Methylcyclohexyl | 2-Chloro-3-trifluoromethylphenyl |
| 1-Methylcyclohexyl | 3-Phenylisoxazol-5-yl |
| 1-Methylcyclohexyl | 3-Methylisoxazol-5-yl |
| 1-Methylcyclohexyl | 4-Chloro-3-methylisoxazol-5-yl |
| 1-Methylcyclohexyl | 4-Chloro-3-isopropylisoxazol-5-yl |
| 1-Methylcyclohexyl | 4-Chloro-3-sec-butylisoxazol-5-yl |
| 1-Methylcyclohexyl | 4-Chloro-3-tert-butylisoxazol-5-yl |
| 1-Methylcyclohexyl | 4-Chloro-3-cyclohexylisoxazol-5-yl |
| 1-Methylcyclohexyl | 4-Chloro-3-phenylisoxazol-5-yl |
| 1-Methylcyclohexyl | 4-Chloro-3-(4-methylphenyl)isoxazol-5-yl |
| 1-Methylcyclohexyl | 4-Chloro-3-(4-chlorophenyl)isoxazol-5-yl |
| 1-Methylcyclohexyl | 4-Chloro-3-(4-fluorophenyl)isoxazol-5-yl |
| 1-Methylcyclohexyl | 4-Chloro-3-(4-trifluoromethylphenyl)isoxazol-5-yl |
| 1-Methylcyclohexyl | 4-Chloro-3-(2,6-difluorophenyl)isoxazol-5-yl |
| 1-Methylcyclohexyl | 2-Phenyloxazol-4-yl |
| 1-Methylcyclohexyl | 2-(4-Fluorophenyl)oxazol-4-yl |
| 1-Methylcyclohexyl | 2-(4-Chlorophenyl)oxazol-4-yl |
| 1-Methylcyclohexyl | 2-(4-Bromophenyl)oxazol-4-yl |
| 1-Methylcyclohexyl | 2-(3-Chlorophenyl)oxazol-4-yl |
| 1-Methylcyclohexyl | 2-(4-Methylphenyl)oxazol-4-yl |
| 1-Methylcyclohexyl | 2-tert-Butyloxazol-4-yl |
| 1-Methylcyclohexyl | 2-(2,4-Dichlorophenyl)oxazol-4-yl |
| 1-Methylcyclohexyl | 2-(4-Methoxyphenyl)oxazol-4-yl |
| 1-Methylcyclohexyl | 2-(4-Chlorophenyl)-5-bromooxazol-4-yl |
| 2,2-Difluorocyclopropyl | 2-Chloro-3-isopropylphenyl |
| 2,2-Difluorocyclopropyl | 2,6-Difluorophenyl |
| 2,2-Difluorocyclopropyl | 2-Chloro-3-trifluoromethylphenyl |
| 2,2-Difluorocyclopropyl | 3-Phenylisoxazol-5-yl |
| 2,2-Difluorocyclopropyl | 3-Methylisoxazol-5-yl |
| 2,2-Difluorocyclopropyl | 4-Chloro-3-methylisoxazol-5-yl |
| 2,2-Difluorocyclopropyl | 4-Chloro-3-isopropylisoxazol-5-yl |
| 2,2-Difluorocyclopropyl | 4-Chloro-3-sec-butylisoxazol-5-yl |
| 2,2-Difluorocyclopropyl | 4-Chloro-3-tert-butylisoxazol-5-yl |
| 2,2-Difluorocyclopropyl | 4-Chloro-3-cyclohexylisoxazol-5-yl |
| 2,2-Difluorocyclopropyl | 4-Chloro-3-phenylisoxazol-5-yl |
| 2,2-Difluorocyclopropyl | 4-Chloro-3-(4-methylphenyl)isoxazol-5-yl |
| 2,2-Difluorocyclopropyl | 4-Chloro-3-(4-chlorophenyl)isoxazol-5-yl |
| 2,2-Difluorocyclopropyl | 4-Chloro-3-(4-fluorophenyl)isoxazol-5-yl |
| 2,2-Difluorocyclopropyl | 4-Chloro-3-(4-trifluoromethylphenyl)isoxazol-5-yl |
| 2,2-Difluorocyclopropyl | 4-Chloro-3-(2,6-difluorophenyl)isoxazol-5-yl |
| 2,2-Difluorocyclopropyl | 2-Phenyloxazol-4-yl |
| 2,2-Difluorocyclopropyl | 2-(4-Fluorophenyl)oxazol-4-yl |
| 2,2-Difluorocyclopropyl | 2-(4-Chlorophenyl)oxazol-4-yl |
| 2,2-Difluorocyclopropyl | 2-(4-Bromophenyl)oxazol-4-yl |
| 2,2-Difluorocyclopropyl | 2-(3-Chlorophenyl)oxazol-4-yl |
| 2,2-Difluorocyclopropyl | 2-(4-Methylphenyl)oxazol-4-yl |
| 2,2-Difluorocyclopropyl | 2-tert-Butyloxazol-4-yl |
| 2,2-Difluorocyclopropyl | 2-(2,4-Dichlorophenyl)oxazol-4-yl |
| 2,2-Difluorocyclopropyl | 2-(4-Methoxyphenyl)oxazol-4-yl |
| 2,2-Difluorocyclopropyl | 2-(4-Chlorophenyl)-5-bromooxazol-4-yl |
| 2,2,3,3-Tetrafluorocyclobutyl | 2-Chloro-3-isopropylphenyl |
| 2,2,3,3-Tetrafluorocyclobutyl | 2,6-Difluorophenyl |
| 2,2,3,3-Tetrafluorocyclobutyl | 2-Chloro-3-trifluoromethylphenyl |
| 2,2,3,3-Tetrafluorocyclobutyl | 3-Phenylisoxazol-5-yl |
| 2,2,3,3-Tetrafluorocyclobutyl | 3-Methylisoxazol-5-yl |
| 2,2,3,3-Tetrafluorocyclobutyl | 4-Chloro-3-methylisoxazol-5-yl |
| 2,2,3,3-Tetrafluorocyclobutyl | 4-Chloro-3-isopropylisoxazol-5-yl |
| 2,2,3,3-Tetrafluorocyclobutyl | 4-Chloro-3-sec-butylisoxazol-5-yl |
| 2,2,3,3-Tetrafluorocyclobutyl | 4-Chloro-3-tert-butylisoxazol-5-yl |
| 2,2,3,3-Tetrafluorocyclobutyl | 4-Chloro-3-cyclohexylisoxazol-5-yl |
| 2,2,3,3-Tetrafluorocyclobutyl | 4-Chloro-3-phenylisoxazol-5-yl |
| 2,2,3,3-Tetrafluorocyclobutyl | 4-Chloro-3-(4-methylphenyl)isoxazol-5-yl |
| 2,2,3,3-Tetrafluorocyclobutyl | 4-Chloro-3-(4-chlorophenyl)isoxazol-5-yl |
| 2,2,3,3-Tetrafluorocyclobutyl | 4-Chloro-3-(4-fluorophenyl)isoxazol-5-yl |
| 2,2,3,3-Tetrafluorocyclobutyl | 4-Chloro-3-(4-trifluoromethylphenyl)isoxazol-5-yl |
| 2,2,3,3-Tetrafluorocyclobutyl | 4-Chloro-3-(2,6-difluorophenyl)isoxazol-5-yl |
| 2,2,3,3-Tetrafluorocyclobutyl | 2-Phenyloxazol-4-yl |
| 2,2,3,3-Tetrafluorocyclobutyl | 2-(4-Fluorophenyl)oxazol-4-yl |
| 2,2,3,3-Tetrafluorocyclobutyl | 2-(4-Chlorophenyl)oxazol-4-yl |
| 2,2,3,3-Tetrafluorocyclobutyl | 2-(4-Bromophenyl)oxazol-4-yl |
| 2,2,3,3-Tetrafluorocyclobutyl | 2-(3-Chlorophenyl)oxazol-4-yl |
| 2,2,3,3-Tetrafluorocyclobutyl | 2-(4-Methylphenyl)oxazol-4-yl |
| 2,2,3,3-Tetrafluorocyclobutyl | 2-tert-Butyloxazol-4-yl |
| 2,2,3,3-Tetrafluorocyclobutyl | 2-(2,4-Dichlorophenyl)oxazol-4-yl |
| 2,2,3,3-Tetrafluorocyclobutyl | 2-(4-Methoxyphenyl)oxazol-4-yl |
| 2,2,3,3-Tetrafluorocyclobutyl | 2-(4-Chlorophenyl)-5-bromooxazol-4-yl |

TABLE C $R^1R^2CH-ON=C(CN)-R^3$     $R^1 = CH_3$     I

| $R^3$ | $R^2$ |
|---|---|
| 2-Methoxyprop-2-yl | 2-Chloro-3-isopropylphenyl |
| 2-Methoxyprop-2-yl | 2,6-Difluorophenyl |
| 2-Methoxyprop-2-yl | 2-Chloro-3-trifluoromethylphenyl |
| 2-Methoxyprop-2-yl | 3-Phenylisoxazol-5-yl |
| 2-Methoxyprop-2-yl | 3-Methylisoxazol-5-yl |
| 2-Methoxyprop-2-yl | 4-Chloro-3-methylisoxazol-5-yl |
| 2-Methoxyprop-2-yl | 4-Chloro-3-isopropylisoxazol-5-yl |
| 2-Methoxyprop-2-yl | 4-Chloro-3-sec-butylisoxazol-5-yl |
| 2-Methoxyprop-2-yl | 4-Chloro-3-tert-butylisoxazol-5-yl |
| 2-Methoxyprop-2-yl | 4-Chloro-3-cyclohexylisoxazol-5-yl |
| 2-Methoxyprop-2-yl | 4-Chloro-3-phenylisoxazol-5-yl |
| 2-Methoxyprop-2-yl | 4-Chloro-3-(4-methylphenyl)isoxazol-5-yl |

TABLE C-continued

| R³ | R² |
|---|---|
| | R¹R²CH—ON=C(CN)—R³    R¹ = CH₃    I |
| 2-Methoxyprop-2-yl | 4-Chloro-3-(4-chlorophenyl)isoxazol-5-yl |
| 2-Methoxyprop-2-yl | 4-Chloro-3-(4-fluorophenyl)isoxazol-5-yl |
| 2-Methoxyprop-2-yl | 4-Chloro-3-(4-trifluoromethylphenyl)-isoxazol-5-yl |
| 2-Methoxyprop-2-yl | 4-Chloro-3-(2,6-difluorophenyl)-isoxazol-5-yl |
| 2-Methoxyprop-2-yl | 2-Phenyloxazol-4-yl |
| 2-Methoxyprop-2-yl | 2-(4-Fluorophenyl)oxazol-4-yl |
| 2-Methoxyprop-2-yl | 2-(4-Chlorophenyl)oxazol-4-yl |
| 2-Methoxyprop-2-yl | 2-(4-Bromophenyl)oxazol-4-yl |
| 2-Methoxyprop-2-yl | 2-(3-Chlorophenyl)oxazol-4-yl |
| 2-Methoxyprop-2-yl | 2-(2-Methylphenyl)oxazol-4-yl |
| 2-Methoxyprop-2-yl | 2-tert-Butyloxazol-4-yl |
| 2-Methoxyprop-2-yl | 2-(2,4-Dichlorophenyl)oxazol-4-yl |
| 2-Methoxyprop-2-yl | 2-(4-Methoxyphenyl)oxazol-4-yl |
| 2-Methoxyprop-2-yl | 2-(4-Chlorphenyl)-5-bromoxazol-4-yl |
| 2-Ethoxyprop-2-yl | 2-Chloro-3-isopropylphenyl |
| 2-Ethoxyprop-2-yl | 2,6-Difluorophenyl |
| 2-Ethoxyprop-2-yl | 2-Chloro-3-trifluoromethylphenyl |
| 2-Ethoxyprop-2-yl | 3-Phenylisoxazol-5-yl |
| 2-Ethoxyprop-2-yl | 3-Methylisoxazol-5-yl |
| 2-Ethoxyprop-2-yl | 4-Chloro-3-methylisoxazol-5-yl |
| 2-Ethoxyprop-2-yl | 4-Chloro-3-isopropylisoxazol-5-yl |
| 2-Ethoxyprop-2-yl | 4-Chloro-3-sec-butylisoxazol-5-yl |
| 2-Ethoxyprop-2-yl | 4-Chloro-3-tert-butylisoxazol-5-yl |
| 2-Ethoxyprop-2-yl | 4-Chloro-3-cyclohexylisoxazol-5-yl |
| 2-Ethoxyprop-2-yl | 4-Chloro-3-phenylisoxazol-5-yl |
| 2-Ethoxyprop-2-yl | 4-Chloro-3-(4-methylphenyl)isoxazol-5-yl |
| 2-Ethoxyprop-2-yl | 4-Chloro-3-(4-chlorphenyl)isoxazol-5-yl |
| 2-Ethoxyprop-2-yl | 4-Chloro-3-(4-fluorphenyl)isoxazol-5-yl |
| 2-Ethoxyprop-2-yl | 4-Chloro-3-(4-trifluormethylphenyl)-isoxazol-5-yl |
| 2-Ethoxyprop-2-yl | 4-Chloro-3-(2,6-difluorphenyl)-isoxazol-5-yl |
| 2-Ethoxyprop-2-yl | 2-Phenyloxazol-4-yl |
| 2-Ethoxyprop-2-yl | 2-(4-Fluorophenyl)oxazol-4-yl |
| 2-Ethoxyprop-2-yl | 2-(4-Chlorophenyl)oxazol-4-yl |
| 2-Ethoxyprop-2-yl | 2-(4-Bromophenyl)oxazol-4-yl |
| 2-Ethoxyprop-2-yl | 2-(3-Chlorophenyl)oxazol-4-yl |
| 2-Ethoxyprop-2-yl | 2-(2-Methylphenyl)oxazol-4-yl |
| 2-Ethoxyprop-2-yl | 2-tert-Butyloxazol-4-yl |
| 2-Ethoxyprop-2-yl | 2-(2,4-Dichlorphenyl)oxazol-4-yl |
| 2-Ethoxyprop-2-yl | 2-(2-Methoxyphenyl)oxazol-4-yl |
| 2-Ethoxyprop-2-yl | 2-(4-Chlorphenyl)-5-bromooxazol-4-yl |
| 2-n-Propoxyprop-2-yl | 2-Chloro-3-isopropylphenyl |
| 2-n-Propoxyprop-2-yl | 2,6-Difluorophenyl |
| 2-n-Propoxyprop-2-yl | 2-Chloro-3-trifluormethylphenyl |
| 2-n-Propoxyprop-2-yl | 3-Phenylisoxazol-5-yl |
| 2-n-Propoxyprop-2-yl | 3-Methylisoxazol-5-yl |
| 2-n-Propoxyprop-2-yl | 4-Chloro-3-methylisoxazol-5-yl |
| 2-n-Propoxyprop-2-yl | 4-Chloro-3-isopropylisoxazol-5-yl |
| 2-n-Propoxyprop-2-yl | 4-Chloro-3-sec-butylisoxazol-5-yl |
| 2-n-Propoxyprop-2-yl | 4-Chloro-3-tert-butylisoxazol-5-yl |
| 2-n-Propoxyprop-2-yl | 4-Chloro-3-cyclohexylisoxazol-5-yl |
| 2-n-Propoxyprop-2-yl | 4-Chloro-3-phenylisoxazol-5-yl |
| 2-n-Propoxyprop-2-yl | 4-Chloro-3-(4-methylphenyl)isoxazol-5-yl |
| 2-n-Propoxyprop-2-yl | 4-Chloro-3-(4-chlorophenyl)isoxazol-5-yl |
| 2-n-Propoxyprop-2-yl | 4-Chloro-3-(4-fluorophenyl)isoxazol-5-yl |
| 2-n-Propoxyprop-2-yl | 4-Chloro-3-(4-trifluoromethylphenyl)-isoxazol-5-yl |
| 2-n-Propoxyprop-2-yl | 4-Chloro-3-(2,6-difluorphenyl)-isoxazol-5-yl |
| 2-n-Propoxyprop-2-yl | 2-Phenyloxazol-4-yl |
| 2-n-Propoxyprop-2-yl | 2-(4-Fluorophenyl)oxazol-4-yl |
| 2-n-Propoxyprop-2-yl | 2-(4-Chlorophenyl)oxazol-4-yl |
| 2-n-Propoxyprop-2-yl | 2-(4-Bromophenyl)oxazol-4-yl |
| 2-n-Propoxyprop-2-yl | 2-(3-Chlorophenyl)oxazol-4-yl |
| 2-n-Propoxyprop-2-yl | 2-(2-Methylphenyl)oxazol-4-yl |
| 2-n-Propoxyprop-2-yl | 2-tert-Butyloxazol-4-yl |
| 2-n-Propoxyprop-2-yl | 2-(2,4-Dichlorophenyl)oxazol-4-yl |
| 2-n-Propoxyprop-2-yl | 2-(2-Methoxyphenyl)oxazol-4-yl |
| 2-n-Propoxyprop-2-yl | 2-(4-Chlorophenyl)-5-bromooxazol-4-yl |

The compounds of the formula I are suitable for effectively controlling pests from the class consisting of the insects, arachnids and nematodes. They may be used as pesticides in crop protection and in the hygiene sector, for the protection of stored materials and in the veterinary sector.

The insect pests include, from the order of the butterflies (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis.*

From the order of the beetles (Coleoptera), for example *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia-japonica, Sitona lineatus* and *Sitophilus granaria.*

From the order of the Diptera, for example *Aedes aegypti, Aedes vexans, Anastrepha ludens, Anopheles maculipennis,*

*Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea* and *Tipula paludosa.*

From the order of the Thysanoptera, for example *Frankliniella fusca, Frankliniella occidentalis, Frankliniella tritici, Scirtothrips citri, Thrips oryzae, Thrips palmi* and *Thrips tabaci.*

From the order of the Hymenoptera, for example *Athalia rosae, Atta cephalotes, Atta sexdens, Atta texana, Hoplocampa minuta, Hoplocampa testudinea, Monomorium pharaonis, Solenopsis geminata* and *Solenopsis invicta.*

From the order of the Heteroptera, for example *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis* and *Thyanta perditor.*

From the order of the Homoptera, for example *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphummaidis, Sappaphis mala, Sappaphis mali, Schizaphis graminum, Schizoneura lanuginosa, Trialeurodes vaporariorum* and *Viteus vitifolii.*

From the order of the Isoptera, for example *Calotermes flavicollis, Leucotermes flavipes, Reticulitermes lucifugus* and *Termes natalensis.*

From the order of the Orthoptera, for example *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus* and *Tachycines asynamorus.*

From the order of the Arachnoidea, for example arachnids (Acarina) such as *Amblyomma americahum, Amglyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius* and *Tetranychus urticae.*

From the class of the nematodes, for example root gall nematodes, e.g. *Meloidogyne hapla, Meloidogyne incognita, Meloidogyne javanica,* cyst-forming nematodes, e.g. *Globodera rostochiensis, Heterodera avenae, Heterodera glycinae, Heterodera schatii, Hetrodera triflolii,* and stem and leaf eelworms, e.g. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus* and *Pratylenchus goodeyi.*

The active ingredients may be used as such, in the form of their formulations or in the application forms prepared therefrom, for example in the form of directly sprayable solutions, powders, suspensions or dispersions, emulsions, oil dispersions, pastes, dusts, broadcasting agents or granules, by spraying, nebulizing, dusting, broadcasting or pouring. The application forms depend entirely on the intended uses; they should in any case ensure a very fine distribution of the novel active ingredients.

Mineral oil fractions having a medium to high boiling point, such as kerosene or diesel oil, as well as coal tar oils and oils of vegetable or animal origin, aliphatic, cyclic and aromatic hydrocarbons, e.g. benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene or isophorone, and strongly polar solvents, e.g. dimethylformamide, dimethyl sulfoxide, N-methylpyrrolidone or water, are suitable for the preparation of directly sprayable solutions, emulsions, pastes or oil dispersions.

Aqueous application forms can be prepared from emulsion concentrates, pastes or wettable powders (sprayable powders, oil dispersions) by adding water. For the preparation of emulsions, pastes or oil dispersions, the substances, as such or in solution in an oil or solvent, may be homogenized in water by means of wetting agents, adherents, dispersants or emulsifiers. However, it is also possible to prepare concentrates consisting of active substance, wetting agents, adherents, dispersants or emulsifiers and possibly solvents or oil, which concentrates are suitable for dilution with water.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkylsulfates, alkylsulfonates, fatty alcohol sulfates and fatty acids and the alkali metal and alkaline earth metal salts thereof, salts of sulfated fatty alcohol glycol ethers, condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenyl polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, broadcasting agents and dusts can be prepared by mixing or milling the active substances together with a solid carrier.

Examples of formulations are:

I. 5 parts by weight of compound No. 1 are thoroughly mixed with 95 parts by weight of finely divided kaolin. A dust which contains 3% by weight of the active ingredient is obtained in this manner.

II. 30 parts by weight of compound No. 2 are thoroughly mixed with a mixture of 92 parts by weight of silica gel powder and 8 parts by weight of liquid paraffin, which was sprayed onto the surface of this silica gel. A formulation of the active ingredient having good adhesion is obtained in this manner.

III. 10 parts by weight of compound No. 4 are dissolved in a mixture which consists of 90 parts by weight of xylene, 6 parts by weight of the adduct of from 8 to 10 mol of ethylene oxide with 1 mol of N-monoethanololeamide, 2 parts by weight of the calcium salt of dodecylbenzenesulfonic acid and 2 parts by weight of the adduct of 40 mol of ethylene oxide with 1 mol of castor oil.

IV. 20 parts by weight of compound No. 13 are dissolved in a mixture which consists of 60 parts by weight of cyclohexanone, 30 parts by weight of isobutanol, 5 parts by weight of the adduct of 7 mol of ethylene oxide with 1 mol of isooctylphenol and 5 parts by weight of the adduct of 40 mol of ethylene oxide with 1 mol of castor oil.

V. 80 parts by weight of compound No. 19 are thoroughly mixed with 3 parts by weight of the sodium salt of diisobutylnaphthalene-alpha-sulfonic acid, 10 parts by weight of the sodium salt of a ligninsulfonic acid obtained from a sulfite waste liquor and 7 parts by weight of silica gel powder, and the mixture is milled in a hammer mill.

Granules, for example coated, impregnated and homogeneous granules, can be prepared by binding the active ingredients to solid carriers. Solid carriers are, for example, mineral earths, such as silica gel, silicas, silicates, talc, kaolin, attaclay, limestone, lime, chalk, bole, loess, clay, dolomite, kieselguhr, calcium sulfate, magnesium sulfate or magnesium oxide, milled plastics, fertilizers, for example ammonium sulfate, ammonium phosphate, ammonium nitrate, ureas and vegetable products, such as cereal flours, bark meal, wood meal and nutshell meal, cellulose powder and other solid carriers.

The formulations contain in general from 0.1 to 95, preferably from 0.5 to 90% by weight of active ingredient.

The active ingredient concentrations in the ready-to-use formulations may be varied within relatively wide ranges. They are in general from 0.0001 to 10%, preferably from 0.01 to 1%.

The active ingredients may also be used successfully by the ultra-low-volume (ULV) method, it being possible to apply formulations containing more than 95% by weight of active ingredient or even the active ingredient without additives.

Under open-air conditions, the application rate of active ingredient is from 0.2 to 10, preferably from 0.5 to 2.0, kg/ha.

Oils of various types, herbicides, fungicides, other pesticides and bacteriocides may be added to the active ingredients, if necessary also immediately before use (tank mix). These agents may be mixed with the agents according to the invention in a weight ratio of from 1:10 to 10:1.

SYNTHESIS EXAMPLES

The methods described in the synthesis examples below are used with appropriate modification of the starting materials in order to obtain further compounds I. The compounds thus obtained are shown in the following tables with physical data.

The examples and methods which follow are intended to illustrate the preparation of the novel active ingredients and intermediates:

Method 1

3-Methoxy-3-methyl-2-oximinobutyronitrile 53.6 g (0.46 mol) of 2-methoxy-2-methylpropionaldehyde oxime in diethyl ether (about 1M) are initially taken at from −5° to 10° C. 35.8 g (0.5 mol) of chlorine gas are passed in, after which stirring is carried out for 1 hour at this temperature, the mixture is evaporated down at 10° C. and the residue is taken up in diethyl ether. 24.7 g (0.5 mol) of sodium cyanide in 375 ml of 20:1 methanol/water are initially taken at 10° C. and the above ether solution is rapidly added dropwise. After 4 hours at room temperature, solid components are removed from the mixture and the solution is washed with 2 times 100 ml of methanol. The combined solutions are evaporated down and the residue is partitioned between methyl tert-butyl ether and water. Drying the organic phase (sodium sulfate) evaporating down and crystallizing (dichloromethane/n-hexane) leads to 41.1 g (63% of theory) of a white powder of melting point 102°–104°–C.

Method 2

4-Chloromethyl-2-(4-fluorophenyl)oxazole 139 g (1 mol) of 4-fluorobenzamide and 127 g (1 mol) of 1,3-dichloroacetone are combined in a reaction vessel with a connected scrubbing tower. The mixture is melted slowly by heating, and the temperature is finally increased to 150° C. This temperature is maintained while stirring until evolution of gas is complete (about 1.5 hours).

The dark reaction mixture is cooled to room temperature, 500 ml of concentrated sulfuric acid are carefully added dropwise and the resulting suspension is stirred for 1.5 hours. The mixture is then poured into ice water while stirring vigorously, and the precipitate is filtered off under suction and washed thoroughly with water. The precipitate is dried and then recrystallized from ethanol.

Yield: 64%; melting point: 71°–74° C.

Example 1

3-Methoxy-3-methyl-2-[[(2',6'-difluorophenyl)methoxy]imino]-butyronitrile 3.55 g (25 mmol) of 3-methoxy-3-methyl-2-oximinobutyronitrile, 5.18 g of potassium carbonate and 4.06 g (25 mmol) of 2,6-difluorobenzyl chloride in 50 ml of dry acetonitrile are stirred for 5 hours at 70° C. and then stirred for 12 hours at room temperature. The solvent is then removed under reduced pressure. The residue is taken up in 200 ml of methyl tert-butyl ether. The solution is washed three times with sodium hydroxide solution and three times with water. The combined organic phases are dried over sodium sulfate and the solvent is distilled off under reduced pressure. The crude product is chromatographed over silica gel using 2:1 cyclohexane/dichloroethane. 6.2 g (92% of theory) of the title compound are obtained as a colorless viscous oil.

IR (cm$^{-1}$): 1595, 1474, 1368, 1273, 1238, 1180, 1064, 1010.

Example 2

3-Methoxy-3-methyl-2-[[(3-methylisoxazol-5-yl)methoxy]imino]-butyronitrile 6.0 g (84% of theory) of the title compound are obtained as a colorless viscous oil by methods similar to that stated in Example 1, from 4.26 g (30 mmol) of 3-methoxy-3-methyl-2-oximinobutyronitrile, 4.14 g of potassium carbonate and 3.95 g (30 mmol) of 5-chloromethyl-3-methylisoxazol in 50 ml of dry acetonitrile as the solvent, after chromatography of the crude product over silica gel using 1:1 cyclohexane/dichloroethane.

IR (cm$^{-1}$): 1445, 1367, 1360, 1273, 1180, 1122, 1062, 1022, 1000.

Example 3

3-Methoxy-3-methyl-2-[[[2-(4-fluorophenyl)oxazol-4-yl]methoxy]imino]-butyronitrile 2.55 g (18 mmol) of 3-methoxy-3-methyl-2-oximinobutyronitrile, 3.72 g of potassium carbonate and 3.8 g (18 mmol) of 4-chloromethyl-2-(4-fluorophenyl)-oxazole in 36 ml of dry 2:1 acetone/dimethylformamide are stirred for i hour at 45° C. and then for 12 hours at room temperature. Working up by a method similar to that stated in Example 1 and chromatographing of the crude product over silica gel using 5:1 cyclohexane/methyl tert-butyl ether give 5.4 g (95% of theory) of the title compound as a crystalline solid.

Melting point: 75°–77° C.

IR (cm$^{-1}$): 1499, 1227, 1070, 1017, 1011, 965, 843.

TABLE 1

$R^1R^2CH-ON=C(CN)-R^3 \quad R^1 = H \quad I$

| Example No. | R$^3$ | R$^2$ | IR data [cm$^{-1}$] |
|---|---|---|---|
| 1.001 | 2-Methoxyprop-2-yl | 2-Chloro-3-isopropylphenyl | 1429, 1366, 1179, 1071, 1059, 1014. |
| 1.002 | 2-Methoxyprop-2-yl | 2,6-Difluorophenyl | 1595, 1474, 1368, 1273, 1238, 1180, 1064, 1010. |
| 1.003 | 2-Methoxyprop-2-yl | 2-Chloro-3-trifluoromethylphenyl | 1437, 1322, 1171, 1140, 1094, 1071, 1041, 1016. |
| 1.004 | 2-Methoxyprop-2-yl | 3-Phenylisoxazol-5-yl | 1443, 1367, 1179, 1069, 1025, 1000, 984. |
| 1.005 | 2-Methoxyprop-2-yl | 3-Methylisoxazol-5-yl | 1445, 1367, 1360, 1180, 1122, 1062, 1022, 1000. |
| 1.006 | 2-Methoxyprop-2-yl | 4-Chloro-3-methylisoxazol-5-yl | 1443, 1384, 1181, 1125, 1069, 1040, 1013, 981. |
| 1.007 | 2-Methoxyprop-2-yl | 4-Chloro-3-isopropylisoxazol-5-yl | 1466, 1367, 1180, 1123, 1070, 1024, 998, 981. |
| 1.008 | 2-Methoxyprop-2-yl | 4-Chloro-3-sec-butylisoxazol-5-yl | 1462, 1368, 1181, 1124, 1070, 1034, 1018, 982. |
| 1.009 | 2-Methoxyprop-2-yl | 4-Chloro-3-tert-butylisoxazol-5-yl | 1367, 1201, 1181, 1123, 1107, 1070, 1022, 995, 981. |
| 1.010 | 2-Methoxyprop-2-yl | 4-Chloro-3-cyclohexylisoxazol-5-yl | 1450, 1367, 1180, 1123, 1070, 1016, 988. |
| 1.011 | 2-Methoxyprop-2-yl | 4-Chloro-3-phenylisoxazol-5-yl | 1180, 1158, 1091, 1070, 1017, 985, 963. |
| 1.012 | 2-Methoxyprop-2-yl | 4-Chloro-3-(4-methylphenyl)isoxazol-5-yl | 1461, 1353, 1181, 1156, 1089, 1069, 1017, 984, 963, 822. |
| 1.013 | 2-Methoxyprop-2-yl | 4-Chloro-3-(4-chlorophenyl)isoxazol-5-yl | 1421, 1180, 1157, 1095, 1069, 1017, 985, 964, 918, 834. |
| 1.014 | 2-Methoxyprop-2-yl | 4-Chloro-3-(4-fluorophenyl)isoxazol-5-yl | 1527, 1458, 1428, 1235, 1180, 1160, 1069, 1017, 842. |
| 1.015 | 2-Methoxyprop-2-yl | 4-Chloro-3-(4-trifluoromethylphenyl)-isoxazol-5-yl | 1326, 1171, 1160, 1129, 1091, 1019. |
| 1.016 | 2-Methoxyprop-2-yl | 4-Chloro-3-(2,6-difluorophenyl)isoxazol-5-yl | 1590, 1474, 1239, 1180, 1157, 1069, 1008, 967, 791. |
| 1.017 | 2-Methoxyprop-2-yl | 2-(4-Fluorophenyl)oxazol-4-yl | 1499, 1227, 1070, 1017, 1011, 965, 843. |
| 1.018 | 2-Methoxyprop-2-yl | 2-(4-Chlorophenyl)oxazol-4-yl | 1485, 1094, 1069, 1013, 1007, 963. |
| 1.019 | 2-Methoxyprop-2-yl | 2-(4-Bromophenyl)oxazol-4-yl | 1480, 1403, 1072, 1015, 1010. |
| 1.020 | 2-Methoxyprop-2-yl | 2-(3-Chlorophenyl)oxazol-4-yl | 1432, 1077, 1063, |

TABLE 1-continued

R¹R²CH—ON=C(CN)—R³  R¹ = H  I

| Example No. | R³ | R² | IR data [cm⁻¹] |
|---|---|---|---|
| 1.021 | 2-Ethoxyprop-2-yl | 4-Chloro-3-methylisoxazol-5-yl | 1050, 959, 937. 1444, 1384, 1356, 1174, 1125, 1067, 1041, 1013, 980. |
| 1.022 | 2-Ethoxyprop-2-yl | 4-Chloro-3-isopropylisoxazol-5-yl | 1366, 1170, 1123, 1110, 1067, 1025, 998, 981. |
| 1.023 | 2-Ethoxyprop-2-yl | 4-Chloro-3-sec-butylisoxazol-5-yl | 1460, 1174, 1124, 1110, 1067, 1034, 1018, 981. |
| 1.024 | 2-Ethoxyprop-2-yl | 4-Chloro-3-tert-butylisoxazol-5-yl | 1367, 1201, 1175, 1123, 1108, 1067, 1023, 996, 981. |
| 1.025 | 2-Ethoxyprop-2-yl | 4-Chloro-3-cyclohexylisoxazol-5-yl | 1450, 1175, 1123, 1067, 1016, 988. |
| 1.026 | 2-Ethoxyprop-2-yl | 4-Chloro-3-phenylisoxazol-5-yl | 1174, 1158, 1067, 1018, 1000, 963. |
| 1.027 | 2-Ethoxyprop-2-yl | 4-Chloro-3-(4-methylphenyl)isoxazol-5-yl | 1353, 1174, 1156, 1089, 1067, 1017, 984, 963, 823. |
| 1.028 | 2-Ethoxyprop-2-yl | 4-Chloro-3-(4-chlorophenyl)isoxazol-5-yl | 1421, 1384, 1171, 1157, 1121, 1108, 1096, 1016, 834. |
| 1.029 | 2-Ethoxyprop-2-yl | 4-Chloro-3-(4-fluorophenyl)isoxazol-5-yl | 1527, 1457, 1429, 1235, 1160, 1089, 1067, 1018, 965, 842. |
| 1.030 | 2-Ethoxyprop-2-yl | 4-Chloro-3-(4-trifluoromethylphenyl)-isoxazol-5-yl | 1326, 1171, 1130, 1114, 1091, 1020. |
| 1.031 | 2-Ethoxyprop-2-yl | 4-Chloro-3-(2,6-difluorophenyl)isoxazol-5-yl | 1634, 1590, 1474, 1284, 1239, 1158, 1065, 1009, 967, 790. |
| 1.032 | 2-Ethoxyprop-2-yl | 2-(4-Fluorophenyl)oxazol-4-yl | 1499, 1367, 1222, 1109, 1067, 1015, 998, 967. |
| 1.033 | 2-Ethoxyprop-2-yl | 2-(4-Chlorophenyl)oxazol-4-yl | 1485, 1117, 1093, 1063, 1013, 995, 960. |
| 1.034 | 2-Ethoxyprop-2-yl | 2-(4-Bromophenyl)oxazol-4-yl | 1480, 1403, 1112, 1071, 1015, 1009, 994, 973, 827. |
| 1.035 | 2-Ethoxyprop-2-yl | 2-(3-Chlorophenyl)oxazol-4-yl | 1462, 1111, 1076, 1066, 1015, 986, 976. |
| 1.036 | 2-n-Propoxyprop-2-yl | 2-(4-Fluorophenyl)oxazol-4-yl | 1499, 1235, 1172, 1157, 1065, 1020, 995. |
| 1.037 | 2-n-Propoxyprop-2-yl | 2-(4-Chlorophenyl)oxazol-4-yl | 1484, 1173, 1108, 1093, 1065, 1015, 995, 978, 838. |
| 1.038 | 2-n-Propoxyprop-2-yl | 2-(4-Bromophenyl)oxazol-4-yl | 1480, 1402, 1073, 1061, 1021, 1011, 995. |
| 1.039 | 2-n-Propoxyprop-2-yl | 2-(3-Chlorophenyl)oxazol-4-yl | 1549, 1463, 1076, 1068, 1016, 988. |
| 1.040 | 2-Isopropoxyprop-2-yl | 4-Chloro-3-methylisoxazol-5-yl | 1384, 1370, 1171, 1125, 1110, 1040, 1010, 998. |
| 1.041 | 2-Isopropoxyprop-2-yl | 4-Chloro-3-isopropylisoxazol-5-yl | 1466, 1384, 1369, 1170, 1123, 1109, 1026, 996. |
| 1.042 | 2-Isopropoxyprop-2-yl | 4-Chloro-3-sec-butylisoxazol-5-yl | 1462, 1384, 1370, 1171, 1123, 1109, 1008, 997. |
| 1.043 | 2-Isopropoxyprop-2-yl | 4-Chloro-3-tert-butylisoxazol-5-yl | 1384, 1369, 1171, 1122, 1107, 1023, 1013, 995, 921. |
| 1.044 | 2-Isopropoxyprop-2-yl | 4-Chloro-3-cyclohexylisoxazol-5-yl | 1450, 1384, 1370, 1171, 1123, 1012. |
| 1.045 | 2-Isopropoxyprop-2-yl | 4-Chloro-3-phenylisoxazol-5-yl | 1384, 1369, 1171, 1158, 1121, 1011. |
| 1.046 | 2-Isopropoxyprop-2-yl | 4-Chloro-3-(4-methylphenyl)isoxazol-5-yl | 1384, 1369, 1171, 1156, 1120, 1010, 822. |

TABLE 1-continued

R¹R²CH—ON=C(CN)—R³    R¹ = H    I

| Example No. | R³ | R² | IR data [cm⁻¹] |
|---|---|---|---|
| 1.047 | 2-Isopropoxyprop-2-yl | 4-Chloro-3-(4-chlorophenyl)isoxazol-5-yl | 1422, 1173, 1157, 1095, 1067, 1017, 985, 964, 834. |
| 1.048 | 2-Isopropoxyprop-2-yl | 4-Chloro-3-(4-fluorophenyl)isoxazol-5-yl | 1527, 1428, 1384, 1235, 1171, 1160, 1089, 1067, 1018, 965, 842. |
| 1.049 | 2-Isopropoxyprop-2-yl | 4-Chloro-3-(4-trifluoromethylphenyl)-isoxazol-5-yl | 1385, 1325, 1171, 1131, 1114, 1091, 1019. |
| 1.050 | 2-Isopropoxyprop-2-yl | 4-Chloro-3-(2,6-difluorophenyl)isoxazol-5-yl | 1590, 1474, 1239, 1171, 1157, 1107, 1009, 967, 791. |
| 1.051 | 2-Isopropoxyprop-2-yl | 2-(4-Fluorophenyl)oxazol-4-yl | 1500, 1373, 1108, 1017, 996, 964. |
| 1.052 | 2-Isopropoxyprop-2-yl | 2-(4-Chlorophenyl)oxazol-4-yl | 1373, 1108, 1094, 1015, 999, 965. |
| 1.053 | 2-Isopropoxyprop-2-yl | 2-(4-Bromophenyl)oxazol-4-yl | 1368, 1175, 1106, 1020, 1011, 982, 833. |
| 1.054 | 2-Isopropoxyprop-2-yl | 2-(3-Chlorophenyl)oxazol-4-yl | 1463, 1436, 1170, 1113, 1018, 983, 975. |
| 1.055 | 2-n-Butoxyprop-2-yl | 4-Chloro-3-methylisoxazol-5-yl | 1383, 1171, 1124, 1070, 1038, 1013, 981. |
| 1.056 | 2-n-Butoxyprop-2-yl | 4-Chloro-3-isopropylisoxazol-5-yl | 1465, 1366, 1169, 1123, 1075, 1024, 997. |
| 1.057 | 2-n-Butoxyprop-2-yl | 4-Chloro-3-sec-butylisoxazol-5-yl | 1171, 1123, 1080, 1035, 1018, 990. |
| 1.058 | 2-n-Butoxyprop-2-yl | 4-Chloro-3-tert-butylisoxazol-5-yl | 1366, 1171, 1122, 1106, 1023, 995, 980. |
| 1.059 | 2-n-Butoxyprop-2-yl | 4-Chloro-3-cyclohexylisoxazol-5-yl | 1450, 1171, 1123, 1069, 1061, 1017, 988. |
| 1.060 | 2-n-Butoxyprop-2-yl | 4-Chloro-3-phenylisoxazol-5-yl | 1170, 1158, 1089, 1075, 1018, 1001, 694. |
| 1.061 | 2-n-Butoxyprop-2-yl | 4-Chloro-3-(4-methylphenyl)isoxazol-5-yl | 1457, 1170, 1156, 1087, 1019, 986, 963. |
| 1.062 | 2-n-Butoxyprop-2-yl | 4-Chloro-3-(4-fluorophenyl)isoxazol-5-yl | 1527, 1457, 1429, 1235, 1160, 1087, 1018, 986, 841. |
| 1.063 | 2-Isobutoxyprop-2-yl | 4-Chloro-3-methylisoxazol-5-yl | 1366, 1172, 1124, 1064, 1040, 1012, 981. |
| 1.064 | 2-Isobutoxyprop-2-yl | 4-Chloro-3-isopropylisoxazol-5-yl | 1467, 1366, 1170, 1123, 1065, 1025, 998, 981. |
| 1.065 | 2-Isobutoxyprop-2-yl | 4-Chloro-3-sec-butylisoxazol-5-yl | 1462, 1172, 1123, 1065, 1036, 1018, 981. |
| 1.066 | 2-Isobutoxyprop-2-yl | 4-Chloro-3-tert-butylisoxazol-5-yl | 1366, 1172, 1122, 1106, 1065, 1022, 995, 980. |
| 1.067 | 2-Isobutoxyprop-2-yl | 4-Chloro-3-cyclohexylisoxazol-5-yl | 1474, 1450, 1366, 1172, 1123, 1064, 1016, 988. |
| 1.068 | 2-Isobutoxyprop-2-yl | 4-Chloro-3-phenylisoxazol-5-yl | 1443, 1171, 1158, 1064, 1017, 1001, 963, 694 |
| 1.069 | 2-Isobutoxyprop-2-yl | 4-Chloro-3-(4-methylphenyl)isoxazol-5-yl | 1366, 1172, 1156, 1089, 1064, 1017, 985, 963. |
| 1.070 | 2-Isobutoxyprop-2-yl | 4-Chloro-3-(4-fluorophenyl)isoxazol-5-yl | 1608, 1528, 1458, 1429, 1236, 1160, 1064, 1018, 842. |
| 1.071 | 2-sec-Butoxyprop-2-yl | 4-Chloro-3-methylisoxazol-5-yl | 1384, 1356, 1169, 1125, 1096, 1039, 1000, 981. |
| 1.072 | 2-sec-Butoxyprop-2-yl | 4-Chloro-3-isopropylisoxazol-5-yl | 1465, 1385, 1169, 1123, 1094, 1025, |

TABLE 1-continued $R^1R^2CH—ON=C(CN)—R^3 \quad R^1 = H \quad I$

| Example No. | $R^3$ | $R^2$ | IR data [cm$^{-1}$] |
|---|---|---|---|
| 1.073 | 2-sec-Butoxyprop-2-yl | 4-Chloro-3-sec-butylisoxazol-5-yl | 997, 981. 1462, 1366, 1169, 1123, 1075, 1024, 997. |
| 1.074 | 2-sec-Butoxyprop-2-yl | 4-Chloro-3-tert-butylisoxazol-5-yl | 1385, 1368, 1169, 1122, 1106, 1022, 996, 980. |
| 1.075 | 2-sec-Butoxyprop-2-yl | 4-Chloro-3-cyclohexylisoxazol-5-yl | 1450, 1385, 1169, 1123, 1036, 1016, 988. |
| 1.076 | 2-sec-Butoxyprop-2-yl | 4-Chloro-3-phenylisoxazol-5-yl | 1443, 1168, 1158, 1121, 1093, 1035, 1017, 962, 695. |
| 1.077 | 2-sec-Butoxyprop-2-yl | 4-Chloro-3-(4-methylphenyl)isoxazol-5-yl | 1385, 1156, 1120, 1093, 1017, 962. |
| 1.078 | 2-sec-Butoxyprop-2-yl | 4-Chloro-3-(4-chlorophenyl)isoxazol-5-yl | 1421, 1385, 1168, 1157, 1121, 1095, 1016, 964, 834. |
| 1.079 | 2-sec-Butoxyprop-2-yl | 4-Chloro-3-(4-fluorophenyl)isoxazol-5-yl | 1527, 1457, 1428, 1235, 1161, 1121, 1092, 1017, 842. |
| 1.080 | 2-Methylthioprop-2-yl | 2-Chloro-3-isopropylphenyl | 1468, 1428, 1364, 1058, 1036, 1017, 1003, 961, 786. |
| 1.081 | 2-Methylthioprop-2-yl | 2,6-Difluorophenyl | 1628, 1595, 1473, 1237, 1063, 1017, 1002, 960, 941, 792. |
| 1.082 | 2-Methylthioprop-2-yl | 2-Chloro-3-trifluoromethylphenyl | 1437, 1321, 1169, 1139, 1113, 1094, 1059, 1018. |
| 1.083 | 2-Methylthioprop-2-yl | 3-Phenylisoxazol-5-yl | 1470, 1441, 1431, 1356, 1023, 996, 928, 907. |
| 1.084 | 2-Methylthioprop-2-yl | 3-Methylisoxazol-5-yl | 1443, 1420, 1369, 1359, 1139, 1112, 1024, 1000, 960, 895. |
| 1.085 | Isopropyl | 2-Chloro-3-isopropylphenyl | 1468, 1428, 1364, 1058, 1035, 1013, 964. |
| 1.086 | Isopropyl | 3-Phenylisoxazol-5-yl | 1469, 1443, 1406, 1024, 1001, 984, 950. |
| 1.087 | Isopropyl | 3-Methylisoxazol-5-yl | 1468, 1446, 1420, 1360, 1058, 1021, 1002, 985. |
| 1.088 | Cyclopropyl | 2-Chloro-3-isopropylphenyl | 1470, 1428, 1363, 1061, 1035, 1011, 969, 939. |
| 1.089 | Cyclopropyl | 2,6-Difluorophenyl | 1473, 1237, 1064, 1045, 1010, 966, 948. |
| 1.090 | Cyclopropyl | 2-Chloro-3-trifluoromethylphenyl | 1436, 1321, 1129, 1139, 1994, 1058, 1029, 1014, 936. |
| 1.091 | Cyclopropyl | 3-Phenylisoxazol-5-yl | 1443, 1406, 1054, 1023, 1001, 983, 950. |
| 1.092 | Cyclopropyl | 3-Methylisoxazol-5-yl | 1445, 1420, 1358, 1056, 1021, 1001, 985, 933. |
| 1.093 | 2-Tetrahydropyranyl | 2-Chloro-3-isopropylphenyl | 1429, 1088, 1059, 1047, 1036, 1007, 903. |
| 1.094 | 2-Tetrahydropyranyl | 2-Chloro-3-trifluoromethylphenyl | 1440, 1320, 1181, 1166, 1138, 1095, 1066, 1044, 974. |
| 1.095 | 2-Tetrahydropyranyl | 3-Phenylisoxazol-5-yl | 1444, 1093, 1085, 1064, 1040, 985, 904. |
| 1.096 | 2-Tetrahydropyranyl | 3-Methylisoxazol-5-yl | 1442, 1418, 1360, 1087, 1047, 1023, 999, 903. |
| 1.097 | 2-Methylthioprop-2-yl | 2-(3-Chlorophenyl)oxazol-4-yl | 1551, 1461, 1434, |

TABLE 1-continued $R^1R^2CH-ON=C(CN)-R^3 \quad R^1 = H \quad I$

| Example No. | $R^3$ | $R^2$ | IR data [cm$^{-1}$] |
|---|---|---|---|
| | | | 1116, 1015, 997, 960, 806, 790, 720. |
| 1.098 | 2-Ethylthioprop-2-yl | 2-(3-Chlorophenyl)oxazol-4-yl | 1551, 1461, 1434, 1114, 1014, 997, 961, 804, 790, 720. |
| 1.099 | 2-isopropylthioprop-2-yl | 2-(3-Chlorophenyl)oxazol-4-yl | 1551, 1464, 1109, 1057, 1021, 994, 980, 795, 778, 722. |
| 1.100 | 2-n-Butylthioprop-2-yl | 2-(3-Chlorophenyl)oxazol-4-yl | 1553, 1434, 1114, 1015, 997, 966, 804, 791, 720. |

Use Examples

The insecticidal action of the compounds of the general formula I can be demonstrated by the following experiments:

The active ingredients were prepared a) as a 0.1% solution in acetone or b) as a 10% strength emulsion in a mixture of 70% by weight of cyclohexanone, 20% by weight of Nekanil® LN (Lutensol® AP6, wetting agent having an emulsifying and dispersant effect and based on ethoxylated alkylphenols) and 10% by weight of Emulphor® EL (Emulan® EL, emulsifier based on ethoxylated fatty alcohols)

and diluted with acetone in the case of a) and with water in the case of b) to give the desired concentration.

After the end of the experiments, the lowest concentration in each case at which the compounds still caused 80–100% inhibition or kill rate (action threshold or minimum concentration) was determined.

A. *Aphis fabae* (Bean Aphid), Contact Effect

Severely infested bush beans (*Vicia faba*) were treated with the aqueous active ingredient formulation.

The kill rate was determined after 24 hours.

In this test, compounds 1,006, 1,024, 1,040, 1.056, 1.065, 1,078, 1,082 and 1.088 had action thresholds of from 1,000 to 200 ppm.

B. *Caenorhabditis elegans* (Pine Nematodes), Contact Effect

The soil of a test vessel was wet with a solution of the active ingredient in acetone, the solvent was evaporated and the soil was then covered with *E. coli* bacteria suspension as a culture medium and was infected with 50 µl of nematode suspension.

The kill rate was determined after 48 hours.

In this test, compounds 1.003, 1,004, 1,005, 1,032, 1.034, 1.084 and 1.083 had action thresholds of 100 ppm.

C. *Dysdercus intermedius* (Cotton Stainer), Contact Effect 200 g of sterile quartz sand were wet with 25 ml of the aqueous active ingredient formulation, after which about 20 larvae in the 3rd larval stage were placed thereon.

After the larvae had hatched in a controlled experiment, the kill rate was determined.

In this test, compounds 1.008, 1,009, 1,010, 1,012, 1.024, 1.025, 1.027, 1,028, 1.040, 1.041, 1.043, 1,044, 1.046, 1.047, 1.056, 1.072 and 1,078 had action thresholds of 1,000 ppm.

D. *Heliothis virescens* (Tobacco Budworm), Contact/Injection Effect

Tobacco plants measuring about 10 cm were treated with the aqueous active ingredient formulation. After drying off, the plants were each assigned 10 larvae in the 3rd stage of development.

The kill rate and prevention of the injection were determined after 48 hours.

In this test, compounds 1.008, 1.009, 1.018, 1.021, 1.022, 1.033 and 1.044 had action thresholds of from 1,000 to 400 ppm.

E. *Meloidogyne incognita* (Root Knot Nematodes), Contact Effect

Tomato seedlings were incubated for 3 weeks in compost severely infected with nematodes. The plants were removed, freed from soil residues and placed for 1 hour in the aqueous active ingredient formulation. Thereafter, the seedlings were planted individually in sterilized soil.

After 6–8 weeks, the growth of the plants and the infestation of the roots were evaluated.

In this test, compounds 1.002, 1.081, 1.082, 1.084, 1.087, 1.089, 1,091, 1.092 and 1.096 had action thresholds of 100 ppm.

F. *Musca domestica* (Housefly), Contact Effect

The soil of a test vessel was wet with a solution of the active ingredient in acetone, the solvent was evaporated off and the soil was then infested with 10 flies.

The kill rate was determined after 4 hours.

In this test, compounds 1.002, 1.003, 1.006, 1.007, 1.011, 1.021, 1.026, 1.040, 1.043, 1.045, 1.056, 1.060, 1.063, 1.080, 1.081, 1.083, 1.084, 1.085, 1.086, 1.089, 1.090 and 1.092 had action thresholds of 1.0 to 100 mg.

G. *Ornithodorus moubata* (Tick), Contact Effect 5 ticks in each case (diameter 1.5–2 mm; after injection of blood) were immersed for about 5 seconds in the aqueous active ingredient formulation.

The kill rate was determined after 48 hours.

In this test, compounds 1.084 and 1.086 had action thresholds of 1.000 ppm.

H. *Plutella maculipennis* (Diamondback Caterpillar), Contact Effect

Leaves of young cabbage plants were wet with the aqueous active ingredient formulation and then placed on a moistened filter. The prepared leaves were then each infested with 10 caterpillars in the 4th stage of development.

The kill rate was determined after 48 hours.

In this test, compounds 1.008, 1.022, 1.023, 1.040, 1.056, 1.057, 1.071 and 1.073 had action thresholds of 1,000 ppm.

I. *Prodenia litura* (Egyptian Cottonleaf Worm), Breeding Test

Five caterpillars in development stage L3 (10–12 mm) which had suffered no detectable damage in the contact test were applied to standard culture medium (3.1 l of water, 80 g of agar, 137 g of beer yeast, 515 g of cornflour, 130 g of wheat germ and conventional additives and vitamins (20 g of Wesson's salt, 5 g of nipagin, 5 g of sotbin, 10 g of cellulose, 80 g of ascorbic acid, 1 g of Lutavit® blend (vitamin), 5 ml of alcoholic biotin solution) which had been previously wet with the aqueous active ingredient formulation.

The observation continued until hatching of the moths in a control experiment without active ingredient.

In this test, compounds 1.009, 1.013, 1.022, 1.023, 1.024, 1.025, 1.044, 1.045, 1.061, 1.071, 1.075, 1.091 and 1.092 had action thresholds of 1.0 mg.

K. *Tetranychus telarius* (Common Spider Mite), Contact Effect

Severely infested potted bush beans which had the second pair of secondary leaves were treated with the aqueous active ingredient formulation.

After 5 days in a greenhouse, the success of the treatment was determined by means of binoculars.

In this test, compounds 1.009, 1.016, 1.062 and 1.074 had action thresholds of from 400 to 1,000 ppm.

We claim:

1. A cyanooxime ether of the formula I $$R^1R^2CH-OH=C(CN)-R^3 \qquad I$$

where $R^1$ is hydrogen or $C_1-C_4$-alkyl;

$R^2$ is a mononuclear to trinuclear aliphatic or aromatic ring system which is bonded via a carbon atom and, in addition to carbon atoms, may contain from one to four nitrogen atoms or from one to three hetero atoms selected from the group consisting of oxygen, sulfur and nitrogen, where this ring system may carry from one to five halogen atoms and/or from one to four of the following radicals:

cyano, cyanato, thiocyanato, nitro, amino, hydroxyl, carboxyl, $C_1-C_6$-alkyl, $C_1-C_4$-haloalkyl, $C_1-C_6$-alkoxy, $C_1-C_4$-haloalkoxy, $C_1-C_4$-alkoxy-$C_1-C_4$-alkyl, $C_1-C_6$-alkylthio, $C_1-C_4$-haloalkylthio, $C_1-C_4$-alkylthio-$C_1-C_4$-alkyl, $C_3-C_{15}$-alkenyl, $C_3-C_{15}$-alkenyloxy, $C_3-C_8$-cycloalkyl, $C_5-C_8$-cycloalkenyl, $C_3-C_8$-cycloalkoxy, $C_5-C_8$-cycloalkenyloxy, $C_1-C_6$-alkylamino, di-$C_1C_6$-alkylamino, $C_1-C_6$-alkylcarbonyl, $C_1-C_6$-alkoxycarbonyl, $C_1-C_6$-alkylaminocarbonyl, di-$C_1-C_6$-alkylaminocarbonyl, $C_1-C_6$-alkylcarboxyl, phenyl, phenoxy, phenylthio, phenylamino, phenyl-$C_1-C_4$-alkyl, phenoxy-$C_1-C_4$-alkyl, phenylthio-$C_1-C_4$-alkyl or phenylamino-$C_1-C_4$-alkyl, where the aromatic rings in turn may carry from one to five halogen atoms and from one to three of the following radicals: cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, or where the aromatic rings in turn may carry from one to five halogen atoms or from one to three of the following radicals: cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, where this ring system may carry from one to four halogen atoms and from one to three of the following radicals= $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, or where the aromatic rings in turn may carry from one to four halogen atoms or from one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

or where this ring system may carry from one to five halogen atoms or from one to four of the following radicals:

cyano, cyanato, thiocyanato, nitro, amino, hydroxyl, carboxyl, $C_1-C_6$-alkyl, $C_1-C_4$-haloalkyl, $C_1-C_6$-alkoxy, $C_1-C_4$-haloalkoxy, $C_1-C_4$-alkoxy-$C_1-C_4$-alkyl, $C_1-C_6$-alkylthio, $C_1-C_4$-haloalkylthio, $C_1-C_4$-alkylthio-$C_1-C_4$-alkyl, $C_3-C_{15}$-alkenyl, $C_3-C_{15}$-alkenyloxy, $C_3-C_8$-cycloalkyl, $C_5-C_8$-cycloalkenyl, $C_3-C_8$-cycloalkoxy, $C_5-C_8$-cycloalkenyloxy, $C_1-C_6$-alkylamino, di-$C_1C_6$-alkylamino, $C_1-C_6$-alkylcarbonyl, $C_1-C_6$-alkoxycarbonyl, $C_1-C_6$-alkylaminocarbonyl, di-$C_1-C_6$-alkylaminocarbonyl, $C_1-C_6$-alkylcarboxyl, phenyl, phenoxy, phenylthio, phenylamino, phenyl-$C_1-C_4$-alkyl, phenoxy-$C_1-C_4$-alkyl, phenylthio-$C_1-C_4$-alkyl or phenylamino-$C_1-C_4$-alkyl, where the aromatic rings in turn may carry from one to five halogen atoms and from one to three of the following radicals: cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, or where the aromatic rings in turn may carry from one to five halogen atoms or from one to three of the following radicals: cyano, nitro, $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio;

a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, where this ring system may carry from one to four halogen atoms and from one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, or where the aromatic rings in turn may carry from one to four halogen atoms or from one to three of the following radicals: $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio, and $R^3$ is unsubstituted or substituted alkyl or an unsubstituted or substituted aliphatic ring system which is bonded via a carbon atom and, in addition to carbon atoms, may contain one or two hetero atoms selected from the group consisting of oxygen, sulfur and nitrogen.

2. A cyanooxime ether of the formula I as claimed in claim 1, wherein $R^3$ is:

$C_1$–$C_8$-alkyl which may carry from one to nine halogen atoms and one of the following radicals: cyano, nitro, amino, $C_1$–$C_6$-alkoxy, $C_1$–$C_4$-haloalkoxy, $C_1$–$C_6$-alkylthio, $C_1$–$C_4$-haloalkylthio, $C_3$–$C_8$-cycloalkyl, $C_3$–$C_8$-cycloalkoxy, di-$C_1$–$C_6$-alkylamino, $C_1$–$C_6$-alkylcarbonyl, $C_1$–$C_6$-alkoxycarbonyl, $C_1$–$C_6$-alkylaminocarbonyl, di-$C_1$–$C_6$-alkylaminocarbonyl, $C_1$–$C_6$-alkylcarboxyl, phenyl, phenoxy, phenylthio, phenyl-$C_1$–$C_4$-alkyl, phenoxy-$C_1$–$C_4$-alkyl, phenylthio-$C_1$–$C_4$-alkyl or phenylamino-$C_1$–$C_4$-alkyl, where the aromatic rings in turn may carry from one to five halogen atoms and from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to five halogen atoms or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;

or $C_1$–$C_8$-alkyl which may carry from one to nine halogen atoms or one of the following radicals: cyano, nitro, amino, $C_1$–$C_6$-alkoxy, $C_1$–$C_4$-haloalkoxy, $C_1$–$C_6$-alkylthio, $C_1$–$C_4$-haloalkylthio, $C_3$–$C_8$-cycloalkyl, $C_3$–$C_8$-cycloalkoxy, di-$C_1$–$C_6$-alkylamino, $C_1$–$C_6$-alkylcarbonyl, $C_1$–$C_6$-alkoxycarbonyl, $C_1$–$C_6$-alkylaminocarbonyl, di-$C_1$–$C_6$-alkylaminocarbonyl, $C_1$–$C_6$-alkylcarboxyl, phenyl, phenoxy, phenylthio, phenyl-$C_1$–$C_4$-alkyl, phenoxy-$C_1$–$C_4$-alkyl, phenylthio-$C_1$–$C_4$-alkyl or phenylamino-$C_1$–$C_4$-alkyl, where the aromatic rings in turn may carry from one to five halogen atoms and from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to five halogen atoms or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;

or an aliphatic ring system which is bonded via a carbon atom and, in addition to carbon atoms, may contain one or two hetero atoms selected from the group consisting of oxygen, sulfur and nitrogen, where this ring system may carry from one to five halogen atoms and from one to four of the following radicals: cyano, nitro, amino, $C_1$–$C_6$-alkyl, $C_1$–$C_4$-haloalkyl, $C_1$–$C_6$-alkoxy, $C_1$–$C_4$-haloalkoxy, $C_1$–$C_4$-alkoxy-$C_1$–$C_4$-alkyl, $C_1$–$C_6$-alkylthio, $C_1$–$C_4$-haloalkylthio, $C_1$–$C_4$-alkylthio-$C_1$–$C_4$-alkyl, $C_3$–$C_8$-cycloalkyl, di-$C_1$–$C_6$-alkylamino, $C_1$–$C_6$-alkylcarboxyl, phenyl, phenoxy, phenylthio, phenyl-$C_1$–$C_4$-alkyl, phenoxy-$C_1$–$C_4$-alkyl, phenylthio-$C_1$–$C_4$-alkyl, where the aromatic rings in turn may carry from one to five halogen atoms and from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to five halogen atoms or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where this ring system may carry from one to five halogen atoms or from one to four of the following radicals: cyano, nitro, amino, $C_1$–$C_6$-alkyl, $C_1$–$C_4$-haloalkyl, $C_1$–$C_6$-alkoxy, $C_1$–$C_4$-haloalkoxy, $C_1$–$C_4$-alkoxy-$C_1$–$C_4$-alkyl, $C_1$–$C_6$-alkylthio, $C_1$–$C_4$-haloalkylthio, $C_1$–$C_4$-alkylthio-$C_1$–$C_4$-alkyl, $C_3$–$C_8$-cycloalkyl, di-$C_1$–$C_6$-alkylamino, $C_1$–$C_8$-alkylcarboxyl, phenyl, phenoxy, phenylthio, phenyl-$C_1$–$C_4$-alkyl, phenoxy-$C_1$–$C_4$-alkyl, phenylthio-$C_1$–$C_4$-alkyl, where the aromatic rings in turn may carry from one to five halogen atoms and from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to five halogen atoms or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio.

3. A cyanooxime ether of the formula I as claimed in claim 1, wherein $R^2$ is phenyl, 4-oxazolyl or 5-oxazolyl, where these rings may carry from one to five halogen atoms and from one to three of the following radicals:

cyano, cyanato, thiocyanato, nitro, amino, hydroxyl, carboxyl, $C_1$–$C_6$-alkyl, $C_1$–$C_4$-haloalkyl, $C_1$–$C_6$-alkoxy, $C_1$–$C_4$-haloalkoxy, $C_1$–$C_4$-alkoxy-$C_1$–$C_4$-alkyl, $C_1$–$C_6$-alkylthio, $C_1$–$C_4$-haloalkylthio, $C_1$–$C_4$-alkylthio-$C_1$–$C_4$-alkyl, $C_3$–$C_{15}$-alkenyl, $C_3$–$C_{15}$-alkenyloxy, $C_3$–$C_8$-cycloalkyl, $C_5$–$C_8$-cycloalkenyl, $C_3$–$C_8$-cycloalkoxy, $C_5$–$C_8$-cycloalkenyloxy, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylaminocarbonyl, di-$C_1$–$C_6$-alkylaminocarbonyl, $C_1$–$C_6$-alkylcarboxyl, phenyl, phenoxy, phenylthio, phenylamino, phenyl-$C_1$–$C_4$-alkyl, phenoxy-$C_1$–$C_4$-alkyl, phenylthio-$C_1$–$C_4$-alkyl or phenylamino-$C_1$–$C_4$-alkyl, where the aromatic rings in turn may carry from one to five halogen atoms and/or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to four halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, where this ring system may carry from one to four halogen atoms and from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to five halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio;

or where these rings may carry from one to five halogen atoms or from one to three of the following radicals:

cyano, cyanato, thiocyanato, nitro, amino, hydroxyl, carboxyl, $C_1$–$C_6$-alkyl, $C_1$–$C_4$-haloalkyl, $C_1$–$C_6$- alkoxy, $C_1$–$C_4$-haloalkoxy, $C_1$–$C_4$-alkoxy-$C_1$–$C_4$-alkyl, $C_1$–$C_6$-alkylthio, $C_1$–$C_4$-haloalkylthio, $C_1$–$C_4$-alkylthio-$C_1$–$C_4$-alkyl, $C_3$–$C_{15}$-alkenyl, $C_3$–$C_{15}$-alkenyloxy, $C_3$–$C_8$-cycloalkyl, $C_5$–$C_8$-cycloalkenyl, $C_3$–$C_8$-cycloalkoxy, $C_5$–$C_8$-cycloalkenyloxy, $C_1$–$C_6$-alkylamino, di-$C_1$–$C_6$-alkylamino, $C_1$–$C_6$-alkylcarbonyl, $C_1$–$C_6$-alkoxycarbonyl, $C_1$–$C_6$-alkylaminocarbonyl, di-$C_1$–$C_6$-alkylaminocarbonyl, $C_1$–$C_6$-alkylcarboxyl, phenyl, phenoxy, phenylthio, phenylamino, phenyl-$C_1$–$C_4$-alkyl, phenoxy-$C_1$–$C_4$-alkyl, phenylthio-$C_1$–$C_4$-alkyl or phenylamino-$C_1$–$C_4$-alkyl, where the aromatic rings in turn may carry from one to five halogen atoms and/or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to five halogen atoms or from one to three of the following radicals: cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, a five-membered or six-membered aromatic ring system which is bonded via a carbon atom and, in addition to carbon atoms, may contain from one to three nitrogen atoms or one or two nitrogen atoms and one oxygen or one sulfur atom or one oxygen or one sulfur atom, where this ring system may carry from one to four halogen atoms and from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, or where the aromatic rings in turn may carry from one to four halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio.

4. A cyanooxime ether of the formula I as claimed in claim 1, wherein $R^3$ is $C_1$–$C_4$-alkyl which may carry from one to nine halogen atoms and one of the following radicals: $C_1$–$C_4$-alkoxy, $C_1$–$C_4$-haloalkoxy, $C_1$–$C_4$-alkylthio, $C_3$–$C_8$-cycloalkyl, $C_3$–$C_8$-cycloalkoxy, phenyl, phenoxy, phenylthio, phenyl-$C_1$–$C_4$-alkyl, phenoxy-$C_1$–$C_4$-alkyl, phenylthio-$C_1$–$C_4$-alkyl, where the aromatic rings in turn may carry from one to five halogen atoms and from one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, or where the aromatic rings in turn may carry from one to five halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

or $C_1$–$C_4$-alkyl which may carry from one to nine halogen atoms or one of the following radicals: $C_1$–$C_4$-alkoxy, $C_1$–$C_4$-haloalkoxy, $C_1$–$C_4$-alkylthio, $C_3$–$C_8$-cycloalkyl, $C_3$–$C_8$-cycloalkoxy, phenyl, phenoxy, phenylthio, phenyl-$C_1$–$C_4$-alkyl, phenoxy-$C_1$–$C_4$-alkyl, phenylthio-$C_1$–$C_4$-alkyl, where the aromatic rings in turn may carry from one to five halogen atoms and from one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, or where the aromatic rings in turn may carry from one to five halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

or a saturated or monounsaturated 3-membered to 7-membered ring system which is bonded via a carbon atom and, in addition to carbon atoms, may carry one or two hetero atoms selected from the group consisting of oxygen, sulfur and nitrogen, where this ring system may carry from one to three of the following radicals: $C_1$–$C_4$-alkyl, $C_1$–$C_4$-alkoxy, $C_1$–$C_4$-alkoxy-$C_1$–$C_4$-alkyl, $C_1$–$C_4$-alkylthio, $C_1$–$C_4$-alkylthio-$C_1$–$C_4$-alkyl, phenyl, phenoxy, phenylthio, phenyl-$C_1$–$C_4$-alkyl, phenoxy-$C_1$–$C_4$-alkyl or phenylthio-$C_1$–$C_4$-alkyl, where the aromatic rings in turn may carry from one to five halogen atoms and from one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio;

or where the aromatic rings in turn may carry from one to five halogen atoms or from one to three of the following radicals: $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio.

5. A cyanooxime ether of the formula I as defined in claim 1 wherein $R^1$ is hydrogen, $R^2$ is 2,6-difluorophenyl and $R^3$ is 2-methoxyprop-2-yl.

6. A cyanooxime ether of the formula I as defined in claim 1 wherein $R^1$ is hydrogen, $R^2$ is 2-chloro-3-trifluoromethylphenyl and $R^3$ is 2-methoxyprop-2-yl.

7. A cyanooxime ether of the formula I as defined in claim 1 wherein $R^1$ is hydrogen, $R^2$ is 3-phenylisoxazol-5-yl and $R^1$ is 2-methoxyprop-2-yl.

8. A cyanooxime ether of the formula I as defined in claim 1 wherein $R^1$ is hydrogen, $R^2$ is 3-methylisoxazol-5-yl and $R^3$ 2-methoxyprop-2-yl.

9. A cyanooxime ether of the formula I as defined in claim 1 wherein $R^1$ is hydrogen, $R^2$ is 2-(4-fluorophenyl)oxazol-4-yl and $R^3$ is 2-ethoxyprop-2-yl.

10. A cyanooxime ether of the formula I as defined in claim 1 wherein $R^1$ is hydrogen, $R^2$ is 2-(4-bromophenyl)oxazol-4-yl and $R^3$ is 2-ethoxyprop-2-yl.

11. A cyanooxime ether of the formula I as defined in claim 1 wherein $R^1$ is hydrogen, $R^2$ is 2-(3-chlorophenyl)oxazol-4-yl and $R^3$ is 2-n-propoxyprop-2-yl.

12. A cyanooxime ether of the formula I as defined in claim 1 wherein $R^1$ is hydrogen, $R^2$ is 2,6-difluorophenyl and $R^3$ is 2-methylthioprop-2-yl.

13. A cyanooxime ether of the formula I as defined in claim 1 wherein $R^1$ is hydrogen, $R^2$ is 2-chloro-3-trifluoromethylphenyl and $R^3$ is 2-methylthioprop-2-yl.

14. A cyanooxime ether of the formula I as defined in claim 1 wherein $R^1$ is hydrogen, $R^2$ is 3-phenylisoxazol-5-yl and $R^3$ is 2-methylthioprop-2-yl.

15. A cyanooxime ether of the formula I as defined in claim 1 wherein $R^1$ is hydrogen, $R^2$ is 3-methylisoxazol-5-yl and $R^3$ is 2-methylthioprop-2-yl.

16. A cyanooxime ether of the formula I as defined in claim 1 wherein $R^1$ is hydrogen, $R^2$ is 3-methylisoxazol-5-yl and $R^3$ is isopropyl.

17. A cyanooxime ether of the formula I as defined in claim 1 wherein $R^1$ is hydrogen, $R^2$ is 2,6-difluorophenyl and $R^3$ is cyclopropyl.

18. A cyanooxime ether of the formula I as defined in claim 1 wherein $R^1$ is hydrogen, $R^2$ is 3-phenylisoxazol-5-yl and $R^3$ is cyclopropyl.

19. A cyanooxime ether of the formula I as defined in claim 1 wherein $R^1$ is hydrogen, $R^2$ is 3-methylisoxazol-5-yl and $R^3$ is cyclopropyl.

20. A cyanooxime ether of the formula I as defined in claim wherein $R^1$ is hydrogen, $R^2$ is 3-phenylisoxazol-5-yl and $R^3$ is 2-tetrahydropyranyl.

21. A pesticidal composition for controlling insects, arachnids and nematodes containing an effective amount of at least one compound of the formula I as defined in claim 1 and inert additives.

22. A method for controlling insects, arachnids and nematodes, wherein the insects, arachnids and nematodes and/or their habitat is or are treated with an effective amount of at least one compound of the formula I as defined in claim 1.

23. A pesticidal composition for controlling insects, arachnids and nematodes containing an effective amount of the compound of the formula I as defined in claim 11 and inert additives.

24. A method for controlling insects, arachnids and nematodes, wherein the insects, arachnids and nematodes and/or their habitat is or are treated with an effective amount of the compound of the formula I as defined in claim 11.

\* \* \* \* \*

UNITED STATES PATENT AND TRADEMARK OFFICE
CERTIFICATE OF CORRECTION

PATENT NO.: 5,489,605

DATED: February 6, 1996

INVENTOR(S): OBERDORF et al.

It is certified that error appears in the above-identified patent and that said Letters Patent is hereby corrected as shown below:

Column 108, claim 1, line 15, after "radicals" delete "=" and replace with a colon --:--.

Column 110, claim 2, line 8, "$C_1$-$C_8$-alkylcarboxyl" should be --$C_1$-$C_6$-alkylcarboxyl--.

Column 112, claim 20, line 66, after "claim" insert --1--.

Signed and Sealed this

Fourth Day of June, 1996

Attest:

BRUCE LEHMAN

*Attesting Officer*    Commissioner of Patents and Trademarks